US012799100B2

(12) United States Patent
Xing et al.

(10) Patent No.: US 12,799,100 B2
(45) Date of Patent: Nov. 17, 2026

(54) N-(1-METHYL-1H-PYRAZOL-4-YL) PYRIDINE-2-AMINE DERIVATIVE COMPOUNDS

(71) Applicant: Technoderma Medicines Inc, Jiaxing (CN)

(72) Inventors: Li Xing, Jiaxing (CN); Guanqun Li, Jiaxing (CN); Xiaolei Wang, Jiaxing (CN); Yuting Cai, Jiaxing (CN); Xiang Jiang, Jiaxing (CN); Xiang Pan, Jiaxing (CN); Wenhao Zhu, Jiaxing (CN); Yang Wang, Jiaxing (CN); Zengquan Wang, Jiaxing (CN)

(73) Assignee: TECHNODERMA MEDICINES INC., Jiaxing (CN)

(*) Notice: Subject to any disclaimer, the term of this patent is extended or adjusted under 35 U.S.C. 154(b) by 1049 days.

(21) Appl. No.: 17/771,070

(22) PCT Filed: Oct. 10, 2020

(86) PCT No.: PCT/CN2020/120134

§ 371 (c)(1),
(2) Date: Apr. 22, 2022

(87) PCT Pub. No.: WO2021/078023

PCT Pub. Date: Apr. 29, 2021

(65) Prior Publication Data

US 2024/0174648 A1 May 30, 2024

(30) Foreign Application Priority Data

Oct. 24, 2019 (CN) ........................ 201911019200.0

(51) Int. Cl.

| | |
|---|---|
| ***C07D 401/14*** | (2006.01) |
| ***C07D 403/12*** | (2006.01) |
| ***C07D 403/14*** | (2006.01) |
| ***C07D 405/14*** | (2006.01) |
| ***C07D 413/14*** | (2006.01) |
| ***C07D 417/14*** | (2006.01) |

(52) U.S. Cl.
CPC ......... *C07D 403/14* (2013.01); *C07D 401/14* (2013.01); *C07D 403/12* (2013.01); *C07D 405/14* (2013.01); *C07D 413/14* (2013.01); *C07D 417/14* (2013.01)

(58) Field of Classification Search
CPC .. C07D 403/14; C07D 401/14; C07D 403/12; C07D 405/14; C07D 413/14; C07D 417/14
See application file for complete search history.

(56) References Cited

U.S. PATENT DOCUMENTS

| | | | | |
|---|---|---|---|---|
| 8,354,422 | B2 | 1/2013 | Clark et al. | |
| 8,536,180 | B2 | 9/2013 | Clark et al. | |
| 8,969,335 | B2 | 3/2015 | Hoelzemann et al. | |
| 9,433,622 | B2 * | 9/2016 | Newton | C07D 471/04 |
| 9,670,208 | B2 | 6/2017 | Blake et al. | |
| 10,081,619 | B2 | 9/2018 | Hopkins et al. | |
| 10,154,995 | B2 | 12/2018 | Blake et al. | |
| 12,509,447 | B2 * | 12/2025 | Xing | C07D 401/14 |
| 2008/0300267 | A1 | 12/2008 | Okram et al. | |

FOREIGN PATENT DOCUMENTS

| | | | | |
|---|---|---|---|---|
| CN | 101218241 | | 7/2008 | |
| CN | 102459264 | | 5/2012 | |
| CN | 103298794 | | 9/2013 | |
| CN | 105848723 | | 8/2016 | |
| CN | 105980387 | | 9/2016 | |
| CN | 106459002 | | 2/2017 | |
| CN | 108368091 | | 8/2018 | |
| CN | 108864057 | | 11/2018 | |
| CN | 110330484 | | 10/2019 | |
| CN | 110330484 | A * | 10/2019 | A61P 1/00 |
| CN | 110627775 | | 12/2019 | |
| CN | 110862380 | | 3/2020 | |
| WO | WO 2012062704 | | 5/2012 | |
| WO | WO 2013/034238 | | 3/2013 | |
| WO | WO-2016027195 | A1 * | 2/2016 | A61K 31/506 |
| WO | WO 2016/201271 | | 12/2016 | |
| WO | WO 2016/201280 | | 12/2016 | |
| WO | WO 2019/222101 | | 11/2019 | |

(Continued)

OTHER PUBLICATIONS

Barreiro et al., Chem Rev, 2011, 111:5215-5246 (Year: 2011).*

(Continued)

*Primary Examiner* — Andrew D Kosar
*Assistant Examiner* — Jonathan D Mahlum
(74) *Attorney, Agent, or Firm* — McDonnell Boehnen Hulbert Berghoff, LLP

(57) ABSTRACT

Provided is a small molecule compound, which is characterized in having the structure represented by the following molecular formula: (I), wherein X1 and X2 are selected from carbon or nitrogen; G1 is a carbocyclic ring or heterocyclic ring having aromaticity; any one or more hydrogen atoms on the ring of G1 are substituted by R1; and R1 is selected from nitrogen-containing groups. The small molecule compound of the present invention can be used as a highly effective and specific JAK kinase inhibitor, specifically a Tyk2 inhibitor; and/or a JAK1 inhibitor, and/or a JAK1/Tyk2 or Tyk2/JAK1, Tyk2/Jak2 dual inhibitor.

1 Claim, No Drawings

(56) References Cited

FOREIGN PATENT DOCUMENTS

| | | | | |
|---|---|---|---|---|
| WO | WO 2020/118683 | | 6/2020 | |
| WO | WO-2020118683 | A1 * | 6/2020 | ........... C07D 493/08 |

OTHER PUBLICATIONS

Shu et al., Eur J Med Chem, 2020, 191:112148 (Year: 2020).*
Patani et al., Chem Rev, 1996, 96:3147-3176 (Year: 1996).*
Shu et al, "Design, synthesis, and pharmacological evaluation of 4- or 6-phenyl-pyrimidine derivatives as novel and selective Janus kinase 3 inhibitors", European Journal of Medicinal Chemistry, 191 (2020) 112148, pp. 1-18.
Li et al., Process Development and Large-Scale Synthesis of BTK Inhibitor BIIB068, Organic Process Research & Development, vol. 24, No. 6, Apr. 22, 2020, pp. 1199-1206.
International Search Report dated Jan. 8, 2021 for International Application No. PCT/CN2020/120134, 6 pages.
International Search Report for Chinese Application No. 2019110192000 filed Oct. 24, 2019, 3 pages.
First Office Action dated Mar. 3, 2021 for Application No. 201911019200.0, 6 pages.
Second Office Action dated Aug. 18, 2021 for Application No. 201911019200.0, 6 pages.

* cited by examiner

N-(1-METHYL-1H-PYRAZOL-4-YL)PYRIDINE-2-AMINE DERIVATIVE COMPOUNDS

CROSS REFERENCE TO RELATED APPLICATION

This application is a U.S. national phase of International Application No. PCT/CN2020/120134, filed on Oct. 10, 2020, which claims priority to Chinese Patent Application No. 201911019200.0, filed Oct. 24, 2019, both of which are incorporated by reference herein in their entirety.

TECHNICAL FIELD

The present invention relates to the field of a small molecule compound, and specifically, to a small molecule compound that can be used to treat, prevent and relieve autoimmune diseases such as rheumatic arthritis, ulcerative colitis or related inflammatory skin diseases such as psoriasis, eczema and vitiligo.

BACKGROUND

Protein kinases catalyze phosphorylation of amino acids at specific sites in proteins, and can be classified into tyrosine kinases, and serine and arginine kinases based on phosphorylation of amino acids. JAKs are a family of intracellular non-receptor tyrosine kinases (Tyrosine Kinase), including four members of JAK1, JAK2, JAK3 and Tyk2. Expressed in hematopoietic cells, leukocytes and intestinal epithelial cells mainly, JAKs play a role for mediating signal transduction of various cytokines involved in inflammatory responses. When cytokines are bound to cell surface receptors, JAKs are activated through autophosphorylation, and the activated JAKs then phosphorylate intracellular portions of the receptors to activate the receptors and recruit members of STAT protein family. Then, STATs are activated by JAKs through phosphorylation to form a dimer, which detached from the receptors, and entered nuclei to regulate gene transcription, thereby affecting biological functions of cells. The JAK (Janus Kinase)-STAT (Signal Transducer and Activator of Transcription) protein signal transduction pathway is a main pathway for intracellular signal transduction stimulated by a combination of the inflammatory cytokine and the receptor. As indicated by numerous evidence, the JAK-STAT signal pathway is critically associated with many diseases, especially autoimmune diseases such as rheumatic arthritis, intestinal diseases, allergic diseases, and the like. Therefore, in drug development, such protein kinases have become the most important targets for disease intervention. Recently, many pharmaceutical companies have been developing new drugs targeting members of the JAK family, but mainly focus on JAK1 and JAK3 inhibitors, particularly rarely on Tyk2 inhibitors.

The JAK-STAT pathway can be activated by more than 50 different cytokines. Proinflammatory cytokines (IL6, TNF-α, IL12 and IL23), anti-inflammatory cytokines (IL4 and IL10), hematopoietic growth factors (g-CSF, EPO and TPO) and metabolic cytokines (leptin and GH) can activate this signal pathway, thereby regulating cell proliferation, differentiation and activation, as well as transcription of various genes for human metabolic homeostasis. The JAK/STAT cascade is a confluence of many extracellular regulatory signals within the cells and therefore, is a central signaling node of the cells. Studies have revealed that a cytokine-mediated signal transduction system activates members of JAK family, such as JAK1, JAK2, JAK3 and TYK2 tyrosine kinases, to phosphorylate cytokine receptors and recruit STAT (signal transducer and activator of transcription) proteins, which finally results in gene expression in the cells. Coupling between JAK members is directly related to upstream cytokines. Under stimulation by different cytokines, different upstream cytokine signals may lead to couplings of JAK1/JAK2, JAK1/JAK3, JAK1/TYK2, JAK2/TYK2 and JAK2/JAK2, with JAK1 couplings as the most common couplings. TYK2 is crucial for signal transduction of type-I interferons (IFN-alpha and IFN-beta), IL-6 and IL-23. Differentiation and functions of immune cells related to inflammatory and autoimmune diseases are essentially associated with TYK2. Usually, TYK2 and family members of the same can appear in forms of TYK2/JAK1, TYK2/JAK2 and TYK2/JAK1/JAK2 couplings after being activated by the signal transduction system. Tyk2 plays a critical role in the signal transduction pathway mediating IL12, IL17 and IL23. Biological antibody drugs targeting IL17 and IL23 have achieved good therapeutic effects on diseases such as psoriasis. It is conceivable that inhibiting activity of JAK kinases, especially TYK2 kinase, by using highly potent small molecules can block a signal pathway mediated by an inflammatory factor, which can control inflammation, effectively treat the autoimmune diseases and/or inflammatory skin diseases and reduce side effects.

SUMMARY

The present invention is intended to develop an optimal JAK kinase inhibitor with high potency and selectivity, especially a Tyk2 inhibitor and/or a JAK1 inhibitor, and/or a dual inhibitor for JAK1/Tyk2 or Tyk2/JAK1 and/or Tyk2/Jak2, which is applicable to treatment of autoimmune diseases such as rheumatic arthritis, ulcerative colitis and inflammatory skin diseases, with indications such as eczema and psoriasis.

According to the present invention, there is provided a small molecule compound, which is a compound represented by the following structural formula or stereoisomer, geometric isomer, tautomer, racemate, hydrate, solvate, a metabolite and a pharmaceutically acceptable salt or a prodrug of the compound:

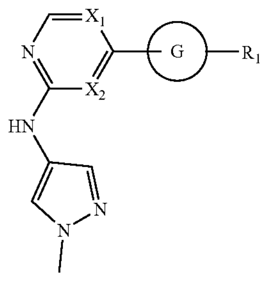

- where $X_1$ and $X_2$ are selected from carbon or nitrogen;
- G1 is aromatic carbocycle or heterocycle with six or more members;
- any one or more hydrogen atoms in the foregoing G1 ring are substituted by $R_1$; and
- $R_1$ is selected from hydrogen, halogen, an alkyl group, a substituted alkyl group, an amino group, an amine group, a substituted amine group, a carboxyl group, an amido group, a substituted amido group, an ester group, a substituted carbonyl group, a cycloalkyl group, a substituted cycloalkyl group, a heterocycloalkyl group, a substituted heterocycloalkyl group, an aryl group, a substituted aryl group, a heteroaryl group and a substituted heteroaryl group.

Further, according to the present invention, there is provided a small molecule compound, where:

G1 has a structure shown in the following general formula:

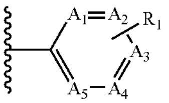

where $A_1$, $A_2$, $A_3$, $A_4$ and $A_5$ are selected from carbon, nitrogen, oxygen or sulfur;

for example,

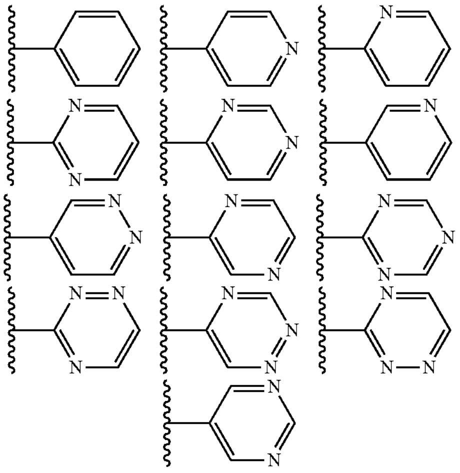

or;

G1 has a structure shown in the following general formula:

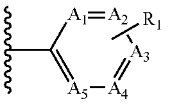

where $A_1$, $A_2$, $A_3$, $A_4$ and $A_5$ are selected from carbon, nitrogen, oxygen or sulfur; and a five-membered aromatic carbocycle/heterocycle or a six-membered aromatic carbocycle/heterocycle is connected in parallel to the foregoing bonds between $A_1$ and $A_2$, $A_2$ and $A_3$, $A_3$ and $A_4$, and $A_4$ and $A_5$;

for example,

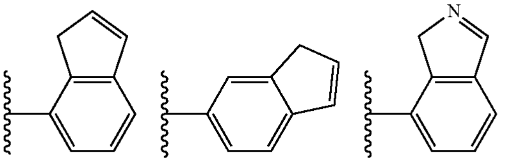

-continued

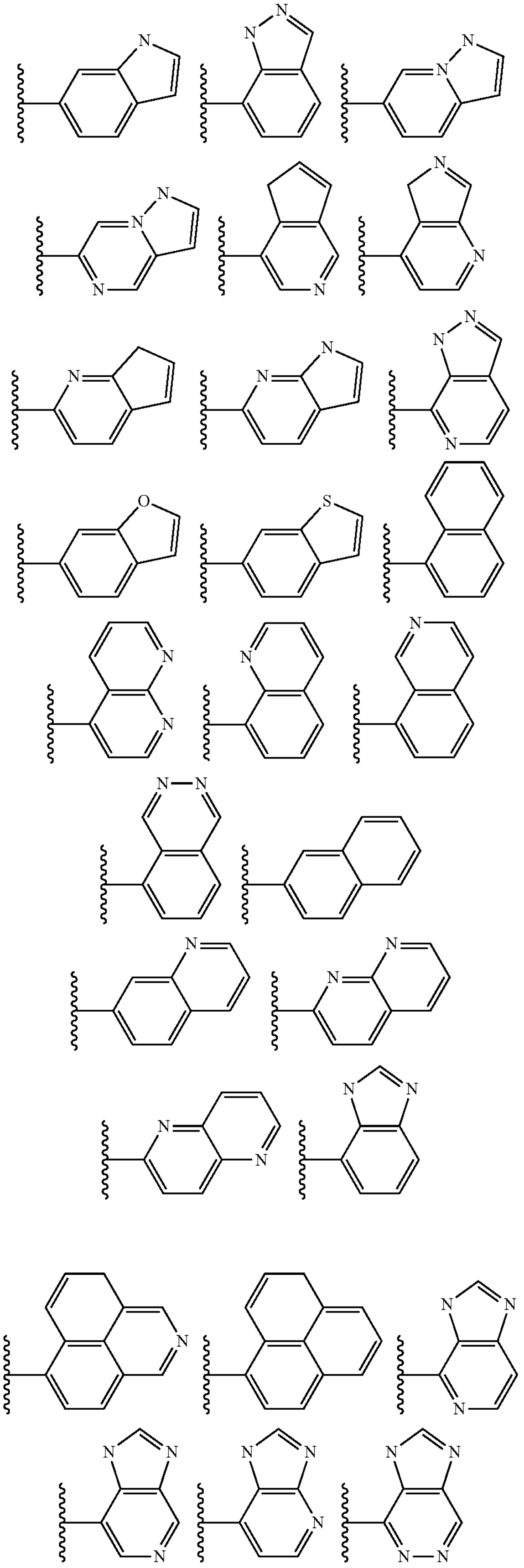

-continued
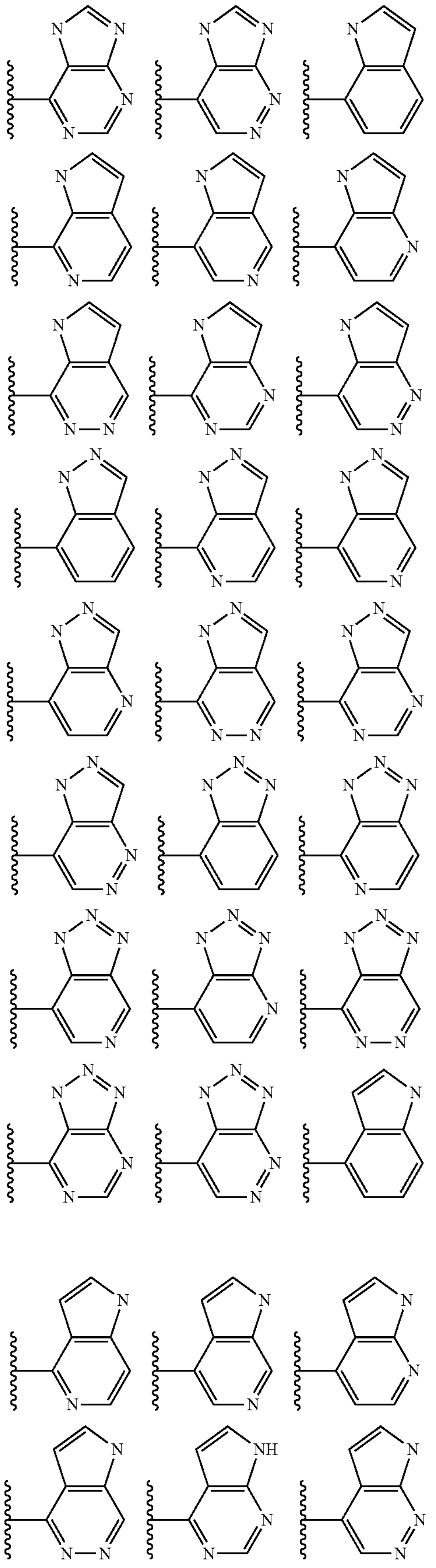
-continued
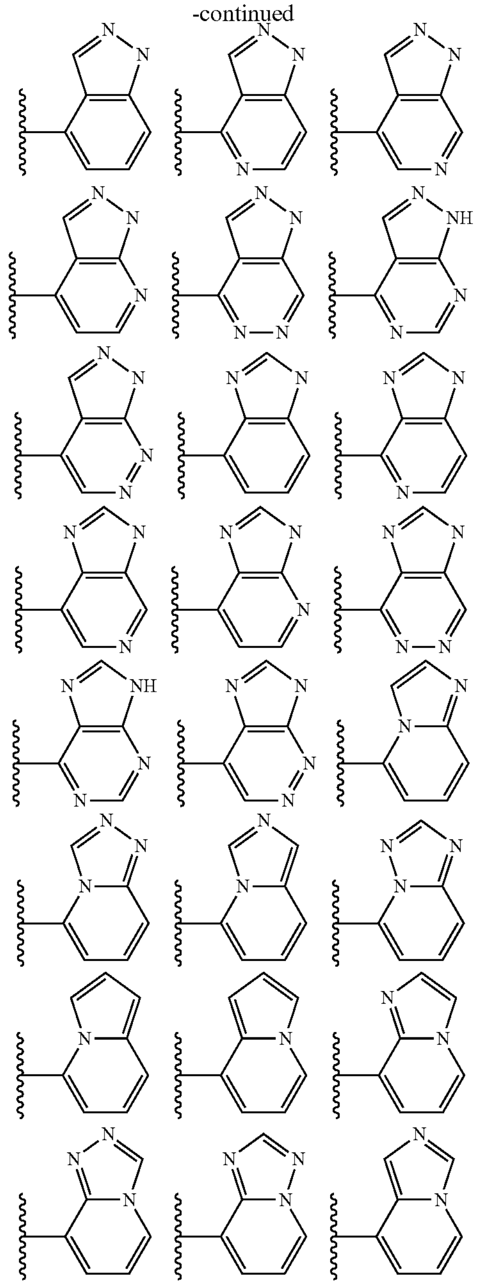
and a similar structure.
Further, according to the present invention, there is provided a small molecule compound, where:
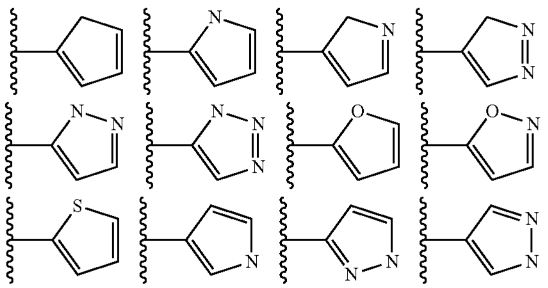

-continued

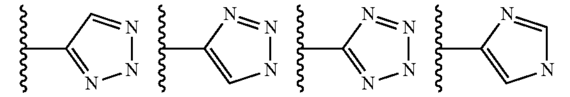
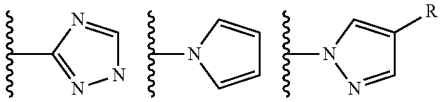
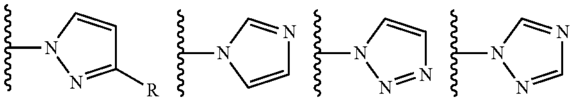
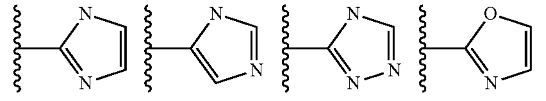
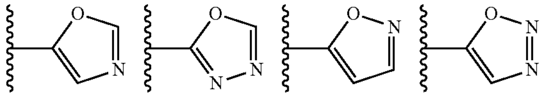
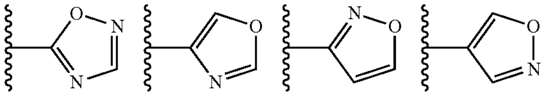
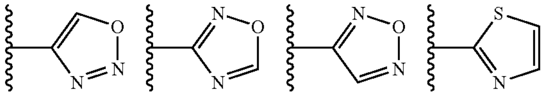
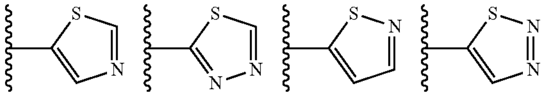
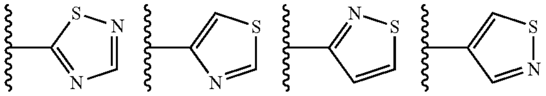
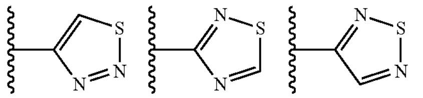

G1 has a structure shown in the following general formula:

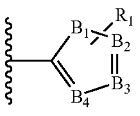

where $B_1$, $B_2$, $B_3$ and $B_4$ are selected from carbon, nitrogen, oxygen or sulfur; and a five-membered aromatic carbocycle/heterocycle or a six-membered aromatic carbocycle/heterocycle is connected in parallel to the foregoing bonds between $B_1$ and $B_2$, $B_2$ and $B_3$, and $B_3$ and $B_4$;

for example,

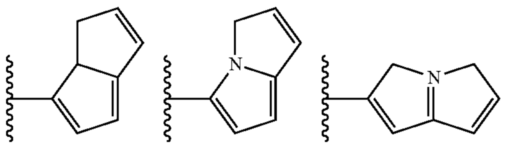

-continued

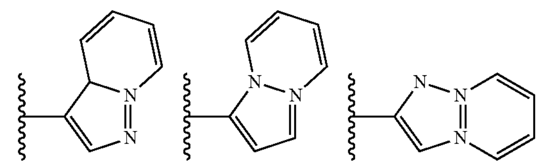
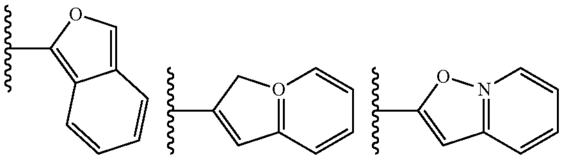
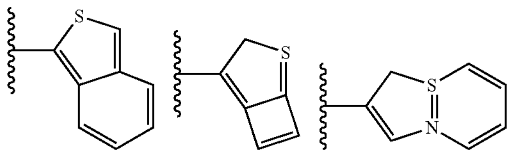

and a similar structure;

or

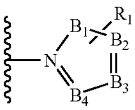

where $B_1$, $B_2$, $B_3$ and $B_4$ are selected from carbon, nitrogen, oxygen or sulfur; and a five-membered aromatic carbocycle/heterocycle or a six-membered aromatic carbocycle/heterocycle is connected in parallel to the foregoing bonds between $B_1$ and $B_2$, $B_2$ and $B_3$, and $B_3$ and $B_4$;

for example,

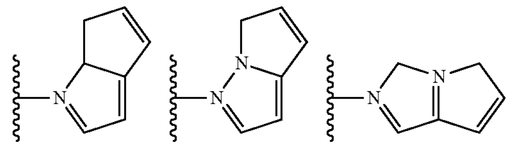
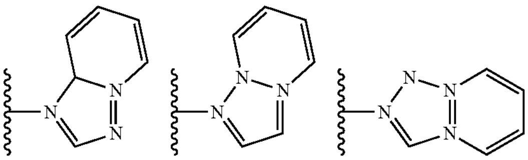
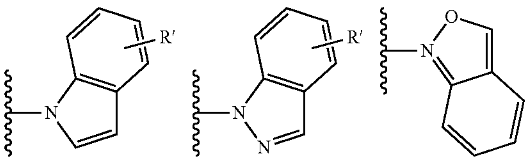
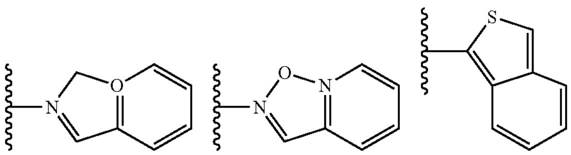

-continued

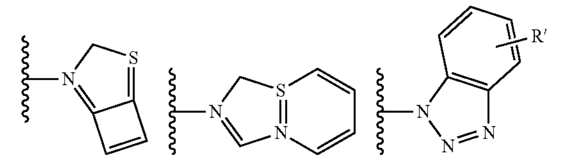

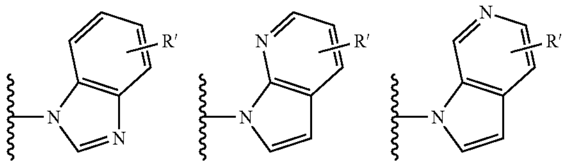

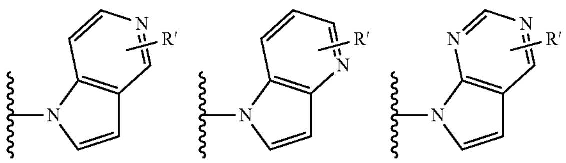

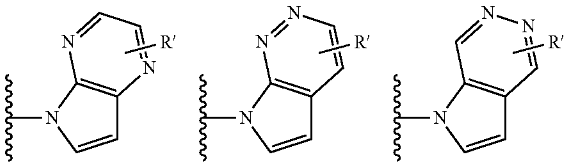

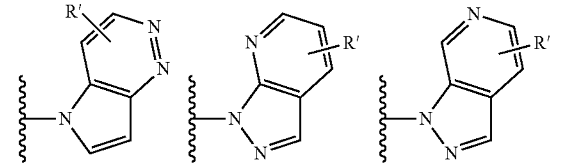

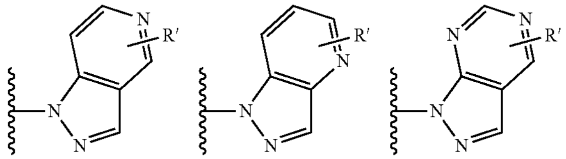

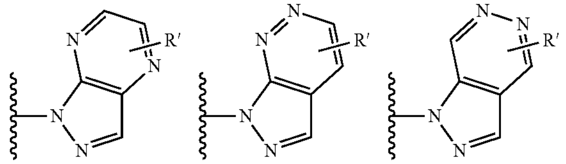

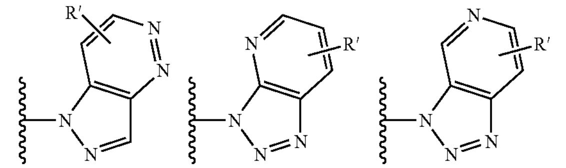

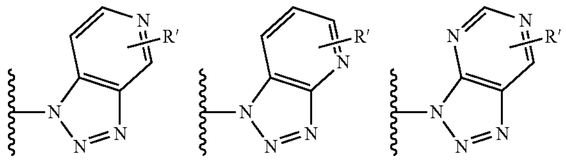

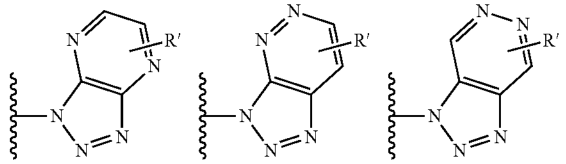

-continued

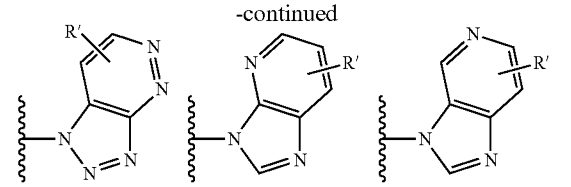

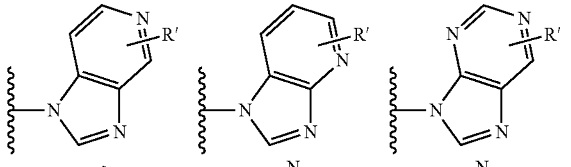

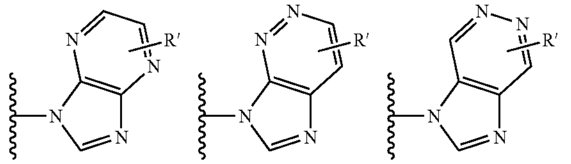

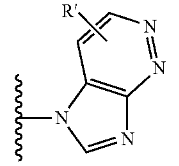

Further, according to the present invention, there is provided a small molecule compound, where:

$R_1$ is

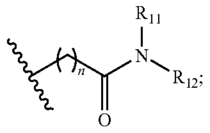

where n is 0 and a natural number;

$R_{11}$ is selected from hydrogen, an alkyl group, a substituted alkyl group, a cycloalkyl group, a substituted cycloalkyl group, a hydroxyl group and an ether group; and $R_{12}$ is selected from hydrogen, an alkyl group, a substituted alkyl group, a cycloalkyl group, a substituted cycloalkyl group, a hydroxyl group and an ether group.

Further, according to the present invention, there is provided a small molecule compound further having such characteristic: $R_1$ is

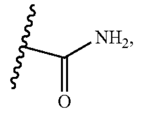 [SMILES: *C(N)=O]

and a product of a reaction with the amido group.

Here, a substance capable of reacting with the amido group is preferably selected from a halogenated compound such as halogenated hydrocarbon, acid halide and sulfonyl halide.

Further, according to the present invention, there is provided a small molecule compound further having such characteristic: $R_1$ is

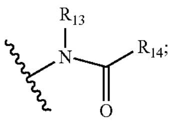

where $R_{13}$ is selected from hydrogen, an alkyl group, a substituted alkyl group, a cycloalkyl group, a substituted cycloalkyl group, a hydroxyl group, an ether group, an aryl group, a substituted aryl group, a heteroaryl group and a substituted heteroaryl group; and $R_{14}$ is selected from hydrogen, an alkyl group, a substituted alkyl group, a cycloalkyl group, a substituted cycloalkyl group, a hydroxyl group, an ether group, an aryl group, a substituted aryl group, a heteroaryl group and a substituted heteroaryl group.

Further, according to the present invention, there is provided a small molecule compound further having such characteristic: $R_1$ is $NH_2$, and a product of a reaction with the $NH_2$ group.

Further, according to the present invention, there is provided a small molecule compound further having such characteristic: $R_1$ is

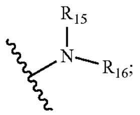

where $R_{15}$ is selected from hydrogen, an alkyl group, a substituted alkyl group, a cycloalkyl group, a substituted cycloalkyl group, a hydroxyl group, an ether group, an aryl group, a substituted aryl group, a heteroaryl group and a substituted heteroaryl group; and $R_{16}$ is selected from hydrogen, an alkyl group, a substituted alkyl group, a cycloalkyl group, a substituted cycloalkyl group, a hydroxyl group, an ether group, an aryl group, a substituted aryl group, a heteroaryl group and a substituted heteroaryl group.

Further, according to the present invention, there is provided a small molecule compound further having such characteristic: $R_1$ is

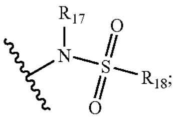

where $R_{17}$ is selected from hydrogen, an alkyl group, a substituted alkyl group, a cycloalkyl group, a substituted cycloalkyl group, a heterocycloalkyl group, a substituted heterocycloalkyl group, a hydroxyl group, an ether group, an aryl group, a substituted aryl group, a heteroaryl group and a substituted heteroaryl group; and $R_{18}$ is selected from hydrogen, an alkyl group, a substituted alkyl group, a cycloalkyl group, a substituted cycloalkyl group, a heterocycloalkyl group, a substituted heterocycloalkyl group, a hydroxyl group, an ether group, an aryl group, a substituted aryl group, a heteroaryl group and a substituted heteroaryl group.

Further, there is provided a small molecule compound, which is a compound represented by the following structural formula or stereoisomer, geometric isomer, tautomer, racemate, hydrate, solvate, a metabolite and a pharmaceutically acceptable salt or a prodrug of the compound:

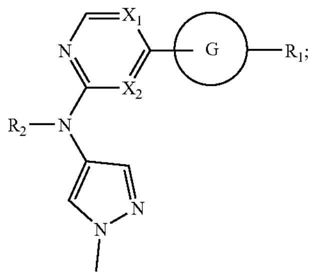

where $R_2$ is selected from an alkyl group, a substituted alkyl group, an ether group, a substituted carbonyl group, a cycloalkyl group, a substituted cycloalkyl group, a heterocycloalkyl group, a substituted heterocycloalkyl group, a sulfone group, a substituted sulfone group, a sulfoxide group and a substituted sulfoxide group.

In the present invention, the alkyl group is usually a linear alkyl group or a branched alkyl group with no more than 6 carbon atoms;

the foregoing substituted alkyl group means that one or more hydrogen atoms on a carbon chain of the alkyl group are substituted by other groups, and the other groups mentioned here may be groups such as the cycloalkyl group (which is substituted in a form similar to

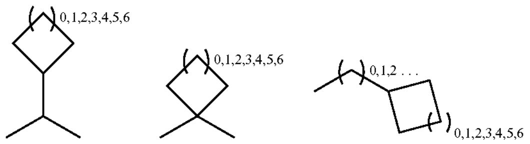

or the like, where any hydrogen atom on the cycloalkyl ring may also be substituted by groups such as halogen, a cyano group, the alkyl group, the hydroxyl group and the carboxyl group), the heterocycloalkyl group (that is, based on the cycloalkyl group mentioned above, at least one carbon atom on the alkyl ring thereof is substituted by oxygen, sulfur or nitrogen), halogen (F, Cl, Br and I), the carboxyl group, the cyano group (—CN), the sulfonic acid group (—$SO_4$), the sulfonyl group (—$SO_2R_a$, where $R_a$ is hydrogen, the alkyl group, the aryl group, or the like), an alkenyl group (—C≡C—$R_b$, where $R_b$ is hydrogen, the alkyl group, the aryl group, or the like), an alkynyl group (—C≡CH and —C≡C$R_b$, where $R_b$ is hydrogen, the alkyl group, the aryl group, or the like), the amido group (—C(O)N$R_xR_y$, where $R_xR_y$ is the alkyl group, the aryl group, or the like), the ester group (—C(O)O—$R_z$, where $R_z$ is the alkyl group, the aryl group, or the like), the aryl group, the heteroaryl group and the ether group ( (

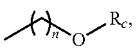

where n is a natural number such as 1, 2, 3 . . . , and $R_c$ is hydrogen, the alkyl group, the aryl group, or the like);

the substituted amine group means that one or more hydrogen atoms on the amine group are substituted by the other groups, and the other groups mentioned here may be groups such as the alkyl group, the cycloalkyl group, the carboxyl group, the cyano group, the sulfonic acid group, the amido group and the ester group; and the foregoing substituted cycloalkyl group means that one or more hydrogen atoms on the cycloalkyl ring are substituted by other groups, and the other groups mentioned here may be groups such as the alkyl group, the substituted alkyl group (same as above), halogen (F, Cl, Br and I), the carboxyl group, the cyano group (—CN), the sulfonic acid group (—$SO_4$), the sulfonyl group (—$SO_2R_a$, where $R_a$ is hydrogen, the alkyl group, the aryl group, or the like), an alkynyl group (—C≡CH and —C≡$CR_b$, where $R_b$ is the alkyl group, the aryl group, or the like), the amido group (—C(O)$NR_xR_y$, where $R_xR_y$ is the alkyl group, the aryl group, or the like), the ester group (—C(O)O—$R_z$, where $R_z$ is the alkyl group, the aryl group, or the like), the aryl group and the heteroaryl group.

The substituted heterocycloalkyl group means that based on the substituted cycloalkyl group, one or more carbon atoms on the ring thereof is substituted by oxygen, sulfur or nitrogen.

The aryl group refers to an aromatic ring or a benzo-aromatic ring with six or more members, such as benzene and naphthalene.

The substituted aryl group refers to an aromatic ring or a benzo-aromatic ring with five or more members, such as benzene, naphthalene and fluorene, one or more hydrogen atoms on the ring are substituted by other groups, and the other groups mentioned here may be groups such as the alkyl group, the substituted alkyl group (same as above), halogen (F, Cl, Br and I), the carboxyl group, the cyano group (—CN), the sulfonic acid group (—$SO_4$), the sulfonyl group (—$SO_2R_a$, where $R_a$ is hydrogen, the alkyl group, the aryl group, or the like), an alkynyl group (—C≡CH and —C≡$CR_b$, where $R_b$ is the alkyl group, the aryl group, or the like), the amido group (—C(O)NRxRy, where RxRy is the alkyl group, the aryl group, or the like), the ester group (—C(O)O—Rz, where Rz is the alkyl group, the aryl group, or the like), the aryl group and the heteroaryl group.

The foregoing heteroaryl group refers to aromatic heterocycle or benzo-aromatic heterocycle with five or more members, such as thiophene, pyrrole, pyridine, furan, imidazole, benzimidazole, and quinoline.

The foregoing substituted heteroaryl group refers to aromatic heterocycle or benzo-aromatic heterocycle with five or more members, such as thiophene, pyrrole, pyridine, furan, imidazole, benzimidazole, and quinoline, one or more hydrogen atoms on the ring are substituted by other groups, and the other groups mentioned here may be groups such as the alkyl group, the substituted alkyl group (same as above), halogen (F, Cl, Br and I), the carboxyl group, the cyano group (—CN), the sulfonic acid group (—$SO_4$), the sulfonyl group (—$SO_2R_a$, where $R_a$ is hydrogen, the alkyl group, the aryl group, or the like), an alkynyl group (—C≡CH and —C≡$CR_b$, where $R_b$ is the alkyl group, the aryl group, or the like), the amido group (—C(O)NRxRy, where RxRy is the alkyl group, the aryl group, or the like), the ester group (—C(O)O—Rz, where Rz is the alkyl group, the aryl group, or the like), the aryl group and the heteroaryl group.

The foregoing amide group has a structure shown in —$CONH_2$; and the foregoing substituted amide group means that one or more hydrogen atoms in the foregoing structure are substituted by other groups, and the other groups mentioned here may be groups such as the alkyl group, the substituted alkyl group (same as above), halogen (F, Cl, Br and I), the carboxyl group, the cyano group (—CN), the sulfonic acid group (—$SO_4$), the sulfonyl group (—$SO_2R_a$, where $R_a$ is hydrogen, the alkyl group, the aryl group, or the like), an alkynyl group (—C≡CH and —C≡$CR_b$, where $R_b$ is the alkyl group, the aryl group, or the like), the amido group (—C(O)NRxRy, where RxRy is the alkyl group, the aryl group, or the like), the ester group (—C(O)O-Rz, where Rz is the alkyl group, the aryl group, or the like), the aryl group and the heteroaryl group.

The foregoing ester group is —C(O)O—$R_z$, where $R_z$ is the alkyl group, the aryl group, or the like.

The foregoing substituted carbonyl groups are several compounds having structures shown below:

R is

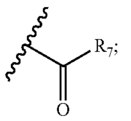

where $R_7$ is the alkyl group (same as above), the substituted alkyl group (same as above), the cycloalkyl group (cyclopropane, cyclobutane, cyclopentane, cyclohexane, cycloheptane, and the like), the substituted cycloalkyl group (that is, one or more hydrogen atoms on the cycloalkyl ring are substituted by halogen, the cyano group, the alkynyl group, for example, in a form shown in a structure of

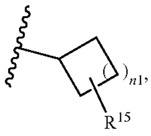

where $R^{15}$ is halogen, the cyano group, the alkynyl group, and the like), the heterocycloalkane group (at least one carbon atom on the 3- to 7-membered ring is substituted by nitrogen, sulfur or oxygen), the substituted heterocycloalkyl group (one or more hydrogen atoms on the heterocycloalkyl ring is substituted by halogen, the cyano group and the alkynyl group), the sulfone group ( ( 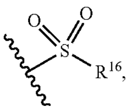

where $R^{16}$ is the alkyl group, halogen, the aryl group, and the like), the sulfoxide group ( (
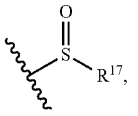

where $R^{17}$ is the alkyl group, halogen, the aryl group, and the like), or the substituted carbonyl group ( (
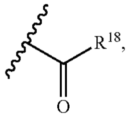

where $R^{17}$ is the alkyl group, the substituted alkyl group, the aryl group, and the like).

The foregoing sulfone group is

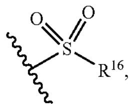

where $R^{16}$ is the alkyl group, the substituted alkyl group (same as above), halogen, the aryl group, the substituted alkyl group (same as above), the ether group, the cycloalkyl group, the substituted cycloalkyl group (same as above), or the like; and the foregoing sulfoxide group is

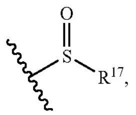

where $R^{17}$ is the alkyl group, halogen, the aryl group, or the like.

Further, according to the present invention, there is provided a small molecule compound further having such characteristic: application for the treatment, prevention and relief of autoimmune-related inflammatory skin diseases. The small molecule compound can be in various dosage forms and can be given through oral route, topical application, and injection.

The present invention achieves a function and an effect:

In the present invention, based on a protein structure of the JAK kinase, especially a protein structure of Tyk2, a small-molecule compound drug is properly designed for a purpose, the synthetic compound is firstly tested for biochemical activity of the JAK kinase, and a SAR (structure-activity relationship) is established based on IC50, a highly-potent inhibitor having IC50 below 200 nM is further subjected to a cytological test, and the selectivity of the compound is determined. Referring to data of the specific activity test, it can be found that several compounds involved in the present invention have a good ability of inhibiting cell activity.

The inhibitor provided in the present invention can also be used for other autoimmune-related skin diseases such as alopecia areata, vitiligo, lupus erythematosus with mainly cutaneous manifestations, lichen planus, lichen *nitidus*, lichen sclerosis et atrophicus, panniculitis, atopic dermatitis, and the like.

The Tyk2 inhibitor, and/or the JAK1 inhibitor, and/or the JAK1/Tyk2 dual inhibitor obtained in the present invention suitable for oral or intravenous administration can still be used for treatment of psoriasis and other autoimmune diseases such as RA, IBD and MS.

DETAILED DESCRIPTION

Example 1: General Method for Synthesizing Compound TDM-180712

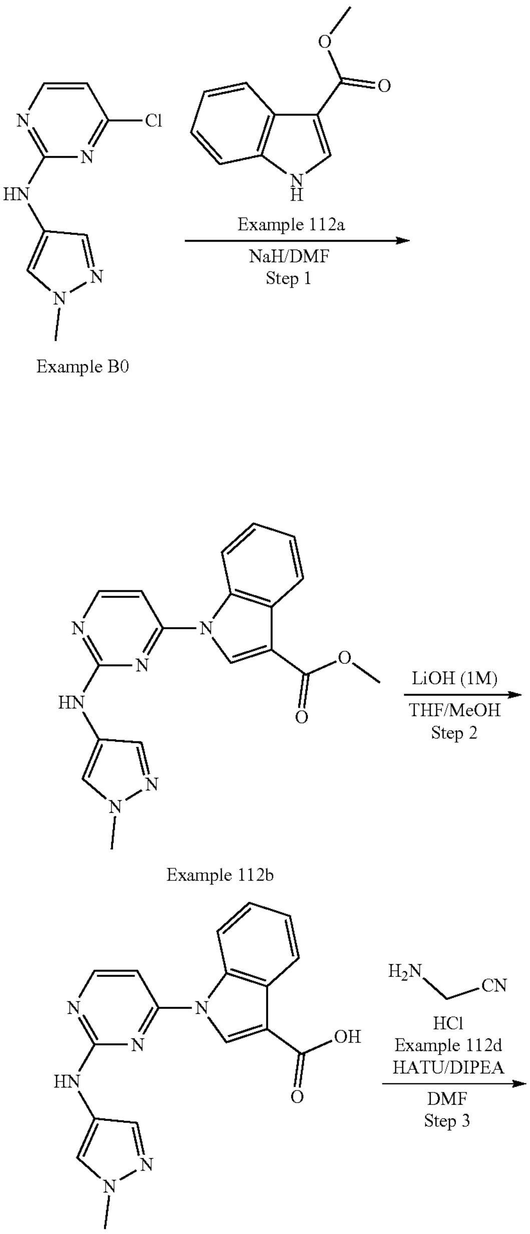

Example B0

Example 112b

Example 112c

-continued

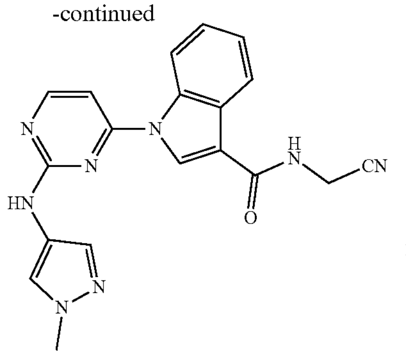

TDM-180712

Step 1: Example 112b

The original compound 112a (namely, 1-methylindole-3-carboxylic acid methyl ester (554 mg, 3.16 mmol) and sodium hydride (183 mg, 4.59 mmol, 60% wt.) were added to a three-necked flask, and nitrogen displacement was employed for the system three times using a water pump. Under an ice bath condition, dry DMF (50 mL) was added via a syringe during stirring, and the mixture was stirred for 30 minutes. A DMF solution (10 mL) of compound B0 (namely, 4-chloro-N-(1-methyl-1H-pyrazol-4-yl)pyrimidin-2-amine (600 mg, 2.87 mmol) was slowly injected into a reaction solution. The resulting reaction solution was refluxed for 4 hours at 100° C. After the reaction completed, the reaction solution was poured into water (30 mL) and extracted with ethyl acetate (60 mL×3). Organic layers were combined, washed with saturated brine, dried over anhydrous magnesium sulfate, concentrated under reduced pressure, and purified via a column (petroleum ether/ethyl acetate=0/100) to obtain the white solid compound 112b, namely 1-(2-((1-methyl-1H-pyrazol-4-yl)amino)pyrimidin-4-yl)-1H-indole-3-carboxylic acid methyl ester (0.6 g, yield: 60%).

LCMS $[M+1]^+$=349.

Step 2: Example 112c

A lithium hydroxide solution (10 mL, 1M) was added to the compound 112b (i.e., 1-(2-((1-methyl-1H-pyrazol-4-yl)amino)pyrimidin-4-yl)-1H-indole-3-carboxylic acid methyl ester (600 mg, 1.72 mmol)) in a solution of tetrahydrofuran (10 mL) and methanol (10 mL). Reaction of the reaction solution lasted 3 hours at 40° C. The mixture was concentrated under reduced pressure to remove the organic solvent, neutralized with HCl (2N) to approximately pH 5, and filtered to collect precipitated solid, ethanol was added to the solid, and the mixture was concentrated via rotary evaporation to remove residual water. A green solid compound 112c (i.e., 1-(2-((1-methyl-1H-pyrazol-4-yl)amino)pyrimidin-4-yl)-1H-indole-3-carboxylic acid (0.5 g, yield: 87%) was obtained. LCMS $[M+1]^+$=335.1.

Step 3: Example 112 (TDM-180712)

N-(cyanomethyl)-1-(2-((1-methyl-1H-pyrazol-4-yl)amino)pyrimidin-4-yl)-1H-indole-3-carboxamide Compound 112d (namely, 2-aminoacetonitrile hydrochloride (55 mg, 0.6 mmol)) and HATU (126 mg, 0.33 mmol) were added to a mixture of compound 112c (namely, N-(cyanomethyl)-1-(2-((1-methyl-1H-pyrazol-4-yl)amino)pyrimidin-4-yl)-1H-indole-3-carboxamide (100 mg, 0.3 mmol)) and DIPEA (155 mg, 1.2 mmol) in DMF (8 mL). The mixture was stirred for 18 hours at room temperature. After the reaction completed, the reaction solution was added into water, and filtered to collect precipitated solid. The solid was slurried with EtOAc/MeOH (approximately 4:1), to obtain an off-white solid compound 112, namely, N-(cyanomethyl)-1-(2-((1-methyl-1H-pyrazol-4-yl)amino)pyrimidin-4-yl)-1H-indole-3-carboxamide (95.3 mg, yield: 85%).

LCMS $[M+1]^+$=373.1

$^1$H NMR (400 MHz, DMSO-$d_6$)) δ 9.74 (s, 1H), 8.96 (s, 1H), 8.80 (s, 1H), 8.57 (d, J=5.6 Hz, 1H), 8.24 (d, J=8.0 Hz, 1H), 7.94 (s, 1H), 7.56 (s, 1H), 7.31-7.45 (m, 2H), 7.04 (d, J=5.6 Hz, 1H), 4.39 (d, J=5.6 Hz, 2H), 3.84 (s, 3H).

Example 2: General Method for Synthesizing Compound 125 (TDM-180725)

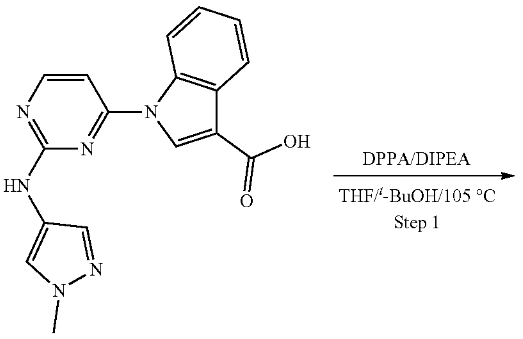

Example 125a

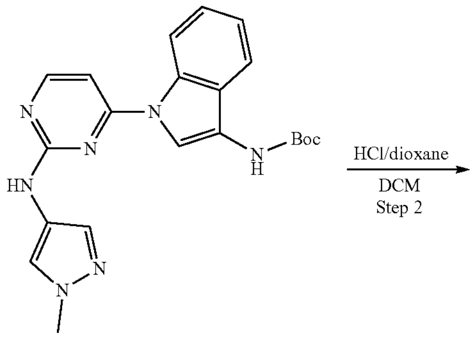

Example 125b

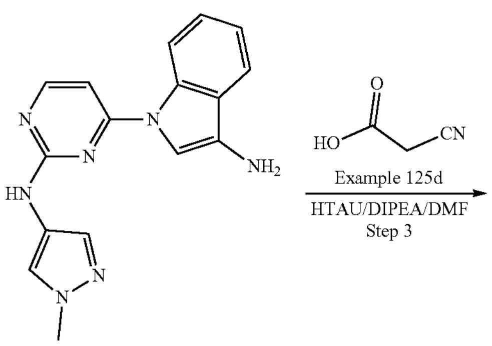

Example 125c

-continued

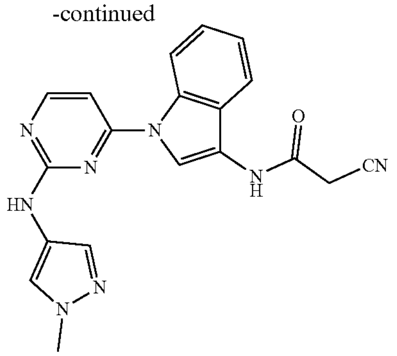

TDM-180725

Step 1: Example 125b (1-(2-((1-methyl-1H-pyrazol-4-yl)amino)pyrimidin-4-yl)-1H-indole-3-yl)carbamate tert-butyl ester Herein, t-BuOH (15 mL) and DPPA (309 mg, 1.13 mmol) were injected into an argon-protected three-necked flask containing a stirring bar and a mixture of compound 125a (0.25 g, 0.75 mmol) and DIPEA (193 mg, 1.5 mmol) in THF (10 mL). The mixture was heated to 105° C. and refluxed for 18 hours. The mixture was subjected to a LCMS test to detect a remaining raw material, then another batch of DIPEA (193 mg) and DPPA (309 mg) was added, and the resulting mixture was stirred at 105° C. under Argon for 20 hours. The reaction mixture was concentrated and purified via column chromatography (petroleum ether/ethyl acetate=0/100) to obtain a yellow solid compound 125b (80 mg, yield: <12.5%). [Note: Reaction reproducibility is poor.]

LCMS $[M+1]^+$=406.2

Step 2: Example 125c 1-(2-((1-methyl-1H-pyrazol-4-yl)amino)pyrimidin-4-yl)-1H-indole-3-amide HCl/1,4-dioxane (3 mL, 4 M) was added to a DCM solution (6 mL) of the compound 125b (80 mg, 0.2 mmol). The mixture was stirred for 26 hours at room temperature. The reaction mixture was concentrated under reduced pressure. A yellow solid compound 125c (60 mg, crude product) was obtained. The crude product was directly used in the next step without purification.

LCMS $[M+1]^+$=306.1

Step 3: Example 125 (TDM-180725)

2-cyano-N-(1-(2-((1-methyl-1H-pyrazol-4-yl)amino)pyrimidin-4-yl)-1H-indole-3-yl) acetamide HATU (114 mg, 0.3 mmol) and compound 125d (51 mg, 0.6 mmol) were added to compound 125c (60 mg, 0.2 mmol) in a solution of DIPEA (129 mg, 1.0 mmol) and DMF (10 mL). The substances were stirred for 16 hours at room temperature. The mixture was poured into $H_2O$, extracted with EtOAc (20 mL×3), and the combined organic layers were washed with $H_2O$ and brine, dried over $Na_2SO_4$, filtered, concentrated, and subjected to column chromatography (EtOAc/MeOH=20) for purification. The resulting crude product was slurried with EtOAc/PE (approximately 3:1), filtered to collect the solid, and dried under vacuum. An orange solid compound 125 (9.5 mg, yield: <10%) was obtained.

LCMS $[M+1]^+$=373.1.

1H NMR (400 MHz, Chloroform-d) δ 10.56 (s, 1H), 9.59 (brs, 1H), 8.87 (brs, 1H), 8.43 (d, J=5.6 Hz, 1H), 7.86-8.00 (m, 2H), 7.53 (s, 1H), 7.27-7.43 (m, 2H), 7.00 (d, J=5.6 Hz, 1H), 4.06 (s, 2H), 3.85 (s, 3H).

Example 3: General Method for Synthesizing Compound 122 (TDM-180722)

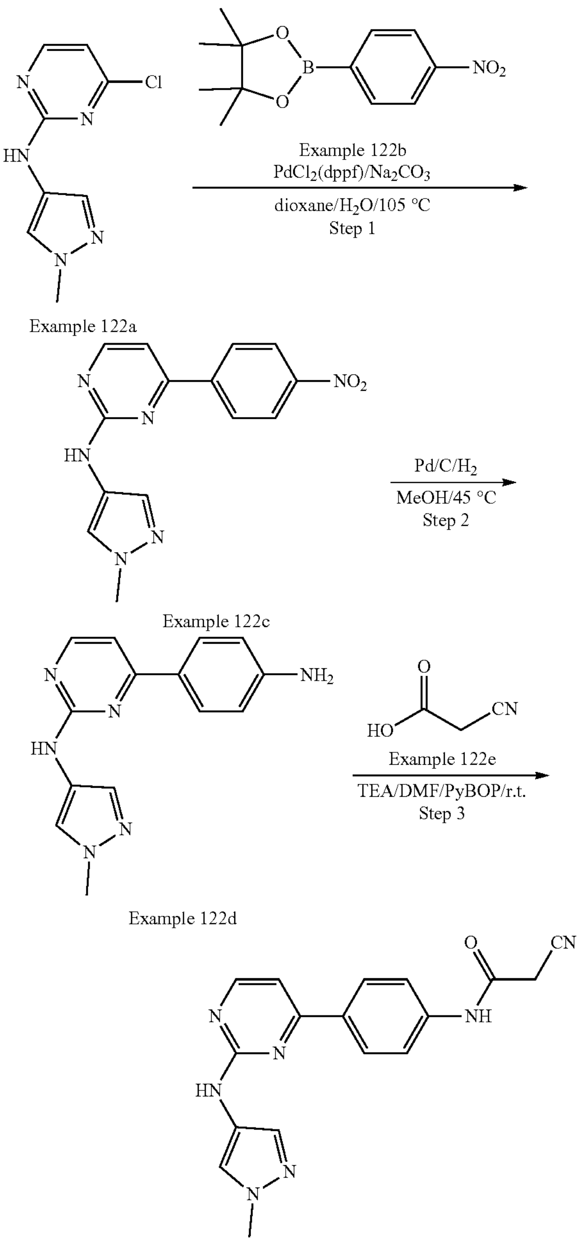

Example 122 (TDM-180722)

Step 1: Example 122c 1,4-dioxane (20 mL) and water (3 mL) were added to a mixture of compound 122a (200 mg, 0.96 mmol) (namely, 4-chloro-N-(1-methyl-1H-pyrazol-4-yl)pyrimidin-2-amine), compound 122b (287 mg, 0.96 mmol) (namely, 4,4,5,5-tetramethyl-2-(4-nitrophenyl)-1,3,2-dioxaborane, [1,1'-bis(diphenylphosphino) ferrocene]palladium dichloride (70.2 mg, 0.096 mmol) and sodium carbonate (210 mg, 1.92 mmol) at room temperature. The mixture was then degassed under vacuum, heated to 105° C. under nitrogen protection and stirred for 3 hours. After the reaction completed, the mixture was concentrated under reduced pressure. The mixture was purified via a silica gel column (petroleum ether:ethyl acetate=25:75) to obtain a red solid compound 122c (242 mg, yield: 56.8%), namely, N-(1-methyl-1H-pyrazol-4-yl)-4-(4-nitrophenyl)pyrimidin-2-amine. LCMS $[M+1]^+$=297.

Step 2: Example 122d

Pd/C was added to a suspension of the compound 122c (100 mg, 0.34 mmol) in methanol (30 mL) at room temperature. The mixture was then degassed under vacuum, heated to 45° C. under hydrogen and stirred for 3 hours. The mixture was filtered, and the filtrate was concentrated under reduced pressure to obtain a white solid compound 112d (57 mg, yield: 63%), namely 4-(4-aminophenyl)-N-(1-methyl-1H-pyrazol-4-yl)pyrimidin-2-amine. LCMS $[M+1]^+$=267.

Step 3: Example 122 (TDM-180722)

Triethylamine (22.7 mg, 0.225 mmol) was added to an N,N-dimethylformamide solution (10 mL) of the compound 122d (40 mg, 0.15 mmol) at room temperature. The mixture was stirred for 5 minutes, and benzotriazol-1-yl-oxytripyrrolidinophosphonium hexafluorophosphate (117 mg, 0.225 mmol) and compound 122e (19.1 mg, 0.225 mmol) (namely, 2-cyano acetic acid) then were added to the mixture and stirred at room temperature for 6 hours. The mixture was extracted with ethyl acetate (50 mL×3), the organic layer was washed with saturated brine (30 mL×6), dried over anhydrous sodium sulfate, and the filtrate was concentrated under reduced pressure, and passed through the silica gel column (ethyl acetate:methanol=20:1) and HPLC for purification, to obtain a yellow solid compound 122, TDM-180722 (13.3 mg, yield: 13.3%), namely, 2-cyano-N-(4-(2-((1-methyl-1H-pyrazol)-4-yl)amino)pyrimidin-4-yl)phenyl) acetamide. LCMS $[M+1]^+$=334

1H NMR (400 MHz, DMSO-$d_6$) δ 10.56 (s, 1H), 9.49 (s, 1H), 8.45 (d, J=5.2 Hz, 1H), 8.14 (d, J=8.7 Hz, 2H), 7.93 (s, 1H), 7.73 (d, J=8.7 Hz, 2H), 7.56 (s, 1H), 7.25 (d, J=5.3 Hz, 1H), 3.97 (s, 2H), 3.84 (s, 3H).

Compounds prepared in a similar method are as follows:

| Structure Structural formula | TDM No. Registration number | LCMS $[M + 1]^+$ | $^1$H-NMR Proton nuclear magnetic resonance spectroscopy |
|---|---|---|---|
| 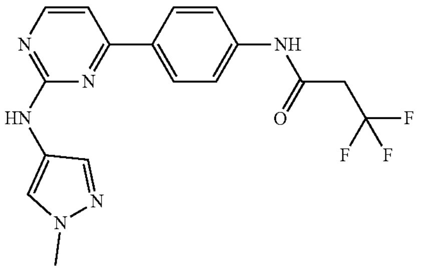 [SMILES: Cn1cc(Nc2nccc(-c3ccc(NC(=O)CC(F)(F)F)cc3)n2)cn1] | TDM-180754 | 377.0 | $^1$H NMR (400 MHz, DMSO-$d_6$) δ 10.57 (s, 1H), 9.50 (s, 1H), 8.45 (d, J = 5.2 Hz, 1H), 8.15 (d, J = 8.7 Hz, 2H), 7.93 (s, 1H), 7.75 (d, J = 8.7 Hz, 2H), 7.56 (s, 1H), 7.25 (d, J = 5.3 Hz, 1H), 3.84 (s, 3H), 3.57 (q, J = 11.1 Hz, 2H). |
| 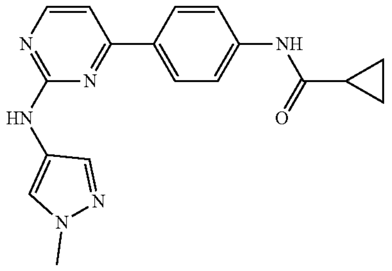 [SMILES: Cn1cc(Nc2nccc(-c3ccc(NC(=O)C4CC4)cc3)n2)cn1] | TDM-180755 | 413.0 | $^1$H NMR (400 MHz, DMSO-$d_6$) δ 10.44 (s, 1H), 9.43 (s, 1H), 8.43 (d, J = 5.1 Hz, 1H), 8.10 (d, J = 8.7 Hz, 2H), 7.92 (s, 1H), 7.76 (d, J = 8.6 Hz, 2H), 7.55 (s, 1H), 7.22 (d, J = 5.2 Hz, 1H), 3.83 (s, 3H), 1.92-1.74 (m, 1H), 0.91-0.76 (m, 4H). |
| 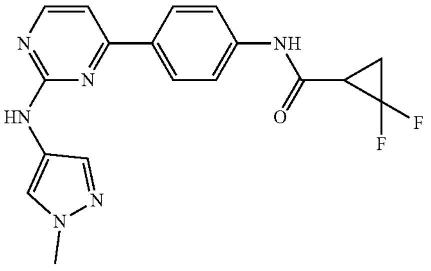 [SMILES: Cn1cc(Nc2nccc(-c3ccc(NC(=O)C4CC4(F)F)cc3)n2)cn1] | TDM-180757 | 371.0 | $^1$H NMR (400 MHz, DMSO-$d_6$) δ 10.67 (s, 1H), 9.45 (s, 1H), 8.44 (d, J = 5.2 Hz, 1H), 8.18-8.08 (m, 2H), 7.92 (s, 1H), 7.76 (d, J = 8.7 Hz, 2H), 7.55 (s, 1H), 7.24 (d, J = 5.3 Hz, 1H), 3.83 (s, 3H), 2.86 (ddd, J = 13.6, 10.8, 8.0 Hz, 1H), 2.10-1.92 (m, 2H). |

-continued

| Structure Structural formula | TDM No. Registration number | LCMS $[M + 1]^+$ | $^1$H-NMR Proton nuclear magnetic resonance spectroscopy |
|---|---|---|---|
| 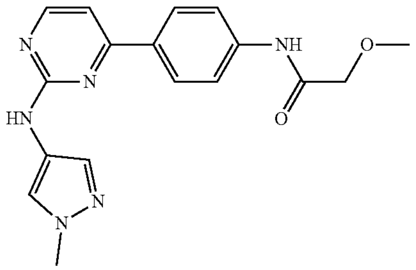 [SMILES: COCC(=O)Nc1ccc(-c2ccnc(Nc3cnn(C)c3)n2)cc1] | TDM-180759 | 339.0 | $^1$H NMR (400 MHz, DMSO-$d_6$) δ 10.02 (s, 1H), 9.51 (s, 1H), 8.44 (d, J = 5.3 Hz, 1H), 8.12 (d, J = 8.7 Hz, 2H), 7.93 (s, 1H), 7.86 (d, J = 8.7 Hz, 2H), 7.56 (s, 1H), 7.26 (d, J = 5.3 Hz, 1H), 4.05 (s, 2H), 3.84 (s, 3H), 3.40 (s, 3H). |
| 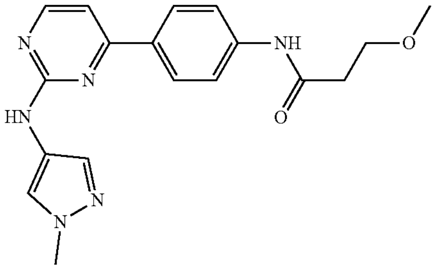 [SMILES: COCCC(=O)Nc1ccc(-c2ccnc(Nc3cnn(C)c3)n2)cc1] | TDM-180799 | 353.2 | $^1$H NMR (400 MHz, DMSO-$d_6$) δ 10.20 (s), 9.43 (s), 8.43 (d, J = 5.2 Hz), 8.10 (d, J = 8.7 Hz), 7.92 (s), 7.77 (d, J = 8.7 Hz), 7.55 (s), 7.22 (d, J = 5.3 Hz), 3.83 (s), 3.64 (t, J = 6.2 Hz), 3.25 (s), 2.59 (t, J = 6.2 Hz). |
| 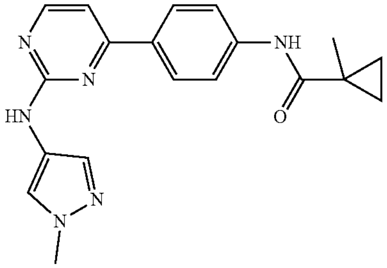 [SMILES: Cn1cc(Nc2nccc(-c3ccc(NC(=O)C4(C)CC4)cc3)n2)cn1] | TDM-180802 | 349.1 | $^1$H NMR (400 MHz, DMSO-$d_6$) δ 9.50 (s, 1H), 9.39 (s, 1H), 8.43 (d, J = 5.3 Hz, 1H), 8.10 (d, J = 8.8 Hz, 2H), 7.93 (s, 1H), 7.83 (d, J = 8.8 Hz, 2H), 7.55 (s, 1H), 7.26 (d, J = 5.3 Hz, 1H), 3.83 (s, 3H), 1.43 (s, 3H), 1.13 (q, J = 3.6 Hz, 2H), 0.67 (q, J = 3.8 Hz, 2H). |
| 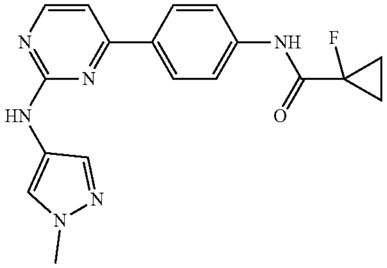 [SMILES: Cn1cc(Nc2nccc(-c3ccc(NC(=O)C4(F)CC4)cc3)n2)cn1] | TDM-180803 | 353.1 | $^1$H NMR (400 MHz, DMSO-$d_6$) δ 9.50 (s, 1H), 9.39 (s, 1H), 8.43 (d, J = 5.3 Hz, 1H), 8.10 (d, J = 8.8 Hz, 2H), 7.93 (s, 1H), 7.83 (d, J = 8.8 Hz, 2H), 7.55 (s, 1H), 7.26 (d, J = 5.3 Hz, 1H), 3.83 (s, 3H), 1.43 (s, 3H), 1.13 (q, J = 3.6 Hz, 2H), 0.67 (q, J = 3.8 Hz, 2H). |
| 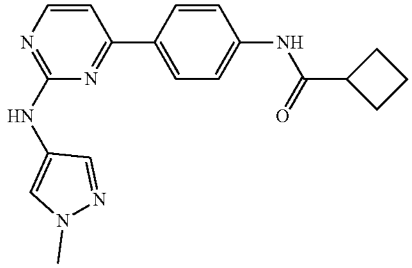 [SMILES: Cn1cc(Nc2nccc(-c3ccc(NC(=O)C4CCC4)cc3)n2)cn1] | TDM-180813 | 349.1 | $^1$H NMR (400 MHz, DMSO-$d_6$) δ 9.98 (s, 1H), 9.49 (s, 1H), 8.43 (d, J = 5.3 Hz, 1H), 8.11 (d, J = 8.8 Hz, 2H), 7.92 (s, 1H), 7.79 (d, J = 8.7 Hz, 2H), 7.56 (s, 1H), 7.24 (d, J = 5.3 Hz, 1H), 3.84 (s, 3H), 3.33-3.19 (m, 1H), 2.34-2.08 (m, 4H), 2.02-1.77 (m, 2H). |

-continued

| Structure Structural formula | TDM No. Registration number | LCMS $[M + 1]^+$ | $^1$H-NMR Proton nuclear magnetic resonance spectroscopy |
|---|---|---|---|
| 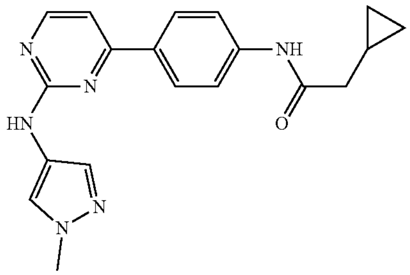 [SMILES: Cn1cc(Nc2nccc(-c3ccc(NC(=O)CC4CC4)cc3)n2)cn1] | TDM-180804 | 349.1 | $^1$H NMR (400 MHz, DMSO-$d_6$) δ 10.06 (s, 1H), 9.43 (s, 1H), 8.43 (d, J = 5.2 Hz, 1H), 8.10 (d, J = 8.7 Hz, 2H), 7.92 (s, 1H), 7.78 (d, J = 8.7 Hz, 2H), 7.55 (s, 1H), 7.23 (d, J = 5.3 Hz, 1H), 3.83 (s, 3H), 2.25 (d, J = 7.0 Hz, 2H), 1.08 (ddd, J = 12.7, 7.9, 5.1 Hz, 1H), 0.54-0.46 (m, 2H), 0.26-0.18 (m, 2H). |
| 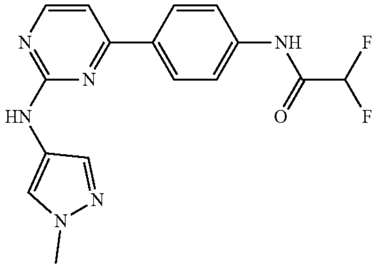 [SMILES: Cn1cc(Nc2nccc(-c3ccc(NC(=O)C(F)F)cc3)n2)cn1] | TDM-180805 | 345.1 | $^1$H NMR (400 MHz, DMSO-$d_6$) δ 10.98 (s, 1H), 9.52 (s, 1H), 8.46 (d, J = 5.2 Hz, 1H), 8.18 (d, J = 8.7 Hz, 2H), 7.93 (s, 1H), 7.85 (d, J = 8.7 Hz, 2H), 7.56 (s, 1H), 7.28 (d, J = 5.3 Hz, 1H), 6.56 (s, 1H), 6.42 (s, 1H), 6.29 (s, 1H), 3.84 (s, 3H). |

TDM-180754, a yellow solid compound 154, namely 3,3,3-trifluoro-N-(4-(2-((1-methyl-1H-pyrazol-4-yl)amino)pyrimidin-4-yl)phenyl)propanamide (6.6 mg, yield: 9.3%).

TDM-180755, an off-white solid compound 155, namely N-(4-(2-((1-methyl-1H-pyrazol-4-yl)amino)pyrimidin-4-yl)phenyl)cyclopropanecarboxamide (30.5 mg, yield: 48.5%).

TDM-180757, a yellow solid compound 157, namely 2,2-difluoro-N-(4-(2-((1-methyl-1H-pyrazol-4-yl)amino)pyrimidin-4-yl)phenyl)cyclopropane-1-carboxamide (32.5 mg, yield: 46.7%).

TDM-180759, a yellow solid compound 159, namely 2-methoxy-N-(4-(2-((1-methyl-1H-pyrazol-4-yl)amino)pyrimidin-4-yl)phenyl)acetamide (46 mg, yield: 51.7%).

TDM-180799, a pale yellow solid compound 199, namely 3-methoxy-N-(4-(2-((1-methyl-1H-pyrazol-4-yl)amino)pyrimidin-4-yl)phenyl)propanamide (8 mg, yield: 12%)

TDM-180802, a yellow solid compound 202, namely 1-methyl-N-(4-(2-((1-methyl-1H-pyrazol-4-yl)amino)pyrimidin-4-yl)phenyl)cyclopropane-1-carboxamide (30.4 mg, yield: 46.4%)

TDM-180803, a yellow solid compound 203, namely 1-fluoro-N-(4-(2-((1-methyl-1H-pyrazol-4-yl)amino)pyrimidin-4-yl)phenyl)cyclopropane-1-carboxamide (43.4 mg, yield: 65.4%)

TDM-180813, a yellow solid compound 213, TDM-180813, namely N-(4-(2-((1-methyl-1H-pyrazol-4-yl)amino)pyrimidin-4-yl)phenyl)cyclobutanemethyl (22.8 mg, 34.8% yield).

TDM-180804, an off-white solid compound 204, namely 2-cyclopropyl-N-(4-(2-((1-methyl-1H-pyrazol-4-yl)amino)pyrimidin-4-yl)phenyl)acetamide (7.4 mg, yield: 11.3%)

TDM-180805, a yellow solid compound 205, namely 2,2-difluoro-N-(4-(2-((1-methyl-1H-pyrazol-4-yl)amino)pyrimidin-4-yl)phenyl)acetamide (10.8 mg, yield: 16.7%)

Example 4: General Method for Synthesizing Compound 191 (TDM-180791)

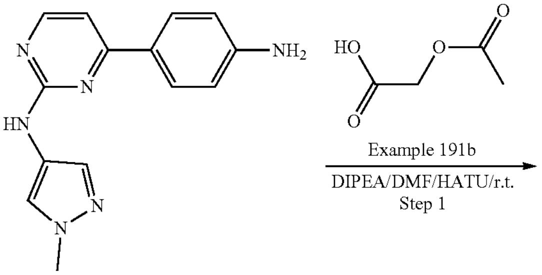

Example 191a

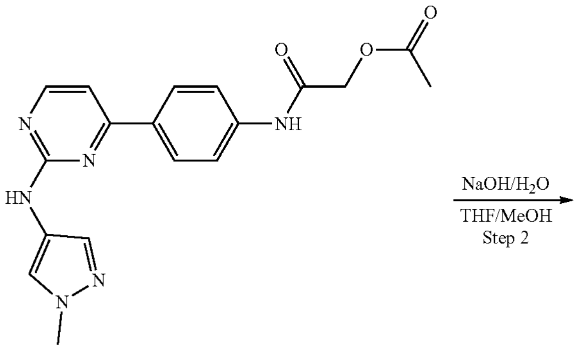

Example 191c

-continued

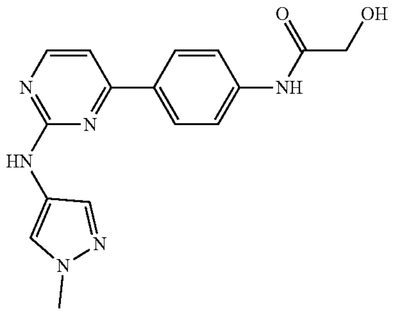

Example 191 (TDM-180791)

Step 1: Example 191c

N,N-diisopropylethylamine (116.3 mg, 0.9 mmol) was added to compound 191a (namely, 4-(4-aminophenyl)-N-(1-methyl-1H-pyrazol-4-yl)pyrimidin-2-amine) (80 mg, 0.3 mmol) in a solution of N,N-dimethylformamide (10 mL) at room temperature, the mixture was stirred for 5 minutes, and then 2-(7-benzotriazole oxide)-N,N,N',N'-tetramethylurea hexafluorophosphate (171 mg, 0.45 mmol) and compound 191b (namely, 2-acetoxyacetic acid) (53 mg, 0.45 mmol) were added into the mixture. The mixture was stirred for 2 hours at room temperature. The mixture was concentrated under reduced pressure to remove the solvent, methanol and petroleum ether were added to the residue, and the suspension was filtered to collect a brown solid compound 191, namely 2-((4-(2-((1-methyl-1H-pyrazol-4-yl)amino)pyrimidin-4-yl)phenyl)amino)-2-oxoethyl acetate (128 mg, crude product). LCMS $[M+1]^+$=367.

Step 2: Example 191 (TDM-180791)

An aqueous solution (10 mL) of sodium hydroxide (100 mg) was added to a mixture solution of compound 191c (128 mg, 0.349 mmol) in tetrahydrofuran (5 mL) and methanol (5 mL). The mixture was stirred for 1 hours at room temperature. The mixture was then concentrated under reduced pressure to remove methanol and tetrahydrofuran, and filtered to collect the precipitate, ethyl acetate and petroleum ether were added to the solid, and the suspension was filtered to collect a white solid compound 191, TDM-180791, namely, 2-hydroxy-N-(4-(2-((1-methyl-1H-pyrazol-4-yl)amino)pyrimidin-4-yl)phenyl)acetamide (60 mg, yield: 46.9%). LCMS $[M+1]^+$=325.1.

1H NMR (400 MHz, DMSO-$d_6$) δ 9.91 (s, 1H), 9.43 (s, 1H), 8.44 (d, J=5.2 Hz, 1H), 8.11 (d, J=8.7 Hz, 2H), 7.96-7.86 (m, 3H), 7.55 (s, 1H), 7.24 (d, J=5.2 Hz, 1H), 5.70 (t, J=6.0 Hz, 1H), 4.04 (d, J=6.0 Hz, 2H), 3.83 (s, 3H).

Example 5: General Method for Synthesizing Compound 213 (TDM-180813)

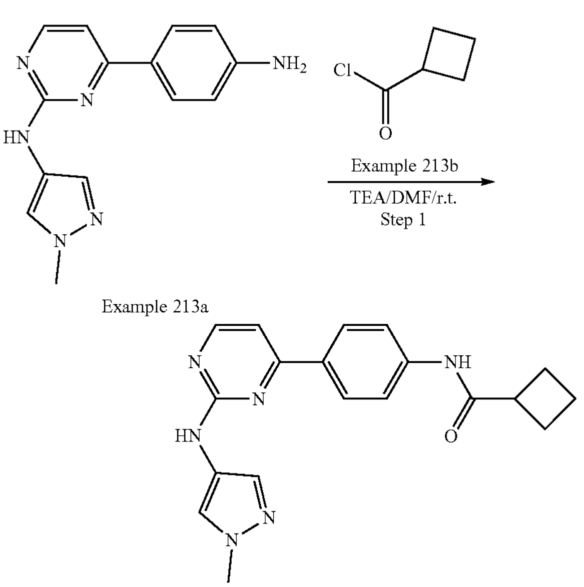

Example 213a

Example 213 (TDM-180813)

Step 1: Example 213

Triethylamine (38 mg, 0.376 mmol) was added to compound 213a (namely, 4-(4-aminophenyl)-N-(1-methyl-1H-pyrazol-4-yl)pyrimidin-2-amine) (50 mg, 0.188 mmol) in a solution of N,N-dimethylformamide (10 mL) at room temperature, and then the compound 213b (26.7 mg, 0.226 mmol) (namely, cyclobutanecarbonyl chloride) was added to the mixture. The mixture was stirred at room temperature for 1 hour, then the mixture was concentrated under reduced pressure and the purified residue was prepared, to obtain a yellow solid compound 213, TDM-180813, namely N-(4-(2-((1-methyl-1H-pyrazol-4-yl)amino)pyrimidin-4-yl)phenyl)cyclobutanemethyl (22.8 mg, 34.8% yield). LCMS $[M+1]^+$=349.1

$^1$H NMR (400 MHz, DMSO-d6) δ 9.98 (s, 1H), 9.49 (s, 1H), 8.43 (d, J=5.3 Hz, 1H), 8.11 (d, J=8.8 Hz, 2H), 7.92 (s, 1H), 7.79 (d, J=8.7 Hz, 2H), 7.56 (s, 1H), 7.24 (d, J=5.3 Hz, 1H), 3.84 (s, 3H), 3.33-3.19 (m, 1H), 2.34-2.08 (m, 4H), 2.02-1.77 (m, 2H).

Example 6: General Method for Synthesizing Compound 167 (TDM-180767)

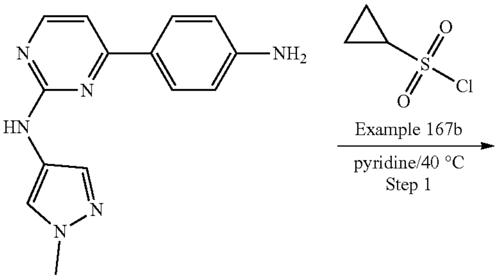

Example 167a

-continued

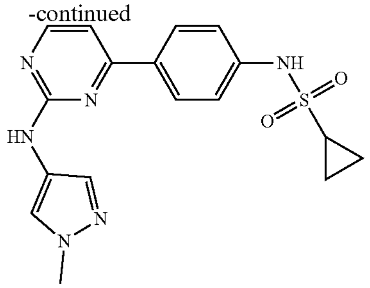

Example 167 (TDM-180767)

Step 1: Example 167 (TDM-180767)

Compound 167b (39.6 mg, 0.282 mmol) (namely, cyclopropanesulfonyl chloride) was added to compound 167a (namely, 4-(4-aminophenyl)-N-(1-methyl-1H-pyrazol-4-yl) pyrimidin-2-amine) (50 mg, 0.188 mmol) in a pyridine solution (5 mL) at room temperature. The mixture was heated to 40° C. and stirred for 16 hours. After the reaction completed, the mixture was concentrated under reduced pressure to remove excess pyridine, the residue was dissolved with hydrochloric acid (2M), and then the solution was neutralized with sodium hydroxide solution, and filtered to collect the precipitate. Ethyl acetate and petroleum ether were added to the precipitate, and the suspension was filtered to collect a pale yellow solid compound 167, TDM-180767, namely N-(4-(2-((1-methyl-1H-pyrazol-4-yl) amino)pyrimidin-4-yl)phenyl)cyclopropanesulfo (49.2 mg, yield: 70.8%). LCMS $[M+1]^+$=371.

1H NMR (400 MHz, DMSO-$d_6$) δ 10.10 (s, 1H), 9.45 (s, 1H), 8.44 (d, J=5.1 Hz, 1H), 8.12 (d, J=8.6 Hz, 2H), 7.92 (s, 1H), 7.55 (s, 1H), 7.39 (d, J=8.6 Hz, 2H), 7.22 (d, J=5.2 Hz, 1H), 3.83 (s, 3H), 2.73 (ddd, J=12.6, 7.6, 5.1 Hz, 1H), 1.05-0.91 (m, 4H).

Compounds prepared in a similar method are as follows:

| Structure Structural formula | TDM No. Registration number | LCMS $[M + 1]^+$ | $^1$H-NMR Proton nuclear magnetic resonance spectroscopy |
|---|---|---|---|
| 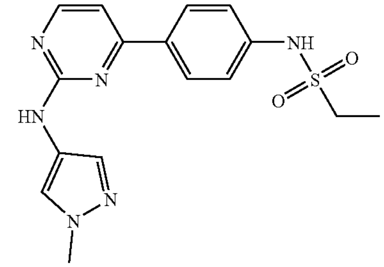 [SMILES: CCS(=O)(=O)Nc1ccc(-c2ccnc(Nc3cnn(C)c3)n2)cc1] | TDM-180768 | 359.0 | $^1$H NMR (400 MHz, DMSO-$d_6$) δ 10.16 (s, 1H), 9.46 (s, 1H), 8.44 (d, J = 5.2 Hz, 1H), 8.12 (d, J = 8.7 Hz, 2H), 7.92 (s, 1H), 7.54 (s, 1H), 7.36 (d, J = 8.7 Hz, 2H), 7.22 (d, J = 5.3 Hz, 1H), 3.83 (s, 3H), 3.19 (q, J = 7.3 Hz, 2H), 1.22 (t, J = 7.3 Hz, 3H). |
| 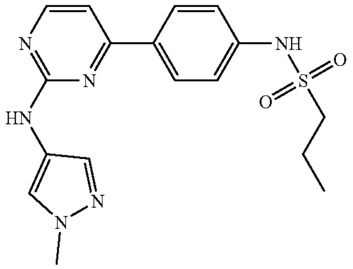 [SMILES: CCCS(=O)(=O)Nc1ccc(-c2ccnc(Nc3cnn(C)c3)n2)cc1] | TDM-180893 | 373.2 | $^1$H NMR (400 MHz, DMSO-$d_6$) δ 10.17 (s, 1H), 9.49 (s, 1H), 8.45 (d, J = 5.2 Hz, 1H), 8.12 (d, J = 8.8 Hz, 2H), 7.93 (s, 1H), 7.55 (s, 1H), 7.36 (d, J = 8.8 Hz, 2H), 7.24 (d, J = 5.2 Hz, 1H), 3.84 (s, 3H), 3.12-3.23 (m, 2H), 1.64-1.81 (m, 2H), 0.95 (t, J = 7.2 Hz, 3H). |
| 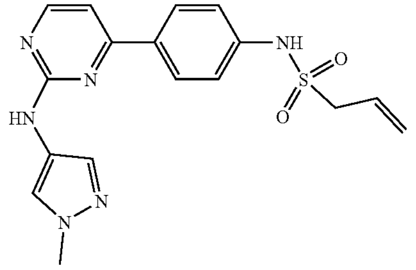 [SMILES: C=CCS(=O)(=O)Nc1ccc(-c2ccnc(Nc3cnn(C)c3)n2)cc1] | TDM-180844 | 371.1 | $^1$H NMR (400 MHz, DMSO-$d_6$) δ 10.26 (s, 1H), 9.49 (s, 1H), 8.45 (d, J = 5.2 Hz, 1H), 8.13 (d, J = 8.8 Hz, 2H), 7.93 (s, 1H), 7.56 (s, 1H), 7.35 (d, J = 8.8 Hz, 2H), 7.48 (s, 1H), 7.24 (d, J = 8.8 Hz, 2H), 5.74-5.87 (m, 1H), 5.27-5.42 (m, 2H), 4.00 (d, J = 7.2Hz, 2H), 3.86 (s, 3H). |

-continued

| Structure Structural formula | TDM No. Registration number | LCMS $[M + 1]^+$ | $^1$H-NMR Proton nuclear magnetic resonance spectroscopy |
|---|---|---|---|
| 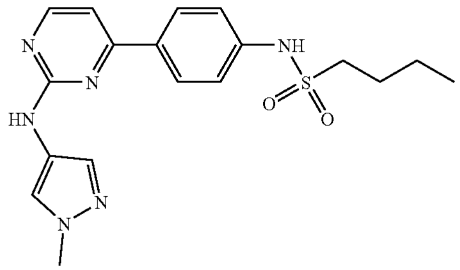 [SMILES: CCCCS(=O)(=O)Nc1ccc(-c2ccnc(Nc3cnn(C)c3)n2)cc1] | TDM-180832 | 378.1 | $^1$H NMR (400 MHz, DMSO-$d_6$) δ 10.17 (s, 1H), 9.48 (s, 1H), 8.44 (d, J = 5.2 Hz, 1H), 8.12 (d, J = 8.6 Hz, 2H), 7.93 (s, 1H), 7.55 (s, 1H), 7.35 (d, J = 8.7 Hz, 2H), 7.23 (d, J = 5.3 Hz, 1H), 3.84 (s, 3H), 3.29 - 3.08 (m, 2H), 1.77-1.51 (m, 2H), 1.36 (dd, J = 14.9, 7.4 Hz, 2H), 0.83 (t, J = 7.4 Hz, 3H). |
| 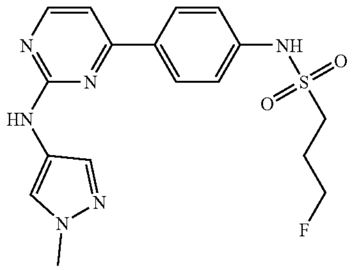 [SMILES: Cn1cc(Nc2nccc(-c3ccc(NS(=O)(=O)CCCF)cc3)n2)cn1] | TDM-180896 | 391.2 | $^1$H NMR (400 MHz, DMSO-$d_6$) δ 10.29 (s, 1H), 9.53 (s, 1H), 8.45 (d, J = 5.2 Hz, 1H), 8.14 (d, J = 8.8 Hz, 2H), 7.94 (s, 1H), 7.56 (s, 1H), 7.37 (d, J = 8.8 Hz, 2H), 7.25 (d, J = 5.2 Hz, 1H), 4.58 (t, J = 6.0 Hz , 1H), 4.46 (t, J = 6.0 Hz, 1H), 3.88 (s, 3H), 3.26-3.35 (m, 2H), 2.00-2.15 (m, 2H). |
| 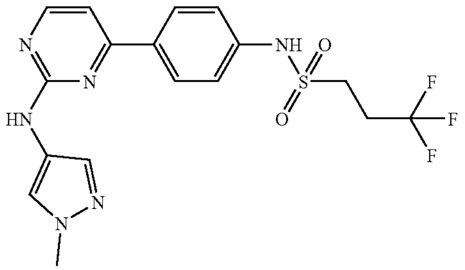 [SMILES: Cn1cc(Nc2nccc(-c3ccc(NS(=O)(=O)CCC(F)(F)F)cc3)n2)cn1] | TDM-180850 | 427.1 | $^1$H NMR (400 MHz, DMSO) δ 10.40 (s, 1H), 9.48 (s, 1H), 8.45 (d, J = 5.2 Hz, 1H), 8.14 (d, J = 8.6 Hz, 2H), 7.92 (s, 1H), 7.55 (s, 1H), 7.38 (d, J = 8.7 Hz, 2H), 7.24 (d, J = 5.3 Hz, 1H), 3.83 (s, 3H), 3.48-3.42 (m, 2H), 2.79-2.70 (m, 2H). |
| 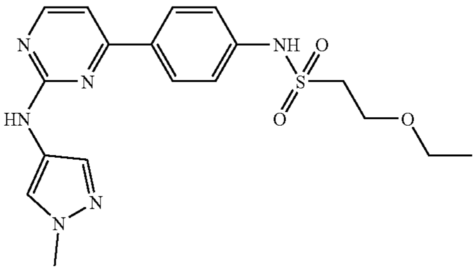 [SMILES: CCOCCS(=O)(=O)Nc1ccc(-c2ccnc(Nc3cnn(C)c3)n2)cc1] | TDM-180834 | 403 | $^1$H NMR (400 MHz, DMSO) δ 10.16 (s, 1H), 9.49 (s, 1H), 8.44 (d, J = 5.2 Hz, 1H), 8.11 (d, J = 8.7 Hz, 2H), 7.93 (s, 1H), 7.55 (s, 1H), 7.35 (d, J = 8.7 Hz, 2H), 7.23 (d, J = 5.3 Hz, 1H), 3.83 (s, 3H), 3.71 (t, J = 6.0 Hz, 2H), 3.45 (t, J = 6.0 Hz, 2H), 3.36 (q, J = 7.0 Hz, 2H), 1.02 (t, J = 7.0 Hz, 3H). |
| 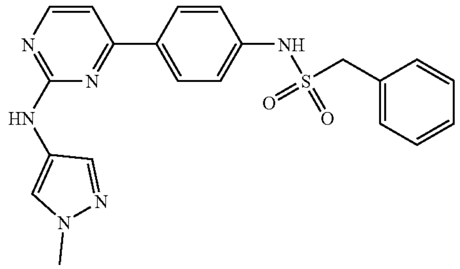 [SMILES: Cn1cc(Nc2nccc(-c3ccc(NS(=O)(=O)Cc4ccccc4)cc3)n2)cn1] | TDM-180820 | 421.1 | $^1$H NMR (400 MHz, DMSO-$d_6$) δ 10.20 (s, 1H), 9.45 (s, 1H), 8.45 (d, J = 5.2 Hz, 1H), 8.12 (d, J = 8.6 Hz, 2H), 7.93 (s, 1H), 7.56 (s, 1H), 7.44-7.21 (m, 8H), 4.57 (s, 2H), 3.83 (d, J = 9.2 Hz, 3H). |
| 3 steps | TDM-180894 | | |

TDM-180768, a pale yellow solid compound 168, namely N-(4-(2-((1-methyl-1H-pyrazol-4-yl)amino)pyrimidin-4-yl)phenyl)ethanesulfonamide (12.7 mg, yield: 18.8%).

TDM-180893, a yellow solid compound 293, namely N-(4-(2-((1-methyl-1H-pyrazol-4-yl)amino)pyrimidin-4-yl)phenyl)propane-1-sulfonamide (22.8 mg, 16% yield).

TDM-180844, a pale green solid compound 244, namely N-(4-(2-((1-methyl-1H-pyrazol-4-yl)amino)pyrimidin-4-yl)phenyl)prop-2-ene-1-sulfonamide (17.9 mg, 12% yield)

TDM-180832, a yellow solid compound 232, TDM-180832, namely N-(4-(2-((1-methyl-1H-pyrazol-4-yl)amino)pyrimidin-4-yl)phenyl)butane-1-sulfonamide (19.6 mg, yield: 13.3%).

TDM-180896, a yellow solid compound 296, namely 3-fluoro-N-(4-(2-((1-methyl-1H-pyrazol-4-yl)amino)pyrimidin-4-yl)phenyl)propane-1-sulfonamide (50.6 mg, 23% yield).

TDM-180850, 3,3,3-trifluoro-N-(4-(2-((1-methyl-1H-pyrazol-4-yl)amino)pyrimidin-4-yl)phenyl)propyl-1-sulfonamide, a yellow solid compound (2.2 mg, yield: 2.3%).

TDM-180834, a yellow solid compound, 2-ethoxyl-N-(4-(2-((1-methyl-1H-pyrazol-4-yl)amino)pyrimidin-4-yl)phenyl)ethyl-1-sulfonamide (Example 234, 36.6 mg, yield: 40.42%).

TDM-180820, a pale yellow solid compound 220, TDM-180820, namely N-(4-(2-((1-methyl-1H-pyrazol-4-yl)amino)pyrimidin-4-yl)phenyl)-1-phenylmethanesulfonamide (16.8 mg, yield: 10.6%).

Example 7: General Method for Synthesizing Compound 294 (TDM-180894)

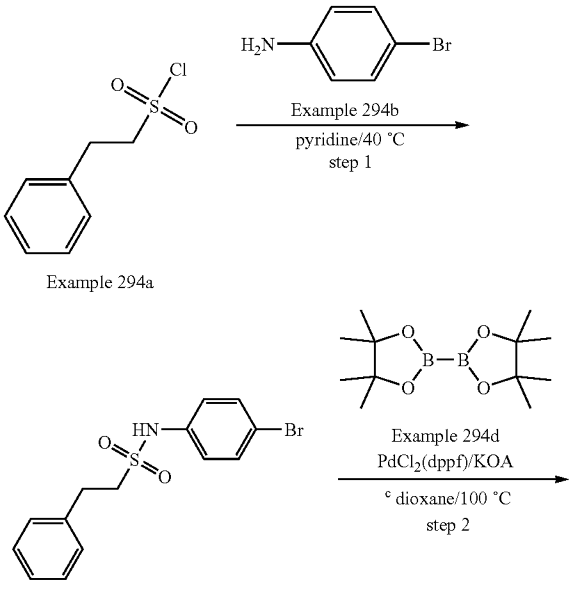

Example 294a

Example 294c

-continued

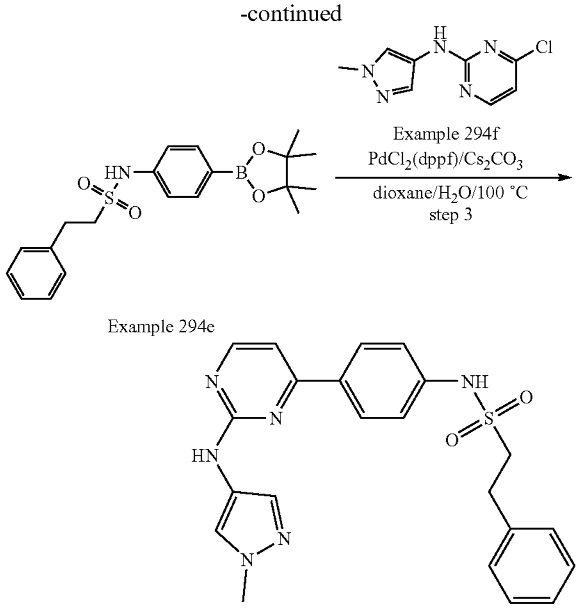

Example 294e

Example 294
(TDM-180894)

Step 1: Example 294c

Compound 294a (namely, 4-bromoaniline) (232 mg, 1.134 mmol) was added to a pyridine solution (5 mL) of the compound 294b (namely, 2-phenylethane-1-sulfonyl chloride (150 mg, 0.872 mmol) at room temperature, and the mixture was heated to 40° C. and stirred for 16 hours. The mixture was concentrated under reduced pressure and the residue was purified via silica gel chromatography (100% dichloromethane) to obtain a white solid compound 294c, namely N-(4-bromophenyl)-2-phenylethane-1-sulfonamide (200 mg, yield: 67.4%). LCMS $[M+1]^+$=340&342

Step 2: Example 294c

Dioxane (18 mL) was added to a mixture of compound 294c (150 mg, 0.441 mmol), compound 294d (namely, bis(pinacolato)diboron) (134.4 mg, 0.529 mmol), 2-(7-benzotriazole oxide)-N,N,N',N'-tetramethylurea hexafluorophosphate (48.4 mg, 0.066 mmol) and potassium acetate (86.4 mg, 0.822 mmol). The mixture was degassed under vacuum, $N_2$ displacement was employed several times, and then the mixture was heated to 100° C. and stirred for 2 hours. The mixture was directly used in the next reaction without purification. LCMS $[M+1]^+$=388

Step 3: Example 294 (TDM-180894)

Compound 294f (92 mg, 0.441 mmol) (namely, 4-chloro-N-(1-methyl-1H-pyrazol-4-yl)pyrimidin-2-amine), 2-(7-benzotriazole oxide)-N,N,N',N'-tetramethyl urea hexafluorophosphate (48.4 mg, 0.066 mmol), cesium carbonate (287 mg, 0.882 mmol) and water (3 mL) were added to the mixture from the second step. The mixture was degassed under vacuum, nitrogen displacement was employed several times, and then the mixture was heated to 100° C. and stirred for 2 hours. The mixture was concentrated under reduced pressure, and the residue was passed through silica gel chromatography (dichloromethane:dichloromethane containing 10% methanol=50:50) and purified to obtain a yellow solid compound 294, TDM-180894, (namely, N-(4-(2-((1-methyl-1H-pyrazol-4-yl)amino)pyrimidin-4-yl)phenyl)-2-phenylethane-1-sulfonamide (25.7 mg, yield: 13.5%). LCMS $[M+1]^+$=435.2

$^1$H NMR (400 MHz, DMSO-$d_6$) δ 10.27 (s, 1H), 9.45 (s, 1H), 8.44 (d, J=5.2 Hz, 1H), 8.13 (d, J=8.6 Hz, 2H), 7.92 (s, 1H), 7.55 (s, 1H), 7.39 (d, J=8.7 Hz, 2H), 7.28-7.12 (m, 6H), 3.83 (s, 3H), 3.51-3.41 (m, 2H), 3.08-2.96 (m, 2H).

Example 7: General Method for Synthesizing Compound 135 (TDM-180735)

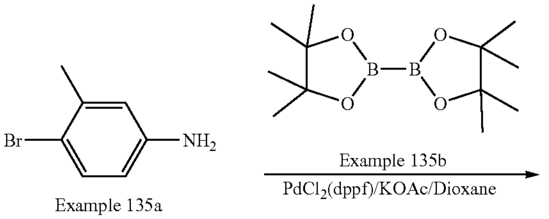

Example 135a

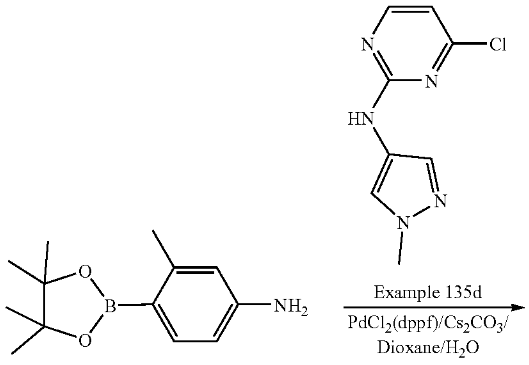

Example 135c

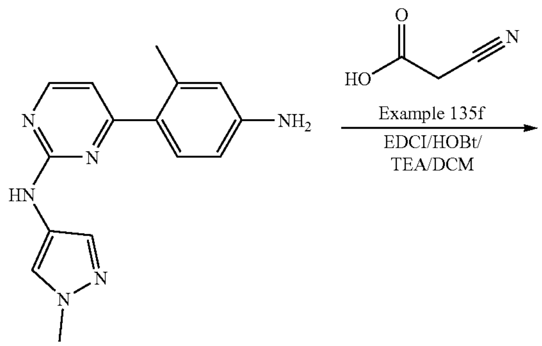

Example 135e

-continued

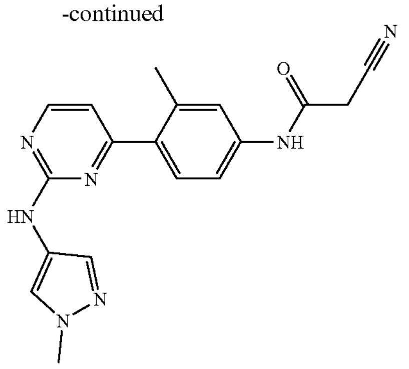

Example 135
(TDM-180735)

Step 1: Example 135c

The compound 135a (1.0 g, 5.37 mmol) was dissolved in 1,4-dioxane (20 mL), the compound 135b (2.73 g, 10.75 mmol), KOAc (1.58 g, 16.12 mmol) and $PdCl_2$ (dppf) (0.39 g, 0.54 mmol) were added to the mixture, nitrogen displacement was employed three times, and then the reaction solution was stirred at 80° C. for 17 hours. The reaction solution was cooled to room temperature and filtered, the filter cake was rinsed with ethyl acetate (20 mL×3) and concentrated, and the concentrate was purified via silica gel chromatography (ethyl acetate:petroleum ether=0-20%) to obtain an off-white solid compound 135c (namely, 3-methyl-4-(4,4,5,5-tetramethyl-1,3,2-dioxaborolane-2-yl) aniline (1.776 g, yield: 94.6%). LCMS $[M+1]^+$=234.1.

Step 2: Example 135e

The compound 135d (1.05 g, 5.01 mmol) was dissolved in 1,4-dioxane (20 mL) and water (4 mL), and the compound 135c (1.17 g, 5.01 mmol), $Na_2CO_3$ (1.06 g, 10.02 mmol) and $PdCl_2$ (dppf) (0.37 g, 0.50 mmol) were added to the mixture. Nitrogen displacement was employed three times, and the reaction solution was then stirred for 3 hours at 95° C. The reaction solution was cooled to room temperature and filtered, the filter cake was rinsed with ethyl acetate (20 mL×3) and concentrated, and the concentrate was purified via silica gel chromatography (ethyl acetate:petroleum ether=0-80%) to obtain a yellow solid compound 135e, (namely, 4-(4-amino-2-methylphenyl)-N-(1-methyl-1H-pyrazol-4-yl)pyrimidin-2-amine (263 mg, 18.8% yield). LCMS $[M+1]^+$=281.4.

Step 3: Example 135 (TDM-180735)

1-(3-dimethylaminopropyl)-3-ethylcarbodiimide hydrochloride (143.6 mg, 0.75 mmol), triethylamine (75.7 mg, 0.75 mmol), 1-hydroxybenzotriazole (101.1 mg, 0.75 mmol) and compound 135f (51.0 mg, 0.6 mmol) were added to a dichloromethane solution (30 mL) of the compound 135e (140 mg, 0.50 mmol), and stirred at room temperature for 17 hours. The reaction solution was concentrated, the concentrate was purified via silica gel chromatography (ethyl acetate:petroleum ether=50-100%) and HPLC, to obtain a yellow solid compound 135 (namely, 2-cyano-N-(3-methyl-4-) 2-((1-methyl-1H-pyrazole-4-yl)amino)pyrimidin-4-yl) phenyl)acetamide (45.4 mg, yield: 18.3%). LCMS: $[M+1]^+$=348.1.

$^1$H NMR (400 MHz, DMSO) δ 10.41 (s, 1H), 9.46 (s, 1H), 8.44 (d, J=5.1 Hz, 1H), 7.85 (s, 1H), 7.66-7.37 (m, 4H), 6.84 (d, J=5.1 Hz, 1H), 3.93 (s, 3H), 3.79 (s, 3H), 2.41 (s, 3H).

Compounds prepared in a similar method are as follows:

| Structure Structural formula | TDM No. Registration number | Lot No. Notebook number | LCMS $[M + 1]^+$ | $^1$H-NMR Proton nuclear magnetic resonance spectroscopy |
|---|---|---|---|---|
| 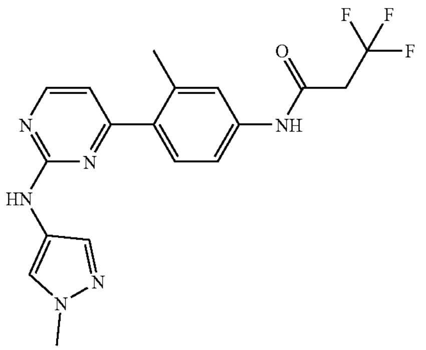 [SMILES: Cc1cc(NC(=O)CC(F)(F)F)ccc1-c1ccnc(Nc2cnn(C)c2)n1] | TDM-180740 | V395-133 | 391.1 | $^1$H NMR (400 MHz, DMSO) δ 10.41 (s, 1H), 9.45 (s, 1H), 8.44 (d, J = 5.1 Hz, 1H), 7.85 (s, 1H), 7.66-7.39 (m, 4H), 6.84 (d, J = 5.1 Hz, 1H), 3.79 (s, 3H), 3.54 (q, J = 11.1 Hz, 2H), 2.41 (s, 3H). |

TDM-180740, a yellow solid compound 136, namely 3,3,3-trifluoro-N-(3-methyl-4-(2-((1-methyl-1H-pyrazol-4-yl)amino)pyrimidin-4-yl)phenyl)propanamide (32.8 mg, yield: 27.6%)

Example 8: General Method for Synthesizing Compound 131 (TDM-180731)

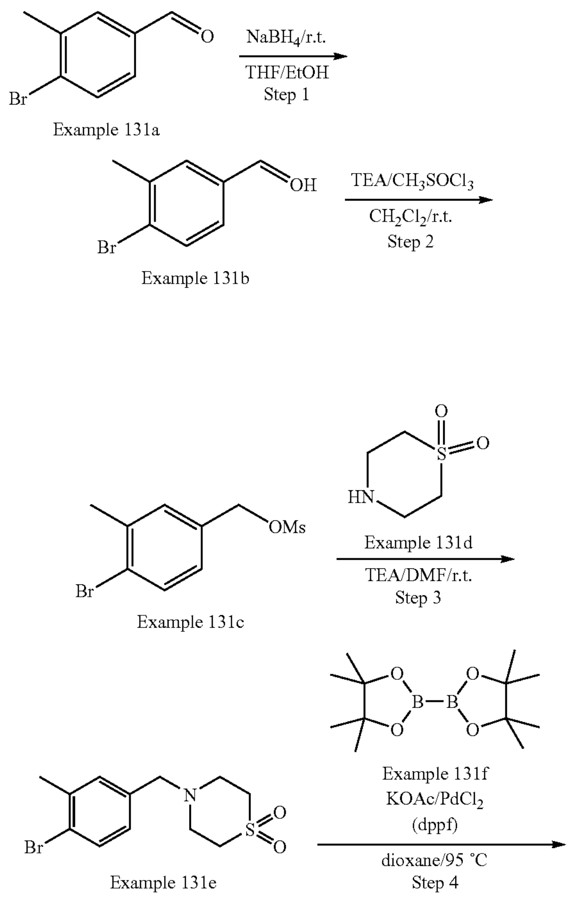

-continued

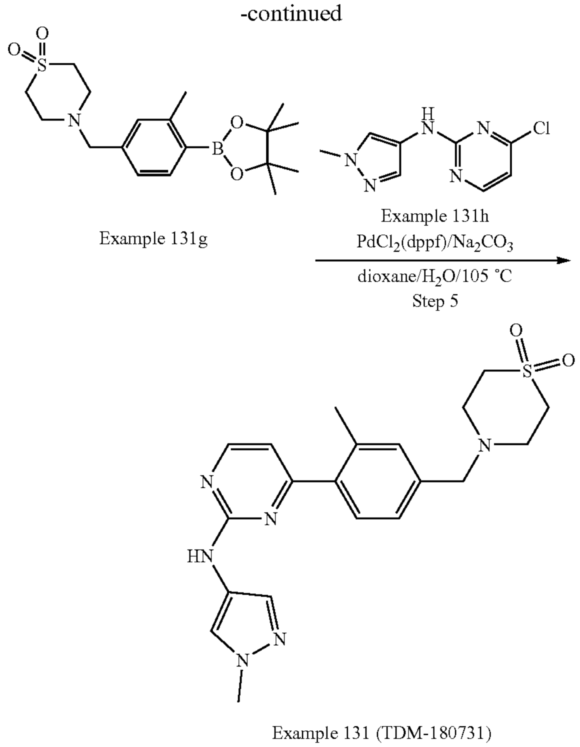

Step 1: Example 131

Sodium borohydride (564 mg, 14.9 mmol) was added to compound 131a (namely, 4-bromo-3-methylbenzaldehyde) (1.2 g, 5.97 mmol) in a mixture solution of tetrahydrofuran (50 mL) and ethanol (5 mL), and the mixture was stirred at room temperature for 4 hours under nitrogen protection. Dilute hydrochloric acid (0.5N) and water were added to the mixture, the mixture was concentrated under reduced pressure to remove excess tetrahydrofuran and ethanol, the residue was extracted with ethyl acetate (50 mL×3), and the organic layer was washed with saturated brine (50 mL). The solution was dried over anhydrous sodium sulfate, and the filtrate was concentrated under reduced pressure to obtain a yellow oily compound 131b (925 mg, yield: 76.3%), namely (4-bromo-3-methylphenyl) methanol.

Step 2: Example 131c

Triethylamine (923 mg, 9.12 mmol) was added to a dichloromethane solution (20 mL) of compound 131b (925 mg, 4.56 mmol), the mixture was cooled to 0° C. and methanesulfonyl chloride (627 mg, 5.47 mmol) was added. The mixture was naturally warmed to room temperature and then stirred for 1.5 hours. Sodium bicarbonate solution was added to the mixture and extracted with dichloromethane (50 mL×3), the organic layer was washed with saturated brine (50 mL) and rinsed with anhydrous sodium sulfate, and the filtrate was concentrated under reduced pressure to obtain a yellow oily compound 131c (1.24 g, yield: 97.4%), namely, 4-bromo-3-methylbenzyl methanesulfonate.

Step 3: Example 131e

Compound 131d (600 mg, 4.44 mmol) (namely, thiomorpholine-1,1-dioxide) and triethylamine (420 mg, 4.15 mmol) were added to compound 131c (1.24 g, 4.44 mmol) in a solution of N,N-dimethylformamide (40 mL). The mixture was stirred for 18 hours at room temperature. After the reaction completed, the mixture was concentrated under reduced pressure to remove N,N-dimethylformamide, water was added to the residue and the solution was extracted with ethyl acetate (50 mL×3), the organic layer was washed with saturated brine (30 mL×4), and dried over anhydrous sodium sulfate, and the filtrate was concentrated under reduced pressure. Petroleum ether and ethyl acetate were added to the residue, and the suspension was filtered to collect the precipitate, to obtain a white solid compound 131e (587 mg, yield: 41.5%), namely 4-(4-bromo-3-methylbenzyl)thiomorpholine1,1-dioxide. LCMS $[M+1]^+$=319.

Step 4: Example 131g

Potassium acetate (115 mg, 1.175 mmol) and [1,1'-bis (diphenylphosphino) ferrocene]palladium dichloride (35.8 mg, 0.049 mmol) were added to a mixture of compound 131e (150 mg, 047 mmol) and compound 131h (143.2 mg, 0.564 mmol), namely 4,4,4',4',5,5,5',5'-octamethyl-2,2'-di(1, 3,2-dioxaborane). 1,4-dioxane was added to the mixture and the mixture was degassed under vacuum, heated to 95° C. under nitrogen protection and stirred for 16 hours. After the reaction completed, the mixture was directly used for the next reaction. LCMS $[M+1]^+$=366.

Step 5: Example 131 (TDM-180731)

Compound 131h (98 mg, 0.47 mmol) (namely, 4-chloro-N-(1-methyl-1H-pyrazol-4-yl)pyrimidin-2-amine, [1,1'-bis (diphenylphosphino) ferrocene]palladium dichloride (34 mg, 0.047 mmol), sodium carbonate (99.6 mg, 0.94 mmol) and water (1.2 mL) were added to the mixture (V834-123). The mixture was degassed under vacuum, heated to 105° C. under nitrogen protection and stirred for 16 hours. After the reaction completed, water was added to the mixture, and the mixture was extracted with ethyl acetate (40 mL×3), and the organic layer was washed with saturated brine (30 mL). The mixture was dried over anhydrous sodium sulfate, and the filtrate was concentrated under reduced pressure. The filtrate was purified via silica gel column (ethyl acetate:methanol=20:1) to obtain a yellow solid compound 131, TDM-180731 (32 mg, yield: 16.6%), namely 4-(3-methyl-4-(2)-((1-methyl-1H-pyrazol-4-yl)amino)pyrimidin-4-yl)benzyl) thiomorpholine-1,1-dioxide. LCMS $[M+1]^+$=413.

1H NMR (400 MHZ, $CDCl_3$) δ 8.43 (d, J=5.1 Hz, 1H), 7.83 (s, 1H), 7.52 (s, 1H), 7.44 (d, J=8.1 Hz, 1H), 7.24 (s, 2H), 7.04 (s, 1H), 6.78 (d, J=5.1 Hz, 1H), 3.89 (s, 3H), 3.68 (s, 2H), 3.06 (d, J=21.7 Hz, 8H), 2.44 (s, 3H).

Example 9: General Method for Synthesizing Compound 183 (TDM-180783)

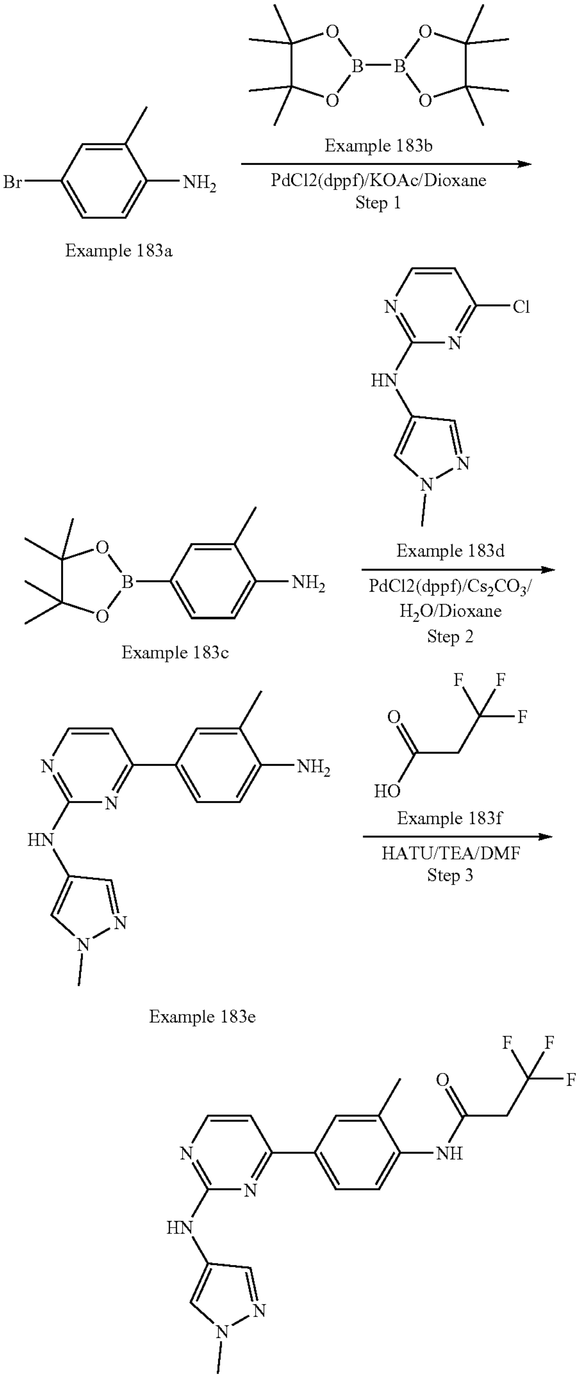

Example 183a

Example 183b

Example 183c

Example 183d

Example 183e

Example 183f

Example 183 (TDM-180783)

Step 1: Example 183c

Compound 183a (1.0 g, 5.37 mmol), compound 183b (2.73 g, 10.75 mmol), potassium acetate (1.58 g, 16.12 mmol) and $PdCl_2$ (dppf) (0.39 g, 0.54 mmol) were added to 1,4-dioxane (20 mL), nitrogen displacement was employed three times, and the mixture was then heated to 90° C. and stirred for 4 hours. The reaction solution was cooled to room temperature and filtered, the filter cake was rinsed with ethyl acetate (15 mL×2), the filtrate was concentrated, and the concentrate was purified via silica gel chromatography (ethyl acetate:petroleum ether=0-80%) to obtain a yellow solid compound 183c (namely, 2-methyl-4-(4,4,5,5-tetramethyl-1,3,2-dioxaborolane-2-yl) aniline (1.21 g, yield: 96.6%). LCMS $[M+1]^+$=234.1.

Step 2: Example 183e

The compound 183d (200 mg, 0.95 mmol), compound 183c (266.9 mg, 1.14 mmol), cesium carbonate (621.6 mg, 1.91 mmol) and $PdCl_2$ (dppf) (69.8 mg, 0.10 mmol) were added to a mixture solution of 1,4-dioxane (10 mL) and water (1 mL), nitrogen displacement was employed three times, and the mixture solution was then heated to 85° C. and stirred for 2 hours. The reaction solution was cooled to room temperature and filtered, the filter cake was washed with ethyl acetate (15 mL×2), the filtrate was concentrated, the concentrate was purified via silica gel chromatography (ethyl acetate:petroleum ether=0-80%) to obtain a crude product, and the crude product was purified via preparative HPLC to obtain a pale yellow solid compound 183e, namely 4-(4-amino-3-methylphenyl)-N-(1-methyl-1H-pyrazol-4-yl) pyrimidin-2-amine (128 mg, yield: 48.4%). LCMS $[M+1]^+$=281.1.

Step 3: Example 183 (TDM-180783)

2-(7-benzotriazole oxide)-N,N,N',N'-tetramethylurea hexafluorophosphate (102.1 mg, 0.269 mmol), triethylamine (27.2 mg, 0.269 mmol) and compound 183f (27.4 mg, 0.21 mmol) were added to compound 183e (50 mg, 0.179 mmol) in a solution of N,N-dimethylformamide (5 mL). The reaction solution was stirred for 2 hours at 30° C. After removal of solvent, the reaction solution was purified via preparative HPLC to obtain a yellow solid compound 183, namely 3,3,3-trifluoro-N-(2-methyl-4-(2-((1-methyl-1H-pyrazol-4-yl)amino)pyrimidin-4-yl)phenyl)propanamide (19.2 mg, yield: 27.3%). LCMS $[M+1]^+$=391.1.

$^1$H NMR (400 MHz, DMSO) δ 9.79 (s, 1H), 9.52 (s, 1H), 8.46 (d, J=5.2 Hz, 1H), 8.03 (s, 1H), 7.98 (d, J=8.4 Hz, 1H), 7.93 (s, 1H), 7.67 (d, J=8.4 Hz, 1H), 7.55 (s, 1H), 7.27 (d, J=5.3 Hz, 1H), 3.83 (s, 3H), 3.62 (q, J=11.2 Hz, 2H), 2.32 (s, 3H).

Compounds prepared in a similar method are as follows:

| Structure Structural formula | TDM No. Registration number | LCMS $[M + 1]^+$ | $^1$H-NMR Proton nuclear magnetic resonance spectroscopy |
|---|---|---|---|
| 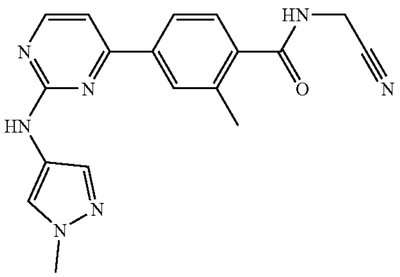 [SMILES: Cc1cc(-c2ccnc(Nc3cnn(C)c3)n2)ccc1C(=O)NCC#N] | TDM-180784 | 348.1 | $^1$HNMR (400 MHz, DMSO) δ 9.76 (s, 1H), 9.48 (s, 1H), 8.46 (d, J = 5.1 Hz, 1H), 8.02 (s, 1H), 7.97 (d, J = 8.4 Hz, 1H), 7.93 (s, 1H), 7.69 (d, J = 8.3 Hz, 1H), 7.55 (s, 1H), 7.26 (d, J = 5.2 Hz, 1H), 4.00 (s, 2H), 3.83 (s, 3H), 2.33 (s, 3H). |

TDM-180784, a yellow solid compound 184, namely N-(cyanomethyl)-2-methyl-4-(2-((1-methyl-1H-pyrazol-4-yl)amino)pyrimidin-4-yl)benzamide (18.1 mg, yield: 27.8%).

Example 10: General Method for Synthesizing Compound 121 (TDM-180721)

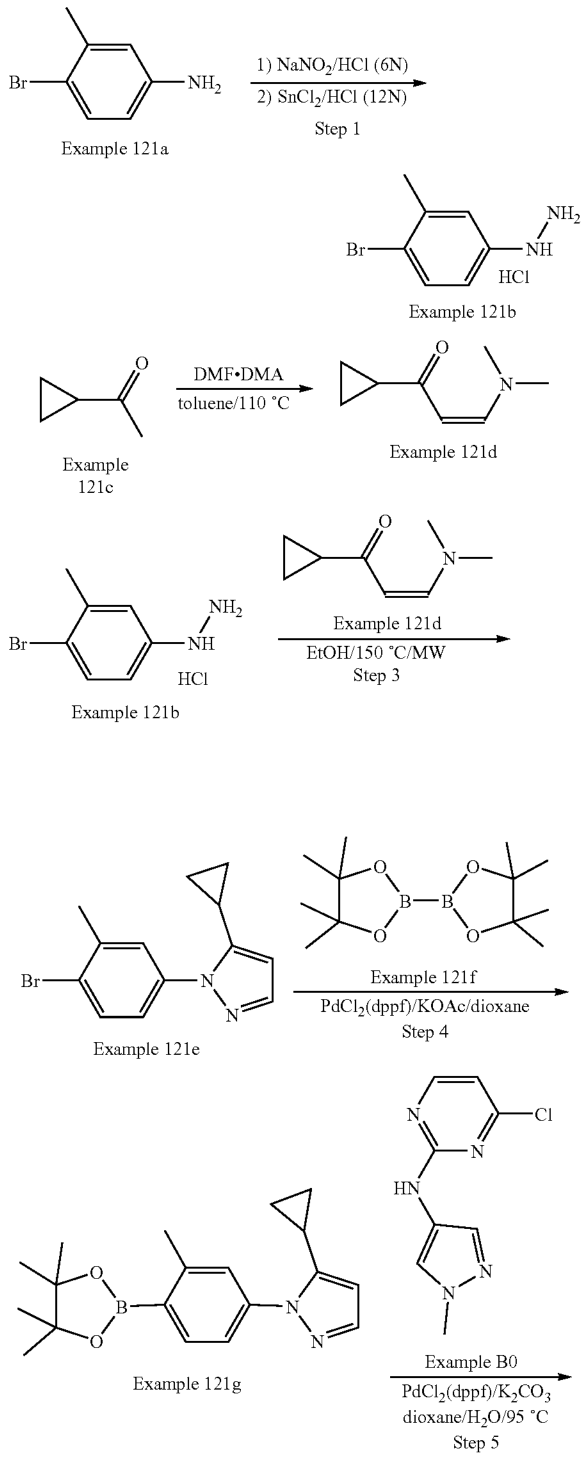

Example 121a

Example 121b

Example 121c

Example 121d

Example 121b

Example 121d

Example 121e

Example 121f

Example 121g

Example B0

-continued

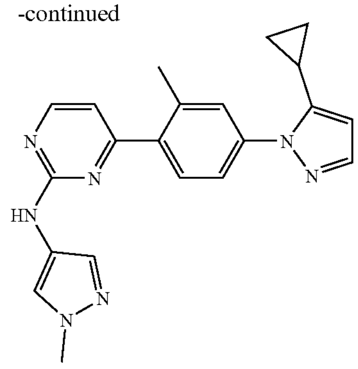

TDM-180721

Step 1: Example 121b (4-bromo-3-methylphenyl) hydrazine hydrochloride

The original compound 121a (3 g, 16.1 mmol) was suspended in HCl (25.5 mL, 6 N) and cooled to 0° C. An aqueous solution (12 mL) of sodium nitrite (1.2 g, 17.4 mmol) was added to the mixture (feeding lasted approximately 5 minutes). The mixture was stirred for 15 minutes at 0° C. HCl solution (7.5 mL, 12 N) of anhydrous stannous chloride (10.8 g, 47.9 mmol) was then added to the mixture. The obtained mixture was stirred for 2 hours at 0° C. The mixture was filtered and the filter cake was washed with cold water to obtain a brown solid compound 121b, namely, (4-bromo-3-methylphenyl) hydrazine hydrochloride (1.89 g, yield: 58.4%).

LCMS $[M+1]^+$=202.

Step 2: Example 121d (Z)-1-cyclopropyl-3-(dimethylamino) prop-2-en-1-one

A mixture of compound 121c (5.5 g, 65 mmol) and DMF·DMA (15 g, 126 mmol) was heated to 115° C. and reacted for 16 hours. The reaction mixture was concentrated under reduced pressure to obtain the crude product compound 121d (900 mg, yield: <15%). The crude product compound was directly used in the next reaction without purification. LCMS $[M+1]^+$=140.2

Step 3: Example 121e 1-(4-bromo-3-methylphenyl)-5-cyclopropyl-1H-pyrazole

The compound 121b (200 mg, 0.84 mmol), the compound 121d (233 mg, 1.68 mmol) and EtOH (6 mL) were added to a microwave tube. The mixture reacted in a sealed microwave tube at 150° C. for 45 minutes. The reactions of different batches were combined, the mixture was concentrated, and purified via a column (petroleum ether/ethyl acetate=0/10) to obtain a yellow oily compound 112e, namely 1-(4-bromo-3-methylphenyl)-5-cyclopropyl-1H-pyrazole (750 mg, yield: 80%).

LCMS $[M+1]^+$=279.

1H NMR (400 MHz, Chloroform-d) δ 7.46-7.67 (m, 3H), 7.32-7.38 (m, 1H), 5.99 (d, J=2.4 Hz, 1H), 2.48 (s, 3H), 1.78-1.86 (m, 1H), 0.98-1.05 (m, 2H), 0.76-0.82 (m, 2H).

Step 4: Example 121g 5-cyclopropyl-1-(3-methyl-4-(4,4,5,5-tetramethyl-1,3,2-dioxaborolane-2-yl)phenyl)-1H-pyrazole The compound 121e (200 mg, 0.72 mmol), the compound 121f (274 mg, 1.08 mmol), PdCl (dppf) (158 mg, 0.22 mmol), KOAc (211 mg, 2.16 mmol) and 1,4-dioxane (20 mL) were added to a three-necked flask, nitrogen displacement was employed 3 times using a water pump. The reaction mixture reacted at 95° C. for 3 hours. The obtained compound 121 g (theoretically, 234 mg) was the reaction mixture. The reaction mixture was directly used for the next reaction.

LCMS $[M+1]^+$=325.2

Step 5: Example 121 (TDM-180721)

4-(4-(5-cyclopropyl-1H-pyrazol-1-yl)-2-methylphenyl)-N-(1-methyl-1H-pyrazol-4-yl)pyrimidin-2-amine 4-(4-(5-cyclopropyl-1H-pyrazol-1-yl)-2-methylphenyl)-N-(1-methyl-1H-pyrazol-4-yl)pyrimidin-2-amine Compound B0 (118 mg, 0.56 mmol), $PdCl_2$ (dppf) (82 mg, 0.11 mmol), $K_2CO_3$ (193 mg, 1.4 mmol), 1,4-oxane (10 mL) and $H_2O$ (5 mL) were added to compound 121g (234 mg, 0.72 mmol). Nitrogen displacement was employed for the mixture three times using a water pump. The reaction mixture reacted at 95° C. for 3 hours. The mixture was concentrated, purified via column chromatography (petroleum ether/ethyl acetate=0/100), and purified again via basic preparation to obtain a pale green solid compound 121 (83.2 mg, yield: 34%).

LCMS $[M+1]^+$=372.1.

$^1$H NMR (400 MHz, Chloroform-d) δ 8.48 (d, J=5.2 Hz, 1H), 7.88 (s, 1H), 7.50-7.67 (m, 5H), 7.01 (br s, 1H), 6.85 (d, J=5.2 Hz, 1H), 6.02 (d, J=1.2 Hz, 1H), 3.91 (s, 3H), 2.53 (s, 3H), 1.87-1.96 (m, 1H), 1.01-1.10 (m, 2H), 0.80-0.87 (m, 2H).

Example 11: General Method for Synthesizing Compound 163 (TDM-180763)

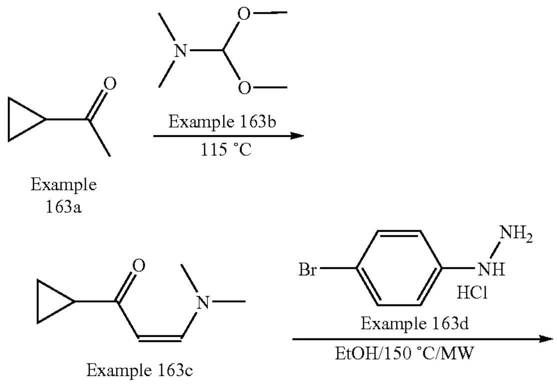

Example 163a

Example 163c

-continued

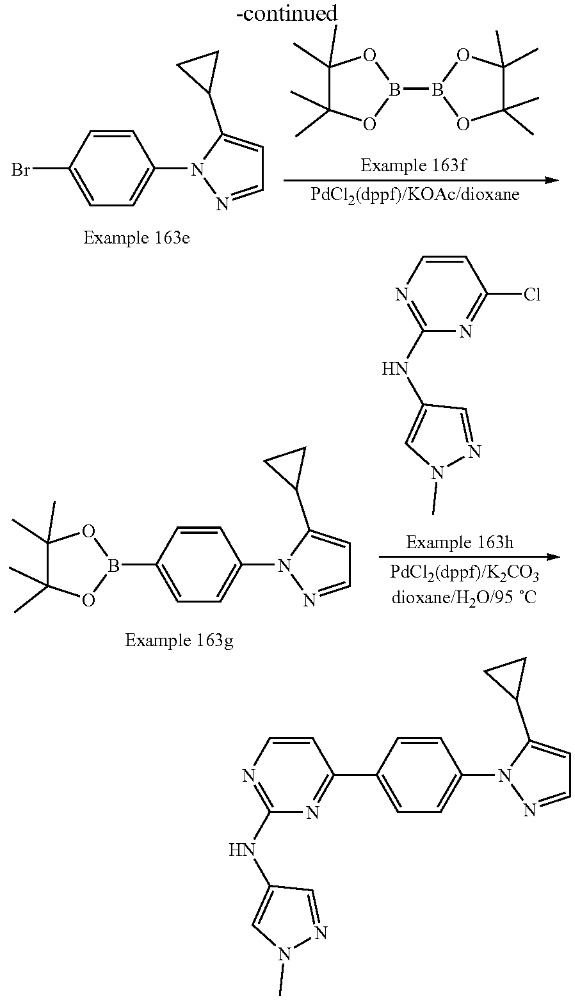

Example 163e

Example 163g

Example 163 (TDM-180763)

Step 1: Example 163c

A mixture solution of compound 163a (5.5 g, 65.4 mmol) and compound 163b (15.6 g, 130.8 mmol) was stirred at 115° C. for 19 hours. The mixture solution was cooled to room temperature, water (50 mL) was added, the mixture solution was extracted with EtOAc (20 mL×4), and organic layers were combined and washed with water (30 mL×2), dried over $MgSO_4$, filtered and evaporated to obtain a yellow oily compound 163c, namely (Z)-1-cyclopropyl-3-(dimethylamino) prop-2-en-1-one (1.23 g, yield: 13.5%). LCMS $[M+1]^+$=140.1.

Step 2: Example 163e

The compound 163d (400 mg, 1.79 mmol) and the compound 163c (498 mg, 3.58 mmol) in EtOH solution (12 mL) was stirred and reacted at 150° C. via microwave irradiation for 45 minutes. The reaction solution was concentrated under reduced pressure, and the residue was purified via silica gel chromatography (flash chromatography) with ethyl acetate:petroleum ether=0%-10% to obtain a yellow solid compound 163e, namely, 1-(4-bromophenyl)-5-cyclopropyl-1H-pyrazole (416 mg, yield: 88.3%). LCMS $[M+1]^+$=264.1.

Step 3: Example 163g

The compound 163e (200 mg, 0.76 mmol), compound 163f (289.7 mg, 1.14 mmol), KOAc (223.6 mg, 2.28 mmol) and $PdCl_2$ (dppf) (55.6 mg, 0.08 mmol) in 1,4-dioxane solution (20 mL) were stirred at room temperature. Nitrogen displacement was employed three times, and the mixture was then heated to 90° C. and stirred for 3 hours. After the reaction completed, the mixture was directly used for the next feeding without processing.

Step 4: Example 163 (TDM-180763)

The compound 163h (122.3 mg, 0.58 mmol), compound 163g (235.1 mg, 0.76 mmol), $K_2CO_3$ (201.3 mg, 1.46 mmol) and $PdCl_2$ (dppf) (85.4 mg, 0.12 mmol) were dissolved in a mixture of 1,4-dioxane (20 mL) and water (5 mL). Nitrogen displacement was employed three times, and the mixture was then heated to 95° C. and stirred for 17 hours. The mixture was cooled to room temperature and filtered, the filter cake was washed with ethyl acetate, and the organic phase was collected and concentrated. The concentrate was purified via preparative HPLC to obtain a pale green solid compound 163, namely 4-(4-(5-cyclopropyl-1H-pyrazol-1-yl)phenyl)-N-(1-methyl-1H-pyrazol-4-yl)pyrimidin-2-amine (29.1 mg, yield: 13.8%). LCMS: $[M+1]^+$=358.2.

$^1$H NMR (400 MHz, DMSO) δ 9.54 (s, 1H), 8.52 (d, J=5.1 Hz, 1H), 8.30 (d, J=8.6 Hz, 2H), 7.93 (s, 1H), 7.85 (d, J=8.7 Hz, 2H), 7.60 (t, J=4.5 Hz, 2H), 7.35 (d, J=5.2 Hz, 1H), 6.19 (d, J=1.3 Hz, 1H), 3.84 (s, 3H), 2.08-1.90 (m, 1H), 1.12-0.94 (m, 2H), 0.88-0.67 (m, 2H).

Example 12: General Method for Synthesizing Compound 182 (TDM-180782)

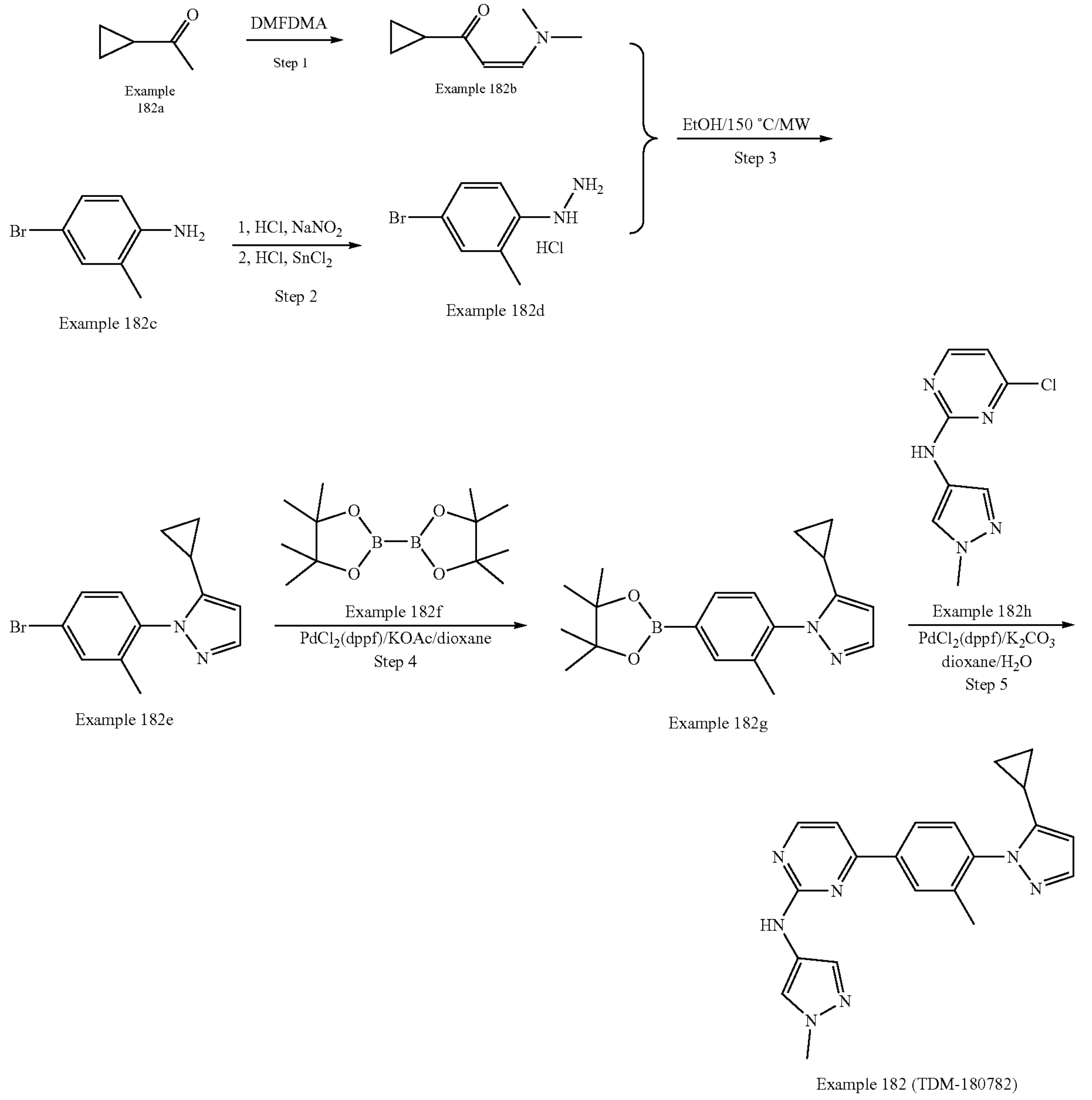

Example 182 (TDM-180782)

Step 1: Example 182b

A mixture solution of the compound 182a (2.75 g, 32.7 mmol) and N,N-dimethylformamide dimethyl acetal (7.8 g, 65.4 mmol) was heated to 115° C., and stirred and held at the temperature for 19 hours. The reaction solution was cooled to room temperature, water (30 mL) was added, the reaction solution was extracted with ethyl acetate (15 mL×4), and organic layers were combined and washed with water (20 mL×2), dried over $MgSO_4$, filtered and concentrated to obtain a yellow oily liquid compound 182b, namely (Z)-1-cyclopropyl-3-(dimethylamino) prop-2-en-1-one (0.4 g, yield: 8.8%). LCMS $[M+1]^+$=140.1.

Step 2: Example 182d

The compound 182c (0.5 g, 2.69 mmol) was dissolved in 6 mol/L hydrochloric acid (4 mL) and cooled to 0° C., an aqueous sodium nitrite solution (0.2 g sodium nitrite and 2 mL aqueous solution) was slowly added, the reaction solution was stirred at 0° C. for 15 minutes, and then stannous chloride dihydrate was added (1.8 g, dissolved in 1.2 mL of 12 mol/L hydrochloric acid). The reaction solution was continuously stirred for 2 hours at 0° C. The reaction solution was filtered, and the filter cake was washed with cold water (10 mL×2). The filter cake was then slurried with dichloromethane (2 mL) and petroleum ether (5 mL) for 15 minutes, filtered and dried to obtain a brown solid compound 182d, namely (4-bromo-2-methylphenyl) hydrazine hydrochloride (290 mg, yield: 45.4%). LCMS $[M+1]^+$=201.1, 203.1.

Step 3: Example 182e

The compound 182d (200 mg, 0.84 mmol) and the compound 182c (234.4 mg, 1.68 mmol) were dissolved in ethanol (6 mL) and heated to 150° C. by microwave and reacted for 45 minutes. The reaction solution was cooled to room temperature and after the solvent was removed, the concentrate was purified via silica gel chromatography (ethyl acetate:petroleum ether=0%-10%) to obtain a yellow solid compound 182e, namely, 1-(4-bromo-2-methylphenyl)-5-cyclopropyl-1H-pyrazole (160 mg, yield: 47.4%). LCMS $[M+1]^+$=277.1, 279.1.

Step 4: Example 182g

The compound 182e (60 mg, 0.22 mmol) and compound 182f (82.5 mg, 0.32 mmol), potassium acetate (63.7 mg, 0.65 mmol) and $PdCl_2$ (dppf) (15.8 mg, 0.02 mmol) were dissolved in 1,4-dioxane (10 mL) and stirred under room temperature. Nitrogen displacement was employed three times, and the reaction solution was then heated to 90° C. and stirred for 5 hours. After being cooled down, the reaction solution was directly used for the next feeding. LCMS $[M+1]^+$=325.1.

Step 5: Example 182 (TDM-180782)

The compound 182h (35 mg, 0.17 mmol), compound 182g (70.3 mg, 0.22 mmol), potassium carbonate (57.6 mg, 0.42 mmol) and $PdCl_2$ (dppf) (24.4 mg, 0.03 mmol) were added to a mixture solution of 1,4-dioxane (12 mL) and water (2 mL). Nitrogen displacement was employed three times, and the reaction solution was heated to 95° C. and stirred for 17 hours. The reaction solution was cooled to room temperature and filtered, the filter cake was washed with ethyl acetate (10 mL×2), and the organic phase was collected and concentrated. The concentrate was subjected to preparative HPLC to obtain a yellow solid compound 182, namely 4-(4-(5-cyclopropyl-1H-pyrazol-1-yl)-3-methylphenyl)-N-(1-methyl-1H-pyrazol-4-yl)pyrimidin-2-amine (7.3 mg, yield: 11.7%). LCMS $[M+1]^+$=372.1.

$^1H$ NMR (400 MHz, DMSO) δ 9.57 (s, 1H), 8.53 (d, J=5.1 Hz, 1H), 8.19 (d, J=1.5 Hz, 1H), 8.11 (d, J=8.2 Hz, 1H), 7.94 (s, 1H), 7.54 (dd, J=22.3, 5.0 Hz, 3H), 7.36 (d, J=5.2 Hz, 1H), 6.07 (d, J=1.7 Hz, 1H), 3.83 (s, 3H), 2.13 (s, 3H), 1.51 (td, J=8.3, 4.2 Hz, 1H), 0.94-0.78 (m, 2H), 0.74-0.61 (m, 2H).

Example 13: General Method for Synthesizing Compound 206 (TDM-180806)

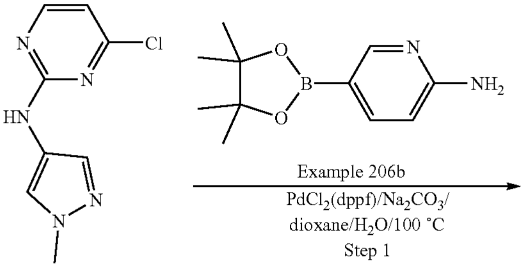

Example 206a

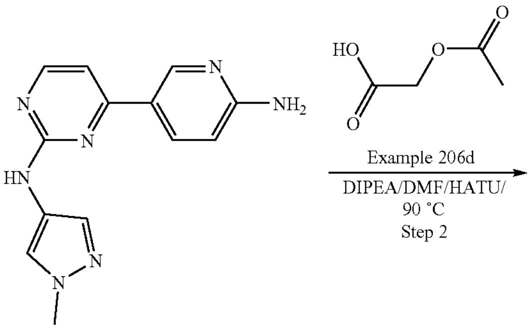

Example 206c

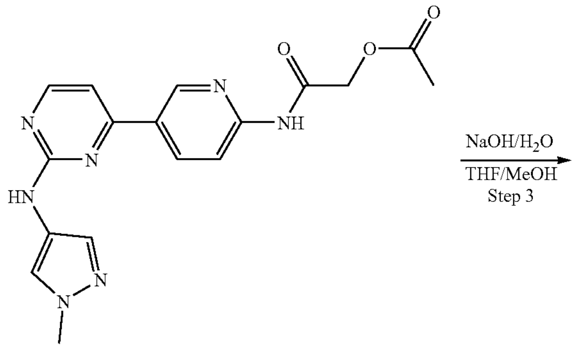

Example 206e

-continued

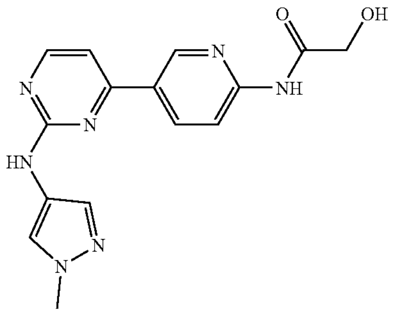

Example 206 (TDM-180806)

Step 1: Example 206c 1,1'-bisdiphenylphosphine ferrocene palladium dichloride (350 mg, 0.479 mmol) and sodium carbonate (1.01 g, 9.57 mmol) were added to a mixture of compound 206a (1 g, 4.785 mmol) (namely, 4-chloro-N-(1-methyl-1H-pyrazol-4-yl)pyrimidin-2-amine and compound 206b (1.05 g, 4.785 mmol) (namely, 5-(4,4,5,5-tetramethyl-1,3,2-dioxaborolane-2-yl)pyridin-2-amine, and water (7 mL) and dioxane (42 mL) were added to the mixture. Nitrogen displacement was then employed several times under vacuum, and the mixture was heated to 100° C. and stirred for 2.5 hours. After the reaction completed, the mixture was concentrated under reduced pressure, and purified via silica gel chromatography (dichloromethane:10% methanol/dichloromethane=50:50) to obtain an off-white solid compound 206c, namely 4-(6-amino-pyridin-3-yl)-N-(1-methyl-1H-pyrazol-4-yl)pyrimidin-2-amine (824 mg, yield: 64.4%). LCMS $[M+1]^+=268$ Step 2: Example 206e N,N-diisopropylethylamine (217.5 mg, 1.683 mmol) was added to compound 206c (150 mg, 0.561 mmol) in a solution of N,N-dimethylformamide (15 mL) at room temperature, the mixture was stirred for 5 minutes, and then 2-(7-benzotriazole oxide)-N,N,N',N'-tetramethylurea hexafluorophosphate (320 mg, 0.842 mmol) and compound 206d (namely, 2-acetoxyacetic acid) (99.4 mg, 0.842 mmol) were added into the mixture. The reaction solution was heated to 90° C. and stirred for 18 hours. The mixture was concentrated under reduced pressure, and the residue was passed through silica gel chromatography (dichloromethane: dichloromethane solution containing 10% methanol=75:25) and purified to obtain a yellow solid compound 206e, (namely, 2-((5-(2-((1-methyl-1H-pyrazol-4-yl)amino)pyrimidin-4-yl)pyridin-2-yl)amino)-2-oxoethyl acetate (165 mg, yield: 80.1%). LCMS $[M+1]^+=368$.

Step 3: Example 206 (TDM-180806)

An aqueous solution (10 mL) of sodium hydroxide (108 mg) was added to a solution of compound 206e (165 mg, 0.45 mmol) in tetrahydrofuran (5 mL) and methanol (5 mL). The mixture was stirred for 1 hours at room temperature. The mixture was concentrated under reduced pressure to remove methanol and tetrahydrofuran, and filtered to collect the precipitate, the solid was purified via silica gel chromatography (ethyl acetate:methanol=20:1) to obtain a pale yellow solid compound 206, TDM-180806, namely, 2-hydroxy-N-(5-(2-((1-methyl-1H-pyrazol-4-yl)amino)pyrimidin-4-yl)pyridin-2-yl) acetamide (4.5 mg, yield: 3.1%). LCMS $[M+1]^+=326.1$.

1H NMR (400 MHz, DMSO-$d_6$) δ 9.98 (s, 1H), 9.54 (s, 1H), 9.09 (d, J=2.0 Hz, 1H), 8.52 (dd, J=20.9, 6.7 Hz, 2H), 8.27 (d, J=8.7 Hz, 1H), 7.94 (s, 1H), 7.54 (s, 1H), 7.33 (d, J=5.2 Hz, 1H), 5.76 (t, J=6.0 Hz, 1H), 4.10 (d, J=5.9 Hz, 2H), 3.83 (s, 3H).

Compounds prepared in a similar method are as follows:

| Structure Structural formula | TDM No. Registration number | LCMS $[M + 1]^+$ | $^1$H-NMR Proton nuclear magnetic resonance spectroscopy |
|---|---|---|---|
| 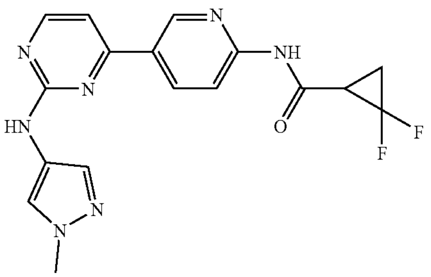 [SMILES: Cn1cc(Nc2nccc(-c3ccc(NC(=O)C4CC4(F)F)nc3)n2)cn1] | TDM-180822 | 372.1 | $^1$H NMR (400 MHz, DMSO-$d_6$) δ 11.29 (s, 1H), 9.54 (s, 1H), 9.11 (d, J = 1.8 Hz, 1H), 8.51 (dd, J = 14.0, 7.0 Hz, 2H), 8.22 (d, J = 8.8 Hz, 1H), 7.93 (s, 1H), 7.54 (s, 1H), 7.33 (d, J = 5.2 Hz, 1H), 3.83 (s, 3H), 3.04 (dt, J = 13.6, 10.0 Hz, 1H), 2.05 (dt, J = 11.8, 8.0 Hz, 2H). |
| 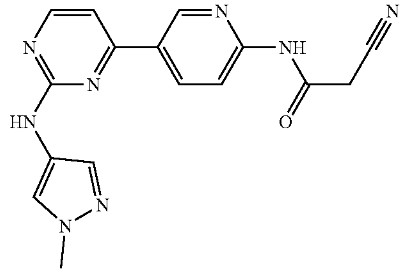 [SMILES: Cn1cc(Nc2nccc(-c3ccc(NC(=O)CC#N)nc3)n2)cn1] | TDM-180833 | 335 | $^1$H NMR (400 MHz, DMSO) δ 11.12 (s, 1H), 9.54 (s, 1H), 9.10 (d, J = 1.9 Hz, 1H), 8.53 (dd, J = 22.7, 6.7 Hz, 2H), 8.18 (d, J = 8.4 Hz, 1H), 7.93 (s, 1H), 7.54 (s, 1H), 7.33 (d, J = 5.2 Hz, 1H), 4.04 (s, 2H), 3.83 (s, 3H). |

-continued

| Structure Structural formula | TDM No. Registration number | LCMS $[M + 1]^+$ | $^1$H-NMR Proton nuclear magnetic resonance spectroscopy |
|---|---|---|---|
| 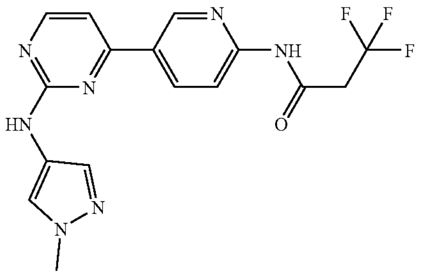 [SMILES: Cn1cc(Nc2nccc(-c3ccc(NC(=O)CC(F)(F)F)nc3)n2)cn1] | TDM-180830 | 378.1 | $^1$H NMR (400 MHz, DMSO-$d_6$) δ 11.14 (s, 1H), 9.55 (s, 1H), 9.11 (d, J = 1.8 Hz, 1H), 8.53 (dd, J = 21.0, 6.3 Hz, 2H), 8.23 (d, J = 8.7 Hz, 1H), 7.93 (s, 1H), 7.54 (s, 1H), 7.34 (d, J = 5.2 Hz, 1H), 3.83 (s, 3H), 3.68 (q, J = 11.1 Hz, 2H). |
| 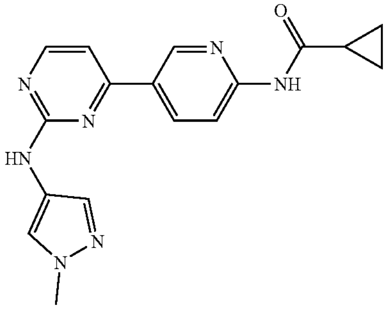 [SMILES: Cn1cc(Nc2nccc(-c3ccc(NC(=O)C4CC4)nc3)n2)cn1] | TDM-180819 | 336.1 | $^1$H NMR (400 MHz, DMSO) δ 11.09 (s, 1H), 9.53 (s, 1H), 9.08 (d, J = 1.9 Hz, 1H), 8.48 (d, J = 5.2 Hz, 2H), 8.23 (d, J = 8.8 Hz, 1H), 7.93 (s, 1H), 7.53 (s, 1H), 7.32 (d, J = 5.2 Hz, 1H), 3.83 (s, 3H), 2.05 (s, 1H), 0.88-0.81 (m, 4H). |
| 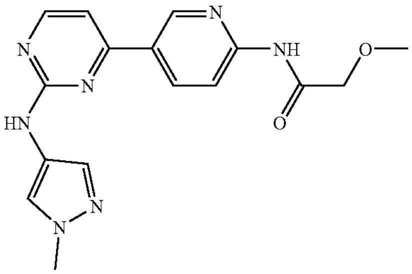 [SMILES: COCC(=O)Nc1ccc(-c2ccnc(Nc3cnn(C)c3)n2)cn1] | TDM-180831 | 340.1 | $^1$H NMR (400 MHz, DMSO-$d_6$) δ 10.32 (s, 1H), 9.54 (s, 1H), 9.09 (d, J = 2.0 Hz, 1H), 8.51 (dd, J = 17.3, 6.6 Hz, 2H), 8.25 (d, J = 8.7 Hz, 1H), 7.93 (s, 1H), 7.54 (s, 1H), 7.33 (d, J = 5.2 Hz, 1H), 4.12 (s, 2H), 3.83 (s, 3H), 3.39 (s, 3H). |
| 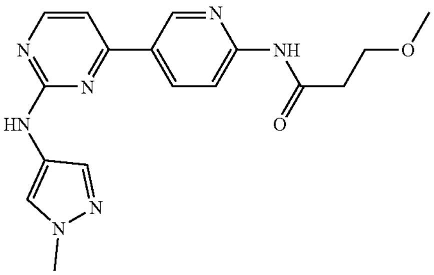 [SMILES: COCCC(=O)Nc1ccc(-c2ccnc(Nc3cnn(C)c3)n2)cn1] | TDM-180814 | 354.1 | $^1$H NMR (400 MHz, DMSO-$d_6$) δ 10.77 (s, 1H), 9.53 (s, 1H), 9.08 (d, J = 1.9 Hz, 1H), 8.49 (t, J = 6.7 Hz, 2H), 8.26 (d, J = 8.8 Hz, 1H), 7.93 (s, 1H), 7.54 (s, 1H), 7.32 (d, J = 5.2 Hz, 1H), 3.83 (s, 3H), 3.64 (t, J = 6.1 Hz, 2H), 3.25 (s, 3H), 2.68 (t, J = 6.1 Hz, 2H). |
| 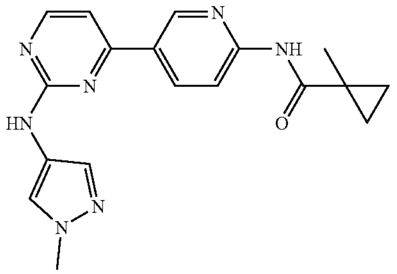 [SMILES: Cn1cc(Nc2nccc(-c3ccc(NC(=O)C4(C)CC4)nc3)n2)cn1] | TDM-180853 | 350.2 | $^1$H NMR (400 MHz, DMSO-$d_6$) δ 9.82 (s, 1H), 9.54 (s, 1H), 9.10 (d, J = 2.1 Hz, 1H), 8.49 (d, J = 5.1 Hz, 2H), 8.19 (d, J = 8.8 Hz, 1H), 7.93 (s, 1H), 7.53 (s, 1H), 7.33 (d, J = 5.2 Hz, 1H), 3.83 (s, 3H), 1.45 (s, 3H), 1.17 (q, J = 3.7 Hz, 2H), 0.70 (q, J = 3.9 Hz, 2H). |

-continued

| Structure Structural formula | TDM No. Registration number | LCMS $[M + 1]^+$ | $^1$H-NMR Proton nuclear magnetic resonance spectroscopy |
|---|---|---|---|
| 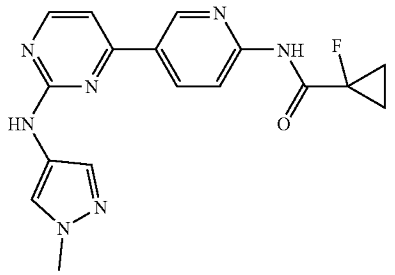 [SMILES: Cn1cc(Nc2nccc(-c3ccc(NC(=O)C4(F)CC4)nc3)n2)cn1] | TDM-180821 | 354.1 | $^1$H NMR (400 MHz, DMSO-$d_6$) δ 10.56 (s, 1H), 9.56 (s, 1H), 9.14 (d, J = 2.0 Hz, 1H), 8.53 (dd, J = 17.9, 6.2 Hz, 2H), 8.19 (d, J = 8.7 Hz, 1H), 7.94 (s, 1H), 7.54 (s, 1H), 7.35 (d, J = 5.2 Hz, 1H), 3.83 (s, 3H), 1.58-1.32 (m, 4H). |
| 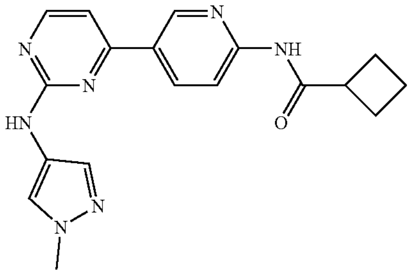 [SMILES: Cn1cc(Nc2nccc(-c3ccc(NC(=O)C4CCC4)nc3)n2)cn1] | TDM-180823 | 350.1 | $^1$H NMR (400 MHz, DMSO-$d_6$) δ 10.61 (s, 1H), 9.54 (s, 1H), 9.07 (d, J = 1.9 Hz, 1H), 8.49 (t, J = 7.1 Hz, 2H), 8.28 (d, J = 8.8 Hz, 1H), 7.93 (s, 1H), 7.54 (s, 1H), 7.32 (d, J = 5.2 Hz, 1H), 3.83 (s, 3H), 3.41 (p, J = 8.3 Hz, 1H), 2.37-2.03 (m, 4H), 2.03-1.74 (m, 2H). |
| 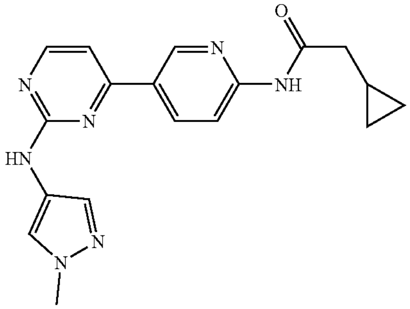 [SMILES: Cn1cc(Nc2nccc(-c3ccc(NC(=O)CC4CC4)nc3)n2)cn1] | TDM-180818 | 350 | $^1$H NMR (400 MHz, DMSO) δ 10.66 (s, 1H), 9.52 (s, 1H), 9.08 (d, J = 1.9 Hz, 1H), 8.48 (d, J = 5.1 Hz, 2H), 8.28 (d, J = 8.8 Hz, 1H), 7.93 (s, 1H), 7.53 (s, 1H), 7.32 (d, J = 5.2 Hz, 1H), 3.83 (s, 3H), 2.33 (d, J = 7.1 Hz, 2H), 1.07 (s, 1H), 0.52-0.42 (m, 2H), 0.21 (dd, J = 6.9, 3.4 Hz, 2H). |
| 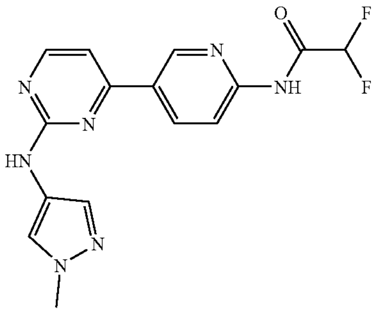 [SMILES: Cn1cc(Nc2nccc(-c3ccc(NC(=O)C(F)F)nc3)n2)cn1] | TDM-180849 | 346 | $^1$H NMR (400 MHz, DMSO) δ 11.63 (s, 1H), 9.57 (s, 1H), 9.15 (d, J = 1.9 Hz, 1H), 8.56 (dd, J = 33.4, 6.5 Hz, 2H), 8.23 (d, J = 8.6 Hz, 1H), 7.94 (s, 1H), 7.54 (s, 1H), 7.36 (d, J = 5.2 Hz, 1H), 6.47 (dd, J = 69.1, 38.1 Hz, 1H), 3.84 (s, 3H). |

TDM-180822, a yellow solid compound 222, namely 2,2-difluoro-N-(5-(2-((1-methyl-1H-pyrazol-4-yl)amino)pyrimidin-4-yl)pyridin-2-yl)cyclopropane-1-carboxamide (19.5 mg, yield: 14%)

TDM-1808332-cyano-N-(5-(2-((1-methyl-1H-pyrazol-4-yl)amino)pyrimidin-4-yl) pyridin-2-yl) acetamide Example 233, white solid compound (18 mg, yield: 18%).

TDM-180830, a yellow solid compound 230, namely 3,3,3-trifluoro-N-(5-(2-((1-methyl-1H-pyrazol-4-yl)amino)pyrimidin-4-yl)pyridin-2-yl)propanamide (9.5 mg, yield: 6.7%)

TDM-180819, N-(5-(2-((1-methyl-1H-pyrazol-4-yl)amino)pyrimidin-4-yl)pyridin-2-yl)cyclopropylcarboxamide, a yellow solid compound (11.9 mg, yield: 11.8%).

TDM-180831, a yellow solid compound 231, namely 2-methoxy-N-(5-(2-((1-methyl-1H-pyrazol-4-yl)amino)pyrimidin-4-yl)pyridin-2-yl) acetamide (35.8 mg, yield: 28%).

TDM-180814, a yellow solid compound 214, namely 3-methoxy-N-(5-(2-((1-methyl-1H-pyrazol-4-yl)amino)pyrimidin-4-yl)pyridin-2-yl)propanamide (18.2 mg, yield: 13.7%)

TDM-180853, a yellow solid compound 253, TDM-180853, namely 1-methyl-N-(5-(2-((1-methyl-1H-pyrazol-4-yl)amino)pyrimidin-4-yl)pyridin-2-yl)cyclopropane-1-carboxamide (3.2 mg, yield: 2.5%).

TDM-180821, a yellow solid compound 221, namely 1-fluoro-N-(5-(2-((1-methyl-1H-pyrazol-4-yl)amino)pyrimidin-4-yl)pyridin-2-yl)cyclopropane-1-carboxamide (54.9 mg, yield: 41.4%)

TDM-180823, a yellow solid compound 223, TDM-180823, namely N-(5-(2-((1-methyl-1H-pyrazol-4-yl)amino)pyrimidin-4-yl)pyridin-2-yl)cyclobutanemethyl (28.3 mg, yield: 43.1%).

TDM-180818, a yellow solid compound, 2-cyclopropyl-N-(5-(2-((1-methyl-1H-pyrazol-4-yl)amino)pyrimidin-4-yl)pyridin-2-yl) acetamide (Example 218, 14.8 mg, yield: 22.7%).

TDM-180849, a pale yellow solid compound, namely 2,2-difluoro-N-(5-(2-((1-methyl-1H-pyrazol-4-yl)amino)pyrimidin-4-yl)pyridin-2-yl) acetamide (Example 249, 17.6 mg, yield: 13.6%).

Example 12: General Method for Synthesizing Compound 253 (TDM-180853)

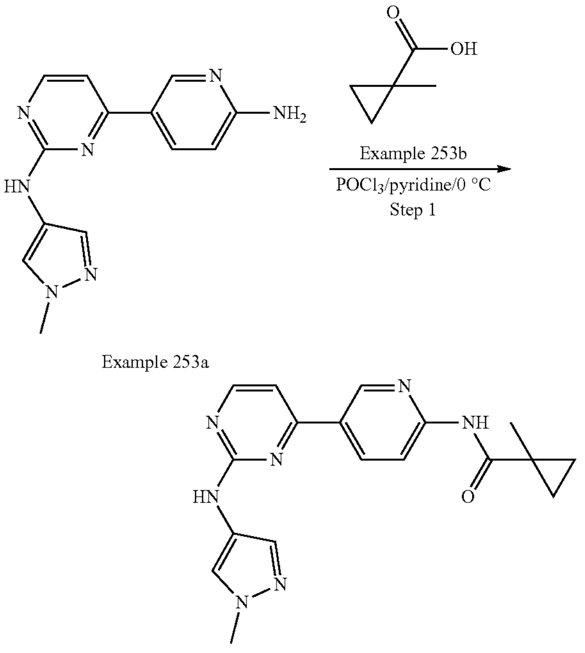

Example 253a

Example 253 (TDM-180853)

Step 1: Example 253

Compound 253b (56.2 mg, 0.561 mmol) (namely, 1-methylcyclopropane carboxylic acid) and phosphorus oxychloride (100 mg, 0.374 mmol) were added to compound 253a (namely, 4-(6-amino-pyridin-3-yl)-N-(1-methyl-1H-pyrazol-4-yl)pyrimidin-2-amine) (100 mg, 0.374 mmol) in a pyridine solution at 0° C. The reaction solution was stirred for one hours at 0° C. The reaction solution was concentrated under reduced pressure, and the residue was passed through silica gel chromatography (dichloromethane:dichloromethane containing 10% methanol=70:30) and purified to obtain a yellow solid compound 253, TDM-180853, (namely, 1-methyl-N-(5-(2-((1-methyl-1H-pyrazol-4-yl)amino)pyrimidin-4-yl)pyridin-2-yl)cyclopropane-1-carboxamide (3.2 mg, yield: 2.5%). LCMS $[M+1]^+$=350.2

$^1$H NMR (400 MHz, DMSO-d6) δ 9.82 (s, 1H), 9.54 (s, 1H), 9.10 (d, J=2.1 Hz, 1H), 8.49 (d, J=5.1 Hz, 2H), 8.19 (d, J=8.8 Hz, 1H), 7.93 (s, 1H), 7.53 (s, 1H), 7.33 (d, J=5.2 Hz, 1H), 3.83 (s, 3H), 1.45 (s, 3H), 1.17 (q, J=3.7 Hz, 2H), 0.70 (q, J=3.9 Hz, 2H).

Example 13: General Method for Synthesizing Compound 223 (TDM-180823)

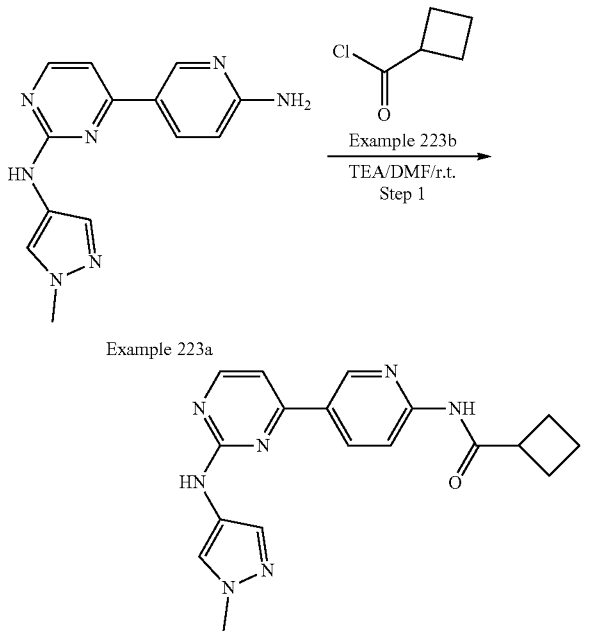

Example 223a

Example 223 (TDM-180823)

Step 1: Example 223

Triethylamine (38 mg, 0.376 mmol) was added to compound 223a (namely, 4-(6-amino-pyridin-3-yl)-N-(1-methyl-1H-pyrazol-4-yl)pyrimidin-2-amine) (50 mg, 0.188 mmol) in a solution of N,N-dimethylformamide (10 mL) at room temperature, and then the compound 223b (26.7 mg, 0.226 mmol) (namely, cyclobutanecarbonyl chloride) was added to the mixture. The mixture was stirred at room temperature for 1 hour, then the mixture was concentrated under reduced pressure and the residue was purified via preparative high-performance liquid chromatography, to obtain a yellow solid compound 223, TDM-180823, namely N-(5-(2-((1-methyl-1H-pyrazol-4-yl)amino)pyrimidin-4-yl)pyridin-2-yl)cyclobutanemethyl (28.3 mg, yield: 43.1%). LCMS $[M+1]^+$=350.1

$^1$H NMR (400 MHz, DMSO-$d_6$) δ 10.61 (s, 1H), 9.54 (s, 1H), 9.07 (d, J=1.9 Hz, 1H), 8.49 (t, J=7.1 Hz, 2H), 8.28 (d, J=8.8 Hz, 1H), 7.93 (s, 1H), 7.54 (s, 1H), 7.32 (d, J=5.2 Hz, 1H), 3.83 (s, 3H), 3.41 (p, J=8.3 Hz, 1H), 2.37-2.03 (m, 4H), 2.03-1.74 (m, 2H).

Example 14: General Method for Synthesizing Compound 295 (TDM-180895)

-continued

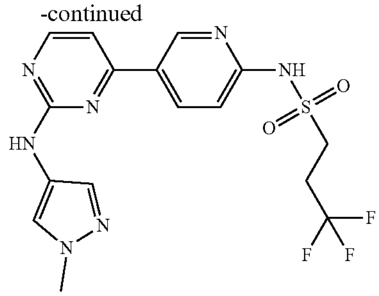

Example 295 (TDM-180895)

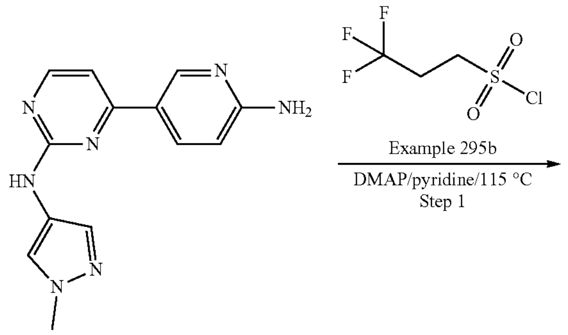

Example 295a

Step 1: Example 295

4-dimethylaminopyridine (13.7 mg, 0.112 mmol) and compound 295b (namely, 3,3,3-trifluoropropane-1-sulfonyl chloride) (220 mg, 1.122 mmol) were added to compound 295a (150 mg, 0.561 mmol) (namely, 4-(6-amino-pyridin-3-yl)-N-(1-methyl-1H-pyrazol-4-yl)pyrimidin-2-amine) in pyridine solution (10 mL). The mixture was heated to 115° C. and stirred for 16 hours. The mixture was concentrated under reduced pressure, and the residue was purified via silica gel chromatography (dichloromethane:dichloromethane containing 10% methanol=60:40) to obtain a yellow solid, methanol and dichloromethane were added to the solid, and the suspension was filtered to collect a yellow solid compound 295, TDM-180895, (namely, 3,3,3-trifluoro-N-(5-(2-((1-methyl-1H-pyrazol-4-yl)amino)pyrimidin-4-yl)pyridin-2-yl) propane-1-sulfonamide (49.1 mg, yield: 20.5%). LCMS $[M+1]^+$=428.2

$^1$H NMR (400 MHz, DMSO-$d_6$) δ 9.52 (s, 1H), 8.92 (s, 1H), 8.48 (d, J=4.9 Hz, 2H), 7.91 (s, 1H), 7.54 (s, 1H), 7.28 (t, J=12.6 Hz, 2H), 3.83 (s, 3H), 3.70 (s, 2H), 2.88-2.67 (m, 2H).

Compounds prepared in a similar method are as follows:

| Structure Structural formula | TDM No. Registration number | LCMS $[M + 1]^+$ | $^1$H-NMR Proton nuclear magnetic resonance spectroscopy |
|---|---|---|---|
| 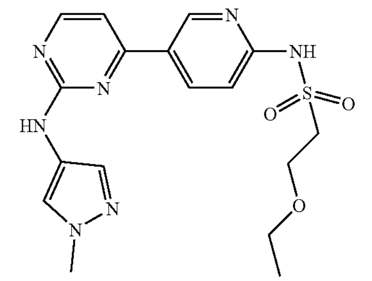 [SMILES: CCOCCS(=O)(=O)Nc1ccc(-c2ccnc(Nc3cnn(C)c3)n2)cn1] | TDM- 180877 | 404.1 | $^1$H NMR (400 MHz, DMSO) δ 9.52 (s, 1H), 8.95 (s, 1H), 8.46 (t, J = 9.1 Hz, 2H), 7.91 (s, 1H), 7.54 (s, 1H), 7.29 (d, J = 5.2 Hz, 1H), 7.16 (d, J = 9.1 Hz, 1H), 3.83 (s, 3H), 3.75 (d, J = 3.4 Hz, 4H), 3.37 (q, J = 7.0 Hz, 2H), 0.98 (t, J = 7.0 Hz, 3H). |
| 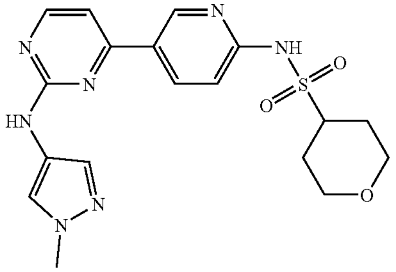 [SMILES: Cn1cc(Nc2nccc(-c3ccc(NS(=O)(=O)C4CCOCC4)nc3)n2)cn1] | TDM- 180875 | 416.1 | $^1$H NMR (400 MHz, DMSO) δ 9.51 (s, 1H), 8.93 (s, 1H), 8.46 (t, J = 7.8 Hz, 2H), 7.91 (s, 1H), 7.55 (s, 1H), 7.28 (d, J = 5.2 Hz, 1H), 7.22 (t, J = 12.2 Hz, 1H), 3.95 (dd, J = 11.2, 3.6 Hz, 2H), 3.83 (s, 3H), 3.33 (t, J = 11.1 Hz, 2H), 1.92 (d, J = 10.7 Hz, 2H), 1.73 (qd, J = 12.4, 4.6 Hz, 2H) |

-continued

| Structure Structural formula | TDM No. Registration number | LCMS $[M + 1]^+$ | $^1H$-NMR Proton nuclear magnetic resonance spectroscopy |
|---|---|---|---|
| 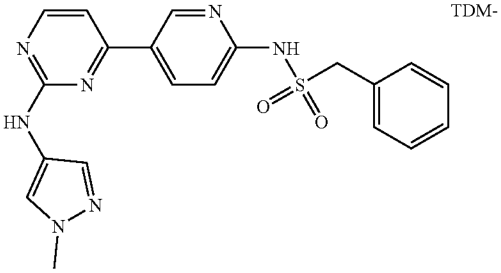 | TDM- 180897 | 422.2 | $^1H$ NMR (400 MHz, DMSO) δ 9.52 (s, 1H), 9.03 (s, 1H), 8.48 (d, J = 5.1 Hz, 1H), 8.42 (d, J = 8.4 Hz, 1H), 7.92 (s, 1H), 7.55 (s, 1H), 7.41-7.20 (m, 6H), 7.06 (d, J = 7.9 Hz, 1H), 4.83 (s, 2H), 3.84 (s, 3H). |

TDM-180877, a yellow solid compound 277, namely 2-ethyoxyl-N-(5-(2-((1-methyl-1H-pyrazol-4-yl)amino)pyrimidin-4-yl)pyridin-2-yl)ethanesulfonamide (3.2 mg, yield: 2.1%).

TDM-180875, a white solid compound 275, namely N-(5-(2-((1-methyl-1H-pyrazol-4-yl)amino)pyrimidin-4-yl)pyridin-2-yl)tetrahydro-2H-pyran-4-sulfonamide (3.2 mg, yield: 2.6%).

TDM-180897, a yellow solid compound 297 namely N-(5-(2-((1-methyl-1H-pyrazol-4-yl)amino)pyrimidin-4-yl)pyridin-2-yl)-1-phenylmethanesulfonamide (6.9 mg, yield: 4.4%).

Example 15: General Method for Synthesizing Compound 229 (TDM-180829)

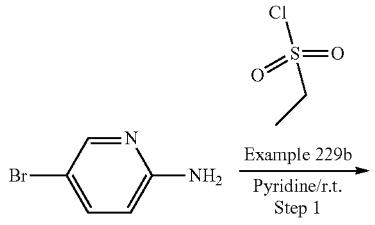

Example 229a

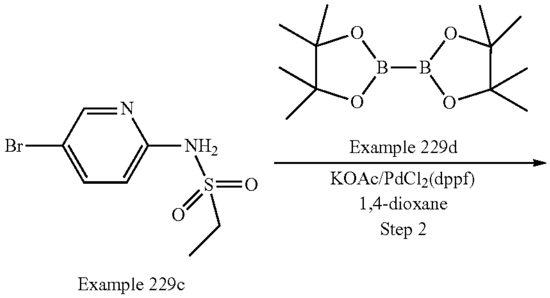

Example 229c

-continued

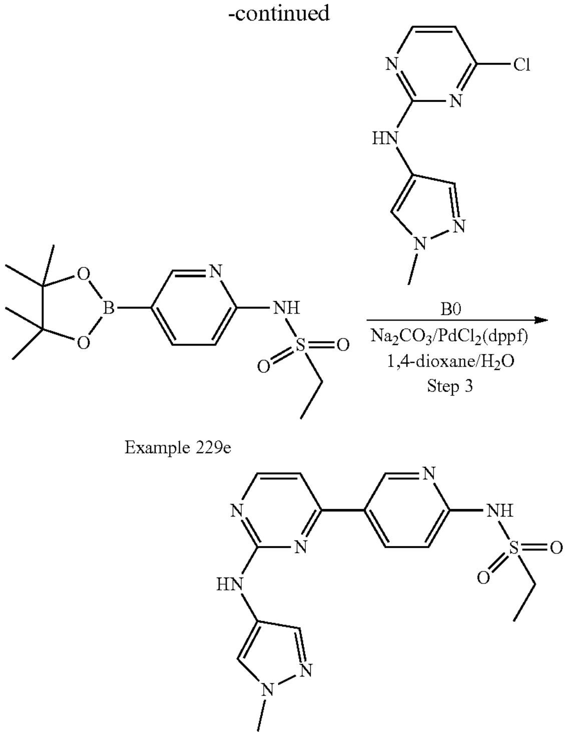

Example 229e

Example 229 (TDM-180829)

Step 1: Example 229c

N-(5-bromopyridin-2-yl)ethanesulfonamide

Compound 229b (625 mg, 4.88 mmol) was added to compound 229a (422 mg, 2.44 mmol) in pyridine solution (10 mL). The reaction solution was stirred for 3 hours at room temperature. The reaction solution was concentrated under reduced pressure, aqueous HCl solution (about 0.5 M) was added, and the solution was filtered to collect a precipitated solid. The orange solid was neutralized to approximately pH 8 with saturated $Na_2CO_3$ solution, and extracted with EtOAc (30 mL×4), the combined organic layers were washed with brine (30 mL×1), dried over $Na_2SO_4$, and filtered, and the concentrated crude product was slurried with DCM/PE (about 1:4). A pale yellow solid compound 229c (380 mg, yield: 59%) was obtained.

LCMS $[M+1]^+$=267.0

Step 2: Example 229e

N-(5-(4,4,5,5-tetramethyl-1,3,2-dioxaborolane-2-yl) pyridin-2-yl)ethanesulfonamide The compound 229c (200 mg, 0.76 mmol), the compound 229d (228 mg, 0.9 mmol), $PdCl_2$ (dppf) (83 mg, 0.11 mmol), KOAc (223 mg, 2.28 mmol) and 1,4-dioxane (20 mL) were added to a three-necked flask. $N_2$ displacement was employed for the mixture 3 times using a water pump. The mixture was heated to 105° C. and reacted for 2 hours. The mixture was concentrated and purified via column chromatography (0-100% EtOAc/PE) to obtain a colorless oily compound 229e (80 mg, yield: 33%).

LCMS $[M+1]^+$=313.1

Step 3: Example 229 (TDM-180829)

N-(5-(2-((1-methyl-1H-pyrazol-4-yl)amino)pyrimidin-4-yl)pyridin-2-3.2 yl)ethanesulfonamide B0 (44 mg, 0.21 mmol), $PdCl_2$ (dppf) (18 mg, 0.03 mmol), $Na_2CO_3$ (56 mg, 0.53 mmol), 1,4-dioxane (10 mL) and $H_2O$ (2 mL) were added to the compound 229e (80 mg, 0.26 mmol). $N_2$ displacement was employed for the mixture 3 times using a water pump. The mixture was heated to 105° C. and stirred for 2 hours. The mixture was concentrated and purified via column chromatography (petroleum ether/EtOAc=0/100), and was then subjected to 10% MeOH in DCM/EtOAc (1:1). The resulting solid was slurried with DCM/PE (about 1:1). A pale green solid compound 229 (4.5 mg, yield: <10%) was obtained.

LCMS $[M+1]^+$=360.1

1H NMR (400 MHz, DMSO-$d_6$) δ 10.96 (br s, 1H), 9.51 (s, 1H), 8.97 (s, 1H), 8.39-8.52 (m, 2H), 7.92 (s, 1H), 7.55 (s, 1H), 7.28 (d, J=5.2 Hz, 1H), 7.16 (d, J=8.8 Hz, 1H), 3.84 (s, 3H), 3.43-3.56 (m, 2H), 1.25 (t, J=7.6 Hz, 3H).

Example 16: General Method for Synthesizing Compound 301 (TDM-180901)

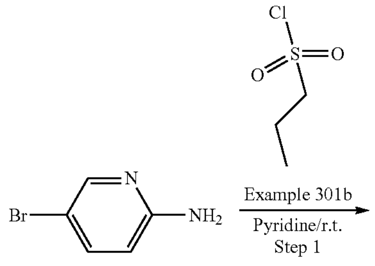

Example 301a

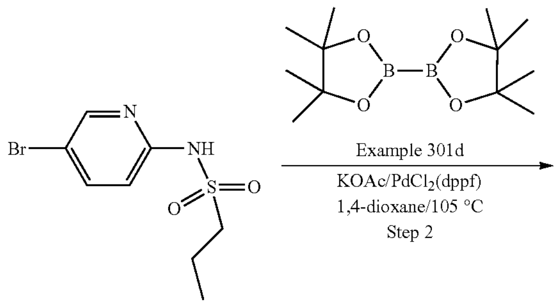

Example 301c

-continued

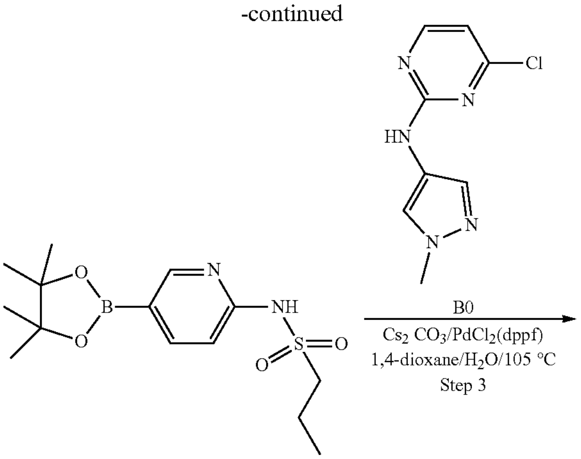

Example 301e

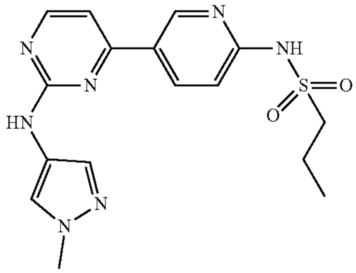

Example 301 (TDM-180901)

Step 1: Example 301c

N-(5-bromopyridin-2-yl) propane-1-sulfonamide

Compound 301b (558 mg, 4.0 mmol) was added to a mixture of compound 301a (340 mg, 2.00 mmol) and pyridine (10 mL). The reaction solution was stirred for 3 hours at room temperature. The reaction solution was concentrated under reduced pressure, $H_2O$ (about 10 mL) was added, and the reaction solution was filtered to collect the precipitated solid, washed with saturated $NaHCO_3$ solution and H2O, and dried. An orange solid compound 301c (260 mg, yield: 46%) was obtained.

LCMS $[M+1]^+$=279

Step 2: Example 301e

N-(5-(4,4,5,5-tetramethyl-1,3,2-dioxaborolane-2-yl) pyridin-2-yl) propane-1-sulfonamide The compound 301c (260 mg, 0.93 mmol), the compound 301d (228 mg, 0.9 mmol), $PdCl_2$ (dppf) (68 mg, 0.09 mmol), KOAc (274 mg, 2.79 mmol) and 1,4-dioxane (20 mL) were added to a three-necked flask. $N_2$ displacement was employed for the mixture 3 times using a water pump. The mixture was heated to 105° C. and reacted for 2 hours. The mixture was concentrated and purified via column chromatography (0-100% EtOAc/PE). A pale yellow solid compound 301e (100 mg, yield: <30%) was obtained. LCMS $[M+1]^+$=327

Step 3: Example 301 (TDM-180901)

N-(5-(2-((1-methyl-1H-pyrazol-4-yl)amino)pyrimidin-4-yl)pyridin-2-yl) propane-1-sulfonamide B0 (100 mg, 0.48 mmol), $PdCl_2$ (dppf) (60 mg), $Cs_2CO_3$ (312 mg, 0.96 mmol), 1,4-dioxane (12 mL) and $H_2O$ (2 mL) were added to the compound 301e (156 mg, 0.48 mmol). $N_2$ displacement was employed for the mixture 3 times using a water pump. The mixture was heated to 108° C. and reacted for 2 hours. The mixture was concentrated and purified via column chromatography (DCM/MeOH=10/1), and the obtained residue was slurried with DCM/PE (about 1:1). A pale yellow solid compound 301 (7.9 mg, yield: <10%) was obtained.

LCMS $[M+1]^+$=374.2

$^1H$ NMR (400 MHz, DMSO-$d_6$) δ 11.13 (brs, 1H), 9.49 (s, 1H), 8.96 (s, 1H), 8.35-8.53 (m, 2H), 7.92 (s, 1H), 7.55 (s, 1H), 7.28 (d, J=5.2 Hz, 1H), 7.12 (d, J=8.8 Hz, 1H), 3.84 (s, 3H), 3.39-3.52 (m, 2H), 1.67-1.80 (m, 2H), 0.98 (t, J=7.6 Hz, 3H).

Example 18: General Method for Synthesizing Compound 303 (TDM-180903)

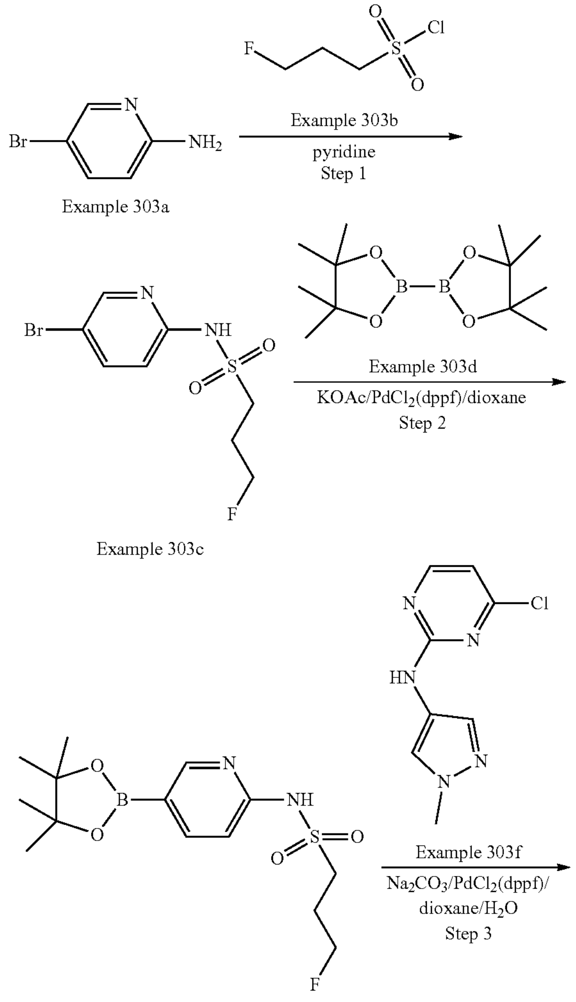

Example 303a

Example 303c

Example 303e

-continued

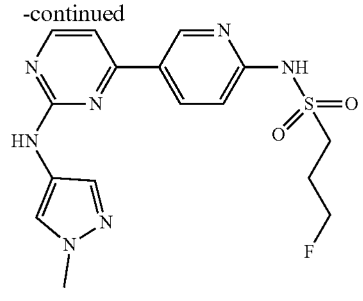

Example 303 (TDM-180903)

Step 1: Example 303

The compound 303a (186 mg, 1.08 mmol) and compound 303b (174 mg, 1.08 mmol) were added to pyridine (4 mL), heated to 50° C. and stirred for 3 hours. After removal of the solvent, a yellow solid compound 303c (namely N-(5-bromopyridin-2-yl)-3-fluoropropane-1-sulfonamide) (28 mg, 8.7%) was obtained through purification using silica gel chromatography (ethyl acetate:petroleum ether=0-20%). LCMS $[M+1]^+$=299.1, 301.1.

Step 2: Example 303e

Compound 303c (40 mg, 0.134 mmol), compound 303d (68 mg, 0.268 mmol), potassium acetate (39.4 mg, 0.402 mmol) and $PdCl_2$ (dppf) (22 mg, 0.03 mmol) were added to a solution of 1,4-dioxane (5 mL), nitrogen displacement was employed three times, and the mixture was then heated to 90° C. and stirred for 17 hours. After being cooled to room temperature, the reaction solution was directly used for the next feeding. LCMS $[M+1]^+$=263.1.

Step 2: Example 303 (TDM-180903)

The compound 303f (30.9 mg, 0.147 mmol), compound 303e (35 mg, 0.134 mmol), sodium carbonate (28 mg, 0.268 mmol) and $PdCl_2$ (dppf) (20 mg, 0.027 mmol) were dissolved in a mixture solution of 1,4-dioxane (5 mL) and water (0.5 mL). Nitrogen displacement was employed three times, and the reaction solution was then heated to 95° C. and stirred for 4 hours. The reaction solution was cooled to room temperature and filtered, the filter cake was washed with ethyl acetate (10 mL×2), the filtrate was concentrated, and the concentrated solution was purified via silica gel chromatography (methanol:dichloromethane=0-3%) to obtain the crude product. The crude product was further purified via preparative HPLC to obtain a yellow solid compound 303, namely 3-fluoro-N-(5-(2-((1-methyl-1H-pyrazol-4-yl)amino)pyrimidin-4-yl)pyridin-2-yl) propane-1-sulfonamide (8.8 mg, yield: 16.8%). LCMS $[M+1]^+$=392.2.

$^1H$ NMR (400 MHz, DMSO) δ 9.51 (s, 1H), 8.95 (s, 1H), 8.46 (t, J=5.7 Hz, 2H), 7.91 (s, 1H), 7.54 (s, 1H), 7.29 (d, J=5.2 Hz, 1H), 7.18 (d, J=6.9 Hz, 1H), 4.61 (t, J=5.9 Hz, 1H), 4.49 (t, J=5.9 Hz, 1H), 3.83 (s, 3H), 3.58 (s, 2H), 2.22-1.99 (m, 2H).

Example 19: General Method for Synthesizing Compound 160 (TDM-180760)

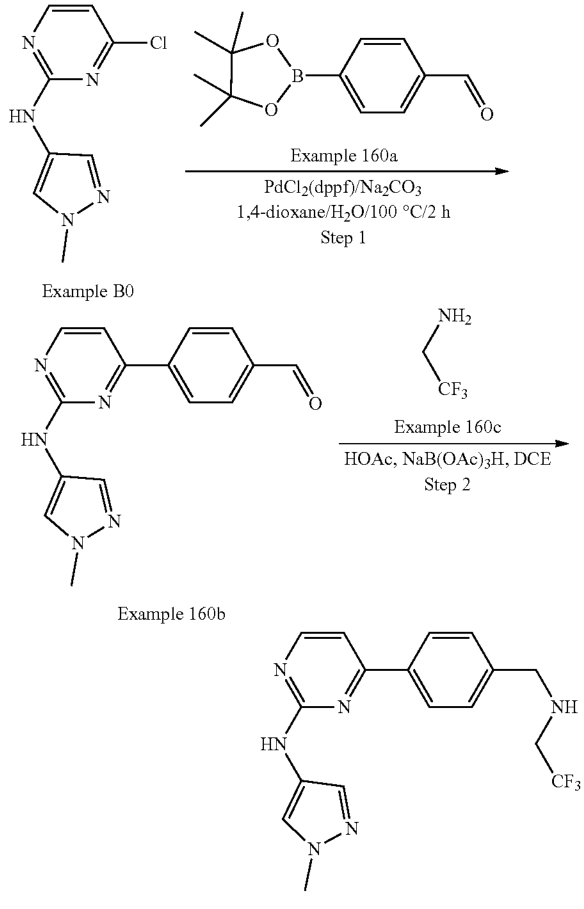

Example B0

Example 160b

TDM-180760

Step 1: Example 160b 4-(2-((1-methyl-1H-pyrazol-4-yl)amino)pyrimidin-4-yl)benzaldehyde Compound B0 (300 mg, 1.44 mmol), $PdCl_2$ (dppf) (73 mg, 0.10 mmol), $Na_2CO_3$ (458 mg, 4.32 mmol), 1,4-dioxane (25 mL) and $H_2O$ (4 mL) were added to compound 160a (400 mg, 1.73 mmol). Nitrogen displacement was employed three times using a water pump. The substances reacted at 100° C. for 2 hours. The reaction mixture was concentrated and purified via column chromatography (petroleum ether/ethyl acetate=0/100) to obtain a yellow solid compound 160b (370 mg, yield: 79%).

LCMS $[M+1]^+$=280.1.

Step 2: Example 160 (TDM-180760)

N-(1-methyl-1H-pyrazol-4-yl)-4-(4-(((2,2,2-trifluoroethyl)amino)methyl)phenyl)pyrimidin-2-amine A mixture of compound 160b (80 mg, 0.07 mmol), compound 160c (115 mg, 1.16 mmol) and HOAc (8 drops) in $ClCH_2CH_2Cl$ (15 mL) was stirred at 35° C. for 1 hour. Then $NaB(OAc)_3H$ (307 mg, 1.45 mmol) was added. The obtained mixture was stirred for 20 hours at 35° C. The mixture was neutralized with saturated $NaHCO_3$. The mixture was extracted with DCM (30 mL×3). The combined organic layers were washed with brine, dried over anhydrous $Na_2SO_4$ and concentrated under reduced pressure. The crude product was slurried with ethyl acetate/petroleum ether (1:2). The mixture was filtered to collect a solid and the solid was dried under vacuum. A pale green solid compound 160 (65.1 mg, yield: 62%) was obtained.

LCMS $[M+1]^+$=363.1.

$^1H$ NMR (400 MHz, DMSO-$d_6$) δ 9.48 (s, 1H), 8.48 (d, J=5.2 Hz, 1H), 8.11 (d, J=8.0 Hz, 2H), 7.93 (s, 1H), 7.56 (br s, 1H), 7.51 (d, J=8.0 Hz, 2H), 7.28 (d, J=5.2 Hz, 1H), 3.89 (d, J=6.0 Hz, 2H), 3.84 (s, 3H), 3.18-3.31 (m, 2H), 2.97-3.10 (m, 1H).

Compounds prepared in a similar method are as follows:

| Structure<br>Structural formula | TDM No.<br>Registration<br>number | LCMS<br>$[M + 1]^+$ | $^1H$-NMR<br>Proton nuclear magnetic resonance<br>spectroscopy |
|---|---|---|---|
| 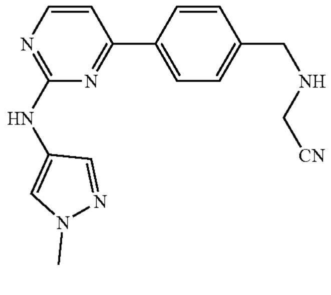 [SMILES: Cn1cc(Nc2nccc(-c3ccc(CNCC#N)cc3)n2)cn1] | TDM-180761 | 320.2 | $^1H$ NMR (400 MHz, CDCL3) δ 8.46 (d, J = 5.2 Hz, 1H), 8.05 (d, J = 8.4 Hz, 2H), 7.90 (s, 1H), 7.58 (s, 1H), 7.51 (d, J = 8.4 Hz, 2H), 7.11 (d, J = 5.2 Hz, 1H), 6.98 (br s, 1H), 4.04 (s, 2H), 3.94 (s, 3H), 3.63 (s, 2H), 1.73 (br s, 1H). |

-continued

| Structure<br>Structural formula | TDM No.<br>Registration<br>number | LCMS<br>[M + 1]+ | $^{1}$H-NMR<br>Proton nuclear magnetic resonance<br>spectroscopy |
|---|---|---|---|
| 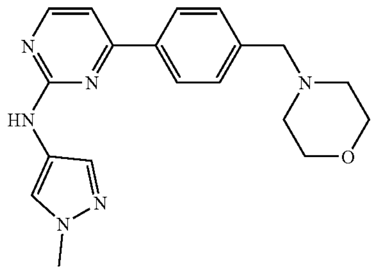 | TDM-180787 | 351.2 | $^{1}$H NMR (400 MHz, DMSO-$d_6$) δ 10.13 (brs, 1H), 9.55 (s, 1H), 8.53 (d, J = 5.2 Hz, 1H), 8.25 (d, J = 8.4 Hz, 2H), 7.92 (s, 1H), 7.69 (d, J = 8.4 Hz, 2H), 7.60 (brs, 1H), 7.33 (d, J = 5.2 Hz, 1H), 4.45 (s, 2H), 3.92-4.05 (m, 2H), 3.84 (s, 3H), 3.57-3.73 (m, 2H), 3.08-3.38 (m, 4H), 0.99 (t, J = 7.2 Hz, 3H). |
| 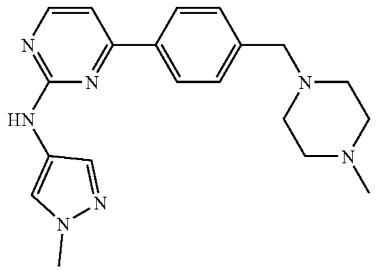 [SMILES: Cn1cc(Nc2nccc(-c3ccc(CN4CCOCC4)cc3)n2)cn1] | TDM-180788 | 364.2 | $^{1}$H NMR (400 MHz, CDCL3) δ 8.45 (d, J = 5.2 Hz, 1H), 8.01 (d, J = 8.0 Hz, 2H), 7.91 (s, 1H), 7.48 (d, J = 8.0 Hz, 2H), 7.10 (d, J = 5.2 Hz, 1H), 6.96 (s, 1H), 3.94 (s, 3H), 3.60 (s, 2H), 2.38-2.75 (m, 8H), 2.34 (s, 3H). |
| 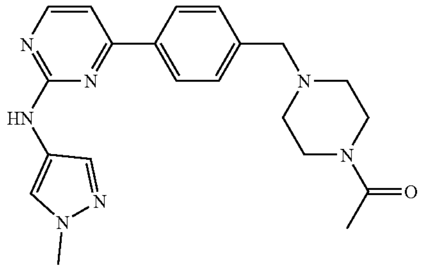 [SMILES: CC(=O)N1CCN(Cc2ccc(-c3ccnc(Nc4cnn(C)c4)n3)cc2)CC1] | TDM-180789 | 392.2 | $^{1}$H NMR (400 MHz, CDCL3) δ 8.46 (d, J = 5.2 Hz, 1H), 8.03 (d, J = 8.0 Hz, 2H), 7.90 (s, 1H), 7.59 (s, 1H), 7.48 (d, J = 8.0 Hz, 2H), 7.11 (d, J = 5.2 Hz, 1H), 6.93 (s, 1H), 3.94 (s, 3H), 3.64-3.70 (m 2H), 3.61 (s, 2H), 3.46-3.53 (m 2H), 2.44-2.54 (m 4H), 2.10 (s, 3H). |

TDM-180761, a white solid compound 161, namely, 2-((4-(2-((1-methyl-1H-pyrazol-4-yl)amino)pyrimidin-4-yl)benzyl)amino) acetonitrile (4.7 mg, yield: <10%).

TDM-180787, an orange solid compound 187 (33 mg, yield: 38%), N-(1-methyl-1H-pyrazol-4-yl)-4-(4-(morpholinomethyl)phenyl)pyrimidine-2-amine.

TDM-180788, an off-white solid compound 188 (28.6 mg, yield: 31%) N-(1-methyl-1H-pyrazol-4-yl)-4-(4-((4-methylpiperazine-1-yl)methyl)phenyl)pyrimidin-2-amine.

TDM-180789, a pale green solid compound 189, 1-(4-(4-(2-((1-methyl-1H-pyrazol-4-yl)amino)pyrimidin-4-yl) benzyl) piperazin-1-yl) ethan-1-one (30.8 mg, yield: 31%).

Example 20: General Method for Synthesizing Compound 134 (TDM-180734)

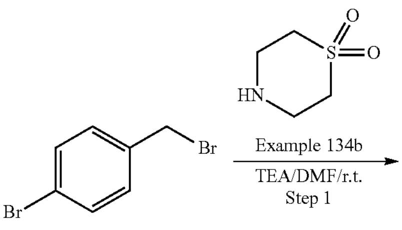

Example 134a

-continued

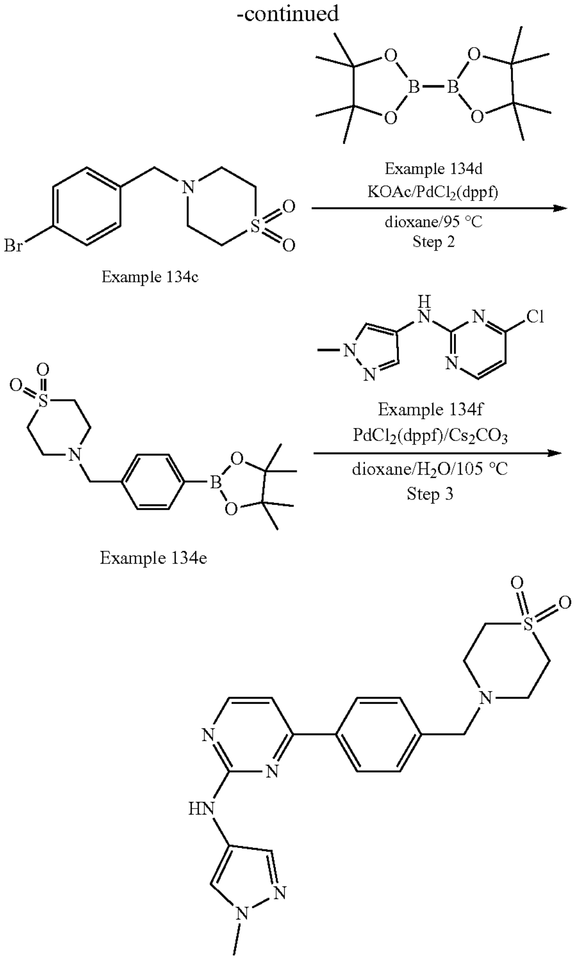

Example 134c

Example 134e

Example 134 (TDM-180734)

Step 1: Example 134c

Triethylamine (303.54 mg, 3 mmol) and compound 134b (namely, thiomorpholine-1,1-dioxide) (297 mg, 2.2 mmol) were added to a tetrahydrofuran solution (20 mL) of compound 134a (500 mg, 2 mmol), namely p-bromobenzyl bromide, and the mixture was stirred at room temperature for 16 hours. The mixture was concentrated under reduced pressure, ethyl acetate and petroleum ether were added to the residue, the mixture was filtered, and the filtrate was concentrated under reduced pressure to obtain a white solid compound 134c (518 mg, yield: 85%), 4-(4-bromobenzyl) thiomorpholine-1,1-dioxide.

Step 2: Example 134e

Potassium acetate (120 mg, 1.225 mmol) and [1,1'-bis (diphenylphosphino) ferrocene]palladium dichloride (35.8 mg, 0.049 mmol) were added to a mixture of compound 134c (150 mg, 049 mmol) and compound 134d (149 mg, 0.588 mmol). 1,4-dioxane (14 mL) was added to the mixture and the mixture was degassed under vacuum, heated to 95° C. under nitrogen protection and stirred for 2 hours. After the reaction completed, the mixture was directly used for the next reaction. LCMS $[M+1]^+$=352.

Step 3: Example 134 (TDM-180734)

Compound 134f (102.4 mg, 0.49 mmol) (namely, 4-chloro-N-(1-methyl-1H-pyrazol-4-yl)pyrimidin-2-amine, [1,1'-bis(diphenylphosphino) ferrocene]palladium dichloride (31.9 mg, 0.047 mmol), cesium carbonate (319 mg, 0.98 mmol) and water (2 mL) were added to the mixture (V834-132). The mixture was degassed under vacuum, heated to 105° C. under nitrogen protection and stirred for 3 hours. After the reaction completed, water was added to the mixture and the mixture was extracted with ethyl acetate (50 mL×3), the organic layer was washed with saturated brine (30 mL), and dried over anhydrous sodium sulfate, and the filtrate was concentrated under reduced pressure. The filtrate was purified via silica gel column (ethyl acetate:methanol=20:1) to obtain a yellow solid compound 134, TDM-180734 (55 mg, yield: 28.2%), namely 4-(4-(2-((1-methyl-1H-pyrazol-4-yl)amino)pyrimidin-4-yl)benzyl) thiomorpholine-1,1-dioxide. LCMS $[M+1]^+$=399.

$^1$H NMR (400 MHZ, $CDCl_3$) δ 8.37 (d, J=5.2 Hz, 1H), 7.95 (d, J=8.2 Hz, 2H), 7.79 (s, 1H), 7.51 (s, 1H), 7.38 (d, J=8.2 Hz, 2H), 7.01 (d, J=5.2 Hz, 1H), 6.94 (s, 1H), 3.85 (s, 3H), 3.66 (s, 2H), 2.98 (dt, J=10.0, 4.0 Hz, 8H).

Example 21: General Method for Synthesizing Compound 119 (TDM-180719)

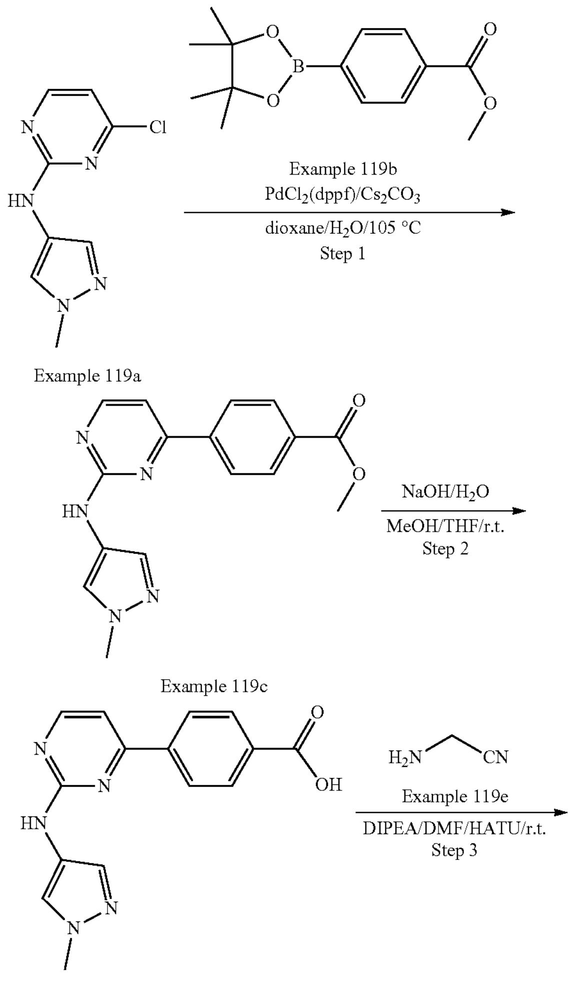

Example 119a

Example 119c

Example 119d

-continued

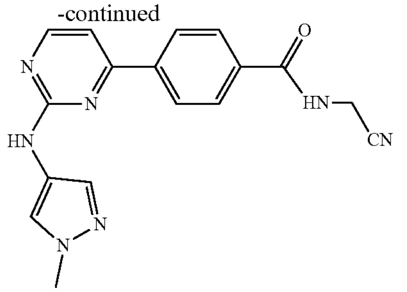

Example 119 (TDM-180719)

Step 1: Example 119c 1,4-dioxane (20 mL) and water (3 mL) were added to a mixture of compound 119a (209 mg, 1 mmol) (namely, 4-chloro-N-(1-methyl-1H-pyrazol-4-yl)pyrimidin-2-amine), compound 119b (314.4 mg, 1.2 mmol) (namely, methyl 4-(4,4,5,5-tetramethyl-1,3,2-dioxaborolane-2-yl) methyl benzoate, [1,1'-bis(diphenylphosphino) ferrocene] palladium dichloride (73.1 mg, 0.1 mmol) and cesium carbonate (651.6 mg, 2 mmol) at room temperature. The mixture was then degassed under vacuum, heated to 105° C. under nitrogen protection and stirred for 3 hours. After the reaction completed, the mixture was concentrated under reduced pressure. The filtrate was purified via silica gel column (petroleum ether:ethyl acetate=30:70) to obtain a yellow solid compound 119c (381 mg, yield: 71.6%), namely methyl 4-(2-((1-methyl-1H-pyrazol-4-yl)amino)pyrimidin-4-yl)methyl benzoate. LCMS $[M+1]^+$=310.

Step 2: Example 119d

An aqueous solution (10 mL) of sodium hydroxide (240 mg, 6 mmol) was added to a mixture solution of compound 119c (185 mg, 0.6 mmol) in methanol (5 mL) and tetrahydrofuran (5 mL) at room temperature. The mixture was then stirred for 2 hours at room temperature. After the reaction completed, the mixture was concentrated under reduced pressure to remove excess methanol and tetrahydrofuran, then the solution was neutralized with hydrochloric acid (2M), and the solution was filtered to collect the precipitate. Ethanol was added to the precipitate, and the residual water was removed via concentration under reduced pressure to obtain a yellow solid compound 119d (173 mg, yield: 97.7%), namely 4-(2-((1-methyl-1H-pyrazol-4-yl)amino) pyrimidin-4-yl)benzoic acid. LCMS $[M+1]^+$=296.

Step 3: Example 119 (TDM-180719)

The compound 119d (80 mg, 0.27 mmol) was dissolved in N,N-dimethyl formamide (10 mL) at room temperature, N,N-diisopropylethylamine (139 mg, 1.08 mmol) was then added, the mixture was stirred for 5 minutes, and then 2-(7-benzotriazole oxide)-N,N,N',N'-tetramethylurea hexafluorophosphate (153.9 mg, 0.405 mmol) and compound 119e (namely, 2-aminoacetonitrile) (37.5 mg, 0.405 mmol) were added into the mixture. The mixture was stirred at room temperature for 16 hours. Water (40 mL) was added to the mixture, the mixture was filtered to collect the precipitate, ethanol was added to the precipitate and the mixture was concentrated under reduced pressure to remove residual water. Ethyl acetate and petroleum ether were added to the residue, and then the mixture was filtered to collect an off-white solid compound 119, TDM-180719 (37.2 mg, yield: 41.3%), namely, N-(cyanomethyl)-4-(2-((1-methyl-1H-pyrazol-4-yl)amino)pyrimidine-4-yl)benzamide. LCMS $[M+1]^+$=334

1H NMR (400 MHz, DMSO-$d_6$) δ 9.58 (s, 1H), 9.35 (t, J=5.2 Hz, 1H), 8.54 (d, J=5.0 Hz, 1H), 8.27 (d, J=8.2 Hz, 2H), 8.04 (d, J=8.2 Hz, 2H), 7.94 (s, 1H), 7.56 (s, 1H), 7.36 (d, J=5.1 Hz, 1H), 4.36 (d, J=5.3 Hz, 2H), 3.84 (s, 3H).

Compounds prepared in a similar method are as follows:

| Structure Structural formula | TDM No. Registration number | LCMS $[M + 1]^+$ | $^1$H-NMR Proton nuclear magnetic resonance spectroscopy |
|---|---|---|---|
| 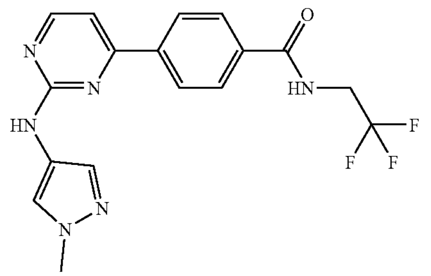 [SMILES: Cn1cc(Nc2nccc(-c3ccc(C(=O)NCC(F)(F)F)cc3)n2)cn1] | TDM-180748 | 377.0 | $^1$H NMR (400 MHz, DMSO-$d_6$)) δ 9.58 (s, 1H), 9.23 (t, J = 6.2 Hz, 1H), 8.54 (d, J = 5.0 Hz, 1H), 8.26 (d, J = 8.3 Hz, 2H), 8.06 (d, J = 8.3 Hz, 2H), 7.94 (s, 1H), 7.56 (s, 1H), 7.36 (d, J = 5.1 Hz, 1H), 4.20-4.04 (m, 2H), 3.84 (s, 3H). |
| 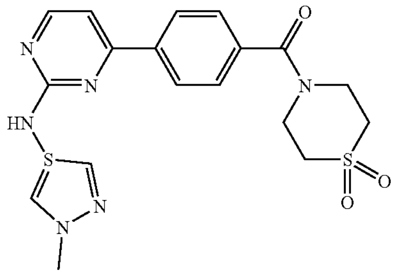 [SMILES: CN1C=S(Nc2nccc(-c3ccc(C(=O)N4CCS(=O)(=O)CC4)cc3)n2)C=N1] | TDM-180749 | 413.0 | $^1$H NMR (400 MHz, DMSO-$d_6$) δ 9.54 (s, 1H), 8.52 (d, J = 5.0 Hz, 1H), 8.22 (d, J = 8.2 Hz, 2H), 7.92 (s, 1H), 7.67 (d, J = 8.2 Hz, 2H), 7.58 (s, 1H), 7.34 (d, J = 5.2 Hz, 1H), 4.04 (s, 2H), 3.83 (s, 3H), 3.74 (s, 2H), 3.28 (s, 4H). |

-continued

| Structure Structural formula | TDM No. Registration number | LCMS $[M + 1]^+$ | $^1$H-NMR Proton nuclear magnetic resonance spectroscopy |
|---|---|---|---|
| 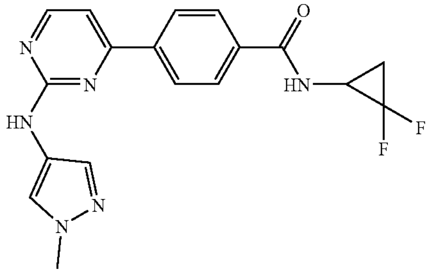 [SMILES: Cn1cc(Nc2nccc(-c3ccc(C(=O)NC4CC4(F)F)cc3)n2)cn1] | TDM-180758 | 371 | $^1$H NMR (400 MHz, DMSO-$d_6$) δ 9.58 (s, 1H), 8.94 (s, 1H), 8.53 (d, J = 5.1 Hz, 1H), 8.25 (d, J = 8.4 Hz, 2H), 8.02 (d, J = 8.4 Hz, 2H), 7.94 (s, 1H), 7.56 (s, 1H), 7.36 (d, J = 5.2 Hz, 1H), 3.83 (s, 3H), 3.50 (d, J = 9.4 Hz, 1H), 1.99 (dt, J = 24.6, 10.1 Hz, 1H), 1.78-1.67 (m, 1H). |
| 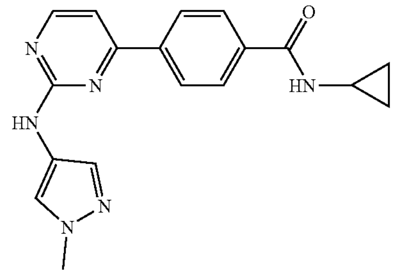 [SMILES: Cn1cc(Nc2nccc(-c3ccc(C(=O)NC4CC4)cc3)n2)cn1] | TDM-180852 | 335.2 | $^1$H NMR (400 MHz, DMSO-$d_6$) δ 9.56 (s, 1H), 8.54 (dd, J = 18.5, 4.6 Hz, 2H), 8.21 (d, J = 8.4 Hz, 2H), 8.01-7.90 (m, 3H), 7.55 (s, 1H), 7.34 (d, J = 5.2 Hz, 1H), 3.83 (s, 3H), 2.88 (td, J = 7.2, 3.9 Hz, 1H), 0.72 (td, J = 7.1, 4.9 Hz, 2H), 0.64-0.55 (m, 2H). |

TDM-180748, a yellow solid compound 148, namely 4-(2-((1-methyl-1H-pyrazol-4-yl)amino)pyrimidin-4-yl)-N-(2,2,2-trifluoroethyl)benzamide (28.5 mg, yield: 60.6%).

TDM-180749, a yellow solid compound 149, namely (1,1-sulfur dioxide) (4-(2-((3-methyl-3H-114,3,4thiadiazol-1-yl)amino)pyrimidin-4-yl)phenyl) methanone (31.4 mg, yield: 60.9%).

TDM-180758, a yellow solid compound 158, namely N-(2,2-difluorocyclopropyl)-4-(2-((1-methyl-1H-pyrazol-4-yl)amino)pyrimidin-4-yl)benzamide (10.6 mg, yield: 16.9%).

TDM-180852, a yellow solid compound 252, namely N-cyclopropyl-4-(2-((1-methyl-1H-pyrazol-4-yl) amino)pyrimidin-4-yl)benzamide (59.3 mg, yield: 74.8%)

Example 22: General Method for Synthesizing Compound 156 (TDM-180756)

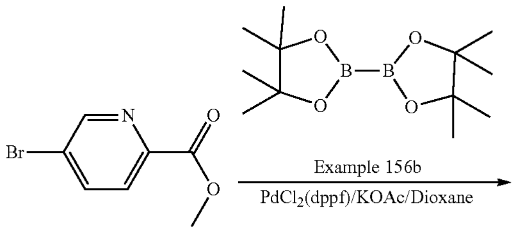

Example 156a

-continued

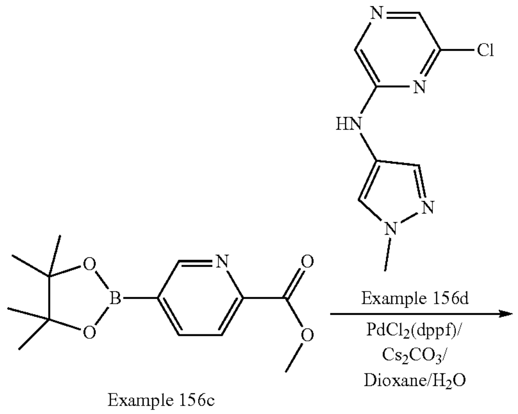

Example 156c

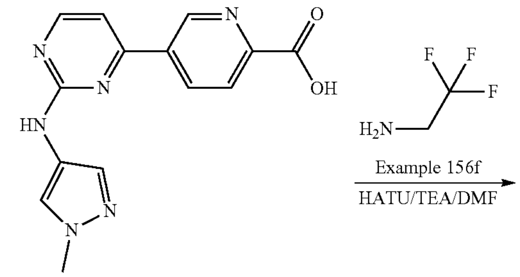

Example 156e

-continued

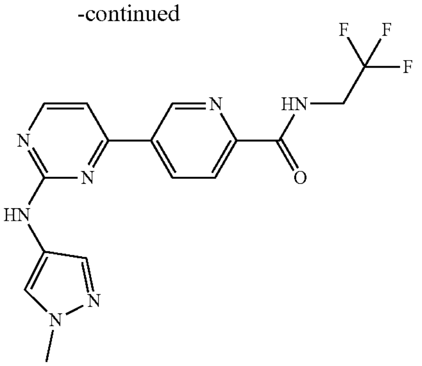

Example 156 (TDM-180756)

Step 1: Example 156c

The compound 156a (500 mg, 2.31 mmol) was dissolved in 1,4-dioxane (20 mL), the compound 156b (705.3 mg, 2.78 mmol), KOAc (453.6 mg, 4.63 mmol) and $PdCl_2$ (dppf) (169.4 mg, 0.23 mmol) were added to the mixture, nitrogen displacement was employed three times, and then the reaction solution was stirred at 90° C. for 3 hours. The mixture was cooled to room temperature, filtered and concentrated, and the concentrate was directly used for feeding in the next reaction. LCMS $[M+1]^+$=264.1.

Step 2: Example 156e

The compound 156d (404.8 mg, 1.93 mmol) was dissolved in 1,4-dioxane (20 mL) and water (5 mL), and the compound 156c, $CS_2CO_3$ (1.57 g, 4.83 mmol) and $PdCl_2$ (dppf) (141.3 mg, 0.19 mmol) were added to the mixture. Nitrogen displacement was employed three times, and the reaction solution was then stirred for 17 hours at 95° C. The reaction solution was cooled to room temperature and filtered, the filter cake was rinsed with ethyl acetate (20 mL×3), the aqueous phase was collected, acidified with hydrochloric acid (1 mol/L), concentrated, dissolved with DMF (20 mL), and filtered, to obtain the filtrate. The solvent was concentrated to obtain a yellow solid compound 156e, namely 5-(2-((1-methyl-1H-pyrazol-4-yl)amino)pyrimidin-4-yl) picolinic acid (380 mg, yield: 66.3%). LCMS $[M+1]^+$= 297.1.

Step 3: Example 156 (TDM-180756)

2-(7-benzotriazole oxide)-N,N,N',N'-tetramethylurea hexafluorophosphate (154.1 mg, 0.41 mmol), triethylamine (40.9 mg, 0.41 mmol) and compound 156f (40.2 mg, 0.41 mmol) were added to compound 156e (80 mg, 0.27 mmol) in a solution of DMF (10 mL). The mixture was stirred for 16 hours at room temperature. The reaction solution was concentrated, and the concentrate was purified via silica gel chromatography (ethyl acetate:petroleum ether=50-100%) to obtain a pale yellow solid compound 156, namely 5-(2-((1-methyl-1H-pyrazole-4-yl)amino)pyrimidin-4-yl)-N-(2,2,2-trifluoroethyl)pyridinecarboxamide (7.0 mg, yield: 6.9%). LCMS: $[M+1]^+$=378.1.

$^1$H NMR (400 MHz, DMSO) δ 9.67 (s, 1H), 9.47 (t, J=6.6 Hz, 1H), 9.38 (s, 1H), 8.71 (d, J=7.4 Hz, 1H), 8.59 (d, J=5.0 Hz, 1H), 8.24 (d, J=8.1 Hz, 1H), 7.94 (s, 1H), 7.57 (s, 1H), 7.47 (d, J=5.1 Hz, 1H), 4.12 (dd, J=9.6, 6.7 Hz, 2H), 3.84 (s, 3H).

Compounds prepared in a similar method are as follows:

| Structure Structural formula | TDM No. Registration number | LCMS $[M + 1]^+$ | $^1$H-NMR Proton nuclear magnetic resonance spectroscopy |
|---|---|---|---|
| 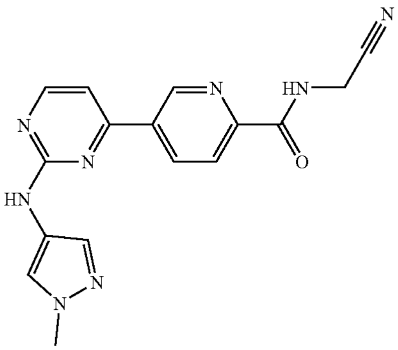 [SMILES: Cn1cc(Nc2nccc(-c3ccc(C(=O)NCC#N)nc3)n2)cn1] | TDM-180762 | 335.1 | $^1$H NMR (400 MHz, DMSO) δ 9.67 (s, 1H), 9.60 (t, J = 5.8 Hz, 1H), 9.38 (s, 1H), 8.71 (d, J = 7.9 Hz, 1H), 8.59 (d, J = 5.1 Hz, 1H), 8.24 (d, J = 8.2 Hz, 1H), 7.94 (s, 1H), 7.57 (s, 1H), 7.47 (d, J = 5.1 Hz, 1H), 4.35 (d, J = 5.9 Hz, 2H), 3.84 (s, 3H). |

-continued

| Structure Structural formula | TDM No. Registration number | LCMS $[M + 1]^+$ | $^1H$-NMR Proton nuclear magnetic resonance spectroscopy |
|---|---|---|---|
| 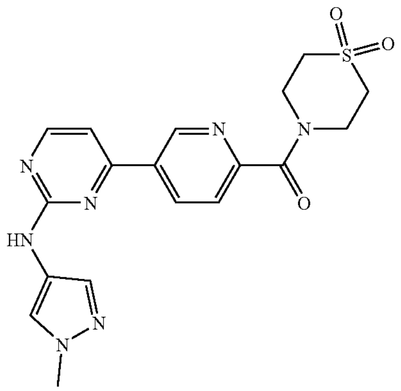 [SMILES: Cn1cc(Nc2nccc(-c3ccc(C(=O)N4CCS(=O)(=O)CC4)nc3)n2)cn1] | TDM-180764 | 414.1 | $^1H$ NMR (400 MHz, DMSO) δ 9.63 (s, 1H), 9.32 (s, 1H), 8.65 (d, J = 7.7 Hz, 1H), 8.57 (d, J = 4.9 Hz, 1H), 7.93 (s, 1H), 7.89 (d, J = 8.2 Hz, 1H), 7.57 (s, 1H), 7.43 (d, J = 5.1 Hz, 1H), 4.09 (d, J = 5.1 Hz, 2H), 3.89 (s, 2H), 3.83 (s, 3H), 3.26 (s, 2H), 3.17 (d, J = 5.2 Hz, 2H). |
| 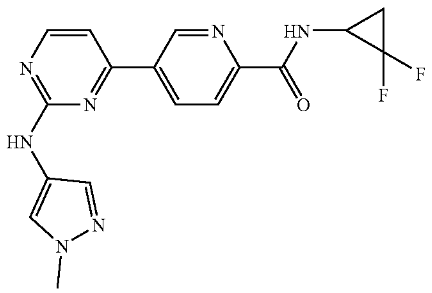 [SMILES: Cn1cc(Nc2nccc(-c3ccc(C(=O)NC4CC4(F)F)nc3)n2)cn1] | TDM-180781 | 372.1 | $^1H$ (400 MHz, DMSO) δ 9.67 (s, 1H), 9.35 (s, 1H), 9.29 (s, 1H), 8.69 (d, J = 7.8 Hz, 1H), 8.59 (d, J = 5.0 Hz, 1H), 8.21 (d, J = 8.2 Hz, 1H), 7.93 (s, 1H), 7.58 (s, 1H), 7.45 (d, J = 5.1 Hz, 1H), 3.84 (s, 3H), 3.52 (d, J = 8.2 Hz, 1H), 2.06-1.82 (m, 2H). |
| 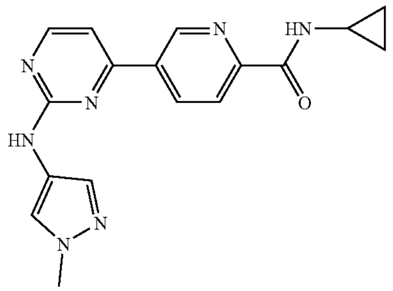 [SMILES: Cn1cc(Nc2nccc(-c3ccc(C(=O)NC4CC4)nc3)n2)cn1] | TDM-180826 | 336.1 | $^1H$NMR (400 MHz, DMSO) δ 9.65 (s, 1H), 9.31 (s, 1H), 8.87 (d, J = 4.9 Hz, 1H), 8.66 (d, J = 6.8 Hz, 1H), 8.57 (d, J = 5.0 Hz, 1H), 8.22-8.12 (m, 1H), 7.92 (s, 1H), 7.58 (s, 1H), 7.43 (d, J = 5.1 Hz, 1H), 3.84 (s, 3H), 3.05-2.79 (m, 1H), 1.09-0.51 (m, 4H). |

TDM-180762, a yellow solid compound 162, namely N-(cyanomethyl)-5-(2-((1-methyl-1H-pyrazol-4-yl) amino)pyrimidin-4-yl)pyridinecarboxamide (21.0 mg, yield: 23.3%)

TDM-180764, a yellow solid compound 164, namely (1,1-sulfur dioxide) (5-(2-((1-methyl-1H-pyrazol-4-yl) amino)pyrimidin-4-yl)pyridin-2-yl) methanone (7.5 mg, yield: 6.7%)

TDM-180781, a pale yellow solid compound 181, namely N-(2,2-difluorocyclo propyl)-5-(2-((1-methyl-1H-pyrazol-4-yl)amino)pyrimidin-4-yl)pyridinecarboxamide (2.3 mg, yield: 2.3%).

TDM-180826, a pale yellow solid compound 226, namely N-cyclopropyl-5-(2-((1-methyl-1H-pyrazol-4-yl) amino)pyrimidin-4-yl)pyridinecarboxamide (28.1 mg, yield: 31.1%).

Example 23: General Method for Synthesizing Compound 120 (TDM-180720)

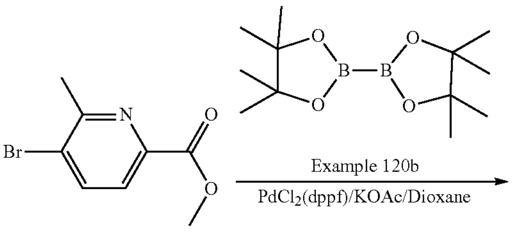

Example 120a

-continued

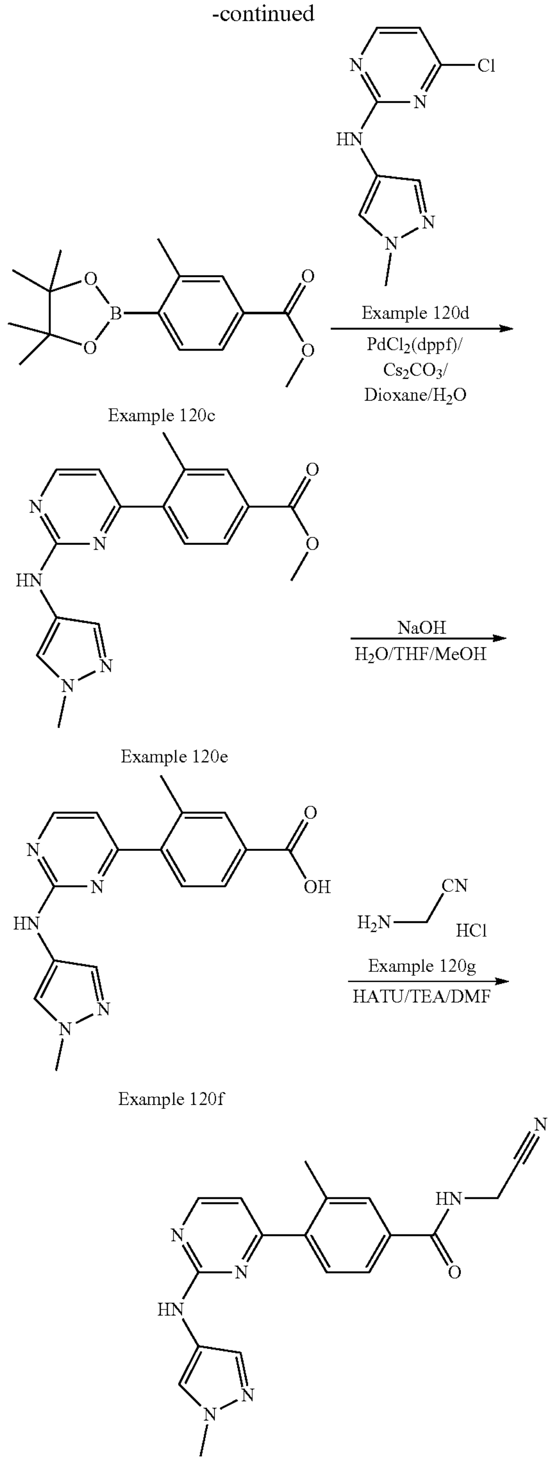

Example 120 (TDM-180720)

Step 1: Example 120c

The compound 120a (1.0 g, 4.365 mmol) was dissolved in 1,4-dioxane (30 mL), the compound 120b (2.22 g, 8.73 mmol), KOAc (1.5 g, 15.277 mmol) and $PdCl_2$ (dppf) (0.32 g, 0.436 mmol) were added to the mixture, nitrogen displacement was employed three times, and then the reaction solution was stirred at 95° C. for 16 hours. The reaction solution was cooled to room temperature, water (60 mL) was added, the reaction solution was extracted with ethyl acetate (30 mL×3), the organic layers were combined, washed with water (30 mL×2), dried over $MgSO_4$, filtered and concentrated. The concentrate was purified via silica gel chromatography (ethyl acetate:petroleum ether=0-10%) to obtain an off-white solid compound 120c (namely, 3-methyl-4-(4,4,5,5-tetramethyl-1,3,2-dioxaborolane-2-yl)methyl benzoate (1.113 g, yield: 92.4%). LCMS $[M+1]^+$=277.1.

Step 2: Example 120e

The compound 120d (0.21 g, 1.0 mmol) was dissolved in 1,4-dioxane (20 mL) and water (3 mL), and the compound 120c (0.33 g, 1.2 mmol), $CS_2CO_3$ (0.65 g, 2.0 mmol) and $PdCl_2$ (dppf) (0.07 g, 0.1 mmol) were added to the mixture. Nitrogen displacement was employed three times, and the reaction solution was then stirred for 16 hours at 85° C. The reaction solution was cooled to room temperature, then water (60 mL) was added, the reaction solution was extracted with ethyl acetate (30 mL×3), and the combined organic layers were washed with water (30 mL×2), dried over $MgSO_4$, and filtered. The solvent was concentrated, and purified via silica gel chromatography (ethyl acetate:petroleum ether=0-50%) to obtain an off-white solid compound 120e, namely 3-methyl-4-(2-((1-methyl-1H-pyrazol-4-yl)amino)pyrimidin-4-yl)methyl benzoate (198 mg, yield: 61.2%). LCMS $[M+1]^+$=323.1.

Step 3: Example 120f

Sodium hydroxide (244.9 mg, 6.12 mmol) was added to the compound 120e (198 mg, 0.61 mmol) in a mixture solution of methanol (5 mL), tetrahydrofuran (5 mL) and water (3 mL). The mixture was stirred for 4 hours at room temperature. After the solvent was removed via concentration, water (15 mL) was added, the mixture was acidified with hydrochloric acid (1 mol/L), extracted with ethyl acetate (15 mL×3), and the organic layers were combined, washed with water (20 mL×2), and dried over $MgSO_4$. The mixture was filtered and concentrated to obtain a yellow solid compound 120f, namely, 3-methyl-4-(2-((1-methyl-1H-pyrazol-4-yl)amino)pyrimidin-4-yl)benzoic acid (168 mg, yield: 89.0%). LCMS: $[M+1]^+$=310.1.

Step 4: Example 120 (TDM-180720)

2-(7-benzotriazole oxide)-N,N,N',N'-tetramethylurea hexafluorophosphate (147.9 mg, 0.39 mmol), triethylamine (78.5 mg, 0.78 mmol) and compound 120g (26.3 mg, 0.28 mmol) were added to compound 120f (80 mg, 0.26 mmol) in a solution of DMF (5 mL). The mixture was stirred for 2 hours at room temperature. The reaction solution was poured into water (15 mL) and stirred for 30 minutes. The reaction solution was filtered, the filter cake was slurried with ethyl acetate (10 mL) for 30 minutes and filtered, and the filter cake was dried to obtain a white solid compound 120, namely N-(cyanomethyl)-3-methyl-4-(2-((1-methyl-1H-pyrazol-4-yl)amino)pyrimidin-4-yl)benzamide (31.4 mg, yield 34.8%). LCMS: $[M+1]^+$=348.1.

$^1H$ NMR (400 MHz, DMSO) δ 9.56 (s, 1H), 9.28 (t, J=5.4 Hz, 1H), 8.51 (d, J=4.9 Hz, 1H), 7.96-7.73 (m, 3H), 7.59 (d, J=7.9 Hz, 1H), 7.49 (s, 1H), 6.89 (d, J=5.0 Hz, 1H), 4.34 (d, J=5.4 Hz, 2H), 3.79 (s, 3H), 2.45 (s, 3H).

Compounds prepared in a similar method are as follows:

| Structure Structural formula | TDM No. Registration number | LCMS $[M + 1]^+$ | $^1$H-NMR Proton nuclear magnetic resonance spectroscopy |
|---|---|---|---|
| 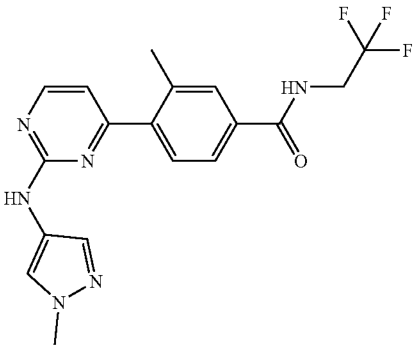 [SMILES: Cc1cc(C(=O)NCC(F)(F)F)ccc1-c1ccnc(Nc2cnn(C)c2)n1] | TDM-180736 | 391.1 | $^1$H NMR (400 MHz, DMSO) δ 9.57 (s, 1H), 9.16 (t, J = 6.2 Hz, 1H), 8.50 (d, J = 5.0 Hz, 1H), 7.93-7.76 (m, 3H), 7.58 (d, J = 8.0 Hz, 1H), 7.49 (s, 1H), 6.89 (d, J = 5.0 Hz, 1H), 4.11 (td, J = 9.7, 6.4 Hz, 2H), 3.79 (s, 3H), 2.45 (s, 3H). |

TDM-180736, a yellow solid compound 136, namely 3-methyl-4-(2-((1-methyl-1H-pyrazol-4-yl)amino)pyrimidin-4-yl)-N-(2,2,2-trifluoroethyl)benzamide (44.5 mg, yield: 42.3%)

Example 24: General Method for Synthesizing Compound 179 (TDM-180779)

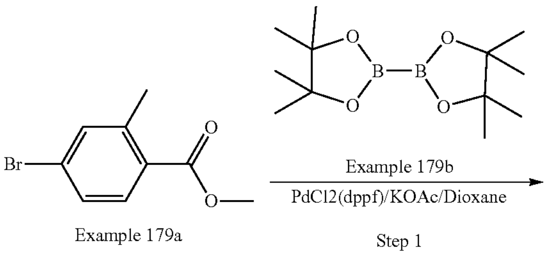

Example 179a

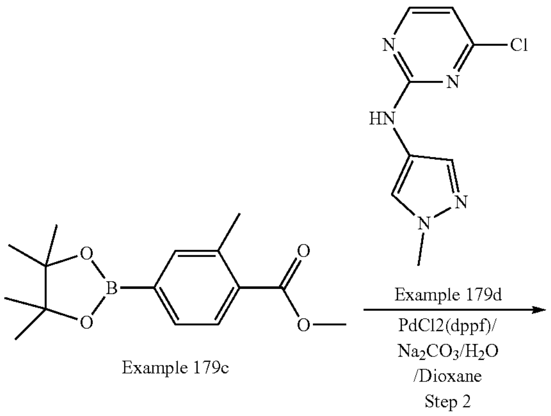

Example 179c

-continued

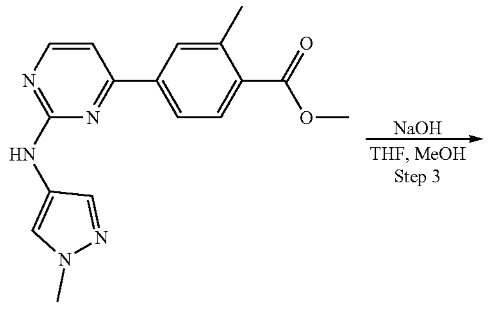

Example 179e

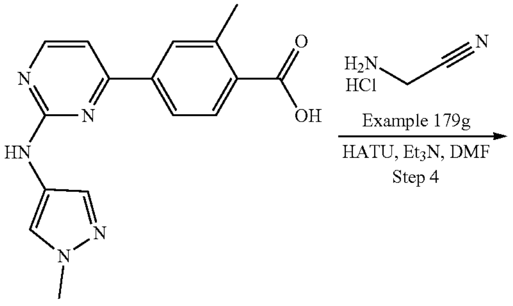

Example 179f

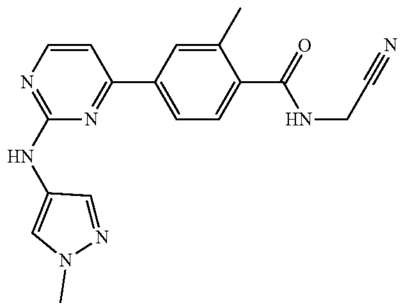
Example 179 (TDM-180779)

Step 1: Example 179c

Compound 179a (500 mg, 2.18 mmol), compound 179b (665.1 mg, 2.62 mmol), potassium acetate (427.8 mg, 4.36 mmol) and $PdCl_2$ (dppf) (159.7 mg, 0.22 mmol) were added to 1,4-dioxane (10 mL), nitrogen displacement was employed three times, and the mixture was then heated to 85° C. and stirred for 6 hours. After being cooled to room temperature, the reaction solution was directly used for feeding in the next step. LCMS $[M+1]^+$=277.1.

Step 2: Example 179e

The compound 179d (380.8 mg, 1.81 mmol), compound 179c (601.8 mg, 2.18 mmol), $Na_2CO_3$ (385.1 mg, 3.63 mmol) and $PdCl_2$ (dppf) (132.9 mg, 0.18 mmol) were added to a mixture solution of 1,4-dioxane (20 mL) and water (5 mL). Nitrogen displacement was employed three times, and the reaction solution was then stirred for 16 hours at 85° C. The reaction solution was cooled to room temperature and filtered, the filter cake was rinsed with ethyl acetate (15 mL×2), the filtrate was concentrated, and the concentrate was purified via silica gel chromatography (ethyl acetate: petroleum ether=0-80%) to obtain a yellow solid compound 179e, namely, 2-methyl-4-(2-((1-methyl-1H-pyrazol-4-yl) amino)pyrimidin-4-yl)methyl benzoate (420 mg, yield: 78.0%). LCMS $[M+1]^+$=297.1.

Step 3: Example 179f

The compound 179e (420 mg, 1.3 mmol) was added to a mixture solution of tetrahydrofuran (10 mL), methanol (10 mL) and water (5 mL), sodium hydroxide (519.5 mg, 12.99 mmol) was added, and then the reaction solution was stirred at 40° C. for 2 hours. The reaction solution was cooled to room temperature, the solvent was removed, water (15 mL) was added, then the mixture was acidified with hydrochloric acid (1 mol/L) and filtered, and the filter cake was dissolved in N,N-dimethyl formamide (10 mL) and concentrated to obtain a yellow solid compound 179f, namely, 2-methyl-4-(2-((1-methyl-1H-pyrazol-4-yl)amino)pyrimidin-4-yl)benzoic acid (387 mg, yield: 96.2%). LCMS $[M+1]^+$=310.2.

Step 4: Example 179 (TDM-180779)

2-(7-benzotriazole oxide)-N,N,N',N'-tetramethylurea hexafluorophosphate (147.5 mg, 0.39 mmol, triethylamine (78.4 mg, 0.78 mmol) and compound 179g (35.9 mg, 0.39 mmol) were added to compound 179f (80 mg, 0.26 mmol) in a solution of N,N-dimethylformamide (5 mL). The reaction solution was then stirred for 16 hours at 40° C. After the solvent was removed, the reaction solution was purified via silica gel chromatography (MeOH/DCM=0%-2%) to obtain the crude product. The crude product was slurried with methanol (5 mL) for 5 minutes and filtered, and the filter cake was dried to obtain a yellow solid compound 179, namely N-(cyanomethyl)-2-methyl-4-(2-((1-methyl-1H-pyrazol-4-yl)amino)pyrimidin-4-yl)benzamide (48.2 mg, yield: 53.5%). LCMS $[M+1]^+$=348.1.

$^1H$ NMR (400 MHz, DMSO) δ 9.56 (s, 1H), 9.11 (t, J=5.6 Hz, 1H), 8.51 (d, J=5.2 Hz, 1H), 8.12-7.97 (m, 2H), 7.92 (s, 1H), 7.54 (d, J=8.1 Hz, 2H), 7.32 (d, J=5.2 Hz, 1H), 4.33 (d, J=5.6 Hz, 2H), 3.83 (s, 3H), 2.46 (s, 3H).

Compounds prepared in a similar method are as follows:

| Structure Structural formula | TDM No. Registration number | LCMS $[M+1]^+$ | 1H-NMR Proton nuclear magnetic resonance spectroscopy |
|---|---|---|---|
| 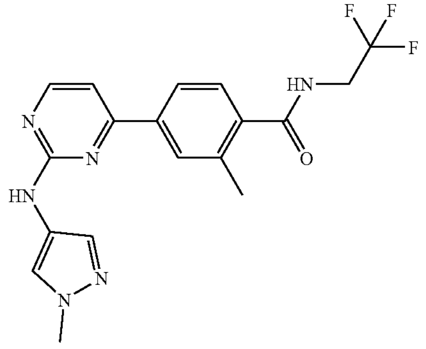 [SMILES: Cc1cc(-c2ccnc(Nc3cnn(C)c3)n2)ccc1C(=O)NCC(F)(F)F] | TDM-180780 | 391.1 | $^1H$ NMR (400 MHz, DMSO) δ 9.56 (s, 1H), 9.07 (t, J = 6.3 Hz, 1H), 8.52 (dd, J = 7.2, 3.3 Hz, 1H), 8.03 (d, J = 10.7 Hz, 2H), 7.92 (s, 1H), 7.68-7.44 (m, 2H), 7.31 (d, J = 5.2 Hz, 1H), 4.22-4.02 (m, 2H), 3.83 (s, 3H), 2.43 (s, 3H). |

TDM-180780, a yellow solid compound 180, namely 2-methyl-4-(2-((1-methyl-1H-pyrazol-4-yl)amino)pyrimidin-4-yl)-N-(2,2,2-trifluoroethyl)benzamide (49.3 mg, yield: 48.5%).

Example 25: General Method for Synthesizing Compound 267 (TDM-180867)

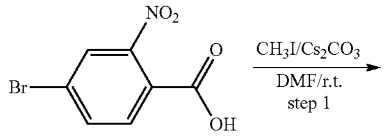

Example 267a

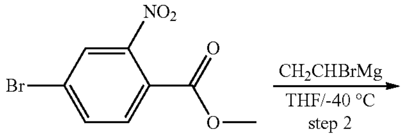

Example 267b

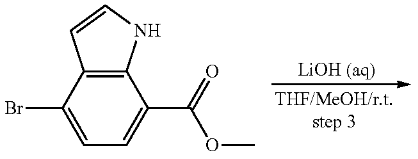

Example 267c

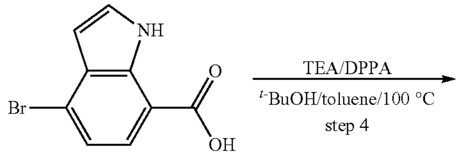

Example 267d

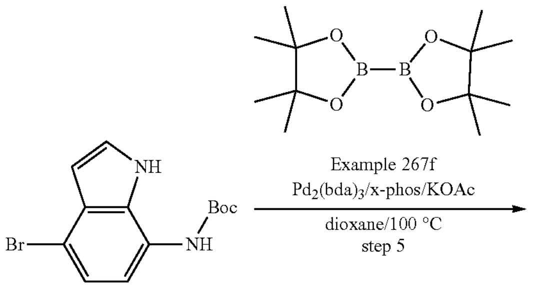

Example 267e

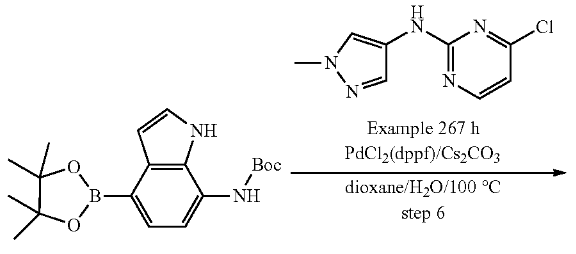

Example 267g

-continued

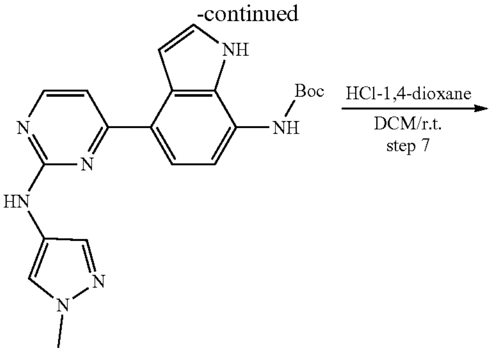

Example 267i

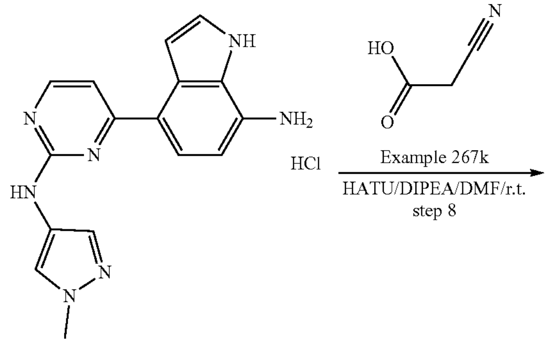

Example 267j

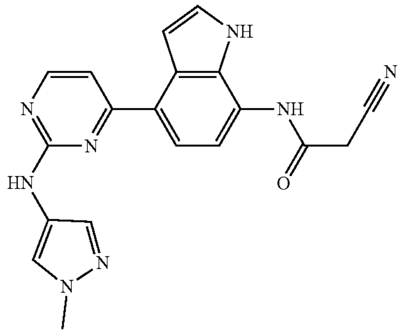

Example 267 (TDM-180867)

Step 1: Example 267b

Cesium carbonate (13.5 g, 40.5 mmol) and iodomethane (3.8 mL, 61 mmol) were added to compound 267a (namely, 4-bromo-2-nitrobenzoic acid) (5 g, 4.07 mmol) in a solution of N,N-dimethylformamide (50 mL). The mixture was stirred at room temperature for 16 hours, then the mixture was concentrated under reduced pressure to remove some solvent, water was added to the residue and the solution was extracted with ethyl acetate (160 mL×2), the extract was washed with saturated brine (60 mL×3), and dried over anhydrous sodium sulfate, the filtrate was concentrated under reduced pressure, and then the residue was purified via silica gel chromatography (petroleum ether:ethyl acetate=91:9) to obtain a white solid compound 267b, namely, methyl 4-bromo-2-nitrobenzoate (4.98 g, yield: 94.2%).

Step 2: Example 267c

A tetrahydrofuran solution (15 mL) of compound 267b (2.5 g, 9.614 mmol) was cooled to −60° C., and vinylmagnesium bromide (1.0 M, in tetrahydrofuran, 34 mL, 34 mmol, equivalent to 3.5) was added dropwise to the solution under nitrogen atmosphere. The reaction solution was stirred for 2 hours at −40° C. Then the reaction solution was subjected to saturated aqueous ammonium chloride solution (30 mL), the obtained mixture was extracted with ethyl acetate (80 mL×3), the combined organic phases were washed with water (60 mL) and brine (60 mL), dried over anhydrous sodium sulfate, and then purified via silica gel chromatography (petroleum ether:ethyl acetate=97:3) to obtain a white solid compound 267c, namely, methyl 4-bromo-1H-indole-7-carboxylate (850 mg, yield: 30%). LCMS $[M+1]^+$=254&256

Step 3: Example 267d

An aqueous solution (12 mL) of lithium hydroxide was added to a mixture solution of compound 267c (800 mg, 3.149 mmol) in methanol (6 mL) and tetrahydrofuran (6 mL) at room temperature. The mixture was stirred for 2.5 hours at room temperature. The reaction solution was concentrated under reduced pressure, water was added to the residue and the mixture was neutralized with dilute hydrochloric acid and then extracted with ethyl acetate (80 mL×3). The organic phases were combined, washed with saturated brine, and dried over anhydrous sodium sulfate. The filtrate was concentrated under reduced pressure, ethyl acetate and petroleum ether were added to the residue, and the mixture was filtered to collect a white solid compound 267d, namely 4-bromo-1H-indole-7-carboxylic acid (360 mg, yield: 44.8%). LCMS $[M+1]^+$=240&242

Step 4: Example 267e

Triethylamine (522.7 mg, 5.165 mmol) was added to toluene solution (20 mL) of the compound 267d (310 mg, 1.291 mmol) at room temperature. Nitrogen displacement was employed for the mixture several times under vacuum, diphenylphosphoryl azide (461.9 mg, 1.678 mmol) was then added, and the reaction solution was heated to 80° C. and stirred for 0.5 hours. Then tert-butanol (191.4 mg, 2.582 mmol) was added to the mixture, and the mixture was heated to 100° C. and stirred for 16 hours. The mixture was concentrated under reduced pressure to remove toluene, and the residue was purified via silica gel chromatography (petroleum ether:ethyl acetate=84:16) to obtain a pale yellow solid 267e, namely, (4-bromo-1H-indol-7-yl)carbamate tert-butyl ester (158 mg, yield: 39.3%). LCMS $[M+1]^+$=255&257

Step 5: Example 267g

Dioxane (12 mL) was added to a mixture of compound 67e (155 mg, 0.5 mmol), compound 267f (namely, bis (pinacolato)diboron) (190 mg, 0.75 mmol), tris(dibenzylideneacetone)dipalladium (91.6 mg, 0.1 mmol), 2-dicyclohexylphosphonium-2,4,6-triisopropylbiphenyl (83.3 mg, 0.2 mmol) and potassium acetate (147 mg, 1.5 mmol). Nitrogen displacement was employed for the mixture several times under vacuum, and then the mixture was heated to 100° C. and stirred for 2.5 hours. The reaction solution was concentrated under reduced pressure, and the residue was purified via silica gel chromatography (petroleum ether:ethyl acetate=94:6) to obtain a dark red solid compound 267g, namely (4-(4,4,5,5-tetramethyl-1,3,2-dioxaborolane-2-yl)-1H-indol-7-yl)carbamate tert-butyl ester (125 mg, crude product). LCMS $[M+1]^+$=359

Step 6: Example 267i 1,1'-bis(diphenylphosphino) ferrocene-palladium dichloride (51 mg, 0.07 mmol) was added to compound 267g (125 mg, 0.349 mmol), compound 267h (namely, 4-chloro-N-(1-methyl-1H-pyrazol-4-yl)pyrimidin-2-amine) (73 mg, 0.349 mmol), cesium carbonate (227 mg, 0.698 mmol) in a mixture solution of dioxane (12 mL) and water (2 mL). Nitrogen displacement was employed for the mixture several times, and then the mixture was heated to 100° C. and stirred for 2.5 hours. The mixture was concentrated under reduced pressure, and the residue was purified via silica gel chromatography (petroleum ether:ethyl acetate=20:80) to obtain a yellow solid compound 267i, (namely, tert-butyl (4-(2-((1-methyl-1H-pyrazol-4-yl)amino)pyrimidin-4-yl)-1H-indol-7-yl)carbamate tert-butyl ester (72 mg, yield: 50.9%). LCMS $[M+1]^+$=406

Step 7: Example 267j 1,4-dioxane hydrochloride (1 mL) was added to a dichloromethane solution (4 mL) of the compound 267i (72 mg, 0.178 mmol). The mixture was stirred at room temperature for 1.5 hours, and the mixture was concentrated under reduced pressure, to obtain an orange solid compound 267i, namely 4-(2-((1-methyl-1H-pyrazol-4-yl)amino)pyrimidin-4-yl)-1H-indol-7-amine hydrochloride (actually 81 mg). LCMS $[M+1]^+$=306.

Step 8: Example 267 (TDM-180867)

N,N-diisopropylethylamine (50.7 mg, 0.392 mmol) was added to compound 267i (30 mg, 0.098 mmol) in a solution of N,N-dimethylformamide (5 mL) at room temperature, the mixture was stirred for 5 minutes, and then 2-(7-benzotriazole oxide)-N,N,N',N'-tetramethylurea hexafluorophosphate (55.9 mg, 0.147 mmol) and compound 267j (9.2 mg, 0.108 mmol) were added into the mixture. The mixture was stirred for 16 hours at room temperature. The mixture was concentrated under reduced pressure, and the residue was passed through silica gel chromatography (dichloromethane: dichloromethane solution containing 10% methanol=30:70) and purified to obtain a yellow solid compound 267, TDM-180867, (namely, 2-cyano-N-(4-(2-((1-methyl-1H-pyrazol-4-yl)amino)pyrimidin-4-yl)-1H-indol-7-yl) acetamide (12.8 mg, yield: 35.1%). LCMS $[M+1]^+$=373.1

$^1$H NMR (400 MHz, DMSO-$d_6$) δ 11.05 (s, 1H), 10.22 (s, 1H), 9.57 (s, 1H), 8.44 (d, J=5.3 Hz, 1H), 7.95 (s, 1H), 7.70 (d, J=7.0 Hz, 1H), 7.59-7.48 (m, 3H), 7.27 (s, 2H), 4.02 (s, 2H), 3.81 (s, 3H).

Compounds prepared in a similar method are as follows:

| Structure Structural formula | TDM No. Registration number | LCMS $[M + 1]^+$ | $^1H$-NMR Proton nuclear magnetic resonance spectroscopy |
|---|---|---|---|
| 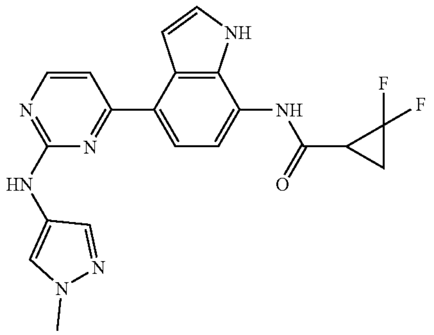 [SMILES: Cn1cc(Nc2nccc(-c3ccc(NC(=O)C4CC4(F)F)c4[nH]ccc34)n2)cn1] | TDM-180868 | 410.1 | $^1H$ NMR (400 MHz, DMSO-$d_6$) δ 11.07 (s, 1H), 10.33 (s, 1H), 9.55 (s, 1H), 8.43 (d, J = 5.3 Hz, 1H), 7.95 (s, 1H), 7.69 (q, J = 8.2 Hz, 2H), 7.58-7.46 (m, 2H), 7.27 (s, 2H), 3.81 (s, 3H), 3.03-2.85 (m, 1H), 2.07 (dd, J = 13.7, 9.1 Hz, 2H). |
| 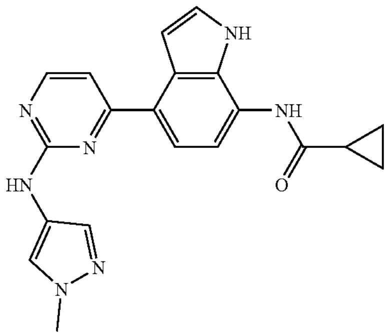 [SMILES: Cn1cc(Nc2nccc(-c3ccc(NC(=O)C4CC4)c4[nH]ccc34)n2)cn1] | TDM-180869 | 374.2 | $^1H$ NMR (400 MHz, DMSO-$d_6$) δ 11.10 (s, 1H), 10.14 (s, 1H), 9.58 (s, 1H), 8.40 (d, J = 5.3 Hz, 1H), 7.95 (s, 1H), 7.70 (s, 2H), 7.55 (d, J = 5.8 Hz, 2H), 7.28 (s, 2H), 3.82 (s, 3H), 1.92 (d, J = 4.8 Hz, 1H), 0.90 (t, J = 6.2 Hz, 4H). |
| 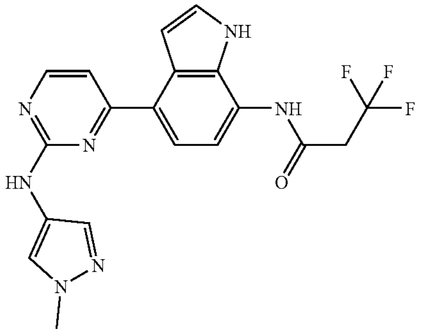 [SMILES: Cn1cc(Nc2nccc(-c3ccc(NC(=O)CC(F)(F)F)c4[nH]ccc34)n2)cn1] | TDM-180870 | 416.1 | $^1H$ NMR (400 MHz, DMSO-$d_6$) δ 11.00 (s, 1H), 10.22 (s, 1H), 9.59 (s, 1H), 8.44 (d, J = 5.0 Hz, 1H), 7.95 (s, 1H), 7.70 (s, 1H), 7.59 (dd, J = 15.4, 7.6 Hz, 3H), 7.27 (s, 2H), 3.81 (s, 3H), 3.65 (q, J = 11.0 Hz, 2H). |

TDM-180868, a yellow solid compound 268, namely 2,2-difluoro-N-(4-(2-((1-methyl-1H-pyrazol-4-yl)amino)pyrimidin-4-yl)-1H-indol-7-yl)cyclopropane-1-carboxamide (13.3 mg, yield: 33.1%)

TDM-180869, a yellow solid compound 269, namely N-(4-(2-((1-methyl-1H-pyrazol-4-yl)amino)pyrimidin-4-yl)-1H-indol-7-yl)cyclopropanecarboxamide (27.6 mg, yield: 56.4%)

TDM-180870, a yellow solid compound 270, namely 3,3,3-trifluoro-N-(4-(2-((1-methyl-1H-pyrazol-4-yl)amino)pyrimidin-4-yl)-1H-indol-7-yl)propanamide (21.4 mg, yield: 39.3%)

Example 26: General Method for Synthesizing Compound 298 (TDM-180898)

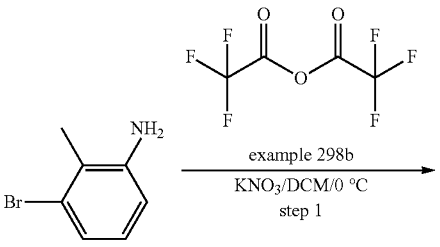

example 298a

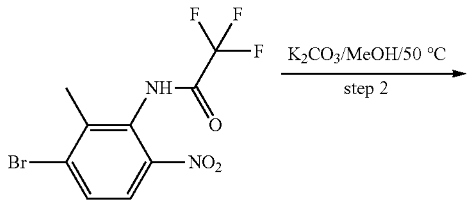

example 298c

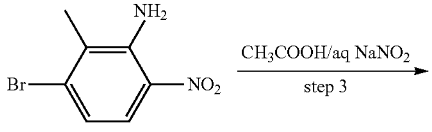

example 298d

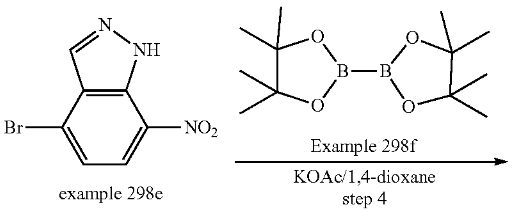

example 298e

-continued

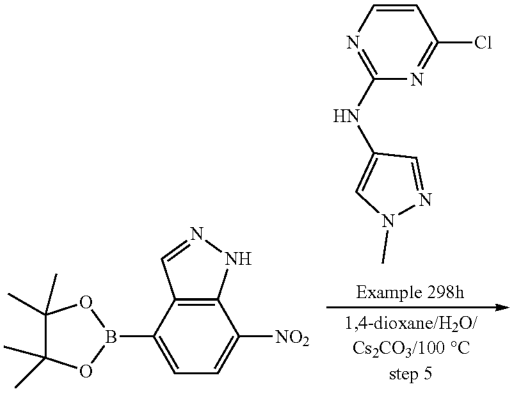

example 298g

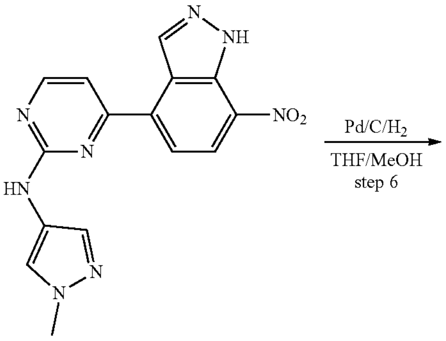

example 298i

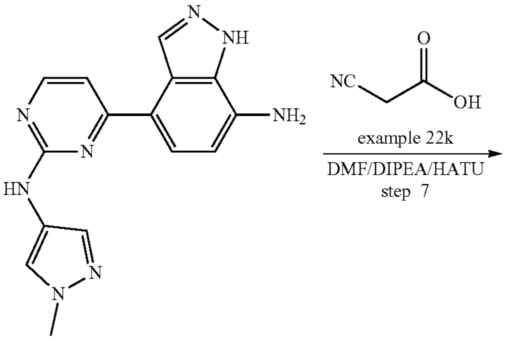

example 298j

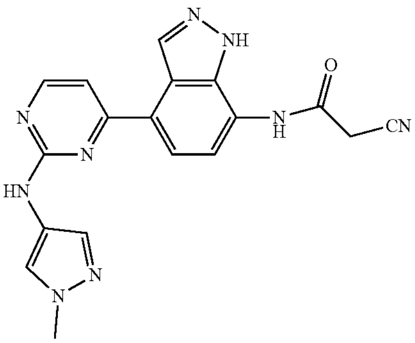

example 298 (TDM-180898)

Step 1: Example 298c

N-(3-bromo-2-methyl-6-nitrophenyl)-2,2,2-trifluoro-acetamide

Compound 298b (16 mL, 113.5 mmol) was added to a dichloromethane solution (80 mL) of compound 298a (8 g, 43 mmol) at 0° C., the reaction solution was stirred at 0° C. for 30 minutes, then solid potassium nitrate (5.43 g, 53.7 mmol) was added, the ice bath was discontinued, and the reaction solution was stirred at room temperature for 4 hours. When it was detected by LCMS that the reaction of the raw material completed, the reaction solution was concentrated and dried under vacuum, water was added to the residue, the mixture was extracted twice with dichloromethane (2*200 mL), the organic phases were combined, dried over anhydrous sodium sulfate, filtered via suction, and dried, and the crude product was passed through the column to obtain a yellow solid compound (example 298c, 4.0972 g, yield: 28.57%). LCMS [M+H]+=327,329.

Step 2: Example 298d 3-bromo-2-methyl-6-nitroaniline

Potassium carbonate (5.2 g, 37.5 mmol) was added to a methanol solution (100 ml) of compound 298c (4.1 g, 12.5 mmol), and the reaction solution was heated to 60° C. and stirred overnight. When it was detected by TLC that the reaction of the raw material completed, after being cooled to room temperature, the reaction solution was slowly added to water and extracted three times with dichloromethane (100 mL*3), the organic phases were combined, dried over anhydrous sodium sulfate, filtered via suction, and dried to obtain a yellow solid compound (example 298d, 2.6111 g, yield: 90.4%). LCMS [M+H]+=231,233.

Step 3: Example 298e 4-bromo-7-nitro-1H-indazole

The compound 298d (2.6111 g, 11.3 mmol) was dissolved in acetic acid solution (100 mL) and cooled to 0° C., and an aqueous solution (15 mL) of sodium nitrite (1.56 g, 22.6 mmol) was added dropwise. After the addition was completed, the mixture was stirred at room temperature for 4 hours. It was revealed by TLC that the reaction of the raw material completed. The reaction solution was slowly poured into ice water, neutralized to neutrality with solid sodium carbonate, the aqueous phase was extracted three times with ethyl acetate (3*150 mL), the organic phases were combined, washed with saturated brine, dried over anhydrous sodium sulfate, filtered via suction, and dried, and the crude product was passed through the column to obtain a yellow solid compound (example 298e, 1.5475 g, yield: 56.4%). LCMS [M+H]+=242,244.

Step 4: Example 298g 7-nitro-4-(4,4,5,5-tetramethyl-1,3,2-dioxaborolane-2-yl)-1H-indazole The compound 298e (1.15 g, 4.75 mmol), compound 298f (1.8 g, 7.127 mmol), tris(dibenzylideneacetone)dipalladium (870 mg, 0.95 mmol), 2-dicyclohexylphosphonium-2',4',6'-triisopropylbiphenyl (905 mg, 1.9 mmol), potassium acetate (1.4 g, 14.25 mmol) and 1,4-dioxane (25 mL) was added to a 250 mL three-necked flask. Nitrogen displacement was employed for the reaction solution several times, and then the reaction solution was heated to 100° C. and stirred for two hours. When it was detected by LCMS that the reaction of the raw material completed, the reaction solution was dried under vacuum, and the crude product was passed through the column to obtain a yellow solid compound (example 298g, 937.9 mg, yield: 68.3%). LCMS [M+H]+=290.

Step 5: Example 298i

N-(1-methyl-1H-pyrazol-4-yl)-4-(7-nitro-1H-indazol-4-yl)pyrimidin-2-amine

The compound 298g (900 mg, 3.11 mmol), compound 298h (650 mg, 3.11 mmol), tris(dibenzylideneacetone)dipalladium (569.5 mg, 0.622 mmol), 2-dicyclohexylphosphonium-2',4',6'-triisopropylbiphenyl (593 mg, 1.244 mmol), cesium acetate (2.533 g, 7.775 mmol), 1,4-dioxane (24 mL) and water (4 mL) was added to a 250 mL three-necked flask. Nitrogen displacement was employed for the reaction solution several times, and then the reaction solution was heated to 100° C. and stirred for two hours. When it was detected by LCMS that the reaction of the raw material completed, the reaction solution was dried under vacuum, and the crude product was passed through the column to obtain a yellow solid compound (example 298i, 450 mg, yield: 43.1%). LCMS [M+H]+=337.

Step 6: Example 298j 4-(2-((1-methyl-1H-pyrazol-4-yl)amino)pyrimidin-4-yl)-1H-indazole-7-amide Pd/C (10%, 16 mg) was added to compound 298i (400 mg, 1.19 mmol) in a solution of methanol (100 mL)/tetrahydrofuran (20 mL) under nitrogen atmosphere. Hydrogen displacement was employed for the reaction solution several times, and the reaction solution was stirred and reacted for 3 hours at 40° C., until it was detected by LCMS that the reaction of the raw material completed. The reaction solution was filtered via suction, the filter cake was washed with methanol, and the filtrate was concentrated and dried to obtain a yellow solid (example 298j, 300 mg, yield: 82.42%). LCMS [M+H]+=307.

Step 7: Example 298 (TDM-180898)

2-cyano-N-(4-(2-((1-methyl-1H-pyrazol-4-yl)amino) pyrimidin-4-yl)-1H-indazole-7-yl) acetamide N,N-diisopropylethylamine (31.6 mg, 0.245 mmol), 2-(7-benzotriazoleoxide)-N,N,N',N'-tetramethylurea hexafluorophosphate (93.1 mg, 0.245 mmol) and compound 298k (15.3 mg, 0.179 mmol) were added to compound 298j (50 mg, 0.163 mmol) in a solution of N,N-dimethylformamide (5 mL). The reaction solution was heated to 90° C. and stirred for 3 hours. When it was detected by LCMS that the reaction of most raw materials completed, the reaction solution was concentrated and dried under vacuum, and the crude product was passed through the column and then prepared to obtain a yellow solid compound (example 298, 10.2 mg, yield: 16.77%), LCMS [M+H]+=374.

$^1$H NMR (400 MHz, DMSO) δ 12.92 (s, 1H), 10.43 (s, 1H), 9.57 (s, 1H), 8.49 (d, J=5.3 Hz, 1H), 7.93 (s, 1H), 7.88 (d, J=7.8 Hz, 1H), 7.73 (s, 1H), 7.55 (s, 1H), 7.37 (d, J=4.7 Hz, 1H), 4.07 (s, 2H), 3.83 (s, 3H).

Compounds prepared in a similar method are as follows:

| Structure Structural formula | TDM No. Registration number | LCMS [M + 1]$^+$ | $^1$H-NMR Proton nuclear magnetic resonance spectroscopy |
|---|---|---|---|
| 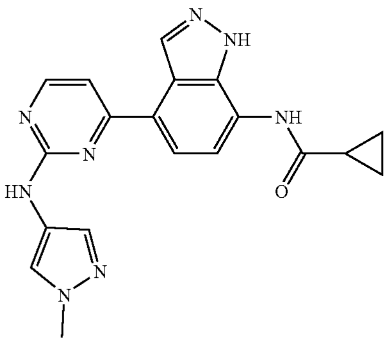 [SMILES: Cn1cc(Nc2nccc(-c3ccc(NC(=O)C4CC4)c4[nH]ncc34)n2)cn1] | TDM-180884 | 375 | $^1$H NMR (400 MHz, DMSO-$d_6$) δ 10.5 (s, 1H), 9.58 (s, 1H), 8.47 (d, J = 5.2 Hz, 1H), 7.81-8.03 (m, 3H), 7.55 (s, 1H), 7.38 (d, J = 5.2 Hz, 1H), 3.83 (s, 3H), 1.89-2.01 (m, 1H), 0.86-1.02 (m, 4H). |
| 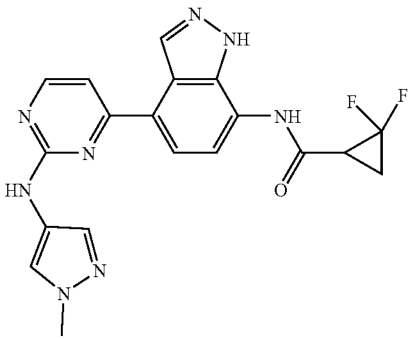 [SMILES: Cn1cc(Nc2nccc(-c3ccc(NC(=O)C4CC4(F)F)c4[nH]ncc34)n2)cn1] | TDM-180899 | 411.1 | $^1$H NMR (400 MHz, DMSO) δ 12.94 (s, 1H), 10.55 (s, 1H), 9.53 (s, 1H), 8.49 (d, J = 5.2 Hz, 1H), 7.93 (s, 1H), 7.87 (s, 2H), 7.53 (d, J = 7.4 Hz, 1H), 7.36 (d, J = 4.9 Hz, 1H), 3.82 (s, 3H), 2.95 (s, 1H), 2.11 (d, J = 6.8 Hz, 2H) |
| 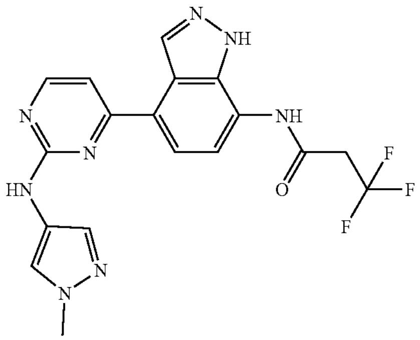 [SMILES: Cn1cc(Nc2nccc(-c3ccc(NC(=O)CC(F)(F)F)c4[nH]ncc34)n2)cn1] | TDM-180900 | 417.2 | $^1$H NMR (400 MHz, DMSO) δ 12.86 (s, 1H), 10.41 (s, 1H), 9.54 (s, 1H), 8.49 (d, J = 5.3 Hz, 1H), 7.94 (s, 1H), 7.88 (d, J = 7.2 Hz, 1H), 7.82 (d, J = 6.7 Hz, 1H), 7.54 (s, 1H), 7.37 (d, J = 4.7 Hz, 1H), 3.83 (s, 3H), 3.71 (s, 2H) |

TDM-180884, N-(4-(2-((1-methyl-1H-pyrazol-4-yl) amino)pyrimidin-4-yl)-1H-indazol-7-yl)cyclopropanemethane, a yellow solid compound (5 mg, yield: 14%)

TDM-180899, 2,2-difluoro-N-(4-(2-((1-methyl-1H-pyrazol-4-yl)amino)pyrimidin-4-yl)-1H-indazol-7-yl)cyclopropane-1-carboxamide, example 299, a yellow solid compound (7.8 mg, yield: 11.82%)

TDM-180900, 3,3,3-trifluoro-N-(4-(2-((1-methyl-1H-pyrazol-4-yl)amino)pyrimidin-4-yl)-1H-indazol-7-yl) propionamide, a yellow solid compound (14.1 mg, yield: 5.78%)

Example 29: General Method for Synthesizing Compound 276 (TDM-180876)

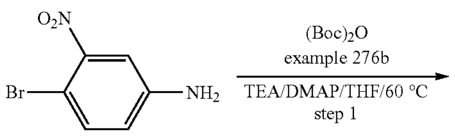

Example 276a

-continued

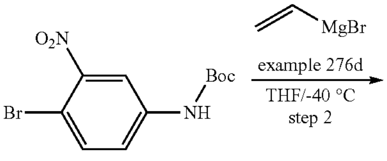

Example 276c

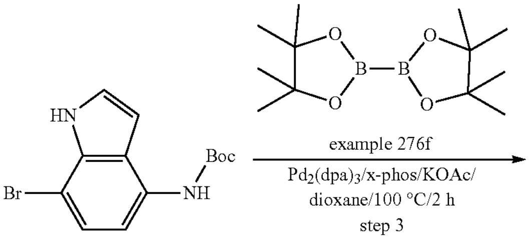

Example 276e

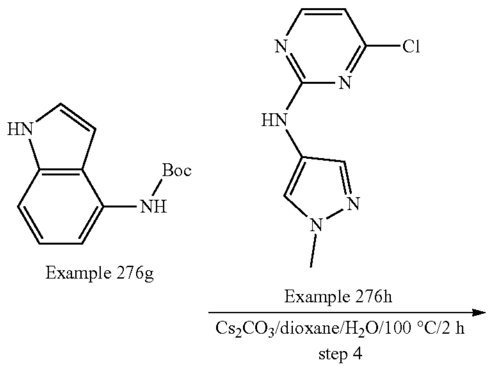

Example 276g

Example 276h

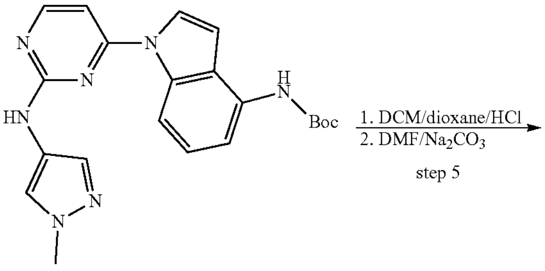

Example 276i

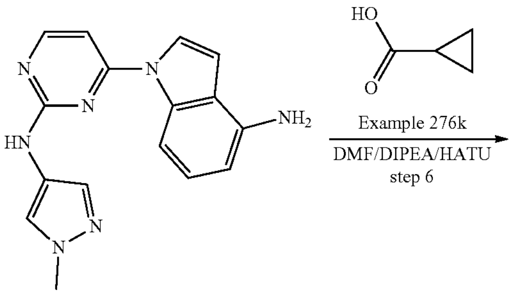

Example 276k

Example 276j

-continued

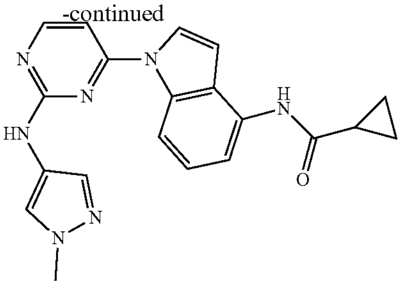

Example 276 (TDM-180876)

Step 1: Example 276c

Tert-butyl (4-bromo-3-nitrophenyl)carbamate 4-dimethylaminopyridine (840 mg, 6.84 mmol), triethylamine (2 g, 20.28 mmol) and compound 276b (3.3 g, 15.2 mmol) were added to compound 276a (2.2 g, 10.14 mmol) in a solution of tetrahydrofuran (20 mL) at 0° C. The reaction solution was heated to 60° C. and stirred overnight until it was detected by TLC that the reaction of the raw material completed. The reaction solution was concentrated to dryness, water (20 mL) was added to the solid residue, ethyl acetate (3*20 mL) was added, the mixture was extracted three times, and the organic phases were combined, washed with saturated brine once, dried over anhydrous sodium sulfate, filtered via suction, and spin-dried. The crude product was passed through the column to obtain a yellow oily substance (example 276c, 2.6278 g; yield: 81.86%). LCMS [M+1]+=261,263.

Step 2: Example 276e

Tert-butyl (7-bromo-1H-indol-4-yl)carbamate

The compound 276d (1.0 M in THF, 83 mL, 82.8 mmol) was slowly added to the compound 276c (2.6278 g, 8.28 mmol) in a solution of tetrahydrofuran (100 mL) at −40° C., and the mixture was stirred and held at −40° C. for 4 hours. LCMS was used for detection, and the product was obtained. MS [M-t-Bu+H]+=255, 257. After the reaction completed, saturated aqueous ammonium chloride solution (150 mL) was added to the mixture for quenching, and the mixture was stirred at room temperature for 1 hour, and then extracted with ethyl acetate. The organic phase was separated, washed with saturated brine, dried over anhydrous sodium sulfate, filtered via suction, and dried. The obtained crude product was passed through the column to obtain a yellow solid compound (example 276e, 989.7 mg, yield: 38.4%). LCMS [M-t-Bu+H]+=255, 257.

Step 3: Example 276g (1H-indole-4-yl)carbamate tert-butyl ester

The compound 276e (989.7 mg, 3.18 mmol), compound 276f (1211 mg, 4.77 mmol), tris(dibenzylideneacetone)dipalladium (582.4 mg, 0.636 mmol), 2-dicyclohexylphosphonium-2',4',6'-triisopropylbiphenyl (606 mg, 1.272 mmol), potassium acetate (935 mg, 9.54 mmol) and 1,4-dioxane (25 mL) were added to a 250 mL three-necked flask. Nitrogen displacement was employed several times, and the reaction solution was heated to 100° C. for two hours. When it was detected by LCMS that the reaction of the raw material completed, the reaction solution was concentrated and dried, and the solid residue was passed through the column to obtain a yellow solid (example 276g, 250 mg, yield: 21.9%). LCMS [M+H]+=177.

Step 4: Example 276i (1-(2-((1-methyl-1H-pyrazol-4-yl)amino)pyrimidin-4-yl)-1H-indole-4-yl)carbamate tert-butyl ester The compound 276g (286 mg, 0.8 mmol), compound 276h (500 mg, 2.4 mmol), tris(dibenzylideneacetone)dipalladium (146.5 mg, 0.16 mmol), 2-dicyclohexylphosphonium-2',4',6'-triisopropylbiphenyl (152.5 mg, 0.32 mmol), cesium carbonate (651.64 mg, 2 mmol), 1,4-dioxane (24 mL) and water (4 mL) was added to a 250 mL three-necked flask. After nitrogen displacement was employed several times, the reaction solution was heated to 100° C. for two hours. When it was detected by LCMS that the reaction of the raw material completed, the reaction solution was concentrated and dried, and the solid residue was passed through the column to obtain a yellow solid (example 276i, 151.6 mg, yield: 46.8%). LCMS [M+H]+=406.

Step 5: Example 276j 1-(2-((1-methyl-1H-pyrazol-4-yl)amino)pyrimidin-4-yl)-1H-indole-4-amide A solution of hydrochloric acid in 1,4-dioxane (3.0 mL, 4 mol/L, 12 mmol) was slowly added dropwise to a solution of compound 276i (151.6 mg, 0.374 mmol) in dichloromethane (15 mL). The reaction solution was stirred for one hours at room temperature. When it was detected by TLC that the reaction completed, the reaction solution was directly dried to obtain the solid. N,N-dimethylformamide (10 mL) solution was added, the mixture was neutralized to neutrality with solid sodium carbonate, the solid was removed via suction filtration, and the filtrate was dried to obtain a yellow solid (example 276j, 110 mg, yield: 96.5%). LCMS [M+H]+= 306.

Step 6: Example 276 (TDM-180876)

N-(1-(2-((1-methyl-1H-pyrazol-4-yl)amino)pyrimidin-4-yl)-1H-indole-4-yl)cyclopropanemethane N,N-diisopropylethylamine (24 mg, 0.1855 mmol), 2-(7-benzotriazole oxide)-N,N,N',N'-tetramethylurea hexafluorophosphate (30 mg, 0.0795 mmol) and compound 276k (5 mg, 0.058 mmol) were added to compound 276j (20 mg, 0.053 mmol) in a solution of N,N-dimethylformamide (5 mL). The reaction solution was stirred at room temperature overnight. When it was detected by LCMS that the reaction of the raw material completed, the product was obtained. LCMS [M+H]+=374. The reaction solution was directly concentrated and dried for preparation, the eluent was distilled under reduced pressure at 45° C. to remove the solvent, and the aqueous phase was lyophilized to obtain a yellow solid (example 276, 8.1 mg, yield: 47.6%). LCMS [M+H]+= 374.

1H NMR (400 MHz, DMSO) δ 9.98 (s, 1H), 9.65 (s, 1H), 8.44 (d, J=5.7 Hz, 1H), 8.08 (s, 1H), 7.93 (s, 1H), 7.78 (d, J=7.8 Hz, 1H), 7.54 (s, 1H), 7.22 (s, 1H), 7.11 (d, J=4.1 Hz, 2H), 3.85 (d, J=15.6 Hz, 3H), 2.06 (s, 1H), 0.84 (t, J=6.2 Hz, 4H).

Compounds prepared in a similar method are as follows:

| Structure Structural formula | TDM No. Registration number | LCMS $[M+1]^+$ | $^1$H-NMR Proton nuclear magnetic resonance spectroscopy |
|---|---|---|---|
| 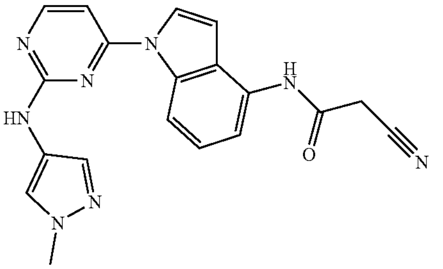 | TDM-180881 | 373.3 | $^1$H NMR (400 MHz, DMSO) δ 10.13 (s, 1H), 9.71 (s, 1H), 8.45 (d, J = 5.8 Hz, 1H), 8.12 (s, 1H), 7.93 (s, 1H), 7.72 (d, J = 7.8 Hz, 1H), 7.56 (d, J = 15.0 Hz, 1H), 7.28 (s, 1H), 7.13 (d, J = 5.8 Hz, 1H), 7.04 (d, J = 3.6 Hz, 1H), 4.03 (d, J = 13.5 Hz, 2H), 3.88-3.79 (m, 3H). |
| 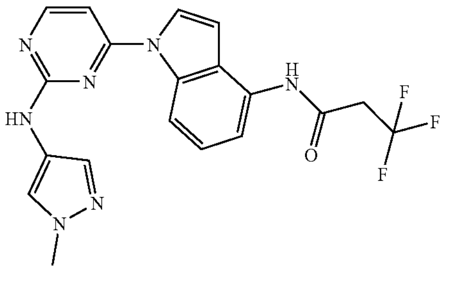 | TDM-180882 | 416.3 | $^1$H NMR (400 MHz, DMSO) δ 10.11 (s, 1H), 9.66 (s, 1H), 8.45 (d, J = 5.7 Hz, 1H), 8.12 (d, J = 3.1 Hz, 1H), 7.93 (s, 1H), 7.72 (d, J = 7.8 Hz, 1H), 7.54 (s, 1H), 7.27 (s, 1H), 7.12 (d, J = 5.7 Hz, 1H), 7.01 (d, J = 3.6 Hz, 1H), 3.83 (s, 3H), 3.68 (q, J = 11.2 Hz, 2H). |

-continued

| Structure Structural formula | TDM No. Registration number | LCMS $[M + 1]^+$ | $^1$H-NMR Proton nuclear magnetic resonance spectroscopy |
|---|---|---|---|
| 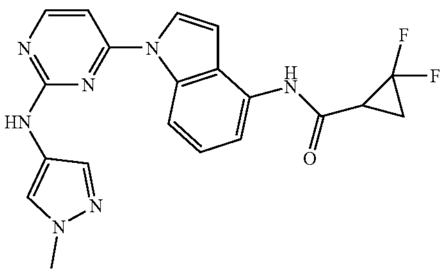 | TDM-180885 | 409.4 | $^1$H NMR (400 MHz, DMSO) δ 10.23 (s, 1H), 9.66 (s, 1H), 8.45 (d, J = 5.8 Hz, 1H), 8.11 (s, 1H), 7.93 (s, 1H), 7.76 (d, J = 7.8 Hz, 1H), 7.54 (s, 1H), 7.26 (s, 1H), 7.12 (d, J = 5.7 Hz, 1H), 7.07 (d, J = 3.6 Hz, 1H), 3.84 (s, 3H), 3.13-2.96 (m, 1H), 2.16-1.91 (m, 2H). |

TDM-180881, a yellow solid compound 281, namely 2-cyano-N-(1-(2-((1-methyl-1H-pyrazol-4-yl)amino) pyrimidin-4-yl)-1H-indol-4-yl) acetamide (5.1 mg, yield: 11.8%)

TDM-180882, a yellow solid compound 282, namely 3,3,3-trifluoro-N-(1-(2-((1-methyl-1H-pyrazol-4-yl) amino)pyrimidin-4-yl)-1H-indol-4-yl)propanamide (5.6 mg, yield: 15.1%)

TDM-180885, a yellow solid compound 285, namely 2,2-difluoro-N-(1-(2-((1-methyl-1H-pyrazol-4-yl) amino)pyrimidin-4-yl)-1H-indol-4-yl)cyclopropane-1-carboxamide (39 mg, yield: 81.41%)

TDM-180911, a white solid compound 311, namely 2-cyclopropyl-N-(1-(2-((1-methyl-1H-pyrazol-4-yl)amino) pyrimidin-4-yl)-1H-indol-4-yl) acetamide (45.7 mg, yield: 53.14%)

Example 30: General Method for Synthesizing Compound 292 (TDM-180892)

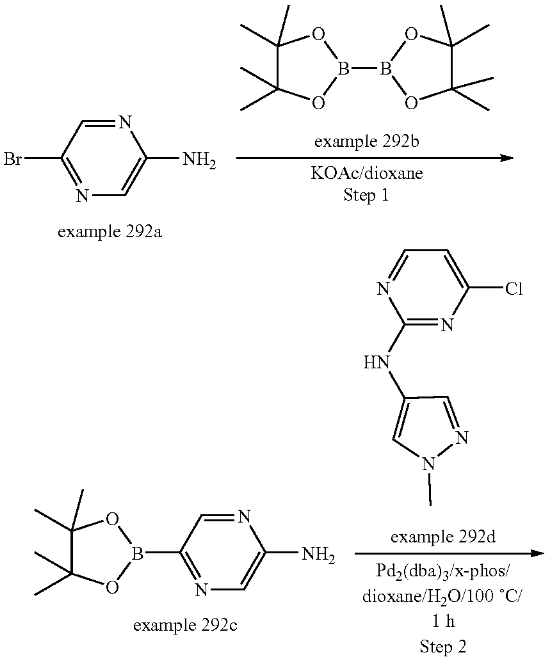

-continued

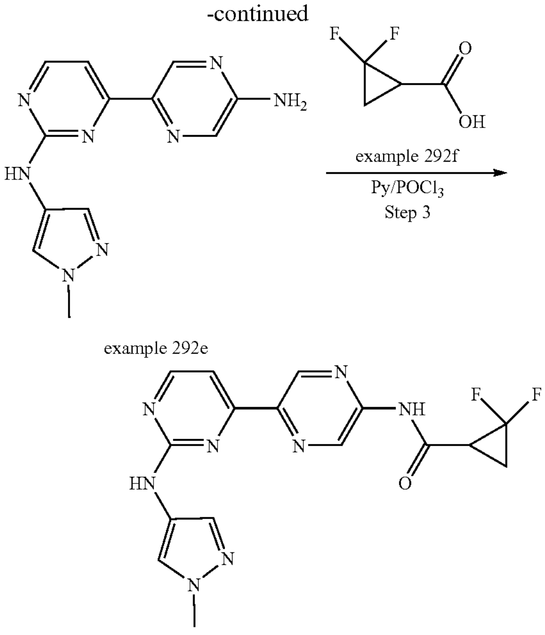

example 292 (TDM-180892)

Step 1: Example 292c 5-(4,4,5,5-tetramethyl-1,3,2-dioxaborolane-2-yl) pyrazin-2-amino The compound 292a (300 mg, 1.72 mmol), compound 292b (656.74 mg, 2.59 mmol), tris(dibenzylideneacetone) dipalladium (315.7 mg, 0.34 mmol), 2-dicyclohexyl phosphonium-2',4',6'-triisopropylbiphenyl (328.7 mg, 0.69 mmol), potassium acetate (422.38 mg, 4.31 mmol) and 1,4-dioxane (24 mL) was added to a 250 mL three-necked flask. Nitrogen displacement was employed for the reaction solution several times, and then the reaction solution was heated to 100° C. and held at the temperature for two hours. When it was detected by LCMS that the reaction of the raw material completed, the reaction solution was directly used in the next reaction without further purification. LCMS (m/z): 140 (MH+ corresponds to boronic acid).

Step 2: Example 292e 4-(5-aminopyrazin-2-yl)-N-(1-methyl-1H-pyrazol-4-yl)pyrimidin-2-amino The compound 292c (381 mg, 1.724 mmol), compound 292d (360 mg, 1.724 mmol), tris(dibenzylideneacetone) dipalladium (158 mg, 0.1724 mmol), 2-dicyclohexylphosphonium-2',4',6'-triisopropylbiphenyl (164 mg, 0.3448 mmol), cesium acetate (1.4 g, 4.31 mmol), 1,4-dioxane (24 mL) and water (4 mL) was added to a 250 mL three-necked flask. Nitrogen displacement was employed for the reaction solution several times, and the reaction solution was stirred, heated to 100° C. and held for one hour. It was detected by LCMS that the reaction of the raw material completed. The reaction solution was directly dried, passed through the column, and eluted with eluent (DCM:MeOH=50:1) to obtain a yellow solid compound (example 292e, 140 mg, yield: 30.3%). LCMS $[M+H]^+=269$.

Step 3: Example 292 (TDM-180892)

2,2-difluoro-N-(5-(2-((1-methyl-1H-pyrazol-4-yl)amino)pyrimidin-4-yl) pyrazin-2-yl)cyclopropane-1-formamide The compound 292f (43.5 mg, 0.36 mmol) was added to a solution of compound 292e (87 mg, 0.32 mmol) in anhydrous pyridine solution (5 mL) at 0° C., and phosphorus oxychloride (74.5 mg, 0.49 mmol) was added dropwise. The reaction solution was held at 0° C. and stirred for three hours. It was detected by LCMS that there were still most raw materials, and a few products were obtained. LCMS [M+H]+=373. The reaction solution was directly concentrated to dryness, water was added, and the reaction solution was extracted three times with DCM:MeOH=10:1 (3*30 mL), dried over anhydrous sodium sulfate, filtered via suction, dried, and passed through the column for preparation to obtain a yellow solid compound (example 292, 5.2 mg, yield: 5.83%). LCMS [M+H]+=373.

$^1$H NMR (400 MHz, DMSO) δ 11.59 (s, 1H), 9.61 (s, 1H), 9.42 (d, J=1.3 Hz, 1H), 9.29 (s, 1H), 8.58 (d, J=5.0 Hz, 1H), 7.96 (s, 1H), 7.57 (s, 1H), 7.50 (d, J=5.0 Hz, 1H), 3.84 (s, 3H), 3.06 (dd, J=22.7, 9.6 Hz, 1H), 2.11 (dd, J=19.0, 8.9 Hz, 2H).

Compounds prepared in a similar method are as follows:

| Structure Structural formula | TDM No. Registration number | LCMS $[M + 1]^+$ | $^1$H-NMR Proton nuclear magnetic resonance spectroscopy |
|---|---|---|---|
| 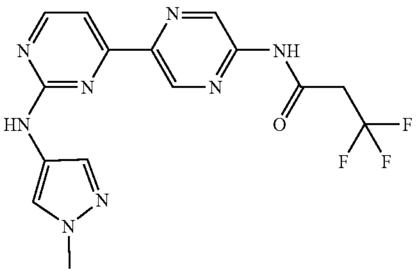 [SMILES: Cn1cc(Nc2nccc(-c3cnc(NC(=O)CC(F)(F)F)cn3)n2)cn1] | TDM-180905 | 379.1 | $^1$H NMR (400 MHz, DMSO) δ 11.44 (s, 1H), 9.62 (s, 1H), 9.41 (d, J = 1.1 Hz, 1H), 9.30 (s, 1H), 8.58 (d, J = 4.9 Hz, 1H), 7.96 (s, 1H), 7.57 (s, 1H), 7.51 (d, J = 5.0 Hz, 1H), 3.84 (s, 3H), 3.74 (q, J = 11.0 Hz, 2H). |

TDM-180905, 3,3,3-trifluoro-N-(5-(2-((1-methyl-1H-pyrazol-4-yl)amino)pyrimidin-4-yl) pyrazin-2-yl)propanamide, example 305, a yellow solid compound (2.3 mg, yield: 2.7%)

Example 31: General Method for Synthesizing Compound 286 (TDM-180886)

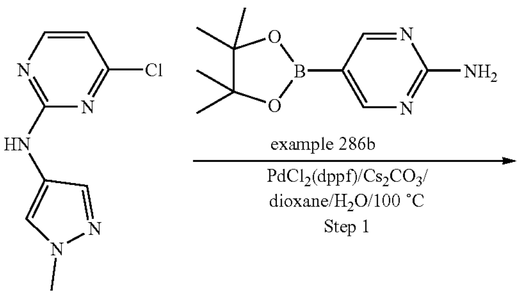

Example 286a

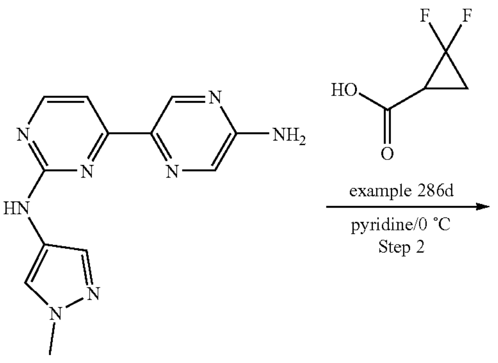

Example 286c

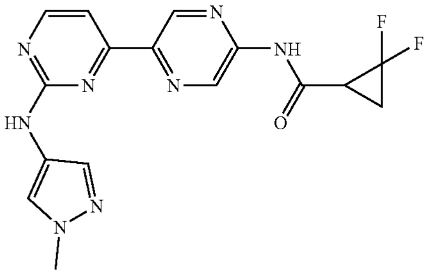

Example 286 (TDM-180886)

Step 1: Example 286c

$N^2$-(1-methyl-1H-pyrazol-4-yl)-[4,5'-bipyrimidine]-2,2'-diamine

The compound 286a (500 mg, 2.392 mmol) (namely, 4-chloro-N-(1-methyl-1H-pyrazol-4-yl)pyrimidin-2-amine), compound 286b (529 mg, 2.392 mmol) (namely, 5-(4,4,5,5-tetramethyl-1,3,2-dioxolane-2-yl)pyrimidin-2-amine), 1,1'-bis(diphenylphosphino)ferrocene-palladium dichloride (174 mg, 0.239 mmol) and cesium carbonate (1.59 g, 4.784 mmol) were added to the three-necked flask. Water (4 mL) and dioxane (24 mL) were added to the mixture. The mixture was then degassed under vacuum, and nitrogen displacement was employed several times. The mixture was heated to 100° C. and stirred for 2 hours. Then the mixture was concentrated under reduced pressure, and purified via silica gel chromatography (dichloromethane: dichloromethane containing 10% methanol=50:50) to obtain a yellow solid compound 286c, namely $N^2$-(1-methyl-1H-pyrazol-4-yl)-[4,5'-bipyrimidine]-2,2'-diamine (418 mg, yield: 65.2%). LCMS $[M+1]^+$=269

Step 2: Example 286 (TDM-180886)

The compound 286d (namely, 2,2-difluorocyclopropane-1-carboxylic acid) (34 mg, 0.282 mmol) and phosphorus oxychloride (85.06 mg, 0.558 mmol) was added to a solution of compound 286c (50 mg, 0.186 mmol) in pyridine (5 mL) at 0° C., and the mixture was stirred for 3 hours. The mixture was then concentrated under reduced pressure, and the residue was passed through silica gel chromatography (dichloromethane:dichloromethane containing 10% methanol=50:50) and purified to obtain a yellow solid compound 286, TDM-180886, namely, 2,2-difluoro-N-(2-((1-methyl-1H-pyrazol-4-yl)amino)-[4,5'-bipyrimidin]-2'-yl)cyclopropane-1 carboxamide (7.1 mg, yield: 10.3%). LCMS $[M+1]^+$= 373.1

$^1$H NMR (400 MHz, DMSO-$d_6$) δ 11.39 (s, 1H), 9.60 (s, 1H), 9.36 (s, 2H), 8.53 (d, J=5.1 Hz, 1H), 7.94 (s, 1H), 7.54 (s, 1H), 7.39 (d, J=5.2 Hz, 1H), 3.83 (s, 3H), 3.21 (dd, J=22.1, 10.1 Hz, 1H), 2.03 (ddd, J=15.8, 12.5, 5.8 Hz, 2H).

Compounds prepared in a similar method are as follows:

| Structure Structural formula | TDM No. Registration number | LCMS $[M + 1]^+$ | $^1$H-NMR Proton nuclear magnetic resonance spectroscopy |
|---|---|---|---|
| 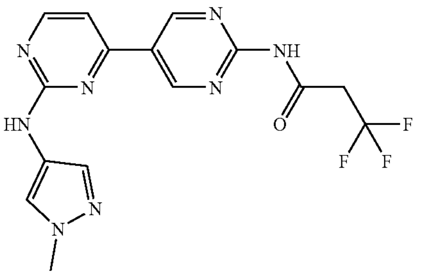 [SMILES: Cn1cc(Nc2nccc(-c3cnc(NC(=O)CC(F)(F)F)nc3)n2)cn1] | TDM-180887 | 379.2 | $^1$H NMR (400 MHz, DMSO-$d_6$) δ 11.25 (s, 1H), 9.60 (s, 1H), 9.36 (s, 2H), 8.54 (d, J = 5.1 Hz, 1H), 7.95 (s, 1H), 7.54 (s, 1H), 7.39 (d, J = 5.2 Hz, 1H), 3.83 (s, 3H), 3.78 (d, J = 11.1 Hz, 2H). |

-continued

| Structure Structural formula | TDM No. Registration number | LCMS [M + 1]+ | $^1$H-NMR Proton nuclear magnetic resonance spectroscopy |
|---|---|---|---|
| 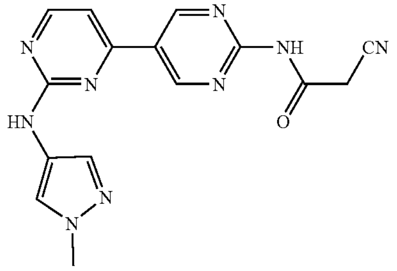 [SMILES: Cn1cc(Nc2nccc(-c3cnc(NC(=O)CC#N)nc3)n2)cn1] | TDM-180902 | 336 | $^1$H NMR (400 MHz, DMSO-$d_6$) δ 11.30 (s, 1H), 9.60 (s, 1H), 9.36 (s, 2H), 8.54 (d, J = 5.2 Hz, 1H), 7.94 (s, 1H), 7.55 (s, 1H), 7.39 (d, J = 5.2 Hz, 1H), 4.24 (s, 2H), 3.84 (s, 3H). |
| 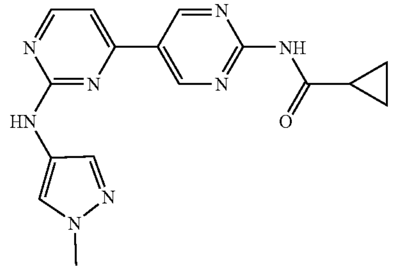 [SMILES: Cn1cc(Nc2nccc(-c3cnc(NC(=O)C4CC4)nc3)n2)cn1] | TDM-180904 | 337.2 | $^1$H NMR (400 MHz, DMSO-$d_6$) δ 11.17 (s, 1H), 9.59 (s, 1H), 9.33 (s, 2H), 8.53 (d, J = 3.9 Hz, 1H), 7.95 (s, 1H), 7.54 (s, 1H), 7.38 (d, J = 5.2 Hz, 1H), 4.24 (s, 2H), 3.84 (s, 3H), 2.14-2.25 (m, 1H), 0.82-0.92 (m, 4H). |

TDM-180887, a yellow solid compound 287, namely 3,3,3-trifluoro-N-(2-((1-methyl-1H-pyrazol-4-yl)amino)-[4,5'-bipyrimidin]-2'-yl)propanamide (8.7 mg, yield: 12.4%)

TDM-180902, a yellow solid compound 302 (52.9 mg, purity: approximately 80%, yield: 42%).

2-cyano-N-(2-((1-methyl-1H-pyrazol-4-yl)amino)-[4,5'-bipyrimidin]-2'-yl) acetamide TDM-180904, a yellow solid compound 304 (25.3 mg, yield: 20%).

N-(2-((1-methyl-1H-pyrazol-4-yl)amino)-[4,5'-bipyrimidin]-2'-yl)cyclopropanecarboxamide

Example 31: General Method for Synthesizing Compound 288 (TDM-180888)

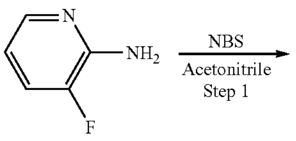

Example 288a

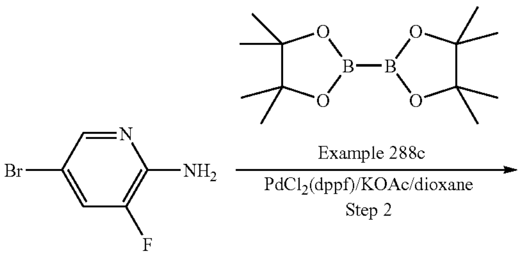

Example 288b

-continued

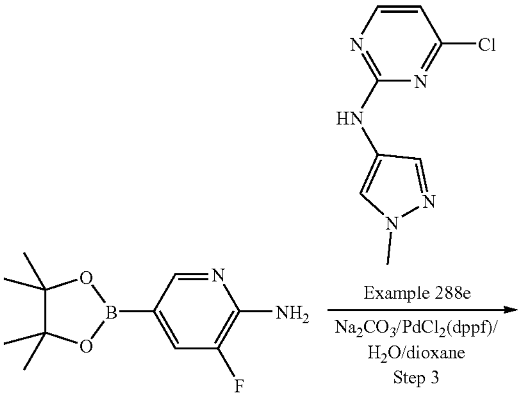

Example 288d

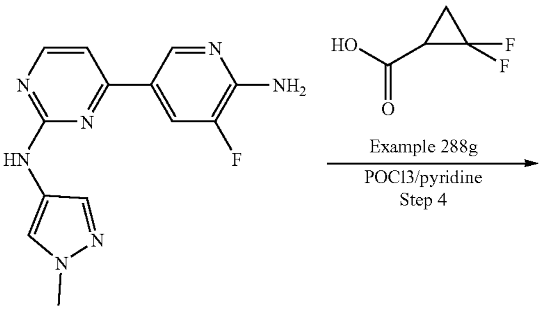

Example 288f

-continued

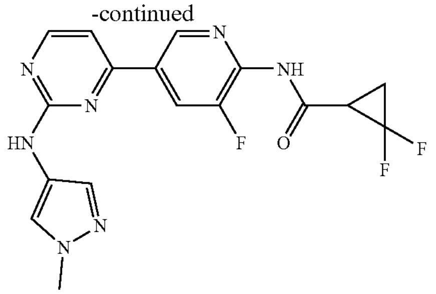

Example 288 (TDM-180888)

Step 1: Example 288b

The compound 288a (0.3 g, 2.68 mmol) was dissolved in acetonitrile (15 mL) and N-bromosuccinimide (0.48 g, 2.68 mmol) was added. The mixture was stirred for 3 hours at room temperature. After removal of the solvent, the mixture was purified via silica gel chromatography (ethyl acetate: petroleum ether=40:60) to obtain a white solid compound 288b, namely 5-bromo-3-fluoropyridin-2-amine (0.436 g, yield: 85.1%). LCMS $[M+1]^+$=191.1.

Step 2: Example 288d

The compound 288b (0.436 g, 2.27 mmol), compound 288c (1.152 g, 4.54 mmol), potassium acetate (0.668 g, 6.81 mmol) and $PdCl_2$ (dppf) (0.166 g, 0.23 mmol) were dissolved in 1,4-dioxane (10 mL). Nitrogen displacement was employed three times. The reaction solution was heated to 90° C. and stirred for 17 hours. The reaction solution was cooled to room temperature and filtered, the filter cake was rinsed with ethyl acetate (15 mL×2), the filtrate was concentrated, and the concentrate was purified via silica gel chromatography (ethyl acetate:petroleum ether=0-50%) to obtain a yellow solid compound 288d, namely, 3-fluoro-5-(4,4,5,5-tetramethyl-1,3,2-dioxaborolane-2-yl)pyridin-2-amine (0.84 g, crude product). LCMS $[M+1]^+$=156.1.

Step 3: Example 288f

The compound 288e (396.1 mg, 1.89 mmol), compound 288d (540 mg, 2.27 mmol), sodium carbonate (300.5 mg, 2.83 mmol) and $PdCl_2$ (dppf) (276.6 mg, 0.38 mmol) were added to a mixture solution of 1,4-dioxane (30 mL) and water (3 mL), nitrogen displacement was employed three times, and the mixture solution was then heated to 105° C. and stirred for 4 hours. The reaction solution was cooled to room temperature and filtered, the filter cake was washed with ethyl acetate (20 mL×2), the filtrate was concentrated, and the concentrate was purified via silica gel chromatography (methanol:dichloromethane=0-3%) to obtain a brown solid compound 288f, namely 4-(6-amino-5-fluoropyridin-3-yl)-N-(1-methyl-1H-pyrazol-4-yl)pyrimidin-2-amine (0.48 g, yield: 88.9%). LCMS $[M+1]^+$=286.1.

Step 4: Example 288 (TDM-180888)

Compound 288g (25.7 mg, 0.21 mmol) was added to compound 288f (50 mg, 0.18 mmol) in pyridine solution (5 mL). $POCl_3$ (40.3 mg, 0.26 mmol) was slowly added at 0° C. The reaction solution was stirred for 2 hours at 0° C. After the solvent was removed, the concentrate was purified via silica gel chromatography (methanol:dichloromethane=0-6%) to obtain the crude product. The crude product was further purified via preparative HPLC to obtain compound 288, namely 2,2-difluoro-N-(3-fluoro-5-(2-((1-methyl-1H-pyrazol-4-yl)amino)pyrimidin-4-yl)pyridin-2-yl)cyclopropanecarboxamide (3.4 mg, yield: 4.7%). LCMS $[M+1]^+$=390.1.

$^1$H NMR (400 MHz, DMSO) δ 11.00 (s, 1H), 9.60 (s, 1H), 9.02 (s, 1H), 8.54 (d, J=5.2 Hz, 1H), 8.42 (dd, J=11.1, 1.8 Hz, 1H), 7.92 (s, 1H), 7.55 (s, 1H), 7.41 (d, J=5.2 Hz, 1H), 3.83 (s, 3H), 2.97 (dt, J=13.5, 9.9 Hz, 1H), 2.04 (dd, J=18.9, 9.1 Hz, 2H).

Compounds prepared in a similar method are as follows:

| Structure Structural formula | TDM No. Registration number | LCMS $[M + 1]^+$ | $^1$H-NMR Proton nuclear magnetic resonance spectroscopy |
|---|---|---|---|
| 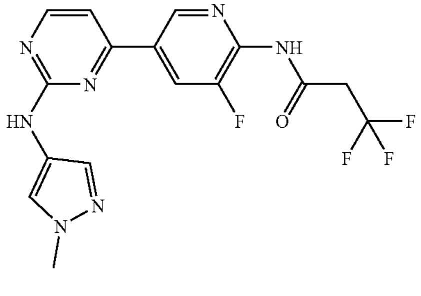 [SMILES: Cn1cc(Nc2nccc(-c3cnc(NC(=O)CC(F)(F)F)c(F)c3)n2)cn1] | TDM-180889 | 396.2 | $^1$H NMR (400 MHz, DMSO) δ 10.90 (s, 1H), 9.60 (s, 1H), 9.03 (d, J = 0.9 Hz, 1H), 8.55 (d, J = 5.0 Hz, 1H), 8.44 (dd, J = 11.1, 1.8 Hz, 1H), 7.92 (s, 1H), 7.55 (s, 1H), 7.41 (d, J = 5.2 Hz, 1H), 3.83 (s, 3H), 3.67 (q, J = 11.1 Hz, 2H). |
| 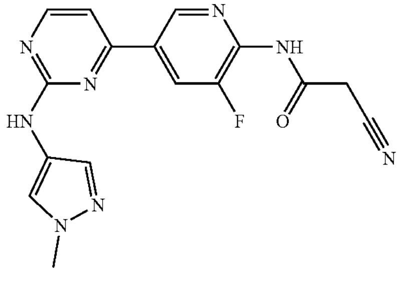 [SMILES: Cn1cc(Nc2nccc(-c3cnc(NC(=O)CC#N)c(F)c3)n2)cn1] | TDM-180890 | 353.2 | $^1$H NMR (400 MHz, DMSO) δ 10.92 (s, 1H), 9.60 (s, 1H), 9.02 (s, 1H), 8.55 (d, J = 5.1 Hz, 1H), 8.44 (dd, J = 11.1, 1.7 Hz, 1H), 7.92 (s, 1H), 7.55 (s, 1H), 7.40 (d, J = 5.2 Hz, 1H), 4.08 (s, 2H), 3.83 (s, 3H). |

-continued

| Structure Structural formula | TDM No. Registration number | LCMS $[M + 1]^+$ | $^1$H-NMR Proton nuclear magnetic resonance spectroscopy |
|---|---|---|---|
| 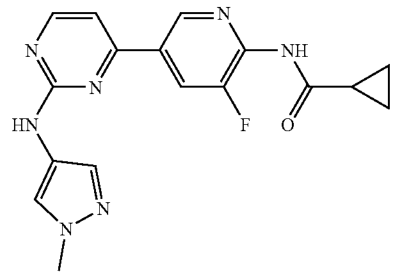 [SMILES: Cn1cc(Nc2nccc(-c3cnc(NC(=O)C4CC4)c(F)c3)n2)cn1] | TDM-180891 | 354.2 | $^1$H NMR (400 MHz, DMSO) δ 10.74 (s, 1H), 9.58 (s, 1H), 9.00 (d, J = 0.9 Hz, 1H), 8.53 (d, J = 5.1 Hz, 1H), 8.38 (dd, J = 11.1, 1.8 Hz, 1H), 7.92 (s, 1H), 7.55 (s, 1H), 7.39 (d, J = 5.2 Hz, 1H), 3.82 (d, J = 5.0 Hz, 3H), 1.95 (ddd, J = 12.5, 7.5, 4.9 Hz, 1H), 0.85 (dq, J = 4.4, 2.8 Hz, 4H). |

TDM-180889, a yellow solid compound 289, namely 3,3,3-trifluoro-N-(3-fluoro-5-(2-((1-methyl-1H-pyrazol-4-yl)amino)pyrimidin-4-yl)pyridin-2-yl)propanamide (7.6 mg, yield: 9.2%).

TDM-180890, a yellow solid compound 290, namely 2-cyano-N-(3-fluoro-5-(2-((1-methyl-1H-pyrazol-4-yl)amino)pyrimidin-4-yl)pyridin-2-yl) acetamide (2.2 mg, yield: 3.0%).

TDM-180891, a yellow solid compound 291, namely N-(3-fluoro-5-(2-((1-methyl-1H-pyrazol-4-yl)amino)pyrimidin-4-yl)pyridin-2-yl)cyclopropanecarboxamide (3.5 mg, yield: 4.7%).

Example 32: General Method for Synthesizing Compound 306 (TDM-180906)

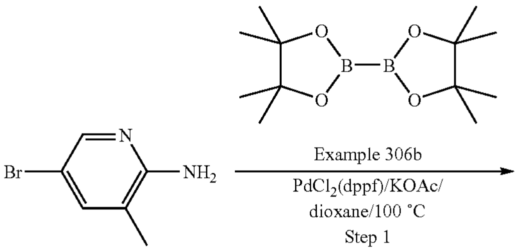

Example 306a

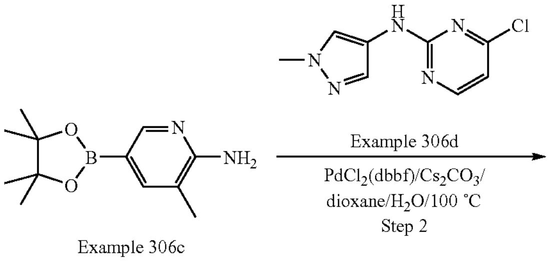

Example 306c

-continued

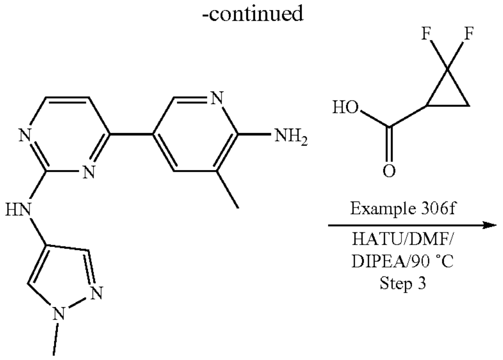

Example 306e

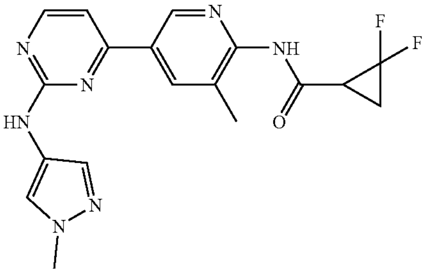

Example 306 (TDM-180906)

Step 1: Example 306c

Dioxane (40 mL) was added to a mixture of compound 306a (1 g, 5.346 mmol) (namely, 5-bromo-3-methylpyridin-2-amine), compound 306b (2.036 g, 8.02 mmol) (namely, bis(pinacolato)diboron), 1,1'-bis(diphenylphosphino) ferrocene-palladium-dichloride (390 mg, 0.535 mmol) and potassium acetate (1.407 g, 10.692 mmol). The mixture was degassed under vacuum, nitrogen displacement was employed several times, and the mixture was heated to 100° C. and stirred overnight. The mixture was directly used in the next reaction without purification. LCMS $[M+1]^+$= 235&153

Step 2: Example 306c

Compound 306d (1.117 g, 5.346 mmol), namely, 4-chloro-N-(1-methyl-1H-pyrazol-4-yl)pyrimidin-2-amine, 1,1'-bis(diphenylphosphino) ferrocene-palladium dichloride (390 mg, 0.535 mmol), cesium carbonate (3.474 g, 10.692 mmol) and water (7 mL) were added to the mixture in the last step. The mixture was degassed under vacuum, nitrogen displacement was employed several times, and then the mixture was heated to 100° C. and stirred for 2 hours. The mixture was concentrated under reduced pressure, and the residue was purified via silica gel chromatography (dichloromethane:dichloromethane containing 10% methanol=60:40) to obtain an off-white solid compound 306e, namely 4-(6-amino-5-methylpyridin-3-yl)-N-(1-methyl-1H-pyrazol-4-yl)pyrimidin-2-amine (240 mg, yield: 16%). LCMS $[M+1]^+$=282

Step 3: Example 306 (TDM-180906)

N,N-diisopropylethylamine (137.6 mg, 1.065 mmol) was added to compound 306e (100 mg, 0.355 mmol) in a solution of N,N-dimethylformamide (10 mL) at room temperature, the mixture was stirred for 5 minutes, and then 2-(7-benzotriazole oxide)-N,N,N',N'-tetramethylurea hexafluorophosphate (202 mg, 0.107 mmol) and compound 306f (namely, 2,2-difluorocyclopropane-1-carboxylic acid) (65 mg, 0.533 mmol) were added into the mixture. The mixture was heated to 90° C. and stirred for 2 hours. The mixture was concentrated under reduced pressure, and the residue was passed through silica gel chromatography (dichloromethane:dichloromethane containing 10% methanol=50:50) and purified (via HCOOH) to obtain a yellow solid compound 306, TDM-180906, (namely, 2,2-difluoro-N-(3-methyl-5-(2-((1-methyl-1H-pyrazol-4-yl)amino)pyrimidin-4-yl)pyridin-2-yl)cyclopropane-1-carboxamide (12 mg, yield: 8.8%). LCMS $[M+1]^+$=386.2

$^1$H NMR (400 MHz, DMSO-$d_6$) δ 10.68 (s, 1H), 9.57 (s, 1H), 9.00 (d, J=2.0 Hz, 1H), 8.52 (d, J=5.1 Hz, 1H), 8.37 (d, J=1.7 Hz, 1H), 7.93 (s, 1H), 7.55 (s, 1H), 7.35 (d, J=5.2 Hz, 1H), 3.83 (s, 3H), 2.95 (ddd, J=13.8, 10.7, 8.2 Hz, 1H), 2.26 (s, 3H), 2.09-1.93 (m, 2H).

Compounds prepared in a similar method are as follows:

| Structure Structural formula | TDM No. Registration number | LCMS $[M + 1]^+$ | $^1$H-NMR Proton nuclear magnetic resonance spectroscopy |
|---|---|---|---|
| 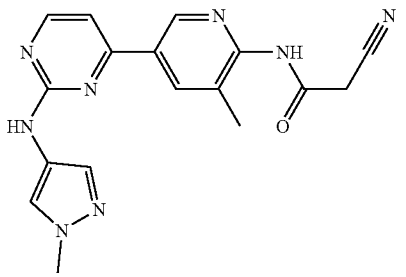 [SMILES: Cc1cc(-c2ccnc(Nc3cnn(C)c3)n2)cnc1NC(=O)CC#N] | TDM-180907 | 349.2 | $^1$H NMR (400 MHz, DMSO-$d_6$) δ 10.55 (s, 1H), 9.57 (s, 1H), 8.99 (d, J = 1.9 Hz, 1H), 8.52 (d, J = 5.1 Hz, 1H), 8.38 (d, J = 1.8 Hz, 1H), 7.93 (s, 1H), 7.55 (s, 1H), 7.35 (d, J = 5.2 Hz, 1H), 4.03 (s, 2H), 3.83 (s, 3H), 2.29 (s, 3H). |
| 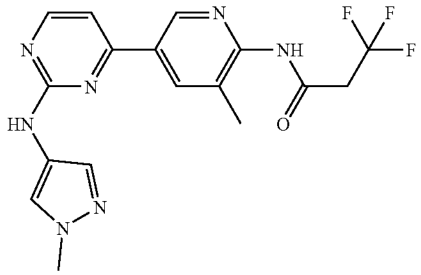 [SMILES: Cc1cc(-c2ccnc(Nc3cnn(C)c3)n2)cnc1NC(=O)CC(F)(F)F] | TDM-180908 | 392.2 | $^1$H NMR (400 MHz, DMSO-$d_6$) δ 10.60 (s, 1H), 9.57 (s, 1H), 9.01 (d, J = 1.7 Hz, 1H), 8.52 (d, J = 5.1 Hz, 1H), 8.38 (d, J = 1.6 Hz, 1H), 7.93 (s, 1H), 7.55 (s, 1H), 7.35 (d, J = 5.2 Hz, 1H), 3.83 (s, 3H), 3.62 (q, J = 11.2 Hz, 2H), 2.27 (s, 3H). |
| 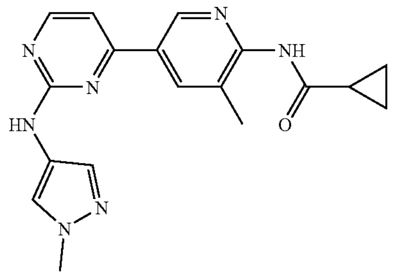 [SMILES: Cc1cc(-c2ccnc(Nc3cnn(C)c3)n2)cnc1NC(=O)C1CC1] | TDM-180910 | 350.2 | $^1$H NMR (400 MHz, DMSO-$d_6$) δ 10.43 (s, 1H), 9.55 (s, 1H), 8.98 (d, J = 2.0 Hz, 1H), 8.50 (d, J = 5.1 Hz, 1H), 8.33 (d, J = 1.8 Hz, 1H), 7.93 (s, 1H), 7.55 (s, 1H), 7.34 (d, J = 5.2 Hz, 1H), 3.83 (s, 3H), 2.24 (s, 3H), 2.00-1.84 (m, 1H), 0.88-0.76 (m, 4H). |

Example 32: General Method for Synthesizing Compound 307 (TDM-180907)

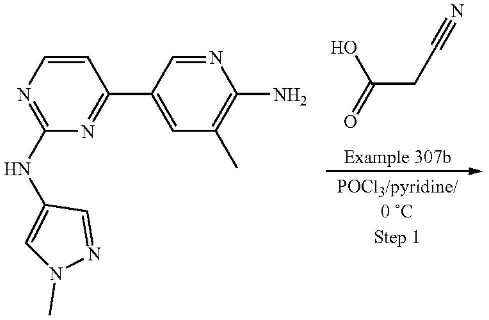

Example 307a

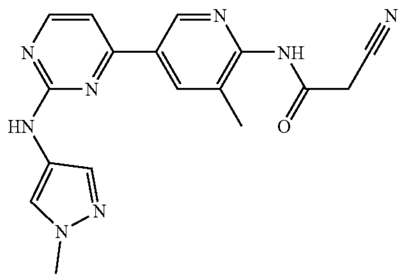

Example 307 (TDM-180907)

Step 1: Example 307 (TDM-180907)

Compound 307b (namely, cyanoacetic acid) (31.8 mg, 0.373 mmol) and phosphorus oxychloride (76.4 mg, 0.498 mmol) were added to compound 307a (namely, 4-(6-amino-5-methylpyridin-3-yl)-N-(1-methyl-1H-pyrazol-4-yl)pyrimidin-2-amine) (70 mg, 0.249 mmol) in a pyridine solution (5 mL) at 0° C. The mixture was stirred for 1 hour. The mixture was concentrated under reduced pressure, the residue was dissolved with dichloromethane solution containing 10% methanol, water was added, the aqueous phase was extracted with dichloromethane solution containing 10% methanol (50 mL×2), the organic phase was washed with saturated brine, and dried over anhydrous sulfuric acid sodium, the filtrate was concentrated under reduced pressure, ethyl acetate and petroleum ether were added to the residue, and the mixture was filtered to collect a yellow solid compound 307, TDM-180907, namely 2-cyano-N-(3-methyl-5-(2-((1-methyl-1H-pyrazol-4-yl)amino)pyrimidin-4-yl)pyridin-2-yl) acetamide (15.2 mg, yield: 17.5%). LCMS $[M+1]^+=349.2$ $^1H$ NMR (400 MHz, DMSO-$d_6$) δ 10.55 (s, 1H), 9.57 (s, 1H), 8.99 (d, J=1.9 Hz, 1H), 8.52 (d, J=5.1 Hz, 1H), 8.38 (d, J=1.8 Hz, 1H), 7.93 (s, 1H), 7.55 (s, 1H), 7.35 (d, J=5.2 Hz, 1H), 4.03 (s, 2H), 3.83 (s, 3H), 2.29 (s, 3H).

TDM-180908

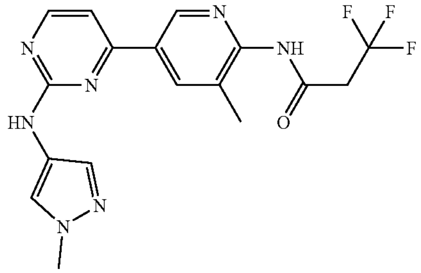 [SMILES: Cc1cc(-c2ccnc(Nc3cnn(C)c3)n2)cnc1NC(=O)CC(F)(F)F]

A yellow solid compound 308, namely 3,3,3-trifluoro-N-(3-methyl-5-(2-((1-methyl-1H-pyrazol-4-yl)amino)pyrimidin-4-yl)pyridin-2-yl)propanamide (27.4 mg, yield: 28.1%).

$^1H$ NMR (400 MHz, DMSO-d6) δ 10.60 (s, 1H), 9.57 (s, 1H), 9.01 (d, J=1.7 Hz, 1H), 8.52 (d, J=5.1 Hz, 1H), 8.38 (d, J=1.6 Hz, 1H), 7.93 (s, 1H), 7.55 (s, 1H), 7.35 (d, J=5.2 Hz, 1H), 3.83 (s, 3H), 3.62 (q, J=11.2 Hz, 2H), 2.27 (s, 3H).

TDM-180910

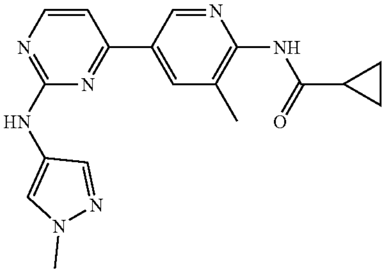 [SMILES: Cc1cc(-c2ccnc(Nc3cnn(C)c3)n2)cnc1NC(=O)C1CC1]

A yellow solid compound 310, namely N-(3-methyl-5-(2-((1-methyl-1H-pyrazol-4-yl)amino)pyrimidin-4-yl)pyridin-2-yl)cyclopropanemethane (11.4 mg, yield: 8%).

$^1H$ NMR (400 MHz, DMSO-d6) δ 10.43 (s, 1H), 9.55 (s, 1H), 8.98 (d, J=2.0 Hz, 1H), 8.50 (d, J=5.1 Hz, 1H), 8.33 (d, J=1.8 Hz, 1H), 7.93 (s, 1H), 7.55 (s, 1H), 7.34 (d, J=5.2 Hz, 1H), 3.83 (s, 3H), 2.24 (s, 3H), 2.00-1.84 (m, 1H), 0.88-0.76 (m, 4H).

Example 33: General Method for Synthesizing Compound 177 (TDM-180777)

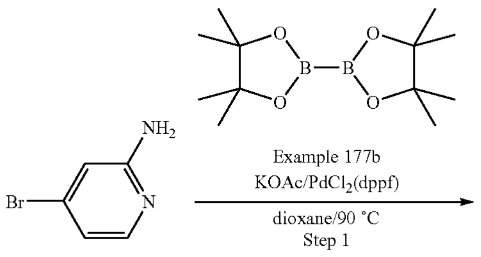

Example 177a

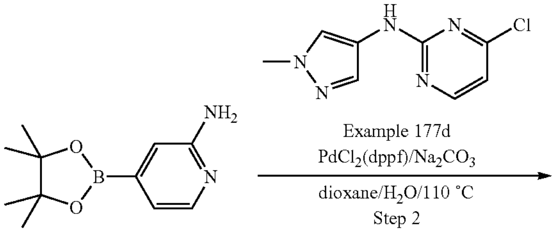

Example 177c

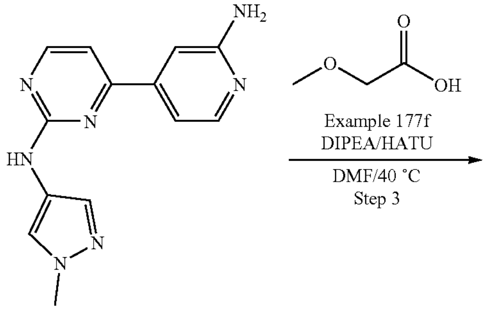

Example 177e

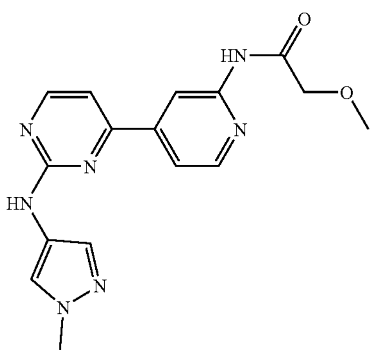

Example 177 (TDM-180777)

Step 1: Example 177c

Potassium acetate (588 mg, 6 mmol) and 1,1'-bis(diphenylphosphino) ferrocene-palladium dichloride (175.4 mg, 0.24 mmol) were added to a mixture of compound 177a (415 mg, 2.4 mmol) (namely, 4-bromopyridin-2-amine) and compound 177b (namely, bis(pinacolato)diboron) (792.3 mg, 3.12 mmol), and then dioxane (50 mL) was added to the mixture. Nitrogen displacement was employed several times under vacuum, and then the mixture was heated to 90° C. and reacted for 8 hours. The reaction solution was directly used for the next reaction. LCMS $[M+1]^+=221$.

Step 2: Example 177e

Compound 177d (415 mg, 2 mmol), namely, 4-chloro-N-(1-methyl-1H-pyrazol-4-yl)pyrimidin-2-amine, 1,1'-bis(diphenylphosphino) ferrocene-palladium dichloride (175.4 mg, 0.24 mmol), sodium carbonate (424 mg, 4 mmol) and water (6 mL) were added to the reaction solution in the last step. Nitrogen displacement was employed for the mixture several times under vacuum, and then the mixture was heated to 110° C. and stirred for 18 hours. The mixture was concentrated under reduced pressure, and purified via silica gel chromatography (dichloromethane:methanol=20:1) to obtain a dark green solid compound 177e, namely 4-(2-aminopyridin-4-yl)-N-(1-methyl-1H-pyrazol-4-yl)pyrimidin-2-amine (90 mg, yield: 16.8%). LCMS $[M+1]^+=268$.

Step 3: Example 177 (TDM-180777)

2-methoxy-N-(4-(2-((1-methyl-1H-pyrazol-4-yl)amino)pyrimidin-4-yl)pyridin-2-yl) acetamide N,N-diisopropylethylamine (72.4 mg, 0.374 mmol) was added to compound 177e (50 mg, 0.187 mmol) in a solution of N,N-dimethylformamide (10 mL) at room temperature, the mixture was stirred for 5 minutes, and then 2-(7-benzotriazole oxide)-N,N,N',N'-tetramethylurea hexafluorophosphate (141.1 mg, 0.374 mmol) and compound 177f (namely, 2-methoxyacetic acid) (33.7 mg, 0.374 mmol) were added into the mixture. The mixture was heated to 40° C. and stirred for 16 hours. The mixture was concentrated under reduced pressure to remove the solvent, water was added to the residue and the solution was extracted with dichloromethane (3×60 mL), the organic phases were combined and washed with saturated brine and dried over sodium sulfate, the filtrate was concentrated under reduced pressure and purified via silica gel chromatography (dichloromethane:dichloromethane solution containing 10% methanol=30:70) and preparation, to obtain an orange solid compound 177, TDM-180777, (namely, 2-methoxy-N-(4-(2-((1-methyl-1H-pyrazol-4-yl)amino)pyrimidin-4-yl)pyridin-2-yl) acetamide) (8.9 mg, yield: 14%). LCMS $[M+1]^+=340.1$.

$^1$H NMR (400 MHz, DMSO-d$_6$) δ 10.25 (s, 1H), 9.73 (s, 1H), 9.10 (s, 1H), 8.59 (d, J=5.0 Hz, 1H), 8.50 (d, J=5.2 Hz, 1H), 8.28 (s, 1H), 7.80 (s, 1H), 7.49 (s, 1H), 7.38 (s, 1H), 4.14 (s, 2H), 3.91 (s, 3H), 3.41 (s, 3H).

Compounds prepared in a similar method are as follows:

| Structure Structural formula | TDM No. Registration number | LCMS $[M + 1]^+$ | $^1$H-NMR Proton nuclear magnetic resonance spectroscopy |
|---|---|---|---|
| 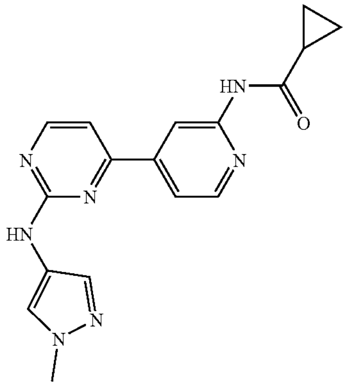 [SMILES: Cn1cc(Nc2nccc(-c3ccnc(NC(=O)C4CC4)c3)n2)cn1] | TDM-180773 | 336 | $^1$H NMR (400 MHz, DMSO-$d_6$) δ 11.03 (s, 1H), 9.71 (s, 1H), 9.16 (br s, 1H), 8.58 (d, J = 4.8 Hz, 1H), 8.48 (d, J = 4.8 Hz, 1H), 8.31 (br s, 1H), 7.55 (brs, 1H), 7.69-7.80 (m, 1H), 7.29-7.50 (m, 2H), 3.89 (s, 3H), 2.00-2.15 (m, 1H), 0.75-0.99 (m, 4H). |
| 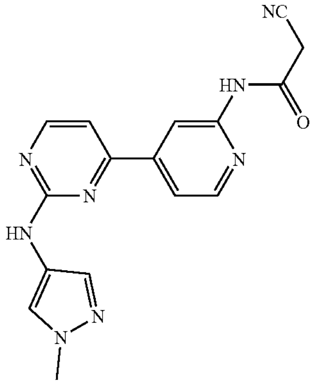 | TDM-180774 | 335.1 | $^1$H NMR (400 MHz, DMSO) δ 11.07 (s, 1H), 9.73 (s, 1H), 9.10 (s, 1H), 8.60 (d, J = 5.0 Hz, 1H), 8.51 (d, J = 5.2 Hz, 1H), 8.31 (s, 1H), 7.82 (s, 1H), 7.48 (s, 1H), 7.40 (s, 1H), 4.07 (s, 2H), 3.94 (s, 3H). |
| 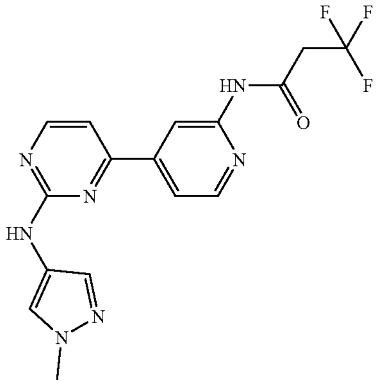 [SMILES: Cn1cc(Nc2nccc(-c3ccnc(NC(=O)CC(F)(F)F)c3)n2)cn1] | TDM-180790 | 378.1 | $^1$H NMR (400 MHz, DMSO-$d_6$) δ 11.09 (s, 1H), 9.74 (s, 1H), 9.14 (s, 1H), 8.59 (d, J = 5.0 Hz, 1H), 8.52 (d, J = 5.2 Hz, 1H), 8.30 (s, 1H), 7.83 (s, 1H), 7.43 (d, J = 18.3 Hz, 2H), 3.90 (s, 3H), 3.72 (dd, J = 21.8, 10.9 Hz, 2H). |
| 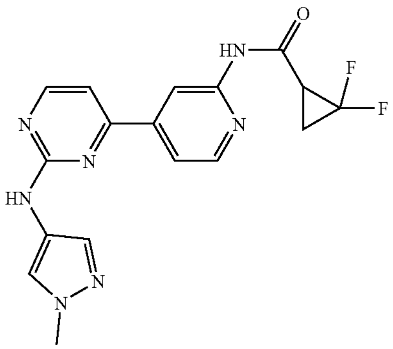 [SMILES: Cn1cc(Nc2nccc(-c3ccnc(NC(=O)C4CC4(F)F)c3)n2)cn1] | TDM-180792 | 372.1 | $^1$H NMR (400 MHz, DMSO-$d_6$) δ 11.24 (s, 1H), 9.72 (s, 1H), 9.12 (s, 1H), 8.59 (d, J = 5.0 Hz, 1H), 8.52 (d, J = 5.2 Hz, 1H), 8.29 (s, 1H), 7.81 (s, 1H), 7.42 (d, J = 20.4 Hz, 2H), 3.87 (s, 3H), 3.07 (dd, J = 22.6, 9.4 Hz, 1H), 2.07 (dd, J = 18.6, 8.9 Hz, 2H). |

TDM-180773, N-(4-(2-((1-methyl-1H-pyrazol-4-yl) amino)pyrimidin-4-yl)-pyrid in-2-yl)cyclopropanemethane, a yellow solid compound 773 (5.9 mg, yield: <10%) [The product was poorly soluble and repurification was attempted via preparative HPLC, but the product was also poorly soluble in DMF.]

TDM-180774, a yellow solid compound 174 (2.5 mg, yield: 3.2%).

2-cyano-N-(4-(2-((1-methyl-1H-pyrazol-4-yl)amino)pyrimidin-4-yl)pyridin-2-yl) acetamide TDM-180790, an orange solid compound 190, namely 3,3,3-trifluoro-N-(4-(2-((1-methyl-1H-pyrazol-4-yl) amino)pyrimidin-4-yl)pyridin-2-yl)propanamide (6.9 mg, yield: 4.9%)

TDM-180792, a yellow solid compound 192, namely 2,2-difluoro-N-(4-(2-((1-methyl-1H-pyrazol-4-yl) amino)pyrimidin-4-yl)pyridin-2-yl)cyclopropane-1-carboxamide (25.4 mg, yield: 14.6%)

Example 34: General Method for Synthesizing Compound 243 (TDM-180843)

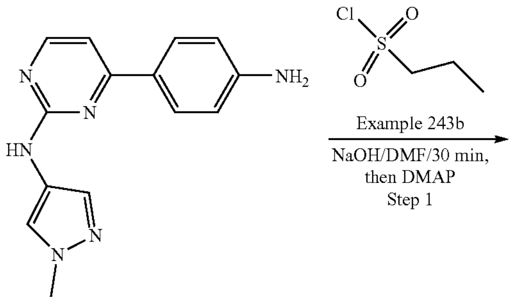

Example 243a

-continued

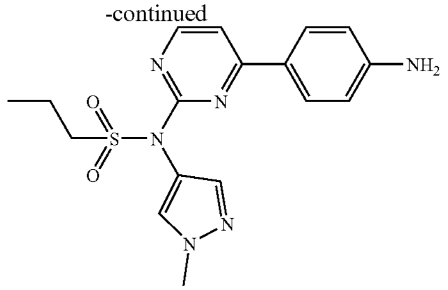

Example 243 (TDM-180843)

Step 1: Example 243 (TDM-180843)

N-(4-(4-aminophenyl)pyrimidin-2-yl)-N-(1-methyl-1H-pyrazol-4-yl) propane-1-sulfonamide NaOH (61 mg, 1.52 mmol) was added to a mixture of compound 243a (100 mg, 0.38 mmol) and DMF (6 mL). The reaction solution was stirred for 0.5 hours at room temperature. DMAP (approximately 5 mg) and compound 243b (162 mg, 1.14 mmol) were then added. The reaction solution was stirred for 1 hours at room temperature. After the reaction completed, the mixture was quenched with $H_2O$ (approximately 10 mL), extracted with EtOAc (approximately 20 mL×3), the organic layers were combined and washed with saturated aqueous LiCl solution (approximately 20 mL×3), dried over $Na_2SO_4$, filtered, concentrated, and purified via preparation (TFA system), and lyophilized. A pale green solid compound 243 (21.8 mg, yield: 15%) was obtained.

LCMS $[M+1]^+$=373.1

$^1$H NMR (400 MHz, DMSO-$d_6$) δ 8.46 (d, J=5.6 Hz, 1H), 7.92 (s, 1H), 7.85 (d, J=8.8 Hz, 2H), 7.54 (d, J=5.6 Hz, 1H), 7.48 (s, 1H), 6.68 (d, J=8.8 Hz, 2H), 3.89-3.98 (m, 2H), 3.86 (s, 3H), 1.79-1.94 (m, 2H), 1.03 (t, J=7.2 Hz, 3H).

Compounds prepared in a similar method are as follows:

| Structure Structural formula | TDM No. Registration number | LCMS $[M + 1]^+$ | $^1$H-NMR Proton nuclear magnetic resonance spectroscopy |
|---|---|---|---|
| 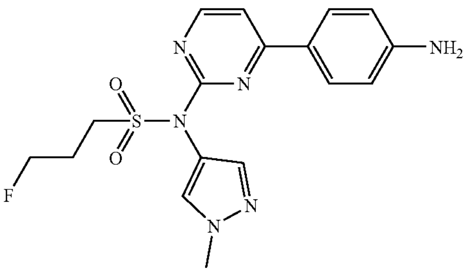 [SMILES: Cn1cc(N(c2nccc(-c3ccc(N)cc3)n2)S(=O)(=O)CCCF)cn1] | TDM-180845 | 391.1 | $^1$H NMR (400 MHz, DMSO-$d_6$) δ 8.47 (d, J = 5.2 Hz, 1H), 7.95 (s, 1H), 7.87 (d, J = 8.8 Hz, 2H), 7.56 (d, J = 5.2 Hz, 1H), 7.51 (s, 1H), 6.69 (d, J = 8.8 Hz, 2H), 4.65 (t, J = 5.6 Hz, 1H), 4.53 (t, J = 6.0 Hz, 1H), 4.05-4.12 (m, 2H), 3.86 (s, 3H), 2.15-2.30 (m, 2H). |
| 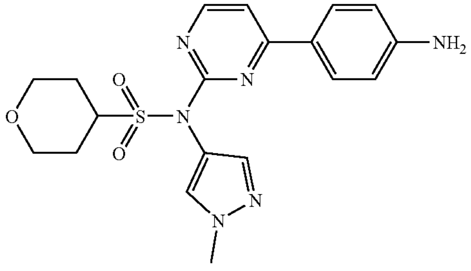 [SMILES: Cn1cc(N(c2nccc(-c3ccc(N)cc3)n2)S(=O)(=O)C2CCOCC2)cn1] | TDM-180848 | 415.1 | $^1$H NMR (400 MHz, DMSO) δ 8.47 (d, J = 5.4 Hz, 1H), 7.91 (s, 1H), 7.83 (d, J = 8.7 Hz, 2H), 7.54 (d, J = 5.5 Hz, 1H), 7.48 (d, J = 0.5 Hz, 1H), 6.67 (d, J = 8.7 Hz, 2H), 4.67 (s, 1H), 4.00 (dd, J = 11.4, 3.5 Hz, 2H), 3.85 (s, 3H), 3.35 (t, J = 11.0 Hz, 2H), 2.12 (d, J = 10.6 Hz, 2H), 1.77 (dd, J = 12.5, 4.4 Hz, 2H). |

-continued

| Structure Structural formula | TDM No. Registration number | LCMS [M + 1]+ | 1H-NMR Proton nuclear magnetic resonance spectroscopy |
|---|---|---|---|
| 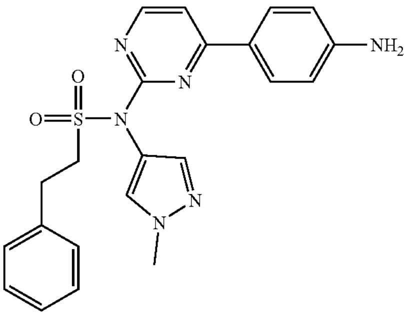 [SMILES: Cn1cc(N(c2nccc(-c3ccc(N)cc3)n2)S(=O)(=O)CCc2ccccc2)cn1] | TDM-180851 | 435.3 | $^1$H NMR (400 MHz, DMSO-$d_6$) δ 8.46 (d, J = 5.4 Hz, 1H), 7.95 (s, 1H), 7.84 (d, J = 8.7 Hz, 2H), 7.53 (dd, J = 7.4, 3.1 Hz, 2H), 7.35-7.27 (m, 4H), 7.26-7.19 (m, 1H), 6.66 (d, J = 8.7 Hz, 2H), 4.31-4.20 (m, 2H), 3.85 (s, 3H), 3.22-3.11 (m, 2H). |

TDM-180845, a pale green solid compound 245 (47.2 mg, yield: 30%).

N-(4-(4-aminophenyl)pyrimidin-2-yl)-3-fluoro-N-(1-methyl-1H-pyrazol-4-yl) propane-1-sulfonamide TDM-180848, a pale yellow solid compound (33.1 mg, yield: 21.3%).

N-(4-(4-aminophenyl)pyrimidin-2-yl)-N-(1-methyl-1H-pyrazol-4-yl)tetrahydro-2H-pyran-4-sulfonamide TDM-180851, a yellow solid compound 251, TDM-180851, namely N-(4-(4-aminophenyl)pyrimidin-2-yl)-N-(1-methyl-1H-pyrazol-4-yl)-2-phenylethane-1-sulfonamide (compound 251, 74.1 mg, yield: 45.4%).

Example 35: General Method for Synthesizing Compound 246 (TDM-180846)

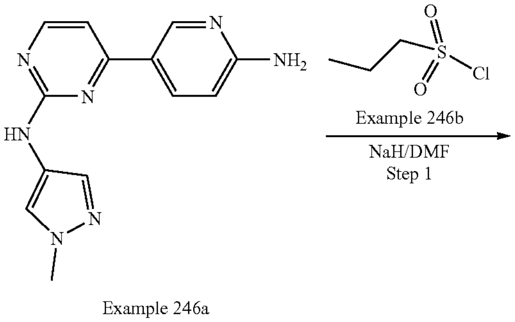

Example 246a

-continued

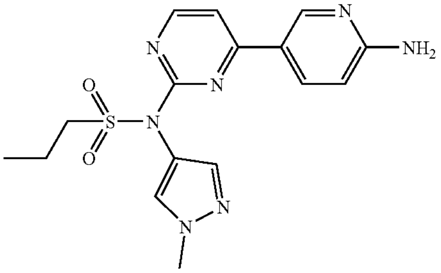

Example 246 (TDM-180846)

Step 1: Example 246 (TDM-180846)

N-(4-(6-aminopyridin-3-yl)pyrimidin-2-yl)-N-(1-methyl-1H-pyrazol-4-yl) propane-1-sulfonamide NaH (72 mg, 1.8 mmol) was added to a mixture of compound 246 (80 mg, 0.3 mmol) and DMF (10 mL). The mixture was stirred for 0.5 hours at room temperature. Compound 246b (128 mg, 0.9 mmol) was then added. The reaction solution was stirred for 3 minutes at room temperature. The mixture was quenched with HCl (1 N HCl) until pH was about 6, and concentrated to remove solvent, MeOH was added to the residue, the mixture was filtered (twice), and the filtrate was prepared and purified (TFA system), and lyophilized. A white solid compound 246 (33.7 mg, yield: 30%) was obtained.

LCMS $[M+1]^+$=374.1

$^1$H NMR (400 MHz, DMSO-$d_6$) δ 8.62-8.72 (m, 2H), 8.28-8.36 (m, 1H), 7.94 (s, 1H), 7.86 (br s, 1H), 7.71 (d, J=5.6 Hz, 1H), 7.50 (s, 1H), 6.91 (d, J=9.2 Hz, 1H), 3.80-3.97 (m, 5H), 1.76-1.93 (m, 1H), 1.03 (t, J=7.6 Hz, 3H).

Compounds prepared in a similar method are as follows:

| Structure Structural formula | TDM No. Registration number | LCMS $[M + 1]^+$ | $^1$H-NMR Proton nuclear magnetic resonance spectroscopy |
|---|---|---|---|
| 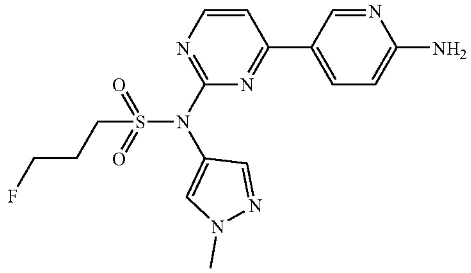 [SMILES: Cn1cc(N(c2nccc(-c3ccc(N)nc3)n2)S(=O)(=O)CCCF)cn1] | TDM-180847 | 392.1 | $^1$H NMR (400 MHz, DMSO-$d_6$) δ 8.62-8.72 (m, 2H), 8.28-8.38 (m, 1H), 7.94 (s, 1H), 7.89 (br s, 1H), 7.63 (d, J = 5.2 Hz, 1H), 7.53 (s, 1H), 6.92 (d, J = 8.8 Hz, 1H), 4.65 (t, J = 5.2 Hz, 1H), 4.53 (t, J = 6.0 Hz, 1H), 4.00-4.10 (m, 2H), 3.87 (s, 3H), 2.15-2.30 (m, 2H). |
| 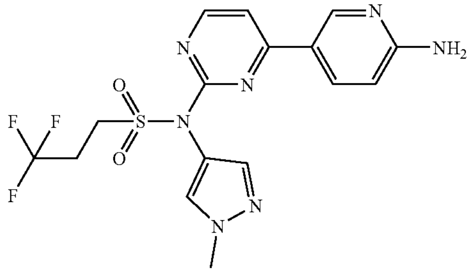 [SMILES: Cn1cc(N(c2nccc(-c3ccc(N)nc3)n2)S(=O)(=O)CCC(F)(F)F)cn1] | TDM-180856 | 428 | $^1$H NMR (400 MHz, DMSO) δ 8.70-8.63 (m, 2H), 8.26 (d, J = 9.2 Hz, 1H), 8.01 (s, 1H), 7.73 (d, J = 5.4 Hz, 1H), 7.58 (s, 1H), 6.84 (d, J = 8.7 Hz, 1H), 4.26-4.19 (m, 2H), 3.86 (s, 3H), 3.01-2.88 (m, 2H). |
| 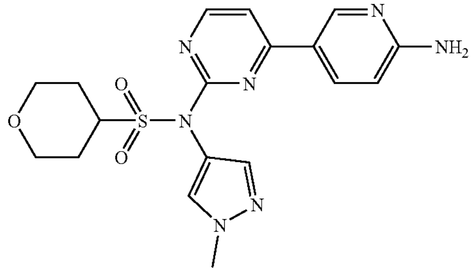 [SMILES: Cn1cc(N(c2nccc(-c3ccc(N)nc3)n2)S(=O)(=O)C2CCOCC2)cn1] | TDM-180857 | 416.2 | $^1$H NMR (400 MHz, DMSO-$d_6$) δ 8.72 (d, J = 2.4 Hz, 1H), 8.53 (d, J = 5.6 Hz, 1H), 7.98-8.06 (m, 1H), 7.93 (s, 1H), 7.61 (d, J = 5.2 Hz, 1H), 7.49 (s, 1H), 6.71 (s, 2H), 6.92 (d, J = 8.8 Hz, 1H), 6.54 (d, J = 8.8 Hz, 1H), 4.57-4.71 (m, 1H), 3.94-4.05 (m, 1H), 3.86 (s, 3H), 3.33-3.42 (m, 2H), 2.05-2.17 (m, 2H), 1.70-1.85 (m, 2H). |

TDM-180847, a pale yellow solid compound 247 (24.5 mg, yield: 21%).

N-(4-(6-aminopyridin-3-yl)pyrimidin-2-yl)-3-fluoro-N-(1-methyl-1H-pyrazol-4-yl) propane-1-sulfonamide TDM-180856, a white solid compound (example 256, 14.2 mg, yield: 11%)

N-(4-(6-aminopyridin-3-yl)pyrimidin-2-yl)-3,3,3-trifluoro-N-(1-methyl-1H-pyrazol-4-yl) propane-1-sulfonamide TDM-180857, a white solid compound 257 (7.9 mg, yield: <10%).

N-(4-(6-aminopyridin-3-yl)pyrimidin-2-yl)-N-(1-methyl-1H-pyrazol-4-yl)tetrahydro-2H-pyran-4-sulfonamide

Example 36: General Method for Synthesizing Compound 276 (TDM-180876)

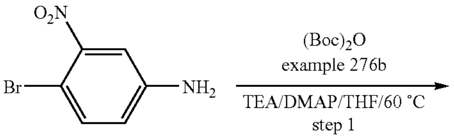

Example 276a

-continued

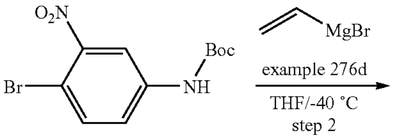

Example 276c

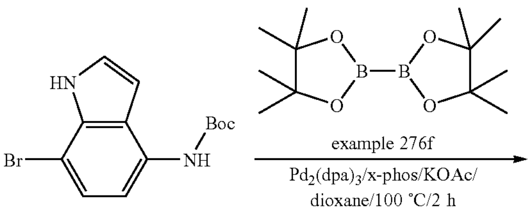

Example 276e step 3

-continued

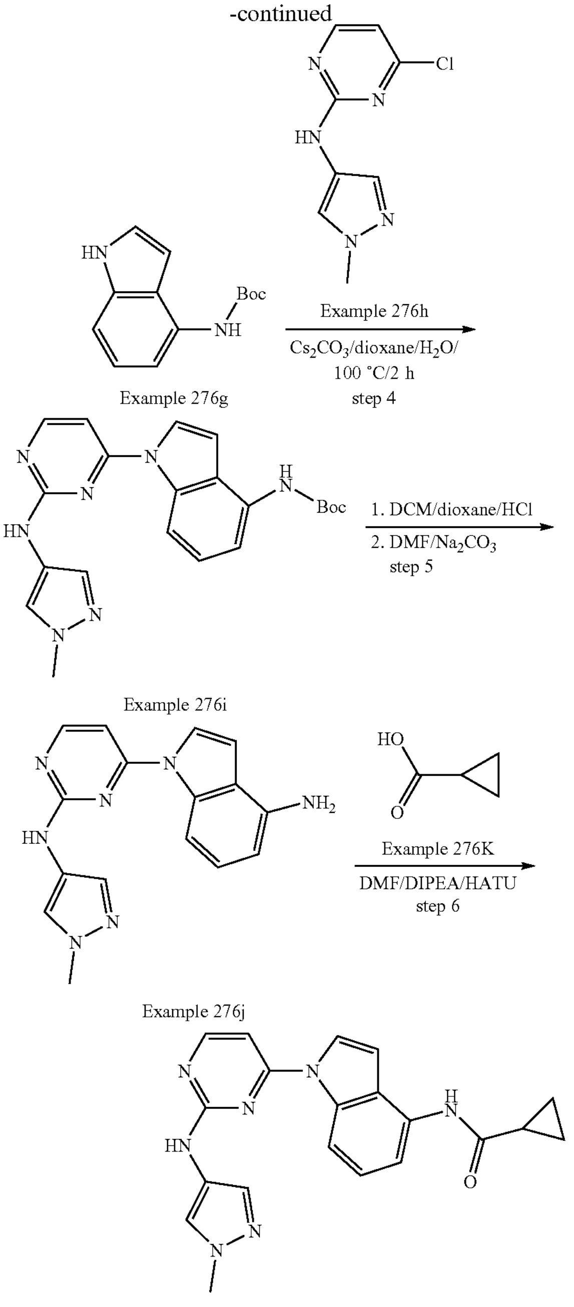

Example 276g

Example 276i

Example 276j

Example 276

Step 1: Example 276c

Tert-butyl (4-bromo-3-nitrophenyl)carbamate 4-dimethylaminopyridine (840 mg, 6.84 mmol), triethylamine (2 g, 20.28 mmol) and compound 276b (3.3 g, 15.2 mmol) were added to compound 276a (2.2 g, 10.14 mmol) in a solution of tetrahydrofuran (20 mL) at 0° C. The reaction solution was heated to 60° C. and stirred overnight until it was detected by TLC that the reaction of the raw material completed. The reaction solution was concentrated to dryness, water (20 mL) was added to the solid residue, ethyl acetate (3*20 mL) was added, the mixture was extracted three times, and the organic phases were combined, washed with saturated brine once, dried over anhydrous sodium sulfate, filtered via suction, and spin-dried. The crude product was passed through the column to obtain a yellow oily substance (example 276c, 2.6278 g, yield: 81.86%). LCMS $[M+1]^+$=261,263.

Step 2: Example 276e

Tert-butyl (7-bromo-1H-indol-4-yl)carbamate

The compound 276d (1.0 M in THF, 83 mL, 82.8 mmol) was slowly added to the compound 276c (2.6278 g, 8.28 mmol) in a solution of tetrahydrofuran (100 mL) at −40° C., and the mixture was stirred and held at −40° C. for 4 hours. LCMS was used for detection, and the product was obtained. MS [M-t-Bu+H]+=255, 257. After the reaction completed, saturated aqueous ammonium chloride solution (150 mL) was added to the mixture for quenching, and the mixture was stirred at room temperature for 1 hour, and then extracted with ethyl acetate. The organic phase was separated, washed with saturated brine, dried over anhydrous sodium sulfate, filtered via suction, and dried. The obtained crude product was passed through the column to obtain a yellow solid compound (example 276e, 989.7 mg, yield: 38.4%). LCMS [M-t-Bu+H]+=255, 257.

Step 3: Example 276g (1H-indole-4-yl)carbamate tert-butyl ester

The compound 276e (989.7 mg, 3.18 mmol), compound 276f (1211 mg, 4.77 mmol), tris(dibenzylideneacetone)dipalladium (582.4 mg, 0.636 mmol), 2-dicyclohexylphosphonium-2',4',6'-triisopropylbiphenyl (606 mg, 1.272 mmol), potassium acetate (935 mg, 9.54 mmol) and 1,4-dioxane (25 mL) were added to a 250 mL three-necked flask. Nitrogen displacement was employed several times, and the reaction solution was heated to 100° C. for two hours. When it was detected by LCMS that the reaction of the raw material completed, the reaction solution was concentrated and dried, and the solid residue was passed through the column to obtain a yellow solid (example 276g, 250 mg, yield: 21.9%). LCMS $[M+H]^+$=177.

Step 4: Example 276i (1-(2-((1-methyl-1H-pyrazol-4-yl)amino)pyrimidin-4-yl)-1H-indole-4-yl)carbamate tert-butyl ester The compound 276g (286 mg, 0.8 mmol), compound 276h (500 mg, 2.4 mmol), tris(dibenzylideneacetone)dipalladium (146.5 mg, 0.16 mmol), 2-dicyclohexylphosphonium-2',4',6'-triisopropylbiphenyl (152.5 mg, 0.32 mmol), cesium carbonate (651.64 mg, 2 mmol), 1,4-dioxane (24 mL) and water (4 mL) was added to a 250 mL three-necked flask. After nitrogen displacement was employed several times, the reaction solution was heated to 100° C. for two hours. When it was detected by LCMS that the reaction of the raw material completed, the reaction solution was concentrated and dried, and the solid residue was passed through the column to obtain a yellow solid (example 276i, 151.6 mg, yield: 46.8%). LCMS [M+H]+=406.

Step 5: Example 276j, 1-(2-((1-methyl-1H-pyrazol-4-yl)amino)pyrimidin-4-yl)-1H-indole-4-amide A solution of hydrochloric acid in 1,4-dioxane (3.0 mL, 4 mol/L, 12 mmol) was slowly added dropwise to a solution of compound 276i (151.6 mg, 0.374 mmol) in dichloromethane (15 mL). The reaction solution was stirred for one hours at room temperature. When it was detected by TLC that the reaction completed, the reaction solution was directly dried to obtain the solid. N,N-dimethylformamide (10 mL) solution was added, the mixture was neutralized to neutrality with solid sodium carbonate, the solid was removed via suction filtration, and the filtrate was dried to obtain a yellow solid (example 276j, 110 mg, yield: 96.5%). LCMS [M+H]+= 306.

Step 6: Example 276

N-(1-(2-((1-methyl-1H-pyrazol-4-yl)amino)pyrimidin-4-yl)-1H-indole-4-yl)cyclopropanemethane N,N-diisopropylethylamine (24 mg, 0.1855 mmol), 2-(7-benzotriazole oxide)-N,N,N',N'-tetramethylurea hexafluorophosphate (30 mg, 0.0795 mmol) and compound 276k (5 mg, 0.058 mmol) were added to compound 276j (20 mg, 0.053 mmol) in a solution of N,N-dimethylformamide (5 mL). The reaction solution was stirred at room temperature overnight. When it was detected by LCMS that the reaction of the raw material completed, the product was obtained. LCMS [M+H]+=374. The reaction solution was directly concentrated and dried for preparation, the eluent was distilled under reduced pressure at 45° C. to remove the solvent, and the aqueous phase was lyophilized to obtain a yellow solid (example 276, 8.1 mg, yield: 47.6%). LCMS [M+H]+= 374.

$^1H$ NMR (400 MHz, DMSO) δ 9.98 (s, 1H), 9.65 (s, 1H), 8.44 (d, J=5.7 Hz, 1H), 8.08 (s, 1H), 7.93 (s, 1H), 7.78 (d, J=7.8 Hz, 1H), 7.54 (s, 1H), 7.22 (s, 1H), 7.11 (d, J=4.1 Hz, 2H), 3.85 (d, J=15.6 Hz, 3H), 2.06 (s, 1H), 0.84 (t, J=6.2 Hz, 4H).

| Structure Structural formula | TDM No. Registration number | LCMS $[M+1]^+$ | $^1H$-NMR Proton nuclear magnetic resonance spectroscopy |
|---|---|---|---|
| 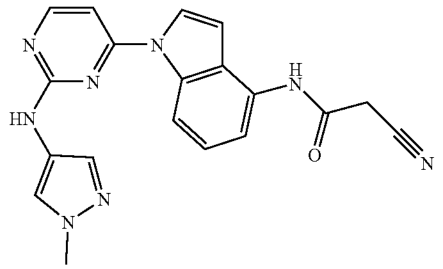 | TDM-180881 | 373.3 | $^1H$ NMR (400 MHz, DMSO) δ 10.13 (s, 1H), 9.71 (s, 1H), 8.45 (d, J = 5.8 Hz, 1H), 8.12 (s, 1H), 7.93 (s, 1H), 7.72 (d, J = 7.8 Hz, 1H), 7.56 (d, J = 15.0 Hz, 1H), 7.28 (s, 1H), 7.13 (d, J = 5.8 Hz, 1H), 7.04 (d, J = 3.6 Hz, 1H), 4.03 (d, J = 13.5 Hz, 2H), 3.88-3.79 (m, 3H). |
| 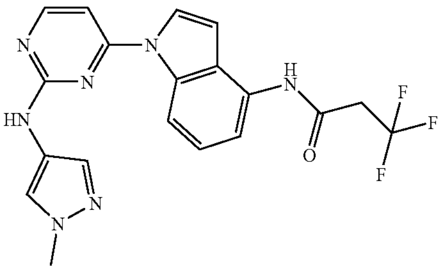 | TDM-180882 | 416.3 | $^1H$ NMR (400 MHz, DMSO) δ 10.11 (s, 1H), 9.66 (s, 1H), 8.45 (d, J = 5.7 Hz, 1H), 8.12 (d, J = 3.1 Hz, 1H), 7.93 (s, 1H), 7.72 (d, J = 7.8 Hz, 1H), 7.54 (s, 1H), 7.27 (s, 1H), 7.12 (d, J = 5.7 Hz, 1H), 7.01 (d, J = 3.6 Hz, 1H), 3.83 (s, 3H), 3.68 (q, J = 11.2 Hz, 2H). |
| 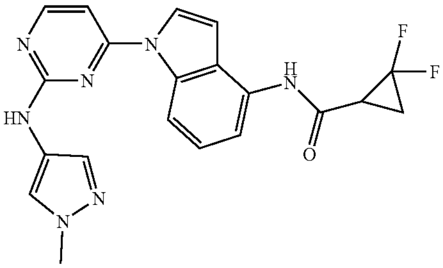 | TDM-180885 | 409.4 | $^1H$ NMR (400 MHz, DMSO) δ 10.23 (s, 1H), 9.66 (s, 1H), 8.45 (d, J = 5.8 Hz, 1H), 8.11 (s, 1H), 7.93 (s, 1H), 7.76 (d, J = 7.8 Hz, 1H), 7.54 (s, 1H), 7.26 (s, 1H), 7.12 (d, J = 5.7 Hz, 1H), 7.07 (d, J = 3.6 Hz, 1H), 3.84 (s, 3H), 3.13-2.96 (m, 1H), 2.16-1.91 (m, 2H). |
| 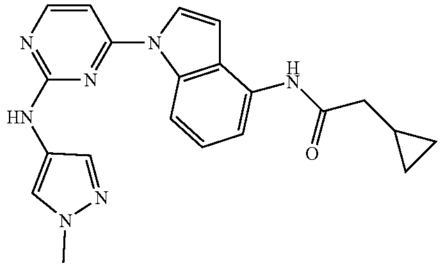 | TDM-180911 | 388.3 | $^1H$ NMR (400 MHz, DMSO) δ 9.60 (s, 2H), 8.45 (d, J = 5.7 Hz, 1H), 8.06 (d, J = 3.2 Hz, 1H), 7.92 (s, 1H), 7.77 (d, J = 7.8 Hz, 1H), 7.53 (s, 1H), 7.23 (s, 1H), 7.09 (d, J = 5.6 Hz, 1H), 7.05 (d, J = 3.6 Hz, 1H), 3.83 (s, 3H), 2.35 (d, J = 7.0 Hz, 2H), 1.19-1.05 (m, 1H), 0.57-0.45 (m, 2H), 0.25 (q, J = 4.8 Hz, 2H). |

-continued

| Structure Structural formula | TDM No. Registration number | LCMS $[M + 1]^+$ | $^1H$-NMR Proton nuclear magnetic resonance spectroscopy |
|---|---|---|---|
| 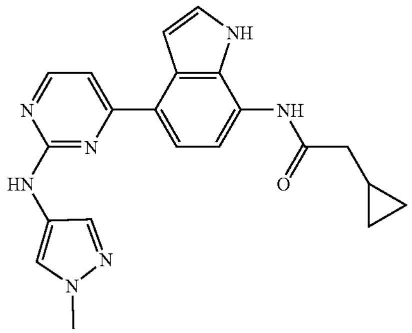 [SMILES: Cn1cc(Nc2nccc(-c3ccc(NC(=O)CC4CC4)c4[nH]ccc34)n2)cn1] | TDM-180920 | 388.3 | $^1H$ NMR (400 MHz, DMSO-$d_6$) δ 11.03 (s, 1H), 9.71 (s, 1H), 9.41 (s, 1H), 8.43 (d, J = 5.2 Hz, 1H), 7.94 (s, 1H), 7.69 (dd, J = 28.8, 8.1 Hz, 2H), 7.54 (dd, J = 5.2, 2.1 Hz, 2H), 7.22 (d, J = 5.2 Hz, 2H), 3.80 (s, 3H), 2.36 (d, J = 7.0 Hz, 2H), 1.15 (ddd, J = 12.3, 7.5, 5.1 Hz, 1H), 0.59-0.47 (m, 2H), 0.28 (t, J = 4.9 Hz, 2H). |
| 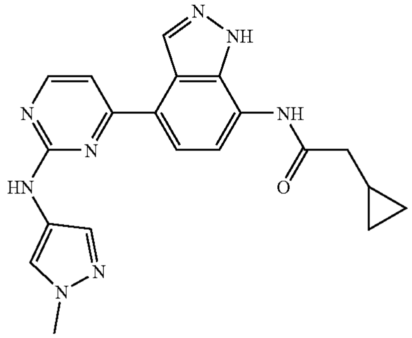 [SMILES: Cn1cc(Nc2nccc(-c3ccc(NC(=O)CC4CC4)c4[nH]ncc34)n2)cn1] | TDM-180917 | 389.2 | $^1H$ NMR (400 MHz, DMSO) δ 12.86 (s, 1H), 9.88 (s, 1H), 9.52 (s, 1H), 8.47 (d, J = 5.3 Hz, 1H), 7.93 (s, 2H), 7.86 (d, J = 7.9 Hz, 1H), 7.54 (s, 1H), 7.35 (d, J = 4.9 Hz, 1H), 3.82 (s, 3H), 2.39 (d, J = 7.0 Hz, 2H), 1.23-1.08 (m, 1H), 0.59-0.48 (m, 2H), 0.27 (q, J = 4.8 Hz, 2H). |

TDM-180881, a yellow solid compound 281, namely 2-cyano-N-(1-(2-((1-methyl-1H-pyrazol-4-yl)amino) pyrimidin-4-yl)-1H-indol-4-yl) acetamide (5.1 mg, yield: 11.8%)

TDM-180882, a yellow solid compound 282, namely 3,3,3-trifluoro-N-(1-(2-((1-methyl-1H-pyrazol-4-yl) amino)pyrimidin-4-yl)-1H-indol-4-yl)propanamide (5.6 mg, yield: 15.1%)

TDM-180885, a yellow solid compound 285, namely 2,2-difluoro-N-(1-(2-((1-methyl-1H-pyrazol-4-yl) amino)pyrimidin-4-yl)-1H-indol-4-yl)cyclopropane-1-carboxamide (39 mg, yield: 81.41%)

TDM-180911, a white solid compound 311, namely 2-cyclopropyl-N-(1-(2-((1-methyl-1H-pyrazol-4-yl)amino) pyrimidin-4-yl)-1H-indol-4-yl) acetamide (45.7 mg, yield: 53.14%)

TDM-180920, a yellow solid compound 320, namely 2-cyclopropyl-N-(4-(2-(1-methyl-1H-pyrazol-4-yl) amino)pyrimidin-4-yl)-1H-indol-7-yl) acetamide (28.9 mg, yield: 45.5%)

TDM-180917, a yellow solid compound 317, namely 2-cyclopropyl-N-(4-(2-((1-methyl-1H-pyrazol-4-yl) amino)pyrimidin-4-yl)-1H-indazol-7-yl) acetamide (5.9 mg, yield: 5.7%)

Example 37: General Method for Synthesizing Compound 326 (TDM-180926)

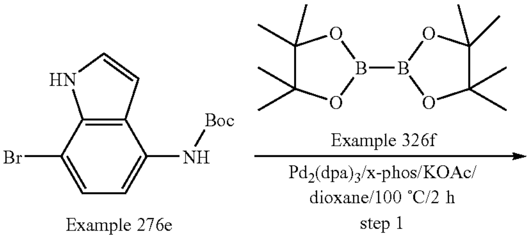

-continued

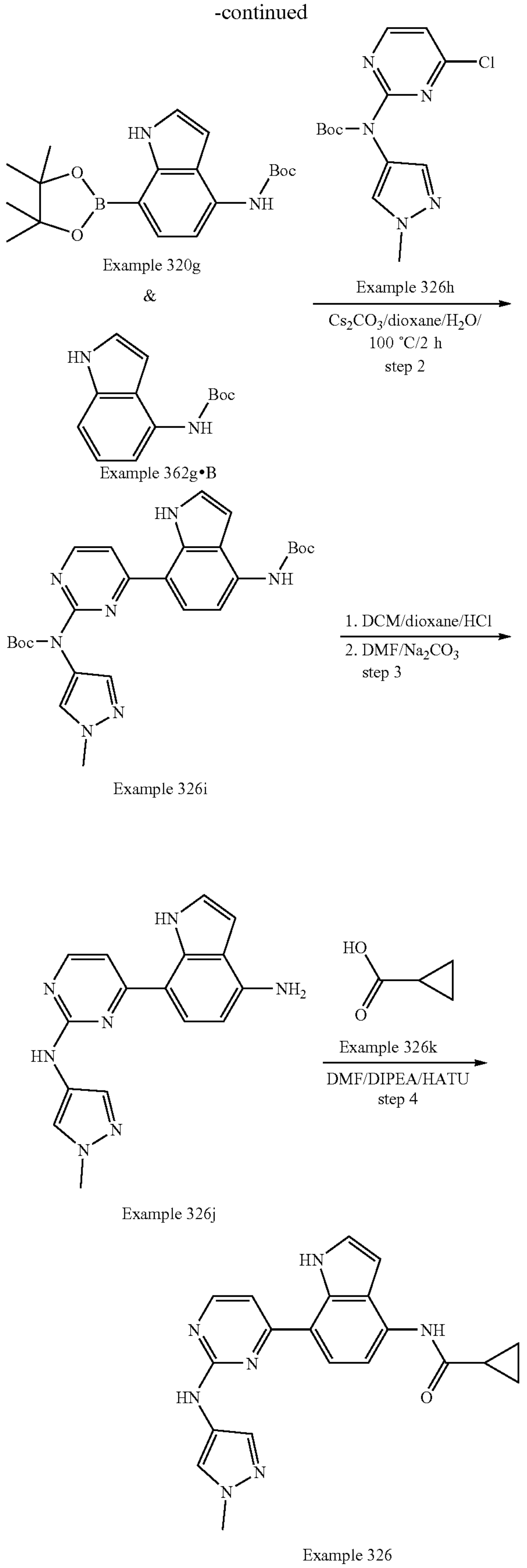

Example 320g

&

Example 362g•B

Example 326h

Example 326i

Example 326k

Example 326j

Example 326

Step 1: Example 326g (7-(4,4,5,5-tetramethyl-1,3,2-dioxaborolane-2-yl)-1H-indol-4-yl)carbamate tert-butyl ester The compound 276e (2100 mg, 6.75 mmol), the compound 326f (2570 mg, 10 mmol), $Pd_2(dba)_3$ (500 mg, 0.54 mmol), X-phos (500 mg, 1.1 mmol), KOAc (1980 mg, 20 mmol) and 1,4-dioxane (60 mL) were added to a three-necked flask. A water pump was used to create a vacuum and Ar displacement was employed. The mixture was heated to 100° C. and stirred for 2 hours. The reaction mixture was concentrated and the residue was purified via silica gel column chromatography (0-100% EtOAc/PE). A purple solid product 326g, (1.5 g, yield: 50%) was obtained, and a brown solid by-product 326g-B (300 mg) was also obtained.

Example 326g LCMS [M+H]+=303.2 $(M\text{-}t\text{-}Bu+H)^+$

Example 326g-B LCMS [M+H]+=177.1 $(M\text{-}t\text{-}Bu+H)^+$ $^1$H NMR (400 MHz, DMSO-$d_6$) δ 11.02 (s, 1H), 8.97 (s, 1H), 7.47 (d, J=1.6 Hz, 1H), 7.35 (d, J=7.2 Hz, 1H), 7.07 (d, J=8.0 Hz, 1H), 6.97 (d, J=8.0 Hz, 1H), 6.74 (d, J=2.4 Hz, 1H), 1.46 (s, 9H).

Step 2: Example 326i (4-(4-((tert-butoxycarbonyl)amino)-1H-indol-7-yl) pyrimidin-2-yl) (1-methyl-1H-pyrazol-4-yl)carbamate tert-butyl ester The compound 326h (1122 mg, 3.63 mmol), $PdCl_2$ (dppf) (100 mg), $Cs_2CO_3$ (2367 mg, 7.26 mmol), 1,4-dioxane (40 mL) and $H_2O$ (8 mL) were added to the compound 326g (1430 mg, 1.1 mmol). The mixture was degassed by using a water pump, and $N_2$ displacement was employed. The mixture was then heated to 100° C. and stirred for 2 hours. The mixture was concentrated and the residue was purified via column chromatography (0-100% EtOAc/PE, 50% DCM contained in EtOAc). The obtained crude product was slurried with EtOAc/PE (approximately, 1:4) to obtain a pale yellow solid compound 326i (1300 mg, yield: 71%).

LCMS $[M+H]^+$=506.3

$^1$H NMR (400 MHz, DMSO-$d_6$) δ 11.72 (s, 1H), 9.46 (s, 1H), 8.62 (d, J=5.2 Hz, 1H), 7.95 (d, J=8.4 Hz, 1H), 7.87 (d, J=5.6 Hz, 1H), 7.84 (brs, 1H), 7.71 (d, J=8.4 Hz, 1H), 7.33-7.38 (m, 1H), 7.47 (d, J=0.4 Hz, 1H), 7.01-7.04 (m, 1H), 3.85 (s, 3H), 1.54 (s, 9H), 1.47 (s, 9H).

Step 3: Example 326j 7-(2-((1-methyl-1H-pyrazol-4-yl)amino)pyrimidin-4-yl)-1H-indole-4-amide HCl/1,4-dioxane (4 mL, 4 M in 1,4-dioxane) was added to a DCM solution (6 mL) of the compound 326i (250 mg, 0.5 mmol). The mixture was stirred for 2 days at room temperature. The mixture was concentrated, the residue was diluted with DMF (6 mL), neutralized with $Na_2CO_3$ (approximately, 3 g) and filtered, and the filtrate was collected and used directly in the next step. 130 mg product (6 mL in DMF, yield: 100%).

LCMS $[M+H]^+$=306.2

Step 4: Example 326

N-(7-(2-((1-methyl-1H-pyrazol-4-yl)amino)pyrimidin-4-yl)-1H-indole-4-yl)cyclopropanecarboxamide DIPEA (77.6 mg, 0.60 mmol), compound 326k (25.8 mg, 0.30 mmol) and HATU (114.1 mg, 0.30 mmol) were added to a solution of compound 326j (60 mg, 0.20 mmol) in DMF (10 mL). The mixture was heated to 45° C. and stirred for 16 hours. The mixture was concentrated under reduced pressure, purified via preparation (FA) and lyophilized to obtain a yellow solid compound 326 (19 mg, yield: 25%).

LCMS $[M+1]^+$=374.2

$^1$H NMR (400 MHz, DMSO-$d_6$) δ 11.92 (s, 1H), 10.06 (s, 1H), 9.63 (s, 1H), 8.43 (d, J=5.5 Hz, 1H), 8.00 (s, 1H), 7.91 (s, 2H), 7.54 (s, 1H), 7.49 (s, 1H), 7.42 (d, J=5.5 Hz, 1H), 7.06-6.96 (m, 1H), 3.85 (s, 3H), 2.24-2.11 (m, 1H), 0.91-0.87 (m, 2H), 0.87-0.82 (m, 2H).

| Structure Structural formula | TDM No. Registra-tion number | LCMS $[M + 1]^+$ | $^1$H-NMR Proton nuclear magnetic resonance spectroscopy |
|---|---|---|---|
| 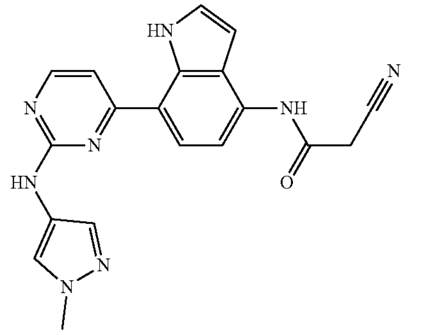 [SMILES: Cn1cc(Nc2nccc(-c3ccc(NC(=O)CC#N)c4cc[nH]c34)n2)cn1] | TDM-180923 | 373.1 | $^1$H NMR (400 MHz, DMSO-$d_6$) δ 11.96 (s, 1H), 10.18 (s, 1H), 9.68 (s, 1H), 8.44 (d, J = 5.5 Hz, 1H), 8.05-7.91 (m, 2H), 7.86 (d, J = 8.3 Hz, 1H), 7.53 (d, J = 9.8 Hz, 2H), 7.45 (d, J = 5.6 Hz, 1H), 6.91 (s, 1H), 4.10 (s, 2H), 3.85 (s, 3H). |
| 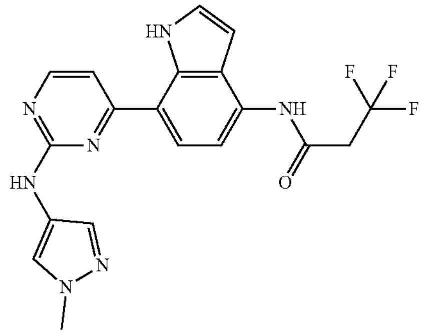 [SMILES: Cn1cc(Nc2nccc(-c3ccc(NC(=O)CC(F)(F)F)c4cc[nH]c34)n2)cn1] | TDM-180924 | 416.1 | $^1$H NMR (400 MHz, DMSO-$d_6$) δ 11.96 (s, 1H), 10.14 (s, 1H), 9.64 (s, 1H), 8.45 (d, J = 5.5 Hz, 1H), 8.08-7.91 (m, 2H), 7.86 (d, J = 8.3 Hz, 1H), 7.54 (s, 2H), 7.44 (d, J = 5.5 Hz, 1H), 6.90 (s, 1H), 3.85 (s, 3H), 3.75 (q, J = 11.2 Hz, 2H). |
| 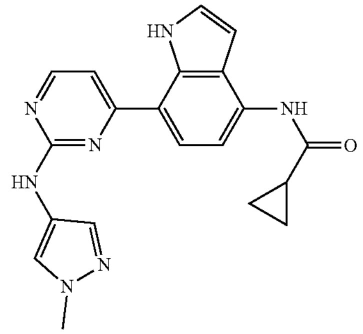 [SMILES: Cn1cc(Nc2nccc(-c3ccc(NC(=O)C4CC4)c4cc[nH]c34)n2)cn1] | TDM-180926 | 374.2 | $^1$H NMR (400 MHz, DMSO-$d_6$) δ 11.92 (s, 1H), 10.06 (s, 1H), 9.63 (s, 1H), 8.43 (d, J = 5.5 Hz, 1H), 8.00 (s, 1H), 7.91 (s, 2H), 7.54 (s, 1H), 7.49 (s, 1H), 7.42 (d, J = 5.5 Hz, 1H), 7.06-6.96 (m, 1H), 3.85 (s, 3H), 2.24-2.11 (m, 1H), 0.91-0.87 (m, 2H), 0.87-0.82 (m, 2H). |
| 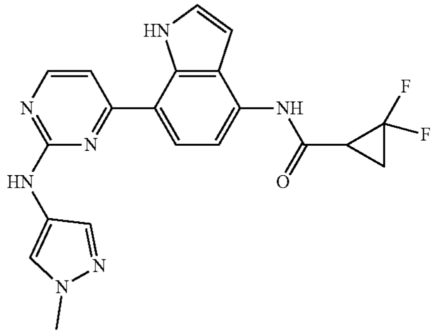 [SMILES: Cn1cc(Nc2nccc(-c3ccc(NC(=O)C4CC4(F)F)c4cc[nH]c34)n2)cn1] | TDM-180929 | 41.2 | $^1$H NMR (400 MHz, DMSO-$d_6$) δ 11.95 (brs, 1H), 10.29 (s, 1H), 9.65 (br s, 1H), 8.45 (d, J = 5.6 Hz, 1H), 8.00 (s, 1H), 7.86-7.97 (m, 2H), 7.54 (brs, 1H), 7.53 (brs, 1H), 7.44 (d, J = 5.2 Hz, 1H), 6.97 (brs, 1H), 3.86 (s, 3H), 3.11-3.24 (m, 1H), 1.98-2.16 (m, 2H). |

-continued

| Structure Structural formula | TDM No. Registration number | LCMS $[M + 1]^+$ | $^1H$-NMR Proton nuclear magnetic resonance spectroscopy |
|---|---|---|---|
| 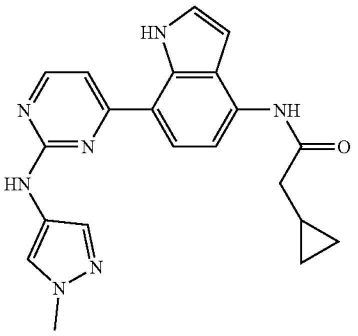 [SMILES: Cn1cc(Nc2nccc(-c3ccc(NC(=O)CC4CC4)c4cc[nH]c34)n2)cn1] | TDM-180933 | 388.2 | $^1H$ NMR (400 MHz, DMSO-$d_6$) δ 11.90 (s, 1H), 9.67 (s, 2H), 8.42 (d, J = 5.5 Hz, 1H), 7.99 (s, 1H), 7.96-7.82 (m, 2H), 7.54 (s, 1H), 7.48 (s, 1H), 7.43 (d, J = 5.6 Hz, 1H), 7.00-6.87 (m, 1H), 3.85 (s, 3H), 2.41 (d, J = 7.0 Hz, 2H), 1.20-1.02 (m, 1H), 0.64-0.43 (m, 2H), 0.25 (d, J = 4.9 Hz, 2H). |

TDM-180923, a yellow solid compound 323, namely 2-cyano-N-(7-(2-(1-methyl-1H-pyrazol-4-yl)amino)pyrimidin-4-yl)-1H-indol-4-yl) acetamide (15.5 mg, yield: 14.1%)

TDM-180924, a yellow solid compound 324, namely 3,3,3-trifluoro-N-(7-(2-((1-methyl-1H-pyrazol-4-yl)amino)pyrimidin-4-yl)-1H-indol-4-yl)propanamide (7.8 mg, yield: 6.4%)

TDM-180926, a yellow solid compound 326, namely N-(7-(2-((1-methyl-1H-pyrazol-4-yl)amino)pyrimidin-4-yl)-1H-indol-4-yl)cyclopropanemethane (19.0 mg, yield: 25%)

TDM-180929, a yellow solid compound 329, namely 2,2-difluoro-N-(7-(2-((1-methyl-1H-pyrazol-4-yl)amino)pyrimidin-4-yl)-1H-indol-4-yl)cyclopropane-1-carboxamide (11.2 mg, yield: 14%)

TDM-180933, a yellow solid compound 333, namely 2-cyclopropyl-N-(7-(2-(1-methyl-1H-pyrazol-4-yl)amino)pyrimidin-4-yl)-1H-indol-4-yl) acetamide (30.3 mg, yield: 39%)

Example 38: General Method for Synthesizing Compound 313 (TDM-180913)

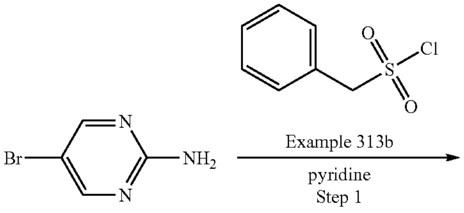

Example 313a

-continued

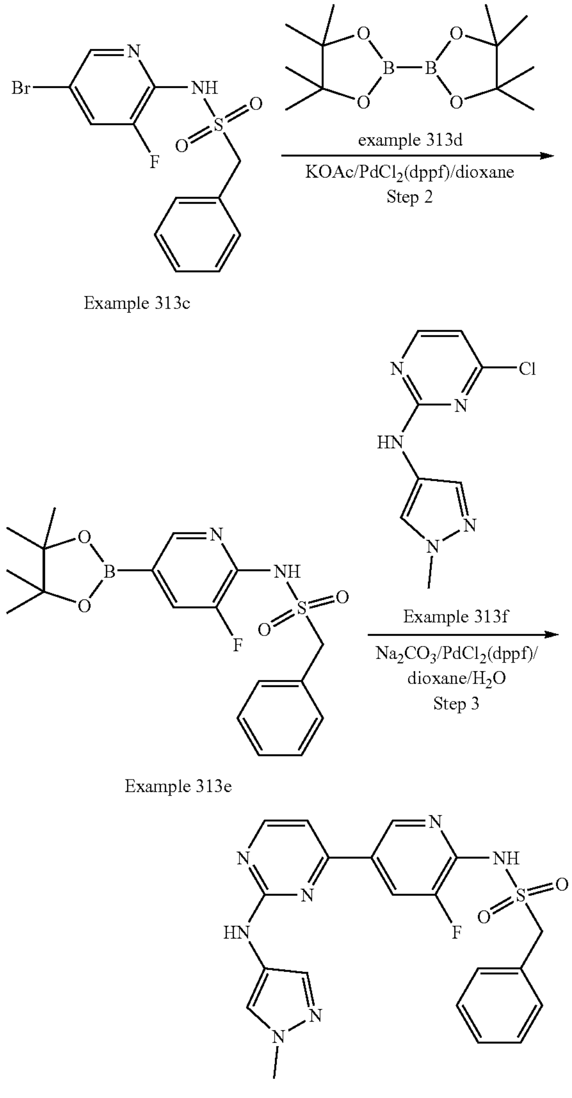

Example 313

Step 1: Example 313c

The compound 313a (192 mg, 1.0 mmol) and compound 313b (190.6 mg, 1.0 mmol) were added to pyridine (4 mL), and the mixture was stirred for 3 hours at room temperature. After removal of the solvent, a yellow solid compound 313c (namely N-(5-bromo-3-fluoropyridin-2-yl)-1-phenylmethanesulfonamide (180 mg, 52.2%) was obtained through purification using silica gel chromatography (ethyl acetate: petroleum ether=0-15%). LCMS $[M+1]^+$=345.1, 347.1.

Step 2: Example 313e

Compound 313c (180 mg, 0.52 mmol), compound 313d (263.9 mg, 1.04 mmol), potassium acetate (152.9 mg, 1.56 mmol) and $PdCl_2$ (dppf) (73 mg, 0.1 mmol) were added to a solution of 1,4-dioxane (10 mL), nitrogen displacement was employed three times, and the mixture was then heated to 90° C. and stirred for 17 hours. The reaction solution was cooled to room temperature and filtered, the filter cake was rinsed with ethyl acetate (10 mL×2), the filtrate was concentrated, and the concentrate was purified via silica gel chromatography (ethyl acetate:petroleum ether=0-20%) to obtain a yellow solid compound 313e (namely, N-(3-fluoro-5-(4,4,5,5-tetramethyl-1,3,2-dioxaborolane-2-yl)-pyridin-2-yl)-1-phenylmethanesulfonamide (138.0 mg, yield: 85.3%). LCMS $[M+1]^+$=311.1.

Step 3: Example 313 (TDM-180913)

The compound 313f (104 mg, 0.496 mmol), compound 303e (138 mg, 0.452 mmol), sodium carbonate (95.4 mg, 0.90 mmol) and $PdCl_2$ (dppf) (66.2 mg, 0.090 mmol) were dissolved in a mixture solution of 1,4-dioxane (10 mL) and water (1 mL). Nitrogen displacement was employed three times, and the reaction solution was then heated to 95° C. and stirred for 4 hours. The reaction solution was cooled to room temperature and filtered, the filter cake was washed with ethyl acetate (15 mL×2), the filtrate was concentrated, and the concentrated solution was purified via silica gel chromatography (methanol:dichloromethane=0-3%) to obtain the crude product. The crude product was dispersed in methanol (1 mL) and slurried, and dried to obtain a yellow solid compound 313, namely N-(3-fluoro-5-(2-((1-methyl-1H-pyrazol-4-yl)amino)pyrimidin-4-yl)pyridin-2-yl)-1-phenylmethanesulfonamide (2.2 mg, yield: 1.1%). LCMS $[M+1]^+$=440.1.

$^1$H NMR (400 MHz, DMSO) δ 11.07 (s, 1H), 9.56 (s, 1H), 9.03 (s, 1H), 8.53 (d, J=4.5 Hz, 1H), 8.36 (d, J=10.9 Hz, 1H), 7.92 (s, 1H), 7.57 (s, 1H), 7.36 (s, 6H), 4.99 (s, 2H), 3.84 (s, 3H).

| Structure Structural formula | TDM NO. Registration number | LCMS $[M + 1]^+$ | $^1$H-NMR Proton nuclear magnetic resonance spectroscopy |
|---|---|---|---|
| 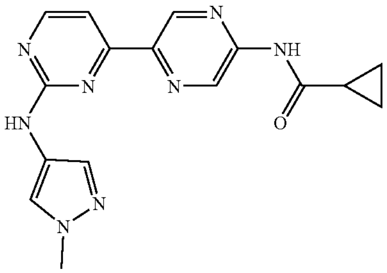 [SMILES: Cn1cc(Nc2nccc(-c3cnc(NC(=O)C4CC4)cn3)n2)cn1] | TDM-180914 | 337.3 | $^1$H NMR (400 MHz, DMSO) δ 11.39 (s, 1H), 9.59 (s, 1H), 9.43 (d, J = 1.3 Hz, 1H), 9.26 (s, 1H), 8.56 (d, J = 5.0 Hz, 1H), 7.96 (s, 1H), 7.56 (s, 1H), 7.48 (d, J = 5.0 Hz, 1H), 3.84 (s, 3H), 2.11-2.04 (m, 1H), 1.26-1.21 (m, 2H), 0.91 (d, J = 6.0 Hz, 3H). |

TDM-180914, a yellow solid compound 314, namely N-(5-(2-((1-methyl-1H-pyrazol-4-yl)amino)pyrimidin-4-yl)pyrazin-2-yl)cyclopropanemethane (3 mg, yield: 2.7%)

Example 39: General Method for Synthesizing Compound 321 (TDM-180921)

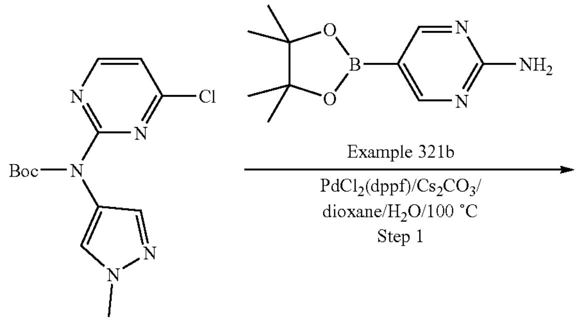

Example 321a

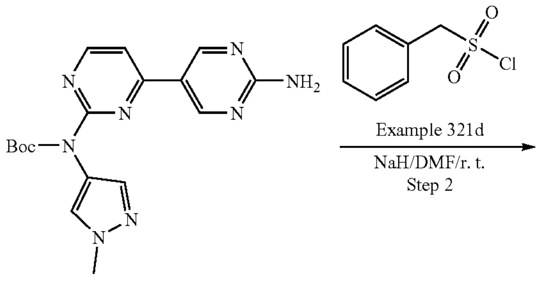

Example 321c

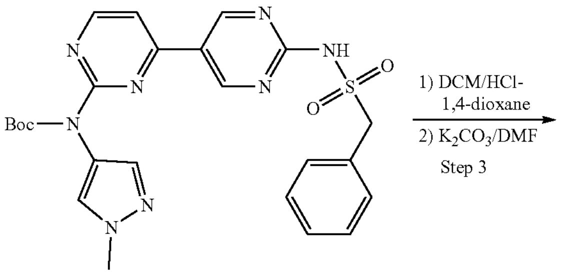

Example 321e

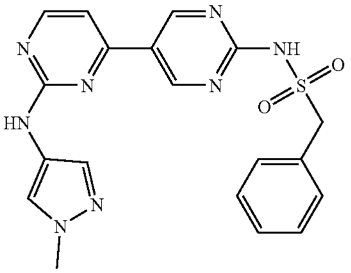

Example 321

Step 1: Example 321c (2'-amino-[4,5'-bipyrimidin]-2-yl) (1-methyl-1H-pyrazol-4-yl)carbamate tert-butyl ester The compound 321a (500 mg, 2.39 mmol), $PdCl_2$ (dppf) (60 mg), $Cs_2CO_3$ (1556 mg, 4.78 mmol), 1,4-dioxane (20 mL) and $H_2O$ (4 mL) were added to the compound 321b (581 mg, 2.63 mmol). The obtained mixture was degassed to vacuum by using a water pump, and nitrogen displacement was employed three times. The reaction solution was heated to 105° C. and stirred for 2 hours. The mixture was concentrated and purified via column chromatography (DCM/MeOH=10/1) to obtain a colorless oily compound 321c (420 mg, yield: 48%).

LCMS $[M+H]^+$=369.

Step 2: Example 321e (1-methyl-1H-pyrazol-4-yl) (2'-((phenylmethyl)sulfonamido)-[4,5'-bipyrimidin]-2-yl)carbamate tert-butyl ester Sodium hydride (14 mg, 0.353 mmol) was added to compound 321c (100 mg, 0.271 mmol) (namely, (2'-amino-[4,5'-bipyrimidin]-2-yl) (1-methyl-1H-pyrazol-4-yl) carbamate tert-butyl ester in a solution of N,N-dimethylformamide (10 mL), and the mixture was stirred at room temperature for 1 hour. Then the compound 321d (namely, benzylsulfonyl chloride) (67.3 mg, 0.353 mmol) was added to the mixture and stirred for 1.5 hours. After the reaction completed, the mixture was added to water (20 mL), then the mixture was concentrated under reduced pressure, and the residue was purified via silica gel chromatography (dichloromethane:dichloromethane containing 10% methanol=70:30), to obtain a pale yellow solid compound 321e, namely, tert-butyl (1-methyl-1H-pyrazol-4-yl) (2'-((phenylmethyl)sulfinamido)-[4,5'-bipyrimidin]-2-yl)carbamate tert-butyl ester (87 mg, yield: 61.4%). LCMS $[M+1]^+$=523.2.

Step 3: Example 321 (TDM-180921)

N-(2-((1-methyl-1H-pyrazol-4-yl)amino)-[4,5'-bipyrimidin]-2'-yl)-1-phenylmethanesulfonamide Hydrochloric acid-1,4-dioxane (0.4 mL, 1.665 mmol) was added to a dichloromethane solution (10 mL) of compound 321e (87 mg, 0.166 mmol), and the mixture was stirred at room temperature overnight. The mixture was concentrated under reduced pressure, N,N-dimethylformamide (10 mL) and potassium carbonate (460 mg, 3.33 mmol) were added to the residue, and the mixture was stirred at room temperature for 4 hours. The mixture was filtered, the filtrate was concentrated under reduced pressure, and the residue was purified with formic acid to obtain a pale yellow solid compound 321, TDM-180921, namely N-(2-((1-methyl-1H-pyrazol-4-yl)amino)-[4,5'-bipyridyl]-2'-yl)-1-phenylmethanesulfonamide (4 mg, yield: 5.7%). TLCMS $[M+1]^+$=423.1.

$^1H$ NMR (400 MHz, DMSO-$d_6$) δ 11.61 (s, 1H), 9.56 (s, 1H), 9.31 (s, 2H), 8.52 (d, J=5.0 Hz, 1H), 7.95 (s, 1H), 7.55 (s, 1H), 7.31 (ddd, J=9.6, 8.2, 4.0 Hz, 6H), 4.92 (s, 2H), 3.84 (s, 3H).

| Structure Structural formula | TDM No. Registration number | LCMS [M + 1]+ | 1H-NMR Proton nuclear magnetic resonance spectroscopy |
|---|---|---|---|
| 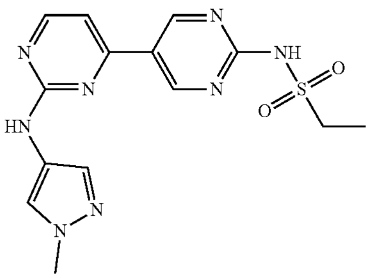 [SMILES: CCS(=O)(=O)Nc1ncc(-c2ccnc(Nc3cnn(C)c3)n2)cn1] | TDM-180919 | 361.1 | $^1H$ NMR (400 MHz, DMSO-$d_6$) δ 9.52 (s, 1H), 9.21 (s, 2H), 8.48 (d, J = 5.1 Hz, 1H), 8.15 (s, 1H), 7.93 (s, 1H), 7.53 (s, 1H), 7.30 (d, J = 5.2 Hz, 1H), 3.83 (s, 3H), 3.51 (q, J = 7.3 Hz, 2H), 1.23 (t, J = 7.4 Hz, 3H). |

TDM-180919, a yellow solid compound 327, namely N-(2-((1-methyl-1H-pyrazol-4-yl)amino)-[4,5'-bipyrimidin]-2'-yl)ethanesulfonamide (3.9 mg, yield: 12%)

General Method for Synthesizing Compound 286-2 (TDM-180886-2)

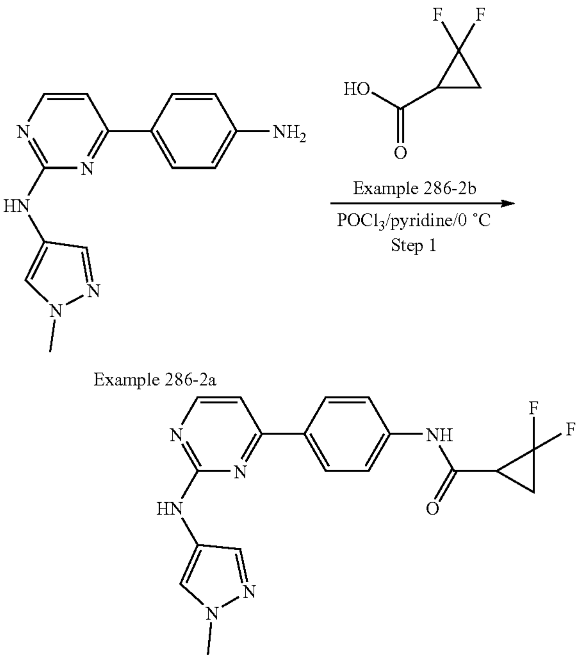

Example 286-2

Step 1: Example 286-2

2,2-difluoro-N-(2-((1-methyl-1H-pyrazol-4-yl)amino)-[4,5'-bipyrimidin]-2'-yl)cyclopropane-1-carboxamide The compound 286-2b (192.5 mg, 1.577 mmol) (namely, 2,2-difluorocyclopropane-1-carboxylic acid and phosphorus oxychloride (403 mg, 2.628 mmol) was added to pyridine solution (20 mL) of the compound 286-2a (350 mg, 1.314 mmol) namely, $N^2$-(1-methyl-1H-pyrazol-4-yl)-[4,5'-bipyrimidine]-2,2'-diamine at 0° C. Then the mixture was stirred for 1.5 hours. The mixture was concentrated under reduced pressure, water was added to the residue, the solution was neutralized with aqueous sodium bicarbonate solution, the solution was concentrated under reduced pressure, and the residue was purified via silica gel chromatography (dichloromethane:dichloromethane containing 10% methanol=50:50) and formic acid to obtain a yellow solid compound 286-2, TDM-180886-2, namely, 2,2-difluoro-N-(2-((1-methyl-1H-pyrazol-4-yl)amino)-[4,5'-bipyrimidin]-2'-yl)cyclopropane-1-carboxamide (76.7 mg, yield: 15.1%). LCMS $[M+1]^+$=373.1.

$^1H$ NMR (400 MHz, DMSO-$d_6$) δ 11.39 (s, 1H), 9.60 (s, 1H), 9.36 (s, 2H), 8.53 (d, J=5.0 Hz, 1H), 7.94 (s, 1H), 7.54 (s, 1H), 7.39 (d, J=5.2 Hz, 1H), 3.83 (s, 3H), 3.21 (dd, J=22.3, 10.4 Hz, 1H), 2.03 (ddd, J=16.2, 12.4, 5.9 Hz, 2H).

Example 41: General Method for Synthesizing Compound 334 (TDM-180934)

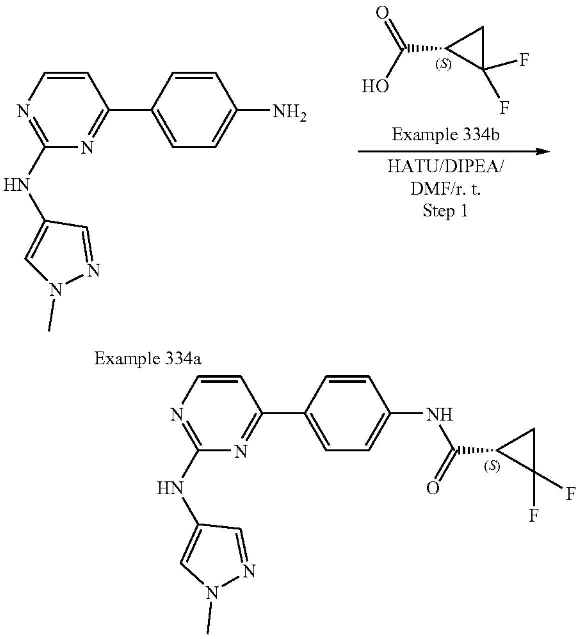

TDM-180934

Step 1: Example 334

N,N-diisopropylethylamine (72.9 mg, 0.564 mmol) was added to compound 334a (namely, 4-(4-aminophenyl)-N-(1-methyl-1H-pyrazol-4-yl)pyrimidin-2-amine) (50 mg, 0.188 mmol) in a solution of N,N-dimethylformamide (5 mL) at room temperature, the mixture was stirred for 5 minutes, and then 2-(7-benzotriazole oxide)-N,N,N',N'-tetramethylurea hexafluorophosphate (93 mg, 0.244 mmol) and compound 334b (namely, (S)-2,2-difluorocyclopropane-1-carboxylic acid) (30 mg, 0.244 mmol) were added into the mixture. The mixture was stirred for 16 hours at room temperature. The mixture was concentrated under reduced pressure to remove some solvent, water was added to the residue, and the solution was extracted with ethyl acetate (40 mL*3). The organic layer was washed with saturated brine (50 mL*5), and dried over anhydrous sodium sulfate. The filtrate was concentrated under reduced pressure, and the residue was purified via formic acid to obtain a yellow solid compound 334, TDM-180934 (43.4 mg, yield: 61.8%), namely(S)-2,2-difluoro-N-(4-(2-(((1-methyl-1H-pyrazol-4-yl)amino)pyrimidin-4-yl)phenyl)cyclopropane-1-carboxamide. LCMS $[M+1]^+$=371.2

$^1$H NMR (400 MHz, DMSO-$d_6$) δ 10.67 (s, 1H), 9.45 (s, 1H), 8.44 (d, J=5.2 Hz, 1H), 8.23-8.05 (m, 2H), 7.92 (s, 1H), 7.76 (d, J=8.7 Hz, 2H), 7.55 (s, 1H), 7.24 (d, J=5.3 Hz, 1H), 3.83 (s, 3H), 2.86 (ddd, J=13.6, 10.8, 8.0 Hz, 1H), 2.13-1.89 (m, 2H).

| Structure Structural formula | TDM No. Registration number | LCMS $[M + 1]^+$ | $^1$H-NMR Proton nuclear magnetic resonance spectroscopy |
|---|---|---|---|
| 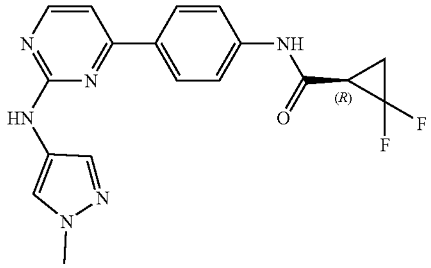 | TDM-180936 | 371.1 | $^1$H NMR (400 MHz, DMSO-$d_6$) δ 10.67 (s, 1H), 9.45 (s, 1H), 8.44 (d, J = 5.2 Hz, 1H), 8.13 (d, J = 8.7 Hz, 2H), 7.92 (s, 1H), 7.76 (d, J = 8.7 Hz, 2H), 7.55 (s, 1H), 7.24 (d, J = 5.3 Hz, 1H), 3.83 (s, 3H), 2.86 (ddd, J = 13.7, 10.8, 8.1 Hz, 1H), 2.02 (ddd, J = 19.9, 12.4, 7.0 Hz, 2H). |

TDM-180936, a yellow solid compound 336, namely (R)-2,2-difluoro-N-(4-(2-((1-methyl-1H-pyrazol-4-yl)amino)pyrimidin-4-yl)phenyl)cyclopropane-1-carboxamide (37.7 mg, yield: 53%).

Example 42: General Method for Synthesizing Compound 335 (TDM-180935)

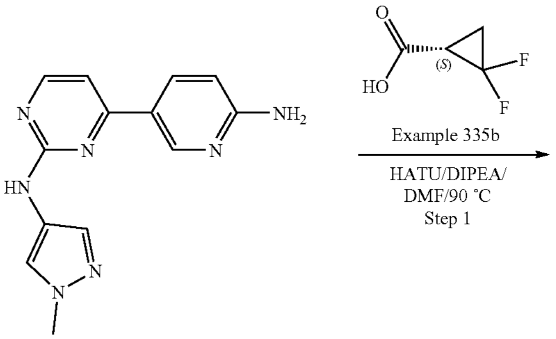

Example 335a

-continued

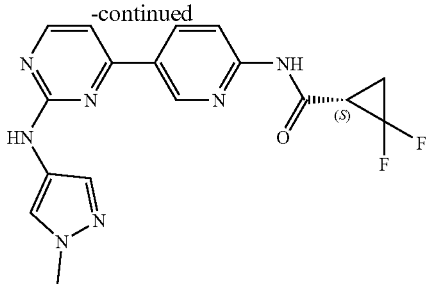

TDM-180935

Step 1: Example 335

N,N-diisopropylethylamine (72.9 mg, 0.564 mmol) was added to compound 335a (namely, 4-(6-aminopyridin-3-yl)-N-(1-methyl-1H-pyrazol-4-yl)pyrimidin-2-amine) (80 mg, 0.299 mmol) in a solution of N,N-dimethylformamide (5 mL) at room temperature, the mixture was stirred for 5 minutes, and then 2-(7-benzotriazole oxide)-N,N,N',N'-tetramethylurea hexafluorophosphate (170 mg, 0.449 mmol) and compound 335b (namely, (S)-2,2-difluorocyclopropane-1-carboxylic acid) (54 mg, 0.449 mmol) were added into the mixture. The mixture was heated to 90° C. and stirred for 16 hours. The mixture was concentrated under reduced pressure to remove some solvent, water was added to the residue, and the solution was extracted with ethyl acetate (60 mL*3). The organic layer was washed with saturated brine (50 mL*5), and dried over anhydrous sodium sulfate. The filtrate was concentrated under reduced pressure, and the residue was purified via formic acid to obtain a yellow solid compound 335, TDM-180935 (21.6 mg, yield: 19.5%), namely(S)-2,2-difluoro-N-(5-(2-((1-methyl-1H-pyrazol-4-yl)amino)pyrimidin-4-yl)pyridin-2-yl)cyclopropane-1-carboxamide. LCMS $[M+1]^+$=372.1

$^1$H NMR (400 MHz, DMSO-$d_6$) δ 11.29 (s, 1H), 9.54 (s, 1H), 9.11 (d, J=2.0 Hz, 1H), 8.51 (dd, J=14.3, 6.9 Hz, 2H), 8.22 (d, J=8.7 Hz, 1H), 7.93 (s, 1H), 7.54 (s, 1H), 7.34 (d, J=5.2 Hz, 1H), 3.83 (s, 3H), 3.04 (dd, J=22.4, 9.9 Hz, 1H), 2.05 (dt, J=11.8, 8.0 Hz, 2H).

| Structure Structural formula | TDM No. Registration number | LCMS $[M + 1]^+$ | $^1$H-NMR Proton nuclear magnetic resonance spectroscopy |
|---|---|---|---|
| 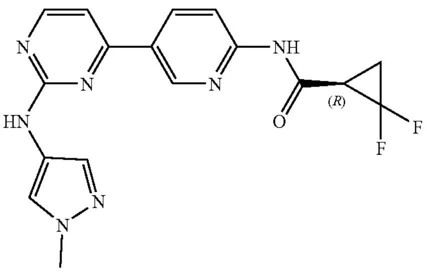 | TDM-180939 | 372.1 | $^1$H NMR (400 MHz, DMSO-$d_6$) δ 11.30 (s, 1H), 9.54 (s, 1H), 9.11 (d, J = 1.6 Hz, 1H), 8.47-8.57 (m, 2H), 8.23 (d, J = 8.8 Hz, 1H), 7.94 (s, 1H), 7.54 (brs, 1H), 7.34 (d, J = 5.2 Hz, 1H), 3.84 (s, 3H), 2.98-3.10 (m, 1H), 1.99-2.12 (m, 2H). |

TDM-180939, a yellow solid compound 339, namely (R)-2,2-difluoro-N-(5-(2-((1-methyl-1H-pyrazol-4-yl)amino)pyrimidin-4-yl)pyridin-2-yl)cyclopropane-1-carboxamide (26.0 mg, yield: 32%).

Assay for Identifying Inhibitory Effects of Compounds on JAK Kinases

Janus kinases (JAK), including JAK1, JAK2, JAK3 and Tyk2, transduce a cytokine-mediated signal through a JAK-STAT pathway. The kinases are 120-140 kDa in size and have 7 determined homology regions: JH1 to JH7. JH1 is an important region for enzymatic activity and has typical characteristics of tyrosine kinases. Phosphorylation of tyrosine leads to a change in the conformation of JAK protein, thereby promoting binding of substrate. The JAK-STAT system includes three main parts: receptors penetrating a cell membrane, Janus kinases binding to the receptors, and signal transducers and activators of transcription (STAT) for transmitting signals to a nucleus and DNA. When cytokines bind to receptors, JAK phosphorylates the receptors and attracts STAT proteins. The STAT proteins are also phosphorylated and combined with one another to form dimers. The dimers enter the nucleus and bind to DNA, thereby leading to gene transcription.

EZ Reader from PerkinElmer can be used to detect the phosphorylation of polypeptide substrates catalyzed by kinases. The device is based on microfluidic techniques, and can directly detect fluorescently labeled substrates and products. The separation step is achieved by controlling the pressure and electric field strength in the microfluidic chip. In kinase assays, a product conversion ratio is usually controlled to be 20-30%. A biological test is used to identify inhibitory effects of compounds on JAKs.

1. Materials

S1.1 Test Compounds

Compound powder was dissolved in DMSO, sealed and stored in a freezer under −20° C. The in-house compound was used as a positive control for JAK1, JAK2 and Tyk2 tests, and Ref2 was used as a positive control for JAK3 tests.

2. Reagent Preparation

S2.1. 1M HEPES buffer: 0.5M HEPES free acid and 0.5M HEPES sodium salt were weighed, dissolved in ultrapure water, diluted to volume, filtered, and stored in a freezer at 4° C.

S2.2. 40 mM ATP solution: The compound was dissolved in 50 mM HEPES buffer, diluted to content of 40 mM, aliquoted, and stored in a freezer at −20° C.

S2.3. 0.5% Tween 20: 100% Tween 20 was diluted with ultrapure water and stored in a freezer at 4° C.

S2.4. 35% bovine serum albumin: 35% bovine serum albumin solution was prepared with ultrapure water, aliquoted, and stored in a freezer at −20° C.

S2.5. 1M dithiothreitol solution: 1M dithiothreitol solution was prepared by using ultrapure water, aliquoted, and stored in a freezer at −20° C.

S2.6. 0.5 mM Jaktide peptide substrate solution: The compound was dissolved with 50 mM HEPES and diluted to 0.5 mM concentration, aliquoted, and stored in a freezer at −20° C.

S2.7. 0.5 mM IRStide peptide substrate solution: The compound was dissolved with 50 mM HEPES and diluted to 0.5 mM concentration, aliquoted, and stored in a freezer at −20° C.

S2.8. Assay buffer: 20 mM HEPES buffer, pH 7.4, 10 mM magnesium chloride, 0.01% bovine serum albumin BSA, 0.0005% Tween-20 and 1 mM dithiothreitol solution.

S2.9. Stop buffer: 180 mM HEPES buffer, 20 mM ethylenediaminetetraacetic acid and 0.2% coating reagent 3.

S2.10. Separation buffer: 100 mM HEPES buffer, 10 mM ethylenediaminetetra acetic acid, 0.0005% Tween 20, 0.1% coating reagent 3 and 1% dimethyl sulfoxide.

3. Method

S3.1. Preparation of Compound Plates

The compound was dissolved in dimethyl sulfoxide and diluted to 10 mM concentration, a certain volume of solution was taken and diluted to 0.6 mM concentration, 10 µL of the 0.6 mM dilution was added to a 384-well microplate, and then was diluted 3-fold with a total of 8 concentration points.

S3.2. Compound Arrangement

| | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| A | HPE1 | cpd1 | cpd2 | cpd3 | cpd4 | cpd5 | cpd6 | cpd7 | cpd8 | cpd9 | cpd10 | cpd11 | cpd12 | cpd13 |
| B | HPE1 | | | | | | | | | | | | | |
| C | HPE1 | | | | | | | | | | | | | |
| D | HPE1 | | | | | | | | | | | | | |
| E | HPE1 | | | | | | | | | | | | | |
| F | HPE1 | | | | | | | | | | | | | |
| G | HPE1 | | | | | | | | | | | | | |
| H | HPE1 | | | | | | | | | | | | | |
| I | HPE2 | cpd1 | cpd2 | cpd3 | cpd4 | cpd5 | cpd6 | cpd7 | cpd8 | cpd9 | cpd10 | cpd11 | cpd12 | cpd13 |
| J | HPE2 | | | | | | | | | | | | | |
| K | HPE2 | | | | | | | | | | | | | |
| L | HPE2 | | | | | | | | | | | | | |
| M | HPE2 | | | | | | | | | | | | | |
| N | HPE2 | | | | | | | | | | | | | |
| O | HPE2 | | | | | | | | | | | | | |
| P | HPE2 | | | | | | | | | | | | | |

| | 15 | 16 | 17 | 18 | 19 | 20 | 21 | 22 | 23 | 24 |
|---|---|---|---|---|---|---|---|---|---|---|
| A | cpd14 | cpd15 | cpd16 | cpd17 | cpd18 | cpd19 | cpd20 | cpd21 | cpd22 | ZPE |
| B | | | | | | | | | | ZPE |
| C | | | | | | | | | | ZPE |
| D | | | | | | | | | | ZPE |
| E | | | | | | | | | | ZPE |
| F | | | | | | | | | | ZPE |
| G | | | | | | | | | | ZPE |
| H | | | | | | | | | | ZPE |
| I | cpd14 | cpd15 | cpd16 | cpd17 | cpd18 | cpd19 | cpd20 | cpd21 | cpd22 | Ref |
| J | | | | | | | | | | Ref |
| K | | | | | | | | | | Ref |
| L | | | | | | | | | | Ref |
| M | | | | | | | | | | Ref |
| N | | | | | | | | | | Ref |
| O | | | | | | | | | | Ref |
| P | | | | | | | | | | Ref |

Positive control (HPE1): Ref1, final concentration: 10 PM

Positive control (HPE1): Ref2, final concentration: 10 µM

Negative control (ZPE): DMSO, final content: 1.6%

Compounds: maximum final concentration: 10 µM; 3-fold dilution, 8 concentration points and 2 duplicates.

4. Procedures

S4.1. 250 nL of the compound was added to each well of the assay microplate by using ECHO, and centrifuged at 1000 rpm for 1 minute.

S4.2. 5 µL of the assay buffer was added and agitated for a few seconds to fully dissolve the compound.

S4.3. 5 µL of 3× substrate solution and 5 µL of 3× kinase solution were added and centrifuged at 800 rpm for 1 minute.

S4.4. Final concentrations of JAK1, JAK2, JAK3 and Tyk2 kinases in the reaction system were 20 nM, 1 nM, 1 nM and 1 nM respectively.

S4.5. Incubation at room temperature, where kinases had time differences, and different batches of kinases had time differences.

S4.6. When 20%-30% of the reaction completed, 15 µL of stop buffer was added to stop the reaction, and centrifuged at 1000 rpm for 2 minutes.

S4.7. The microplates were placed on EZ Reader for reading.

S4.8. Readings on EZ Reader were calculated by using a peak height, where product conversion ratio (%)=product/(product+substrate)*100.

5. Data Processing: IC50 Calculation

A graphing software Xlfit was used to form a concentration curve of the test compound, and an IC50 value was calculated.

IC50 values for the compounds shown in the above examples that are obtained by using the method are listed in the table below.

IC50 values for the compounds shown in the above examples are listed in the table below. "A" means ">10 µM"; "B" means ">1 µM and <10 µM"; "C" means "≥0.1 µM and <1 µM"; and "D" means "<0.1 µM".

| No. | Tyk2/µM | JAK1/µM | JAK2/µM | JAK3/µM |
|---|---|---|---|---|
| TDM-180748 | C | C | C | B |
| TDM-180749 | B | B | B | A |
| TDM-180754 | C | D | D | B |

-continued

| No. | Tyk2/μM | JAK1/μM | JAK2/μM | JAK3/μM |
|---|---|---|---|---|
| TDM-180755 | D | D | D | B |
| TDM-180756 | C | C | C | B |
| TDM-180757 | D | D | D | C |
| TDM-180758 | B | C | B | B |
| TDM-180759 | B | B | B | A |
| TDM-180760 | C | C | B | A |
| TDM-180761 | C | C | B | A |
| TDM-180762 | C | C | C | B |
| TDM-180763 | B | 10 | B | A |
| TDM-180764 | B | B | B | A |
| TDM-180767 | C | C | C | B |
| TDM-180768 | C | C | C | B |
| TDM-180773 | A | A | | |
| TDM-180774 | A | A | | |
| TDM-180777 | A | A | | |
| TDM-180779 | B | B | | |
| TDM-180780 | C | C | B | >10 |
| TDM-180781 | B | B | | |
| TDM-180782 | B | A | | |
| TDM-180783 | B | C | | |
| TDM-180784 | B | C | | |
| TDM-180787 | B | B | | |
| TDM-180788 | B | B | | |
| TDM-180789 | B | A | | |
| TDM-180790 | A | A | | |
| TDM-180791 | B | C | | |
| TDM-180792 | A | A | | |
| TDM-180799 | B | C | | |
| TDM-180801 | C | C | C | B |
| TDM-180802 | C | C | C | A |
| TDM-180803 | C | C | C | A |
| TDM-180804 | C | C | C | B |
| TDM-180805 | C | C | C | B |
| TDM-180806 | B | B | | |
| TDM-180813 | B | C | C | A |
| TDM-180814 | B | C | C | B |
| TDM-180818 | C | C | C | B |
| TDM-180819 | C | C | C | B |
| TDM-180820 | D | D | D | D |
| TDM-180821 | C | C | C | A |
| TDM-180822 | D | D | D | C |
| TDM-180823 | B | C | B | B |
| TDM-180826 | B | B | | |
| TDM-180827 | B | B | C | A |
| TDM-180828 | B | B | B | A |
| TDM-180829 | B | B | | |
| TDM-180830 | C | D | C | C |
| TDM-180831 | A | B | | |
| TDM-180832 | C | C | C | B |
| TDM-180833 | C | C | C | B |
| TDM-180834 | C | D | D | B |
| TDM-180844 | C | C | C | B |
| TDM-180849 | C | C | C | B |
| TDM-180850 | C | C | C | A |
| TDM-180852 | B | B | | |
| TDM-180853 | B | B | | |
| TDM-180867 | C | C | | |
| TDM-180868 | D | D | | |
| TDM-180869 | C | C | | |
| TDM-180870 | C | D | | |
| TDM-180875 | B | C | | |
| TDM-180876 | C | D | | |
| TDM-180877 | B | C | | |
| TDM-180881 | C | D | | |
| TDM-180882 | C | D | | |
| TDM-180884 | C | C | | |
| TDM-180885 | C | D | | |
| TDM-180886 | C | D | | |
| TDM-180887 | B | C | | |
| TDM-180888 | C | C | | |
| TDM-180889 | B | C | | |
| TDM-180890 | B | C | | |
| TDM-180891 | B | B | | |
| TDM-180892 | B | C | | |
| TDM-180893 | C | C | | |
| TDM-180894 | C | C | | |
| TDM-180895 | A | B | | |
| TDM-180896 | C | C | | |
| TDM-180897 | C | C | | |
| TDM-180898 | C | C | | |
| TDM-180899 | C | D | | |
| TDM-180900 | C | D | | |
| TDM-180901 | A | B | | |
| TDM-180902 | B | B | | |
| TDM-180903 | B | B | | |
| TDM-180904 | B | B | | |
| TDM-180905 | B | C | | |
| TDM-180906 | B | C | | |
| TDM-180907 | B | B | | |
| TDM-180908 | B | C | | |
| TDM-180910 | A | B | | |
| TDM-180911 | B | C | | |
| TDM-180913 | A | A | | |
| TDM-180914 | B | B | | |
| TDM-180917 | C | C | | |
| TDM-180919 | A | A | | |
| TDM-180920 | C | C | | |
| TDM-180921 | A | A | | |
| TDM-180923 | A | C | | |
| TDM-180924 | B | C | | |
| TDM-180926 | A | A | | |
| TDM-180929 | A | B | | |
| TDM-180933 | A | B | | |
| TDM-180934 | D | D | | |
| TDM-180935 | D | D | | |
| TDM-180936 | C | D | | |
| TDM-180939 | C | D | | |

The invention claimed is:

1. A JAK1/Tyk2 dual inhibitor represented by the structural formula:

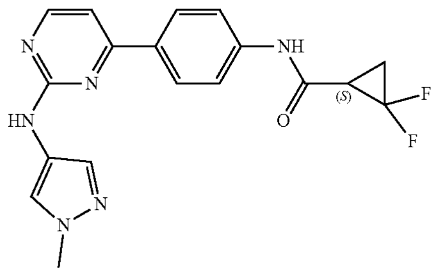

or

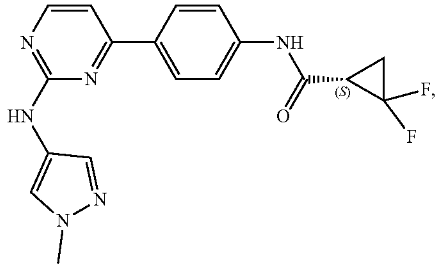

or stereoisomer, geometric isomer, tautomer, racemate, hydrate, solvate, or pharmaceutically acceptable salt thereof.

* * * * *